US012398130B2

(12) United States Patent
Quattropani et al.

(10) Patent No.: US 12,398,130 B2
(45) Date of Patent: Aug. 26, 2025

(54) ACID ADDITION SALTS OF PIPERAZINE DERIVATIVES

(71) Applicant: Asceneuron SA, Lausanne (CH)

(72) Inventors: Anna Quattropani, Rolle (CH); Santosh S. Kulkarni, Bangalore (IN); Awadut Gajendra Giri, Bangalore (IN); Dawn V. Toronto, Saint Lamain (FR); David Malcolm Crowe, Reading (GB)

(73) Assignee: Asceneuron SA, Lausanne (CH)

( * ) Notice: Subject to any disclaimer, the term of this patent is extended or adjusted under 35 U.S.C. 154(b) by 0 days.

(21) Appl. No.: 18/062,295

(22) Filed: Dec. 6, 2022

(65) Prior Publication Data

US 2023/0120169 A1   Apr. 20, 2023

Related U.S. Application Data

(62) Division of application No. 16/877,284, filed on May 18, 2020, now Pat. No. 11,591,327, which is a division of application No. 16/079,162, filed as application No. PCT/EP2017/054278 on Feb. 24, 2017, now Pat. No. 10,696,668.

(30) Foreign Application Priority Data

Feb. 25, 2016 (IN) .............................. 201621006638

(51) Int. Cl.
  *C07D 417/14* (2006.01)
  *C07D 405/12* (2006.01)
  *C07D 405/14* (2006.01)
  *C07D 417/12* (2006.01)
  *C07D 513/04* (2006.01)

(52) U.S. Cl.
  CPC ......... *C07D 417/14* (2013.01); *C07D 405/12* (2013.01); *C07D 405/14* (2013.01); *C07D 417/12* (2013.01); *C07D 513/04* (2013.01)

(58) Field of Classification Search
  CPC .. C07D 417/12; C07D 417/14; C07D 405/12; C07D 405/14; C07D 513/04
  See application file for complete search history.

(56) References Cited

U.S. PATENT DOCUMENTS

| | | | |
|---|---|---|---|
| 3,299,067 | A | 1/1967 | Regnier et al. |
| 3,457,263 | A | 7/1969 | Regnier et al. |
| 3,485,757 | A | 12/1969 | Shapiro et al. |
| 3,489,757 | A | 1/1970 | Koppe et al. |
| 4,600,025 | A | 7/1986 | Grigg et al. |
| 5,935,974 | A | 8/1999 | Rae et al. |
| 7,582,769 | B2 | 9/2009 | Murray et al. |
| 7,666,875 | B2 | 2/2010 | Gallagher, Jr. et al. |
| 8,008,326 | B2 | 8/2011 | Borza et al. |
| 8,952,166 | B2 | 2/2015 | Ding et al. |
| 9,120,781 | B2 | 9/2015 | Li et al. |
| 10,336,775 | B2 | 7/2019 | Quattropani et al. |
| 10,344,021 | B2 | 7/2019 | Quattropani et al. |
| 10,556,902 | B2 | 2/2020 | Quattropani et al. |
| 10,696,668 | B2 | 6/2020 | Quattropani et al. |
| 10,995,090 | B2 | 5/2021 | Quattropani et al. |
| 11,046,712 | B2 | 6/2021 | Quattropani et al. |
| 11,213,525 | B2 | 1/2022 | Quattropani et al. |
| 11,261,183 | B2 | 3/2022 | Quattropani et al. |
| 11,591,327 | B2 | 2/2023 | Quattropani et al. |
| 11,612,599 | B2 | 3/2023 | Quattropani et al. |
| 11,731,972 | B2 | 8/2023 | Quattropani et al. |
| 11,795,165 | B2 | 10/2023 | Quattropani et al. |
| 12,016,852 | B2 | 6/2024 | Quattropani et al. |
| 12,157,734 | B2 | 12/2024 | Quattropani et al. |
| 12,187,741 | B2 | 1/2025 | Quattropani et al. |
| 12,195,455 | B2 | 1/2025 | Quattropani et al. |
| 2004/0106645 | A1 | 6/2004 | Blackburn et al. |
| 2006/0287340 | A1 | 12/2006 | Moriya et al. |
| 2007/0027328 | A1 | 2/2007 | Aronhime et al. |
| 2008/0300276 | A1 | 12/2008 | Borza et al. |
| 2009/0012078 | A1 | 1/2009 | Andrews et al. |
| 2009/0163545 | A1 | 6/2009 | Goldfarb |
| 2010/0022517 | A1 | 1/2010 | Richards et al. |
| 2011/0053982 | A1 | 3/2011 | Fay et al. |
| 2011/0060012 | A1 | 3/2011 | Meyers et al. |
| 2011/0060019 | A1 | 3/2011 | Murray et al. |
| 2012/0208808 | A1 | 8/2012 | Buchstaller et al. |
| 2016/0031871 | A1 | 2/2016 | Yu et al. |
| 2021/0198250 | A1 | 7/2021 | Quattropani et al. |
| 2021/0206766 | A1 | 7/2021 | Quattropani et al. |

(Continued)

FOREIGN PATENT DOCUMENTS

CN  103435606 A  12/2013
EP  2301936 A1  3/2011

(Continued)

OTHER PUBLICATIONS

Abdel-Magid, A. F. et al. "Reductive Amination of Aldehydes and Ketones with Sodium Triacetoxyborohydride. Studies on Direct and Indirect Reductive Amination Procedures", J. Org. Chem., 1996, 61, 3849-3862.

Aitipamula, S. et al. "Polymorphs, Salts, and Cocrystals: What's in a Name?", Cryst. Growth Des., 2012, 12(5), 2147-2152.

Albertson, N. F. "Alkylation with Non-ketonic Mannich Bases. Aminothiazoles and Pyrrole", J. Am. Chem. Soc., 1948, 70(2), 669-670.

Andres, J. I. et al. "Synthesis, Evaluation, and Radiolabeling of New Potent Positive Allosteric Modulators of the Metabotropic Glutamate Receptor 2 as Potential Tracers for Positron Emission Tomography Imaging", J. Med. Chem., 2012, 55, 8685-8699.

(Continued)

*Primary Examiner* — Erich A Leeser
(74) *Attorney, Agent, or Firm* — COOLEY LLP

(57) ABSTRACT

The invention relates to acid addition salts of piperazine derivatives, as well as solid forms, such as polymorphic forms, thereof, which are useful as pharmaceutical ingredients and, in particular, as glycosidase inhibitors.

6 Claims, 21 Drawing Sheets

(56) References Cited

U.S. PATENT DOCUMENTS

| | | |
|---|---|---|
| 2021/0213005 A1 | 7/2021 | Quattropani et al. |
| 2022/0143042 A1 | 5/2022 | Quattropani et al. |
| 2022/0177470 A1 | 6/2022 | Quattropani et al. |
| 2022/0380358 A1 | 12/2022 | Quattropani et al. |
| 2022/0411440 A1 | 12/2022 | Quattropani et al. |
| 2024/0285615 A1 | 8/2024 | Beher et al. |
| 2025/0115604 A1 | 4/2025 | Quattropani et al. |

FOREIGN PATENT DOCUMENTS

| | | | |
|---|---|---|---|
| EP | 2687507 A1 | 1/2014 | |
| FR | 1311316 A | 12/1962 | |
| GB | 1061247 A | 3/1967 | |
| JP | 2010270034 A | 12/2010 | |
| JP | 2012514605 A | 6/2012 | |
| JP | 2013512252 A | 4/2013 | |
| RU | 2251548 C2 | 5/2005 | |
| WO | WO-9321181 A1 | 10/1993 | |
| WO | WO-9743279 A1 | 11/1997 | |
| WO | WO-9846590 A1 | 10/1998 | |
| WO | WO-9921850 A1 | 5/1999 | |
| WO | WO-02094799 A2 | 11/2002 | |
| WO | WO-03092678 A1 | 11/2003 | |
| WO | WO-2004002481 A1 | 1/2004 | |
| WO | WO-2004005293 A2 | 1/2004 | |
| WO | WO-2004022558 A2 | 3/2004 | |
| WO | WO-2004094380 A1 | 11/2004 | |
| WO | WO-2005110982 A2 | 11/2005 | |
| WO | WO-2006092049 A1 | 9/2006 | |
| WO | WO-2007008541 A2 | 1/2007 | |
| WO | WO-2007115077 A2 | 10/2007 | |
| WO | WO-2007135398 A1 | 11/2007 | |
| WO | WO-2007146122 A2 | 12/2007 | |
| WO | WO-2008012623 A1 | 1/2008 | |
| WO | WO-2008025170 A1 | 3/2008 | |
| WO | WO-2009011904 A1 | 1/2009 | |
| WO | WO-2009053373 A1 | 4/2009 | |
| WO | WO-2009131926 A1 | 10/2009 | |
| WO | WO-2010018868 A1 | 2/2010 | |
| WO | WO-2010021381 A1 | 2/2010 | |
| WO | WO-2010022517 A1 | 3/2010 | |
| WO | WO-2010026989 A1 | 3/2010 | |
| WO | WO-2010080874 A1 | 7/2010 | |
| WO | WO-2010089127 A1 | 8/2010 | |
| WO | WO-2010101949 A1 | 9/2010 | |
| WO | WO-2010108115 A1 | 9/2010 | |
| WO | WO-2010108268 A1 | 9/2010 | |
| WO | WO-2010151318 A1 | 12/2010 | |
| WO | WO-2011066352 A1 | 6/2011 | |
| WO | WO-2011140640 A1 | 11/2011 | |
| WO | WO-2012037298 A1 | 3/2012 | |
| WO | WO-2012061927 A1 | 5/2012 | |
| WO | WO-2012062157 A1 | 5/2012 | |
| WO | WO-2012062759 A1 | 5/2012 | |
| WO | WO-2012083435 A1 | 6/2012 | |
| WO | WO-2012117219 A1 | 9/2012 | |
| WO | WO-2013028715 A1 | 2/2013 | |
| WO | WO-2013066729 A1 | 5/2013 | |
| WO | WO-2014023723 A1 | 2/2014 | |
| WO | WO-2014032187 A1 | 3/2014 | |
| WO | WO-2014159234 A1 | 10/2014 | |
| WO | WO-2015083028 A1 | 6/2015 | |
| WO | WO-2015128333 A1 | 9/2015 | |
| WO | WO-2015164508 A1 | 10/2015 | |
| WO | WO 2016/030443 * | 3/2016 | ........... C07D 403/12 |
| WO | WO-2016030443 A1 | 3/2016 | |
| WO | WO-2017001660 A1 | 1/2017 | |
| WO | WO-2017076900 A1 | 5/2017 | |
| WO | WO-2017087858 A1 | 5/2017 | |
| WO | WO-2017087863 A1 | 5/2017 | |
| WO | WO-2017091818 A1 | 6/2017 | |
| WO | WO-2017106254 A1 | 6/2017 | |
| WO | WO-2017144633 A1 | 8/2017 | |
| WO | WO-2017144635 A1 | 8/2017 | |
| WO | WO-2017144639 A1 | 8/2017 | |
| WO | WO-2017223243 A1 | 12/2017 | |
| WO | WO-2018026371 A1 | 2/2018 | |
| WO | WO-2018109198 A1 | 6/2018 | |
| WO | WO-2018109202 A1 | 6/2018 | |
| WO | WO-2018140299 A1 | 8/2018 | |
| WO | WO-2018141984 A1 | 8/2018 | |
| WO | WO-2018153507 A1 | 8/2018 | |
| WO | WO-2018153508 A2 | 8/2018 | |
| WO | WO-2018154133 A1 | 8/2018 | |
| WO | WO-2018217558 A1 | 11/2018 | |

OTHER PUBLICATIONS

Ansari, S. A. et al. "The Role of Insulin Resistance and Protein O-GlcNAcylation in Neurodegeneration", Front. Neurosci., 2019, 13, Article 473, 9 pages.

Apsunde, T. D. et al. "Microwave-Assisted Iridium-Catalyzed Synthesis of Nicotine and Anabasine Derivatives", Synthesis, 2013, 45(15), 2120-2124.

Aube, J. et al. "Intramolecular Schmidt reaction of alkyl azides", J. Am. Chem. Soc. 1991, 113(23), 8965-8966.

Augustine, J. K. et al. "Propylphosphonic anhydride (T3P®): an efficient reagent for the one-pot synthesis of 1,2,4-oxadiazoles, 1,3,4-oxadiazoles, and 1,3,4-thiadiazoles", Tetrahedron, 2009, 65, 9989-9996.

Bastin, R. J. et al., "Salt Selection and Optimisation Procedures for Pharmaceutical New Chemical Entities", Org. Proc. Res. Dev., 2000, 4(5), 427-435.

Berge, S. M. et al. "Pharmaceutical Salts", J. Pharm. Sci., 1977, 1-19.

Biscoe, M. R. et al. "A New Class of Easily Activated Palladium Precatalysts for Facile C-N Cross-Coupling Reactions and Low Temperature Oxidative Addition of Aryl Chlorides", J. Am. Chem. Soc., 2008, 130, 6686-6687.

Bohnert, T. et al. "Plasma Protein Binding: From Discovery to Development", J. Pharm. Sci., 2013, 102, 2953-2994.

Bras, N. F. et al. "Glycosidase inhibitors: a patent review (2008-2013)", Expert Opin. Ther. Pat., 2014, 24(8), 857-874.

Bundgaard, H. "Design and Application of Pro-drugs", A Textbook of Drug Design and Development, edited by Krogsgaard-Larsen and H. Bundgaard, 1991, Chapter 5, 113-191.

Bundgaard, H. "Design of prodrugs: Bioreversible derivatives for various functional groups and chemical entities", Design of Prodrugs, 1985, 1 page.

Calcagno, A. M. "Comparison of Drug Transporter Levels in Normal Colon, Colon Cancer, and Caco-2 Cells: Impact on Drug Disposition and Discovery", Mol. Pharm., 2006, 3(1), 87-93.

CAS Registry (Online) Nos. 948053-91-6; 540512-02-5; 697229-62-2; 346662-52-0; 345992-64-5 (STN database summary sheets) Sep. 26, 2007, 16 pages.

"Chemical Encyclopedia", vol. 4, pp. 990-993, 1988. (Machine translation attached).

Chen, W. "Redox-Neutral α-Arylation of Amines", Org. Lett., 2014, 16(3), 2014, 730-732.

Chen, Y. et al. "Discovery of new acetylcholinesterase and butyrylcholinesterase inhibitors through structure-based virtual screening", RSC Adv., 2017, 7(6), 3429-3438.

Chrovian, C. C. et al "A Dipolar Cycloaddition Reaction To Access 6-Methyl-4,5,6,7-tetrahydro-1H-[1,2,3]triazolo[4,5-c]pyridines Enables the Discovery Synthesis and Preclinical Profiling of a P2X7 Antagonist Clinical Candidate", J. Med. Chem., 2018, 61(1), p. 207-223.

Collet, A. "Resolution of Racemates: Did you say 'Classical?'", Angew. Chem. Int. Ed., 1998, 37(23), 3239-3241.

Dai, W. et al. "Highly Chemoselective and Enantioselective Catalytic Oxidation of Heteroaromatic Sulfides via High-Valent Manganese(IV)-Oxo Cation Radical Oxidizing Intermediates", ACS Catal., 2017, 7, 4890-4895.

Damasio, A. R. "Alzheimer's Disease And Related Dementias", Cecil Textbook of Medicine, 20th Edition, vol. 2, 1996, 1992-1996.

Dassanayaka, S. et al. "O—GlcNAc and the cardiovascular system", Pharmacol. Ther., 2014, 142, 62-71.

Database PubChem Compound, NCBI; Apr. 9, 2016; XP002768133, Database accession No. CID 118902929, 10 pages.

(56) References Cited

OTHER PUBLICATIONS

Database Pubchem Compound (Online) NCBI; Jan. 24, 2012, XP002768130, Database accession No. CID 54914491, 11 pages.
Database PubChem Compound (Online) NCBI; May 28, 2009; XP002768131, Database accession No. CID 28798635, 9 pages.
Database Registry, Chemical Abstracts Service, Jan. 11, 2017, XP002768132, Database accession No. 2055841-81-9, 4 pages.
Database Registry, Chemical Abstracts Service, 2016, CID120907609, 10 pages.
Database Registry (online) Chemical abstract service, Columbus, Ohio, US; Dec. 6, 2011, "Piperazine, 1-[1-(1,3-benzodioxol-5-yl)ethyl]-4-(5-bromo-6-methoxy-2-pyridinyl)-", Database accession No. 1349611-60-4, 1 page.
Dorfmueller, H. C. et al. "Cell-Penetrant, Nanomolar O—GlcNAcase Inhibitors Selective against Lysosomal Hexosaminidases", Chem. Biol., 2010, 17, 1250-1255.
Dubois, B. et al. "Advancing research diagnostic criteria for Alzheimer's disease: the IWG-2 criteria", Lancet Neurol., 2014, 13, 614-629.
Dubois, B. et al. "Preclinical Alzheimer's disease: Definition, natural history, and diagnostic criteria", Alzheimers Dement., 2016, 12, 292-323.
Dyatkin, A.B. et al. "Determination of the Absolute Configuration of a Key Tricyclic Component of a Novel Vasopressin Receptor Antagonist by Use of Vibrational Circular Dichroism", Chirality, 2002, 14, 215-219.
Ellman, J. A. et al. "N-tert-Butanesulfinyl !mines: Versatile Intermediates for the Asymmetric Synthesis of Amines", Acc. Chem. Res., 2002, 35, 984-995.
Fleury-Bregeot, N. et al. "Suzuki-Miyaura Cross-Coupling of Potassium Alkoxyethyltri-fluoroborates: Access to Aryl/Heteroarylethyloxy Motifs", J. Org. Chem. 2012, 77(22), 10399-10408.
Fors, B. P. et al. "A Highly Active Catalyst for Pd-Catalyzed Amination Reactions: Cross-Coupling Reactions Using Aryl Mesylates and the Highly Selective Monoarylation of Primary Amines Using Aryl Chlorides", J. Am. Chem. Soc., 2008, 130, 13552-13554.
Frehel, D. et al. "New synthesis of 5,6,7,8-tetrahydro-4H-thieno[2,3-d]azepine", J. Heterocycl. Chem., 1985, 22, 1011-1016.
Frings, M. et al. "Sulfoximines from a Medicinal Chemist's Perspective: Physicochemical and in vitro Parameters Relevant for Drug Discovery", Eur. J. Med. Chem., 2017, 126, 225-245.
Goho, A. "Tricky Business", Science News, 2004, 166(8), 122-124.
Golub, T. R. et al., "Molecular classification of cancer: class discovery and class prediction by gene expression monitoring", Science, 1999, 286, 531-537.
Gong, C. X. et al. "O—GlcNAcylation: A regulator of tau pathology and neurodegeneration", Alzheimers Dement., 2016, 12, 1078-1089.
Gould, P. L. "Salt selection for basic drugs", Int. J. Pharm., 1986, 33, 201-217.
Graham, D. L. et al. "Increased O—GlcNAcylation reduces pathological tau without affecting its normal phosphorylation in a mouse model of tauopathy", Neuropharmacology, 2014, 79, 307-313.
Gujjar, R. et al. "Lead Optimization of Aryl and Aralkyl Amine-Based Triazolopyrimidine Inhibitors of Plasmodium falciparum Dihydroorotate Dehydrogenase with Antimalarial Activity in Mice", J. Med. Chem., 2011, 54(11), 3935-3949.
Gura et al. "Systems for Identifying New Drugs are Often Faulty", Science, 1997, 278,1041-1042.
Haleblian, J. "Characterization of Habits and Crystalline Modification of Solids and Their Pharmaceutical Applications", J. Pharm. Sci., 1975, 64(8), 1269-1288.
Haleblian, J. et al."Pharmaceutical Applications of Polymorphism", J. Pharm. Sci., 1969, 58(8), 911-929.
Hemming, K. "Product Class 6: 1,2,4-Oxadizoles", Sci. Synth., 2004, 13(6), 127-184.
Yamanaka, H. et al. Chemical Abstract, "Separation of Optical Isomers", Japan, Gakkai Shopping Santa, 1989, 21 pages.
Hulikal, V. "Deuterium Labeled Compounds in Drug Discovery Process", Abstract, Bioorganics and Applied Materials Pvt Ltd., 2010, 1 page.
Jakopin, Z. et al. "Recent Advances in the Synthesis of 1,2,4- and 1,3,4-Oxadiazoles", Curr. Org. Chem., 2008, 12(10), 850-898.
Johnson, J. J. et al. "Relationships Between Drug Activity in NCI Preclinical in vitro and in vivo Models and Early Clinical Trials", Brit. J. Cancer., 2001, 84, 1424-1431.
Kempson, J. "Name Reactions in Heterocyclic Chemistry II", John Wiley & Sons. Eds. Jie Jack Li and E. J. Corey, 2011, 299-308.
Kim, E. J. "Chemical Arsenal for the Study of O—GlcNAc", Molecules, 2011, 16, 1987-2022.
Kim, E. J. et al. "Enzymatic characterization of O—GlcNAcase isoforms using a fluorogenic GlcNAc substrate", Carbohydrate Research, 2006, 341(8), 971-982.
Kim, Y. et al. "Discovery of β-Arrestin Biased Ligands of 5-HT7R", J. Med. Chem. 2018, 61, 7218-7233.
Knapp, S. et al. "An Allosamizoline/ Glucosamine Hybrid NAGase Inhibitor", Synlett, 1997, 5, 435-436.
Layzer, R. B. "Degenerative Diseases Of The Nervous System", Cecil Textbook of Medicine, 20th Edition, vol. 2, 1996, 2050-2057.
Lefebvre, T. "Recall sugars, forget Alzheimer's", Nat. Chem. Bio., 2012, 8(4), 325-326.
Legros, J. et al. "Applications of Catalytic Asymmetric Sulfide Oxidations to the Syntheses of Biologically Active Sulfoxides", Adv. Synth. Catal., 2005, 347, 19-31.
Liu, X. et al. "Rational Use of Plasma Protein and Tissue Binding Data in Drug Design", J. Med. Chem., 2014, 57, 8238-8248.
Mariappa, D. et al. "A mutant O—GlcNAcase as a probe to reveal global dynamics of the *Drosophila* O—GlcNAc developmental proteome", Biochem. J., 2015, 470(2), 255-262.
Marotta, N. P. et al., "O—GlcNAc modification blocks the aggregation and toxicity of the Parkinson's disease associated protein α-synuclein", Nat. Chem., 2015, 7(11), 913-920.
Marwaha, A. et al. "Bioisosteric Transformations and Permutations in the Triazolopyrimidine Scaffold To Identify the Minimum Pharmacophore Required for Inhibitory Activity against Plasmodium falciparum Dihydroorotate Dehydrogenase", J. Med. Chem., 2012, 55(17), 7425-7436.
Masuda, N. et al. "Studies of nonnucleoside HIV-1 reverse transcriptase inhibitors. Part 1: Design and synthesis of thiazolidenebenzenesulfonamides", Bioorg. Med. Chem., 2004, 12, 6171-6182.
Merchant, R. R. et al. "Regioselective Preparation of Saturated Spirocyclic and Ring-Expanded Fused Pyrazoles", J. Org. Chem., 2014, 79(18), 8800-8811.
Micksch, M. et al. "Synthesis of 1,2-Diaryl- and 1-Aryl-2-alkylimidazoles with Sterically Demanding Substituents", Eur. J. Org. Chem. 2013, 27, 6137-6145.
Miller III, B. R. et al. "Design of e-pharmacophore models using compound fragments for the trans-sialidase of Trypanosoma cruzi: screening for novel inhibitor scaffolds", J. Mol. Graph. Model., 2013, 45, 84-97.
Mittur, A. "Piribedil: Antiparkinsonian Properties and Potential Clinical Utility in Dopaminergic Disorders", Curr. Drug Ther., 2011, 6, 17-34.
Moradi-Afrapoli, F. et al. "In vitro α-glucosidase inhibitory activity of phenolicconstituents from aerial parts of Polygonum hyrcanicum", Daru Journal of Pharmaceutical Sciences, 2012, 20(1), 37, 6 pages.
Motiwala, H. F. et al. "Remodeling and Enhancing Schmidt Reaction Pathways in Hexafluoroisopropanol", J. Org. Chem., 2016, 81(8), 1593-1609.
Nandi, A. et al. "Global Identification of O—GlcNAc-Modified Proteins", Anal. Chem., 2006, 78, 452-458.
Nelson, P. T. et al. "Correlation of Alzheimer Disease Neuropathologic Changes With Cognitive Status: A Review of the Literature", J. Neuropathol. Exp. Neurol., 2012, 71(5), 362-381.
Nettekoven, M. et al. "Synthetic Access to 2-Amido-5-aryl-8-methoxy-triazolopyridine and 2-Amido-5-morpholino-8-methoxy-triazolopyridine Derivatives as Potential Inhibitors of the Adenosine Receptor Subtypes", Synthesis, 2003, 1649-1652.
Obach, R. S. "Prediction of human clearance of twenty-nine drugs from hepatic microsomal intrinsic clearance data: and examination

(56) References Cited

OTHER PUBLICATIONS of in vitro half-life approach and nonspecific binding to microsomes", Drug. Metab. Dispos., 1999, 27(11), 1350-1359.
Okamura, H. et al. "Rhodium-Catalyzed Imination of Sulfoxides and Sulfides: Efficient Preparation of N-Unsubstituted Sulfoximines and Sulfilimines", Org. Lett., 2004, 6, 1305-1307.
O'Mahony, G. E. et al. "Synthesis of enantioenriched sulfoxides", Arkivoc, 2011, 1-110.
Orain, D. et al. "Synthesis of Orthogonally Protected 2,6-Diazaspiro[3.5]nonane and 2,6-Diazaspiro[3.4]octane Analogues as Versatile Building Blocks in Medicinal Chemistry", Synlett, 2015, 26(13), 1815-1818.
Papillon, J. P. N. et al. "Discovery of N-[5-(6-Chloro-3-cyano-1-methyl-1H-indol-2-yl)-pyridin-3-ylmethyl]-ethanesulfonamide, a Cortisol-Sparing CYP11B2 Inhibitor that Lowers Aldosterone in Human Subjects", J. Med. Chem., 2015, 58, 9382-9394.
Park, M.-J. et al. "High Glucose-induced O—GlcNAcylated Carbohydrate Response Element-binding Protein (ChREBP) Mediates Mesangial Cell Lipogenesis and Fibrosis", J. Biol. Chem., 2014, 289, 13519-13530.
Pearce, H. L. et al. "Failure Modes in Anticancer Drug Discovery and Development", Cancer Drug Design and Discovery. Neidle, ed. Boston: Elsevier. (2008):424-435.
Reddy, K. R. et al. "Synthesis of Chiral Benzimidazole-Pyrrolidine Derivatives and their Application in Organocatalytic Aldol and Michael Addition Reactions", Synth. Commun., 2007, 37(24), 4289-4299.
Rouhi, A. M. et al. "The Right Stuff: From Research and Development to the Clinic, Getting Drug Crystals Right is Full of Pitfalls", Chem. Eng. News., 2003, 32-35.
Ryan, P. et al. "O—GlcNAc Modification Protects against Protein Misfolding And Aggregation in Neurodegenerative Disease", ACS Chem. Neurosci., 2019, 10(5), 2209-2221.
Santacruz, K. et al. "Tau Suppression in a Neurodegenerative Mouse Model Improves Memory Function", Science, 2005, 309, 476-481.
Serajuddin, A. T. M. "Salt Formation to Improve Drug Solubility", Adv. Drug Deliv. Rev., 2007, 59(7), 603-616.
Shan, X. et al. "Reduced protein O-glycosylation in the nervous system of the mutant SOD1 transgenic mouse model of amyotrophic lateral sclerosis", Neurosci. Lett., 2012, 516, 296-301.
Shen, Q. et al. "Hydroxycoumarin Derivatives: Novel and Potent α-Glucosidase Inhibitors", J. Med. Chem., 2010, 53(23), 8252-8259.
Shirude, P. et al. "Lead Optimization of 1,4-Azaindoles as Antimycobacterial Agents", J. Med. Chem., 2014, 57(13), 5728-5737.
Silverman, R. B. "Prodrugs and Drug Delivery Systems", The Organic Chemistry of Drug Design and Drug Action. Academic Press, Inc., 2004, Chapter 8, 352-401.
Simone, J. V. "Introduction", Cecil Textbook of Medicine. 20th Ed., vol. I . J. Claude Bennet and F. Plum (Eds.) W.B. Sauders Co., 1997, 1004-1010.
Sippy, K. B. et al. "Preparation and characterization of N-(3-pyridinyl) spirocyclic diamines as ligands for nicotinic acetylcholine receptors", Bioorganic & Med. Chemistry Letters, 2009, 19(6), 1682-1685.
Skedelj, V. et al. "Discovery of the first inhibitors of bacterial enzyme D-aspartate ligase from Enterococcus faecium (Aslfm)", Eur. J. Med. Chem., 2013, 67, 208-220.
Smith, P. W. et al. "New spiropiperidines as potent and selective non-peptide tachykinin NK2 receptor antagonists", J. Med. Chem., 1995, 38, 3772-3779.
Song, S. et al. "Efficient and Practical Oxidative Bromination and Iodination of Arenes and Heteroarenes with DMSO and Hydrogen Halide: A Mild Protocol for Late-Stage Functionalization", Org. Lett., 2015, 17(12), 2886-2889.
Sperling, R. A. et al. "Toward defining the preclinical stages of Alzheimer's disease: Recommendations from the National Institute on Aging—Alzheimer's Association workgroups on diagnostic guidelines for Alzheimer's disease", Alzheimers Dement., 2011, 7, 280-292.
Spillantini, M. G. et al. "Tau pathology and neurodegeneration", Lancet Neurol., 2013, 12, 609-622.
Tamura, B. K. et al. "Weight Loss in Patients with Alzheimer's Disease", J. Nutr. Elder., 2008, 26(3-4), 21-38.
Tan, H. et al. "Rational Screening Approach for Classical Chiral Resolution under Thermodynamic Equilibrium: A Case Study of Diphenyl-Substituted N-Methyl-Piperazine", Org. Process Res. Dev., 2011, 15(1), 53-63.
Tanuwidjaja, J. et al. "One-Pot Asymmetric Synthesis of Either Diastereomer of tert-Butanesulfinyl-protected Amines from Ketones", J. Org. Chem., 2007, 72, 626-629.
The Merck Manual, "Acute Leukemia", (Online Edition), 2013, 6 pages.
The U. S. Pharmacopeia 38—National Formulary 35 Chapter 941, Characterization of crystalline and partially crystalline solids by X-ray powder diffraction (XRPD) Official May 1, 2015, 427-431.
Thiel, O. R. et al. "Practical Synthesis of a Vanilloid Receptor-1 Antagonist", J. Org. Chem., 2008, 73(9), 3508-3515.
Trapannone, R. et al. "O—GlcNAc transferase inhibitors: current tools and future challenges", Biochem. Soc. Trans., 2016, 44(1), 88-93.
Vasudevan, A. et al. "Identification of aminopiperidine benzamides as MCHr1 antagonists", Bioorganic & Medicinal Chemistry Letters, 2005, 15(14), 3412-3416.
Volpe, D. A. "Application of Method Suitability for Drug Permeability Classification", The AAPS Journal, 2010, 12(4), 670-678.
Wall, G. M. "Pharmaceutical Applications of Drug Crystal Studies", Pharm. Manuf., 1986, 3, 32-42.
Wang, Z. et al. "Enrichment and Site Mapping of O-Linked N-Acetylglucosamine by a Combination of Chemical/Enzymatic Tagging, Photochemical Cleavage, and Electron Transfer Dissociation Mass Spectrometry", Mol. Cell Proteomics, 2010, 9(1), 153-160.
Waterman, K. C. "Improved Protocol and Data Analysis for Accelerated Shelf-Life Estimation of Solid Dosage Forms", Pharm. Res., 2007, 24(4), 780-790.
Weinberg, K. et al. "Synthesis and differential functionalisation of pyrrolidine and piperidine based spirodiamine scaffolds", Tetrahedron, 2013, 69(23), 4694-4707.
Wermuth, C. G. et al. "Designing Prodrugs and Bioprecursors I: Carrier Prodrugs", The Practice of Medicinal Chemistry: Chapter 31, Academic Press, 1996, 671-696.
Wiessner et al. "A novel non-carbohydrate o-linked beta-n-acetylglucosaminidase inhibitor increases tau o-glcnacylation In vivo", Abstracts of the Annual Meeting of the Society for Neuroscience, Society for Neuroscience, 2013, 43, 2 pages.
Williams, D. R. et al. "Pathological tau burden and distribution distinguishes progressive supranuclear palsy-parkinsonism from Richardson's syndrome", Brain, 2007, 130, 1566-1576.
Xu, D. et al. "The synthesis of chiral tridentate ligands from l-proline and their application in the copper(II)-catalyzed enantioselective Henry reaction", Tetrahedron Asymmetry, 2017, 28(7), 954-963.
Yoshida, M. et al. "Study of biodegradable copoly(L-lactic acid/glycolic acid) formulations with controlled release of Z-100 for application in radiation therapy", Int. J. Pharm., 1995, 115, 61-67.
Youngdale, G. A. et al. "Synthesis and pharmacological activity of 3-(2-pyrrolidinyl)indoles", J. Med. Chem., 1964, 7, 415-427.
Yu, Y. J. et al. "One-Pot Synthesis of Spirocyclic or Fused Pyrazoles from Cyclic Ketones: Calcium Carbide as the Carbon Source in Ring Expansion", Org. Chem. 2017, 82(18), 9479-9486.
Yuzwa, S. A. et al. "O—GlcNAc and neurodegeneration: biochemical mechanisms and potential roles in Alzheimer's disease and beyond", Chem. Soc. Rev., 2014, 43, 6839-6858.
Yuzwa, S. A. et al. "A potent mechanism-inspired O—GlcNAcase inhibitor that blocks phosphorylation of tau in vivo", Nat. Chem. Biol., 2008, 4(8), 483-490.
Yuzwa, S. A. et al. "Increasing O—GlcNAc slows neurodegeneration and stabilizes tau against aggregation", Nat. Chem. Biol., 2012, 8(4), 393-399.

(56) References Cited

OTHER PUBLICATIONS

Yuzwa, S. A. et al. "Mapping O—GlcNAc modification sites on tau and generation of a site-specific O—GlcNAc tau antibody", Amino Acids, 2011, 40, 857-868.
Zenzola, M. et al. "Transfer of Electrophilic NH Using Convenient Sources of Ammonia: Direct Synthesis of NH Sulfoximines from Sulfoxides", Angew. Chem. Int. Ed., 2016, 55, 7203-7207.
Zhang, C. et al. "Nontraditional Reactions of Azomethine Ylides: Decarboxylative Three-Component Couplings of α-Amino Acids", J. Am. Chem. Soc., 2010, 132(6), 2, 1798-1799.
U.S. Appl. No. 18/913,906, filed Oct. 11, 2024 by Quattropani et al.
U.S. Appl. No. 18/957,245, filed Nov. 22, 2024, by Quattropani et al.
U.S. Appl. No. 18/957,291, filed Nov. 22, 2024, by Quattropani et al.
CAS Registry Entry: 890335-15-6 (STN data summary sheet). Entered STN: Jul. 3, 2006, 1 pg.
Addis et al. "Efficient Conversion of Astrocytes to Functional Midbrain Dopaminergic Neurons Using a Single Polycistronic Vector", (2011) PLoS One: e28719 (8 pages).
Alenghat T. et al. "Histone deacetylase 3 coordinates commensal bacteria-dependent intestinal homeostasis", (2013) Nature 504:153-157.
Boxer et al. "Davunetide in patients with progressive supranuclear palsy: a randomised, double-blind, placebo-controlled phase 2/3 trial", Lancet Neurol. 2014;13(7):676-85.
Boxer et al., "Advances in progressive supranuclear palsy: new diagnostic criteria, biomarkers, and therapeutic approaches", Lancet 16:552-563, 2017.
Chen et al. "Protective Effects of Glucosamine on Oxidative-Stress and Ischemia/Reperfusion-Induced Retinal Injury", (2015), Invest Ophthalmol. Vis Sci. 56(3):1506-1516.
Co-pending U.S. Appl. No. 18/570,861, inventors Beher; Dirk et al., filed on Dec. 15, 2023.
Fleming et al. "Early and Progressive Sensorimotor Anomalies in Mice Overexpressing Wild-Type Human alpha-Synuclein", 2004, The Journal of Neuroscience, 24 (42):9434-40.
Gilbert S. et al. "Enterocyte STAT5 promotes mucosal wound healing via suppression of myosin light chain kinase-mediated loss of barrier function and inflammation", (2012) EMBO Mol. Med.4: 109-124.
Han et al. "Direct Reprogramming of Fibroblasts into Neural Stem Cells by Defined Factors", (2012) Cell Stem Cell 10: 465-472.
Hinz et al., "Molecular Genetics of Neurodegenerative Dementias", Cold Spring Harbor Perspectives in Biology, 2017, 9:a023705 (23 pages).
Höglinger et al., "Identification of common variants influencing risk of the tauopathy progressive supranuclear palsy", Nature Genetics 43 :699-705, 2011.
Höglinger et al. (2017) "Longitudinal magnetic resonance imaging in progressive supranuclear palsy: A new combined score for clinical trials", Movement Disorders, 32(6):842-852.
Höglinger et al. (2017) "Clinical diagnosis of progressive supranuclear palsy: The movement disorder society criteria", Movement Disorders, 32:853-64.
Kim J. et al. "Direct reprogramming of mouse fibroblasts to neural progenitors", (2011) Proc Natl Acad Sci USA 108(19):7838-7843.
Kuhn J. et al. "Deep Brain Stimulation of the Nucleus Basalis of Meynert in Early Stage of Alzheimer's Dementia", (2015) Brain Stimulation 8:838-839.
Levine et al.(2019) "α-Synuclein O—GlcNAcylation alters aggregation and toxicity, revealing certain residues as potential inhibitors of Parkinson's disease", Proc. Natl. Acad. Sci. USA 116(5):1511-1519.
Lim et al. "Generation of Dopamine Neurons from Rodent Fibroblasts through the Expandable Neural Precursor Cell Stage", (2015) J. Biol. Chem. 290:17401-17414.

Lozano et al. (2016) "A Phase II Study of Fornix Deep Brain Stimulation in Mild Alzheimer's Disease", Journal of Alzheimer's Disease, 54 :777-787.
Lujan E. et al. "Direct conversion of mouse fibroblasts to self-renewing, tripotent neural precursor cells", (2012) Proc Natl Acad Sci USA 109 :2527-2532.
Matsui T. et al. "Neural Stem Cells Directly Differentiated from Partially Reprogrammed Fibroblasts Rapidly Acquire Gliogenic Competency", (2012) Stem Cells 30: 1109-1119.
Mayer, P. "On the Staining of Mucus", (1897), Mitt. Zool. Stn. Neape., 12, p. 303-330.
Mirzadeh Z. et al. "The rationale for deep brain stimulation in Alzheimer's disease", (2016) J. Neural Transm (Vienna) 123: 775-783.
Opposition Arguments, Notice of Opposition, Indian Pharmaceutical Alliance, in Patent Application No. 202127010343 dated Nov. 3, 2021 filed by Asceneuron S.A. (Applicant), dated Feb. 6, 2024, 26 pages.
Paul S. et al. "Evaluation of a PET Radioligand to Image O—GlcNAcase in Brain and Periphery of Rhesus Monkey and Knock-Out Mouse", J. Nucl. Med. 2019, 60(1), 129-134.
Racine R.J. "Modification of Seizure Activity by Electrical Stimulation: I. After-Discharge Threshold", Electroencephalography and Clinical Neurophysiology 32(3), 269-279 (1972).
Rockenstein E, et al. "Differential Neuropathological Alterations in Transgenic Mice Expressing alpha-synuclein From The Platelet-derived Growth Factor and Thy-1 Promoters", Journal of Neuroscience Research 68:568-578 (2002).
Sanchez et al. "Human and rodent temporal lobe epilepsy is characterized by changes in OGlcNAc homeostasis that can be reversed to dampen epileptiform activity", (2019) Neurobiology of Disease 124: 531-543.
Sankar T et al. "Deep Brain Stimulation Influences Brain Structure in Alzheimer's Disease", (2015) Brain Stimulation 8:645-654.
Sheng C. et al. "Direct reprogramming of Sertoli cells into multipotent neural stem cells by defined factors" (2012) Cell Res 22: 208-218.
Stamelou M et al. (2016) "Power calculations and placebo effect for future clinical trials in progressive supranuclear palsy", Mov Disord. 31 (5):742-747.
Tolosa et al. (2014) "A phase 2 trial of the GSK-3 inhibitor tideglusib in progressive supranuclear palsy", Movement Disorders 29(4):470-478.
Vierbuchen T. et al. "Direct conversion of fibroblasts to functional neurons by defined factors", (2010) Nature 463:1035-1041.
Wahlund et al. (2001) "A new rating scale for age-related white matter changes applicable to MRI and CT", Stroke, 32(6):1318-1322.
Zhang S. Z. et al. "Modeling Neurological Disease by Rapid Conversion of Human Urine Cells into Functional Neurons", (2016) Stem Cells International, 2016: 2452985 (9 pages).
Zhao J. et al. "Neuronal Transcription Factors Induce Conversion of Human Glioma Cells to Neurons and Inhibit Tumorigenesis", (2012) PLoS ONE7:5e41506 (11 pages).
Zhao M, et al. "Deficiency in intestinal epithelial O—GlcNAcylation predisposes to gut inflammation", (2018) EMBO Mol. Med. 10: e8736 (18 pages).
Katritzky et al., "Tautomerism in drug discovery". Journal of Computer-aided Molecular Design. (Jun. 2010); 24: 475-84.
Kharkevich "Pharmacology", 2010, pp. 73-74, 10th ed. M.: GEOTAR-Media.
Mashkovsky "Medicinal Drugs", 2001, p. 11, vol. 1, 14th Ed., S.B. Divov, Moscow, 2 pages.
Office Action issued in Russian Application No. 2024100814/04(001517), mailed Nov. 29, 2024, with English translation, 26 pages.
Pokrovsky "The Small Medical Encyclopedia". 1992, vol. 3, pp. 100-103. The Comprehensive Russian Encyclopedia.
Zhulenko "Pharmacology", 2008, pp. 34-35, M.: Koloss, in non-English, Russian only.

* cited by examiner

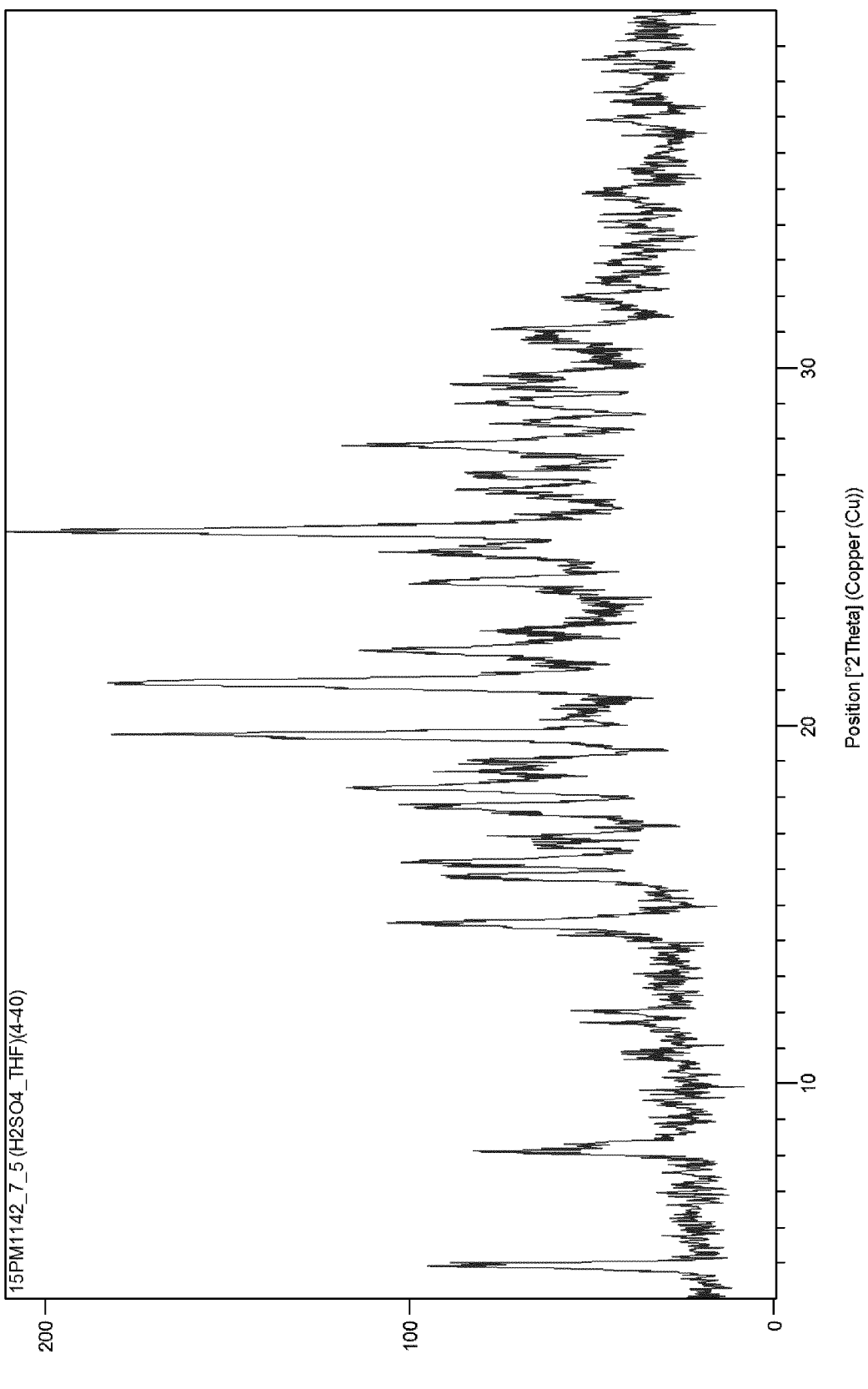
Figure 1: Characteristic X-ray powder diffraction pattern of crystalline Example 69 sulphate salt obtained in THF

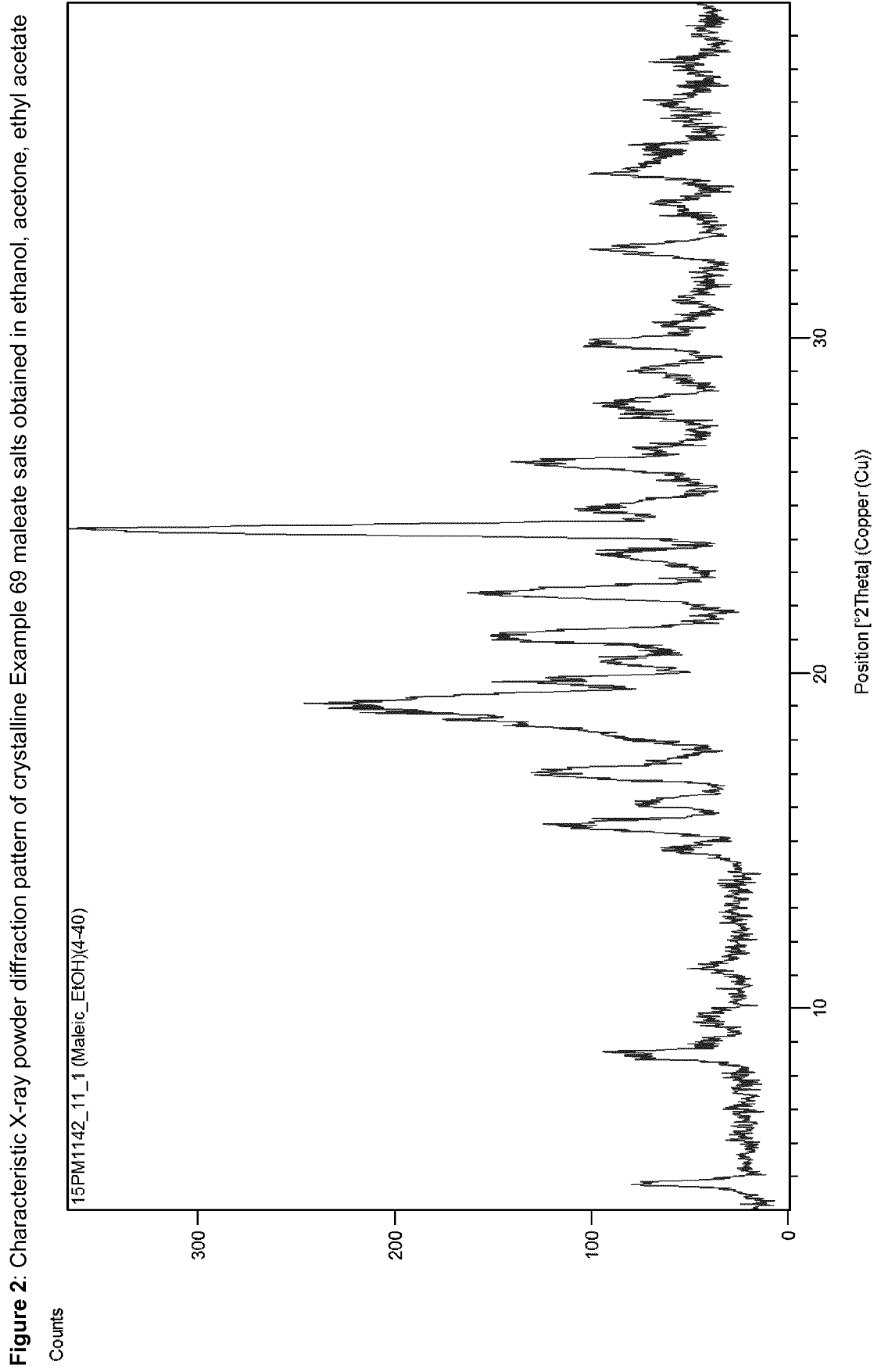
Figure 2: Characteristic X-ray powder diffraction pattern of crystalline Example 69 maleate salts obtained in ethanol, acetone, ethyl acetate

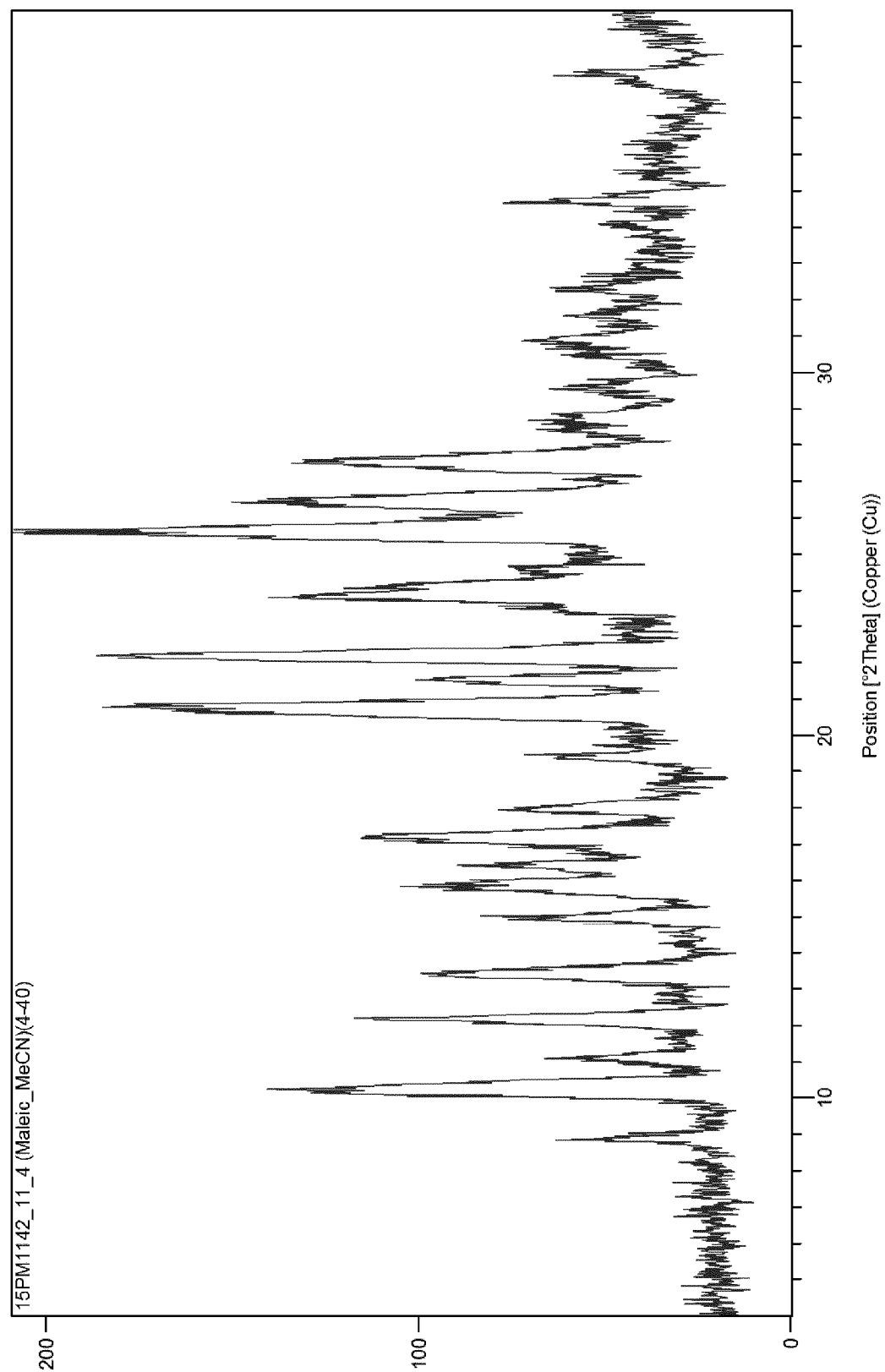
Figure 3: Characteristic X-ray powder diffraction pattern of crystalline Example 69 maleate salt obtained in MeCN

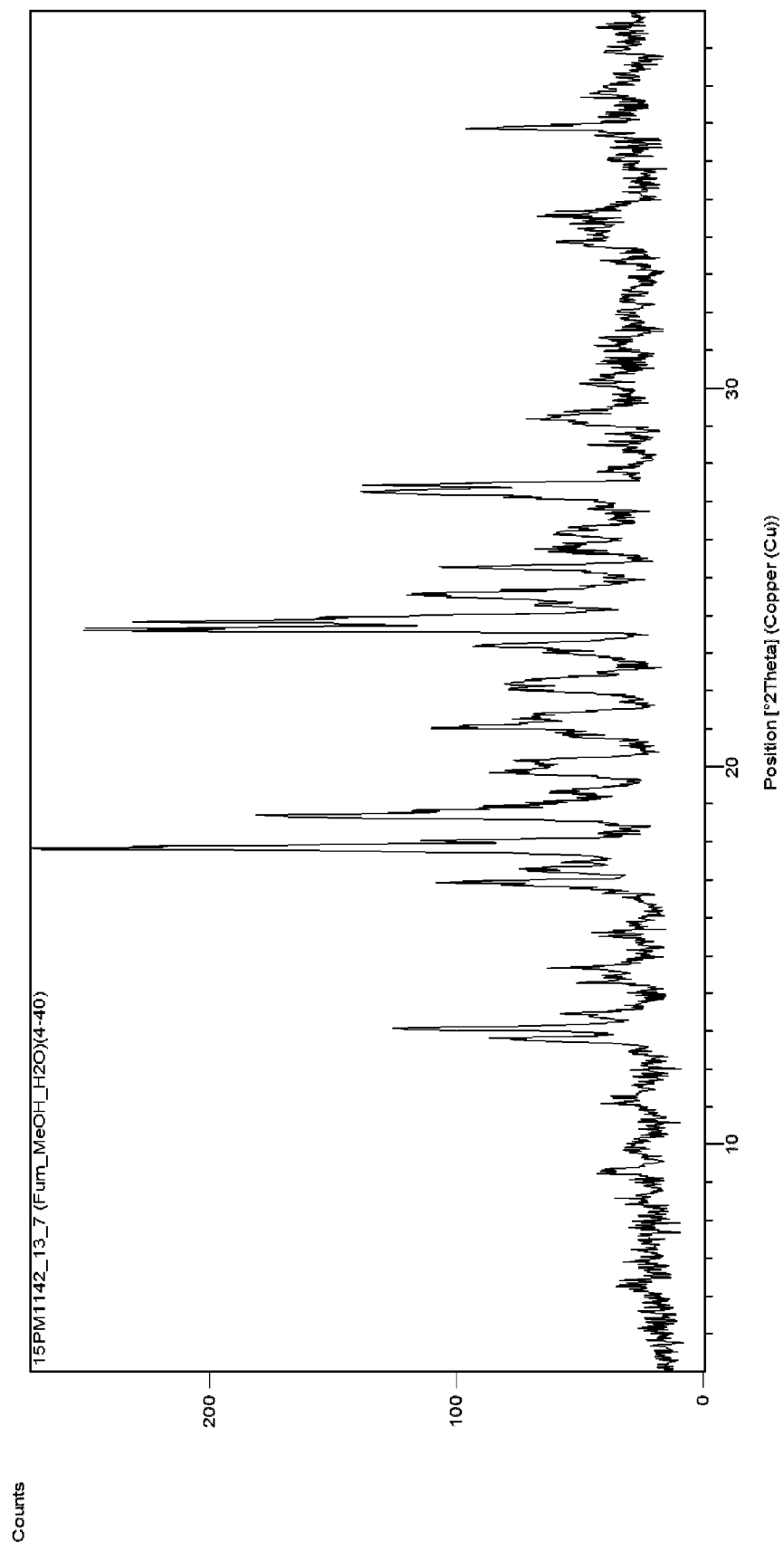
Figure 4: Characteristic X-ray powder diffraction pattern of crystalline Example 69 fumarate salt obtained in alcohol / water mixtures

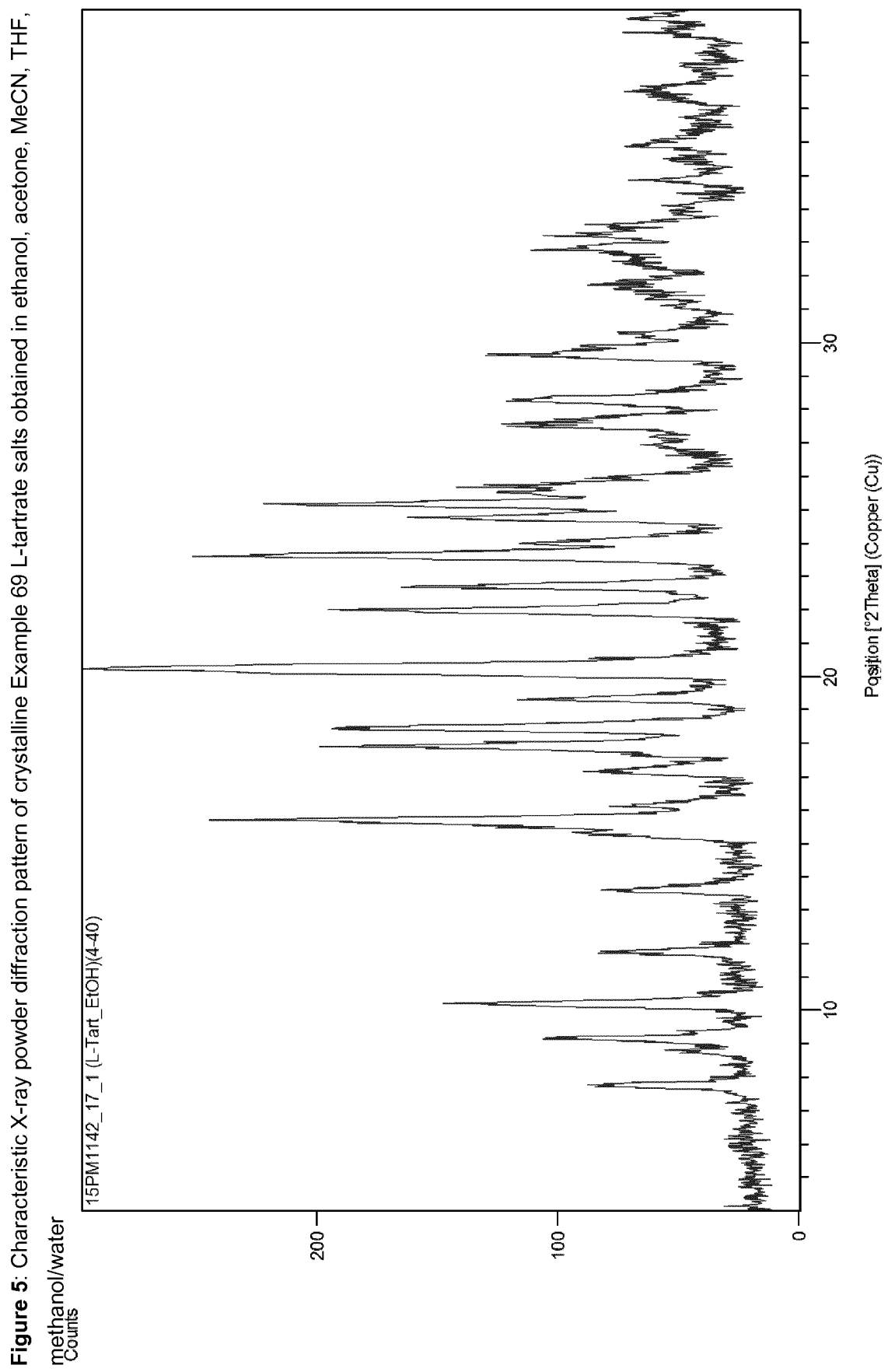
Figure 5: Characteristic X-ray powder diffraction pattern of crystalline Example 69 L-tartrate salts obtained in ethanol, acetone, MeCN, THF, methanol/water

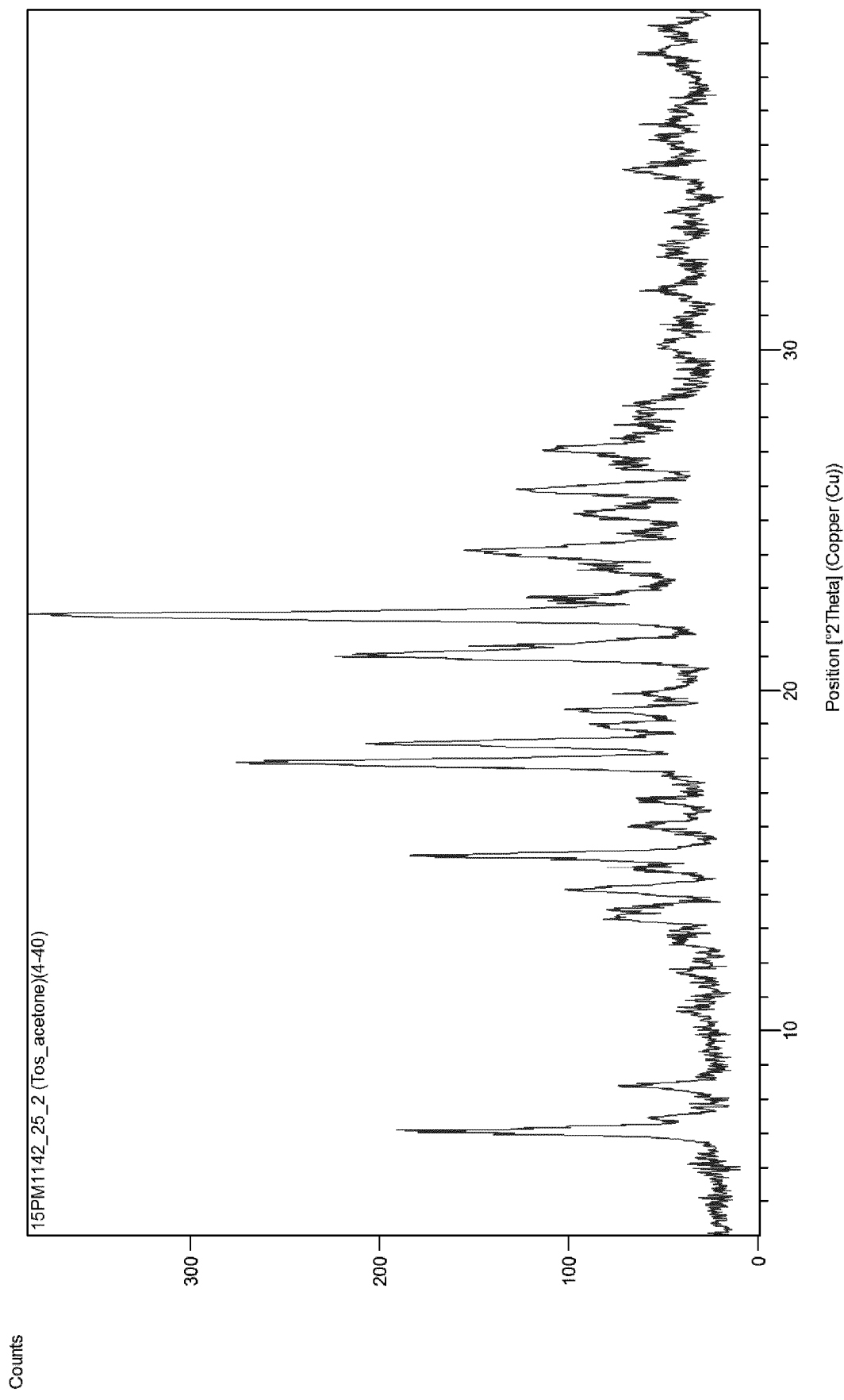
Figure 6: Characteristic X-ray powder diffraction pattern of crystalline Example 69 Tosylate salts obtained in acetone, MeCN

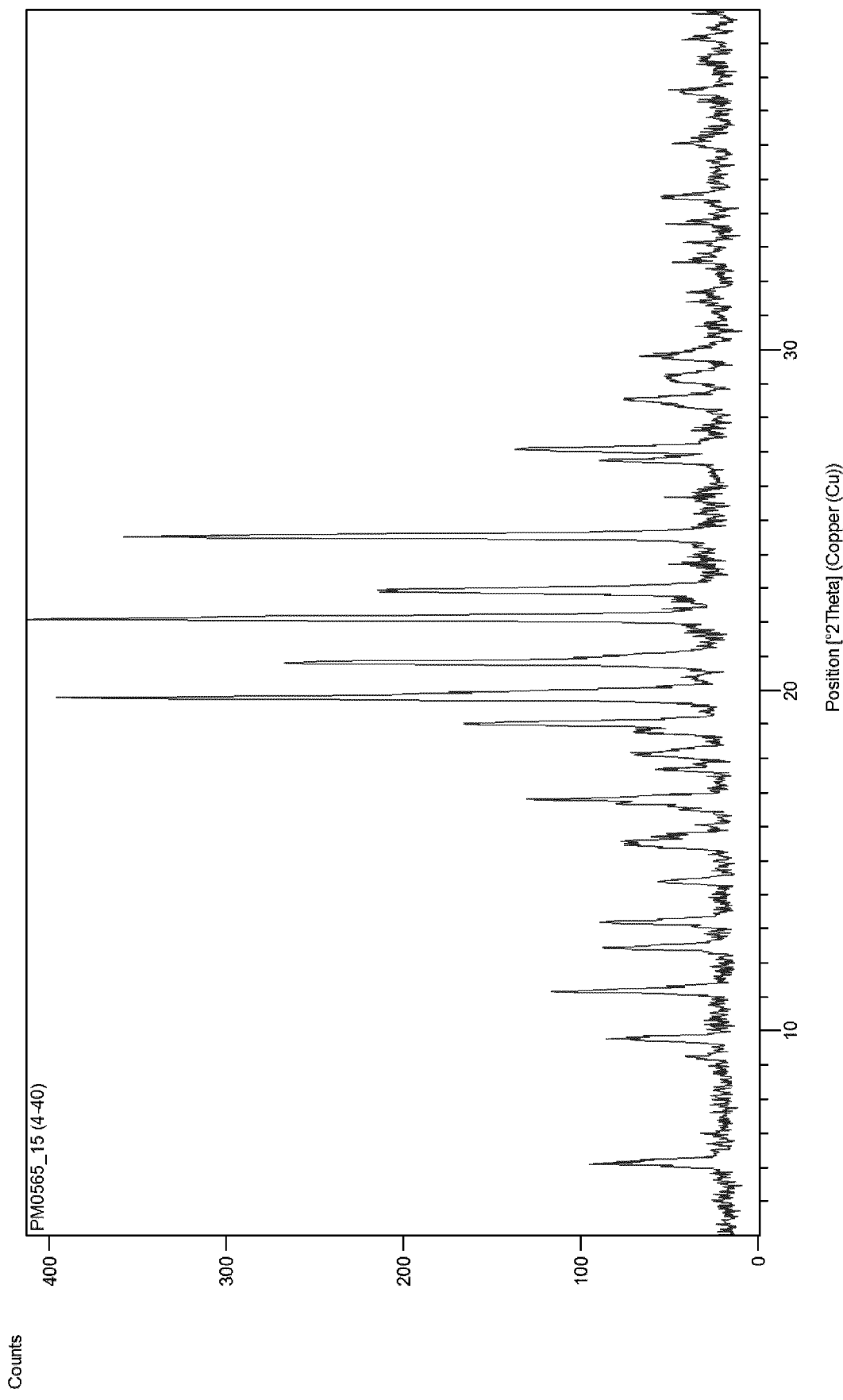
Figure 7: Characteristic X-ray powder diffraction pattern of crystalline Example 69 free base

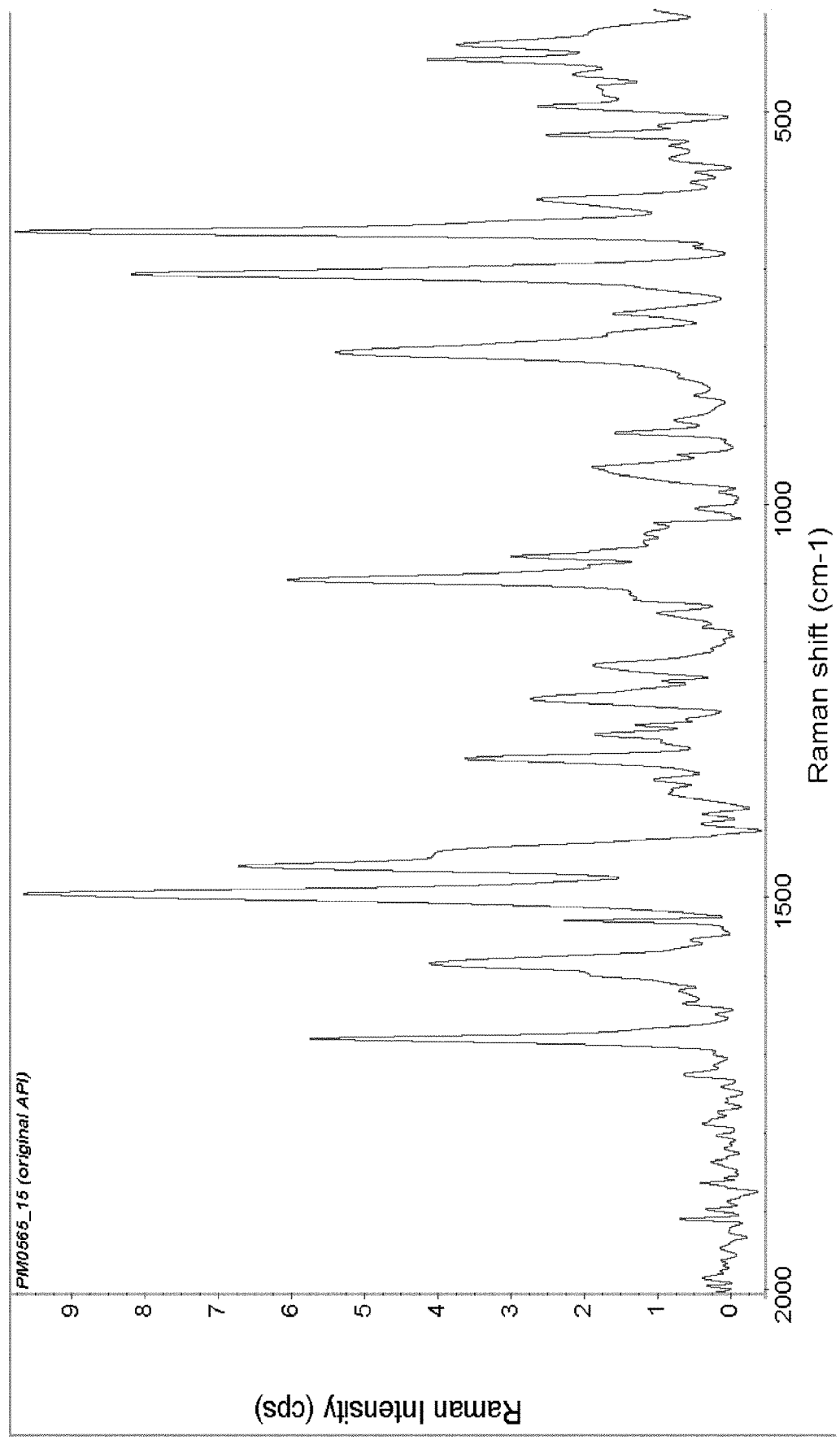
Figure 8: Characteristic Raman spectrum of crystalline Example 69 free base

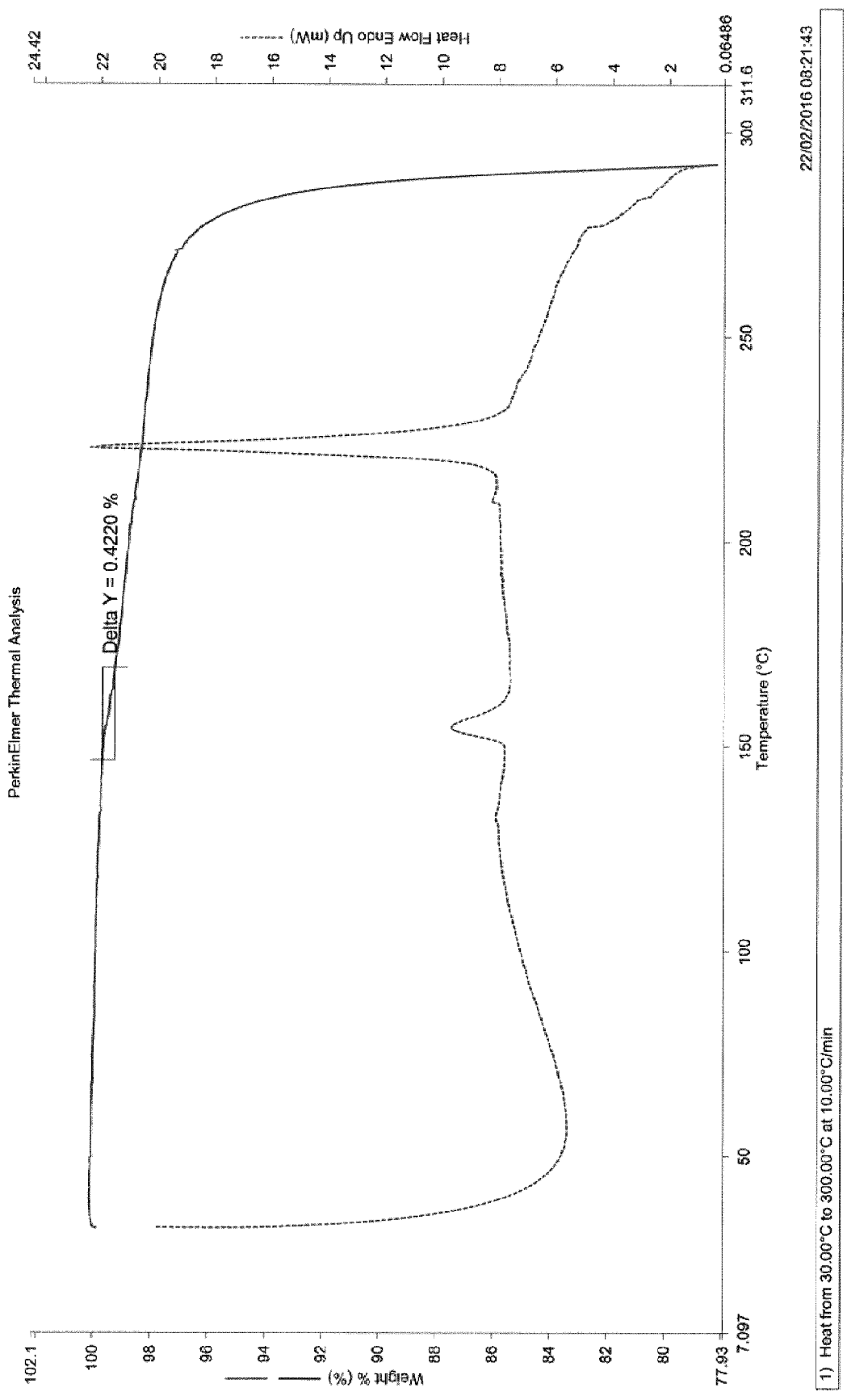
Figure 9: Characteristic STA thermogram of crystalline Example 69 free base

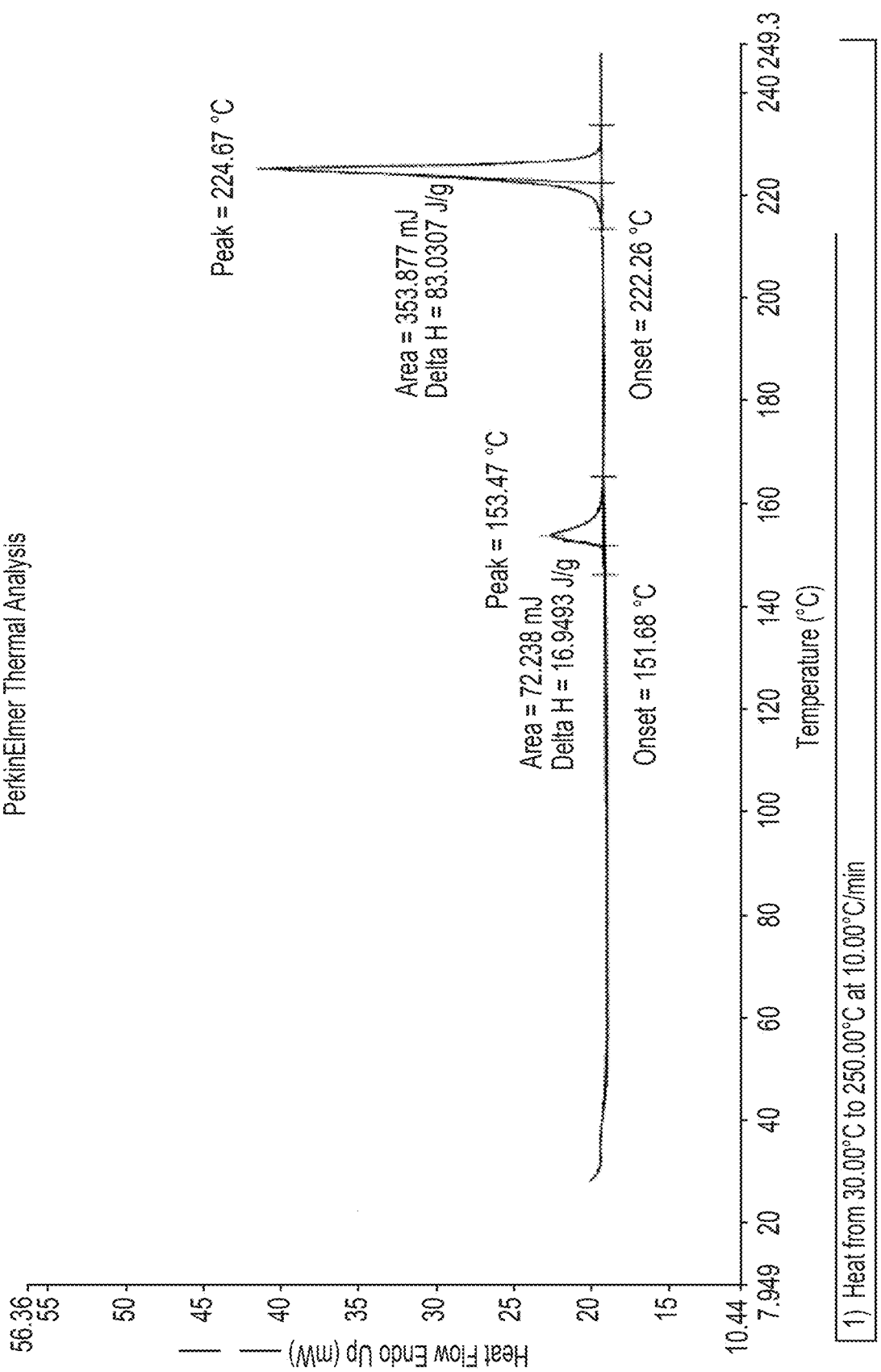
Figure 10: Characteristic DSC thermogram of crystalline Example 69 free base

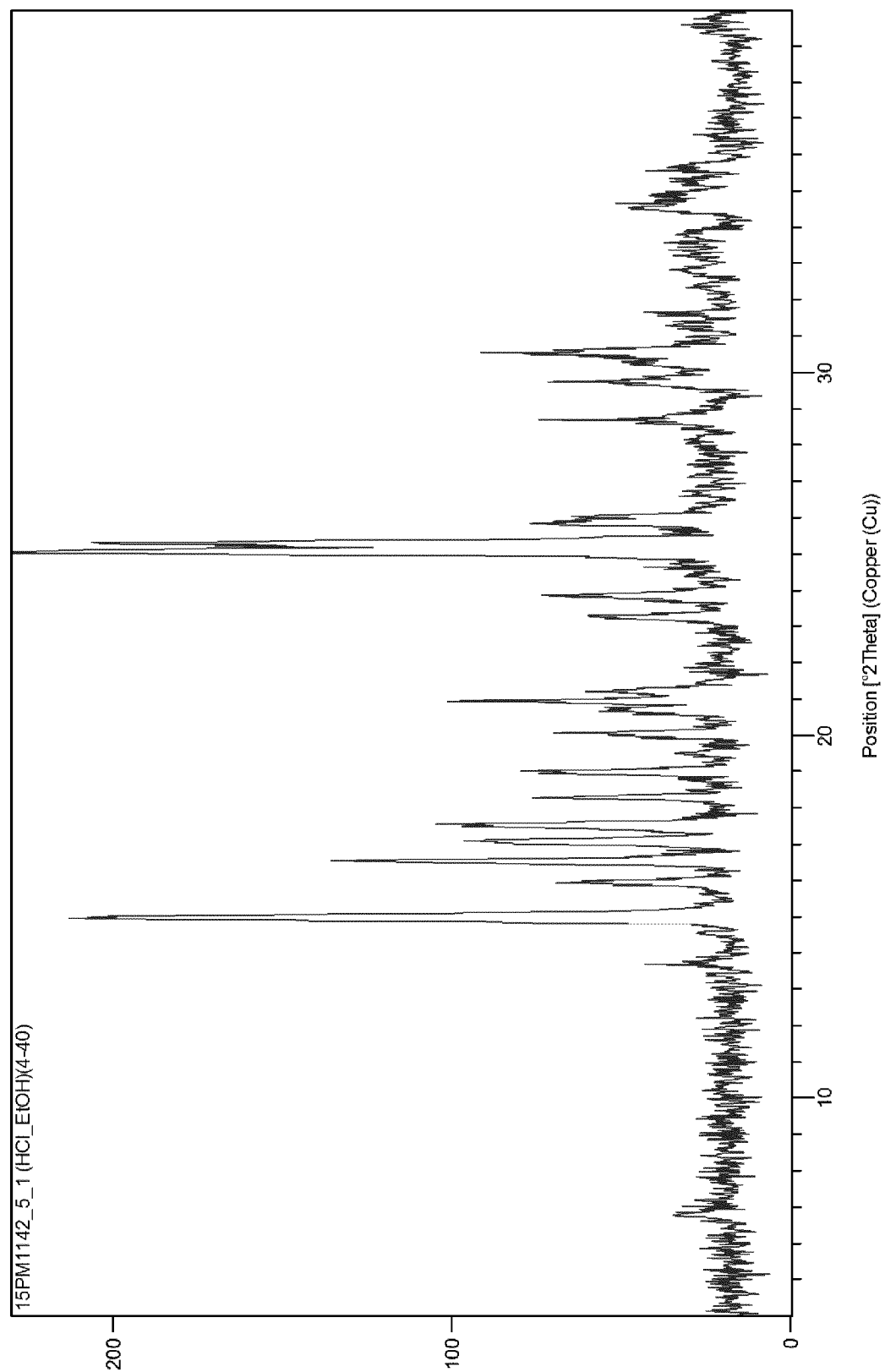
Figure 11: Characteristic X-ray powder diffraction pattern of crystalline Example 69 hydrochloride salt

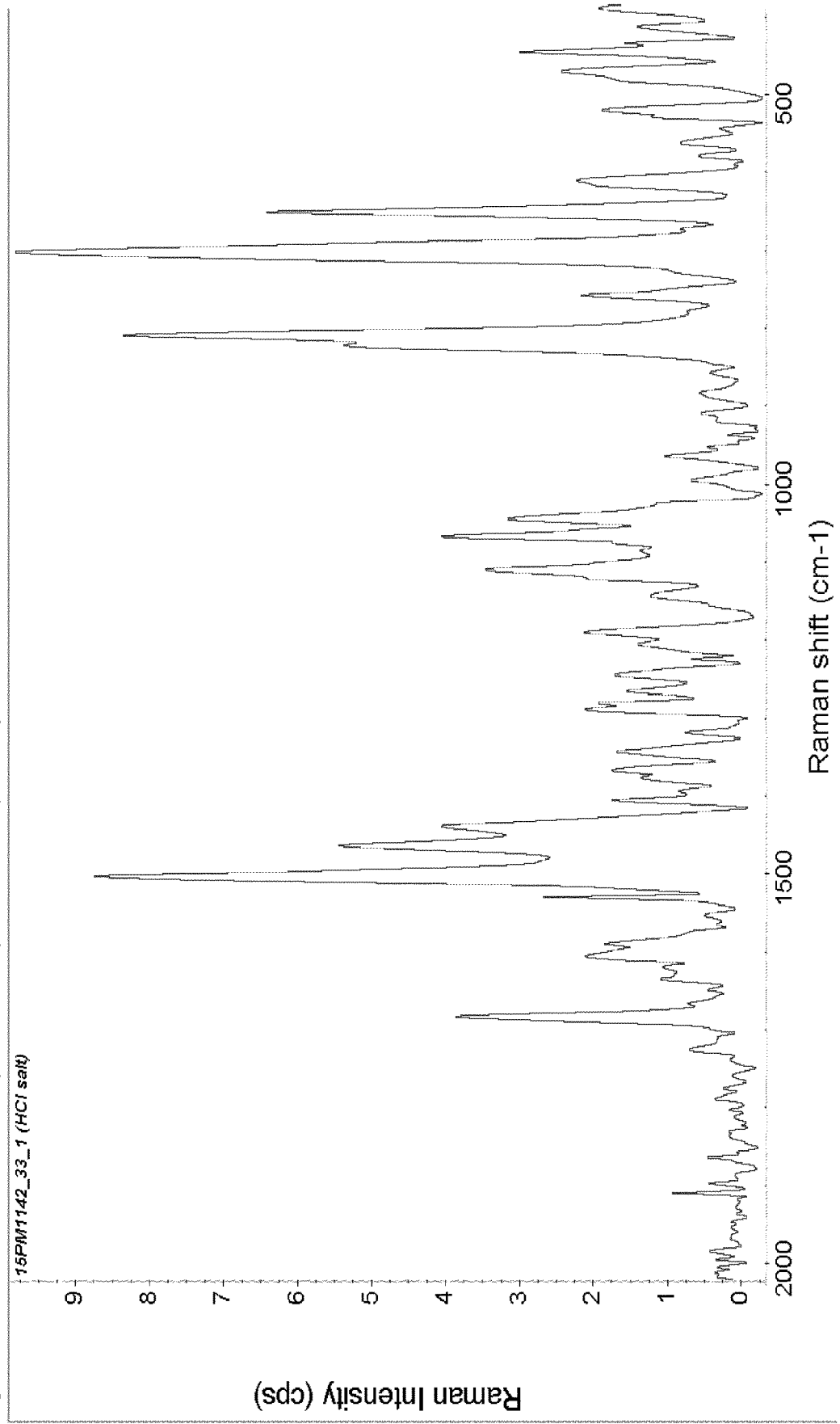
Figure 12: Characteristic Raman spectrum of crystalline Example 69 hydrochloride salt

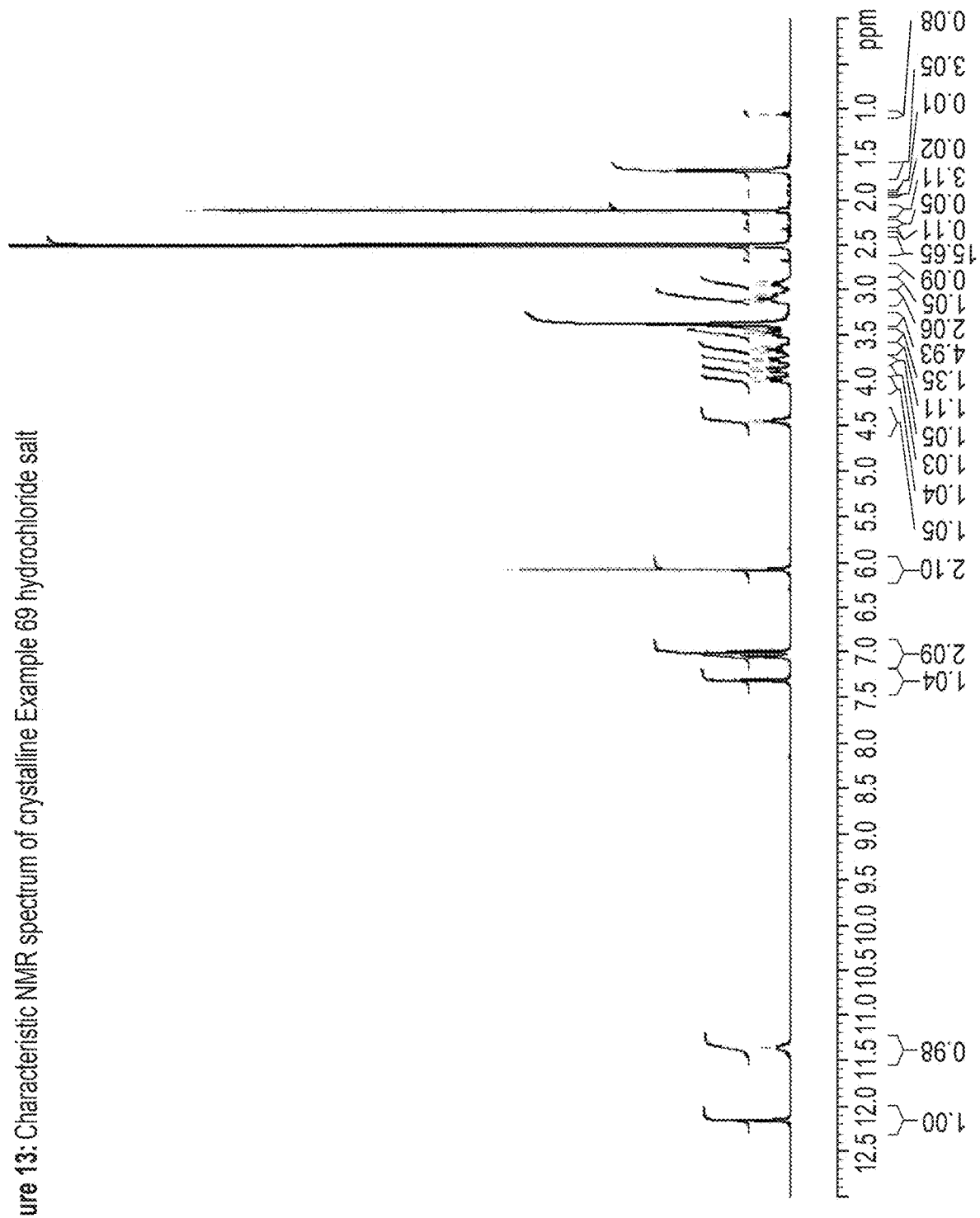
Figure 13: Characteristic NMR spectrum of crystalline Example 69 hydrochloride salt

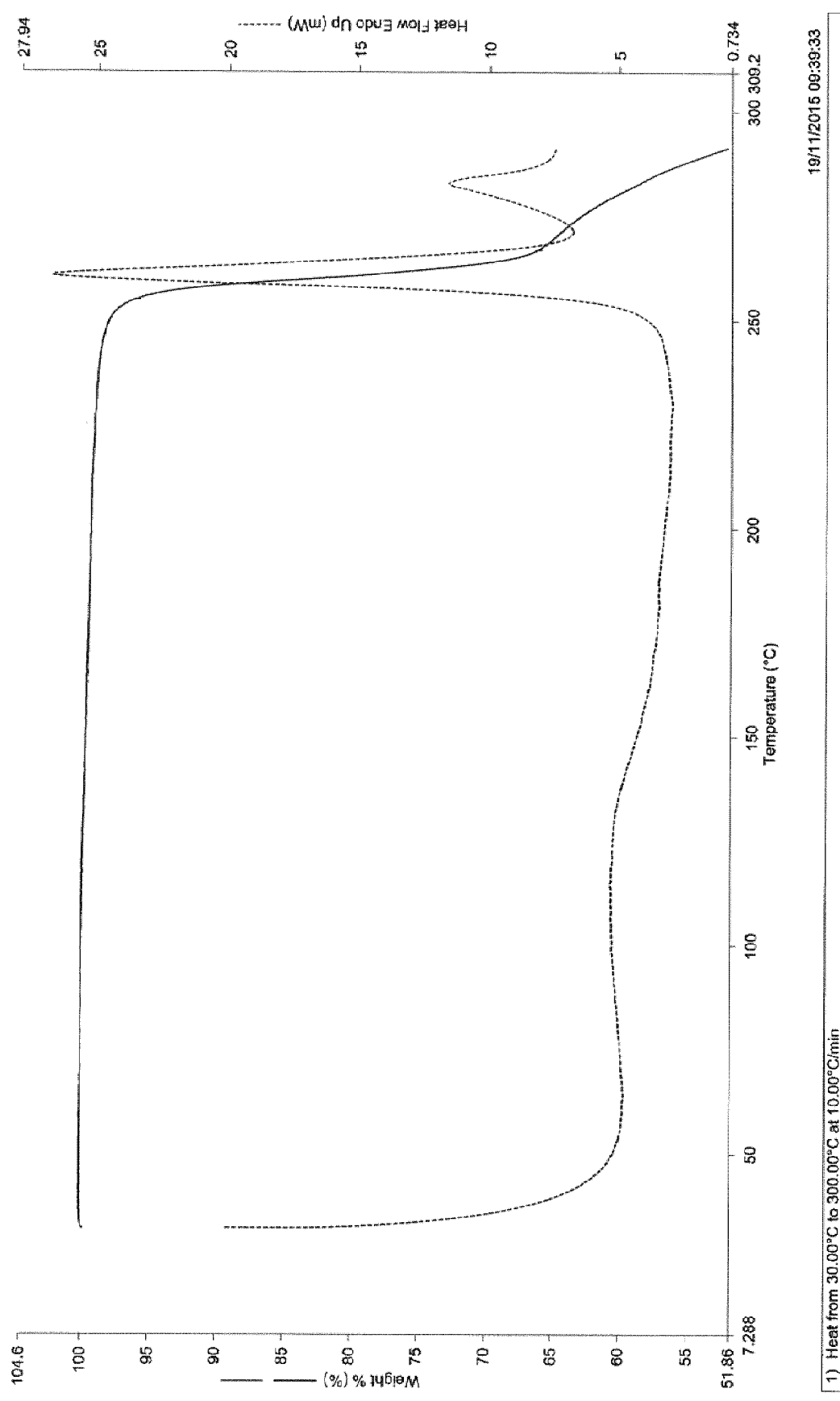
Figure 14: Characteristic STA thermogram of crystalline Example 69 hydrochloride salt

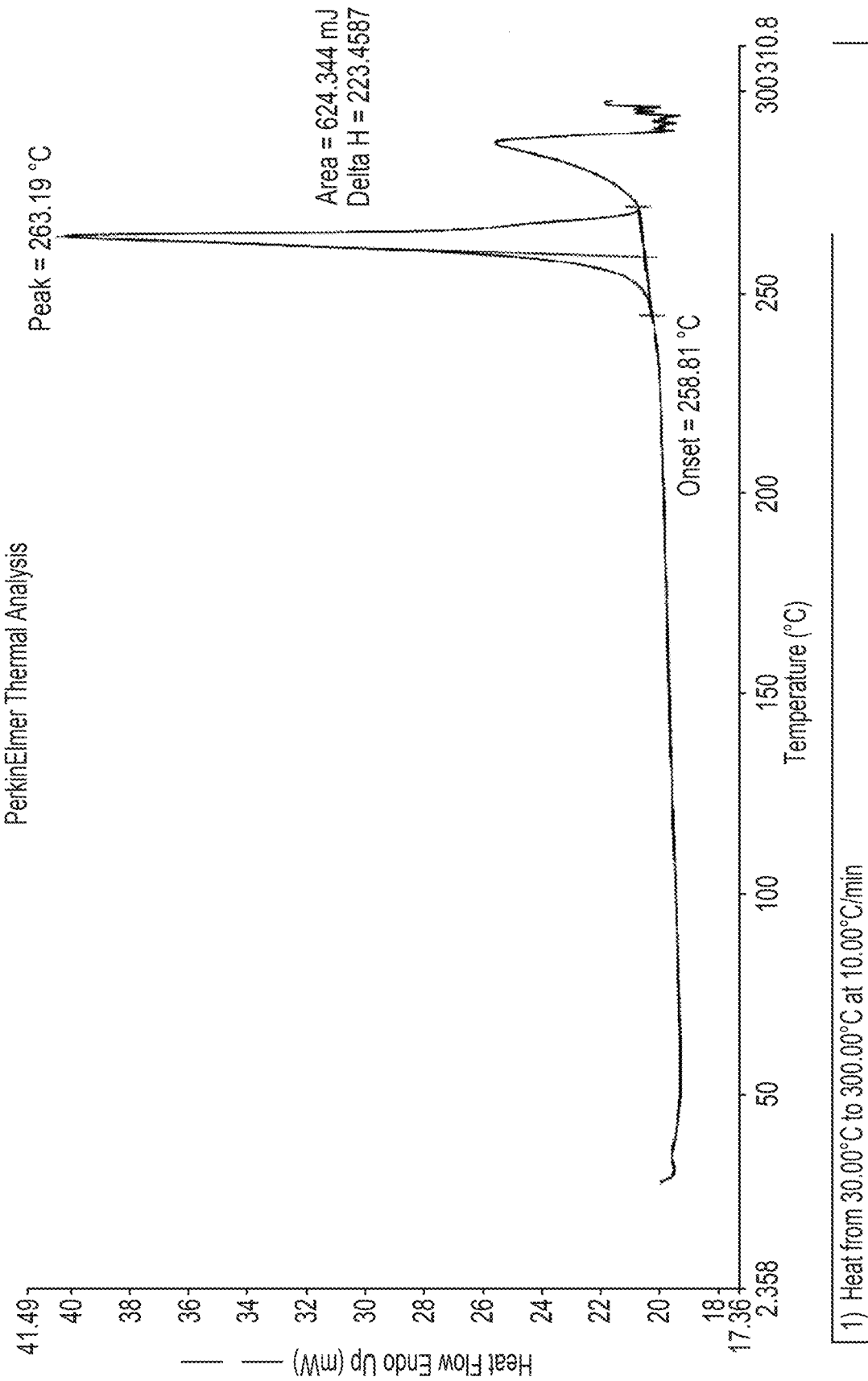

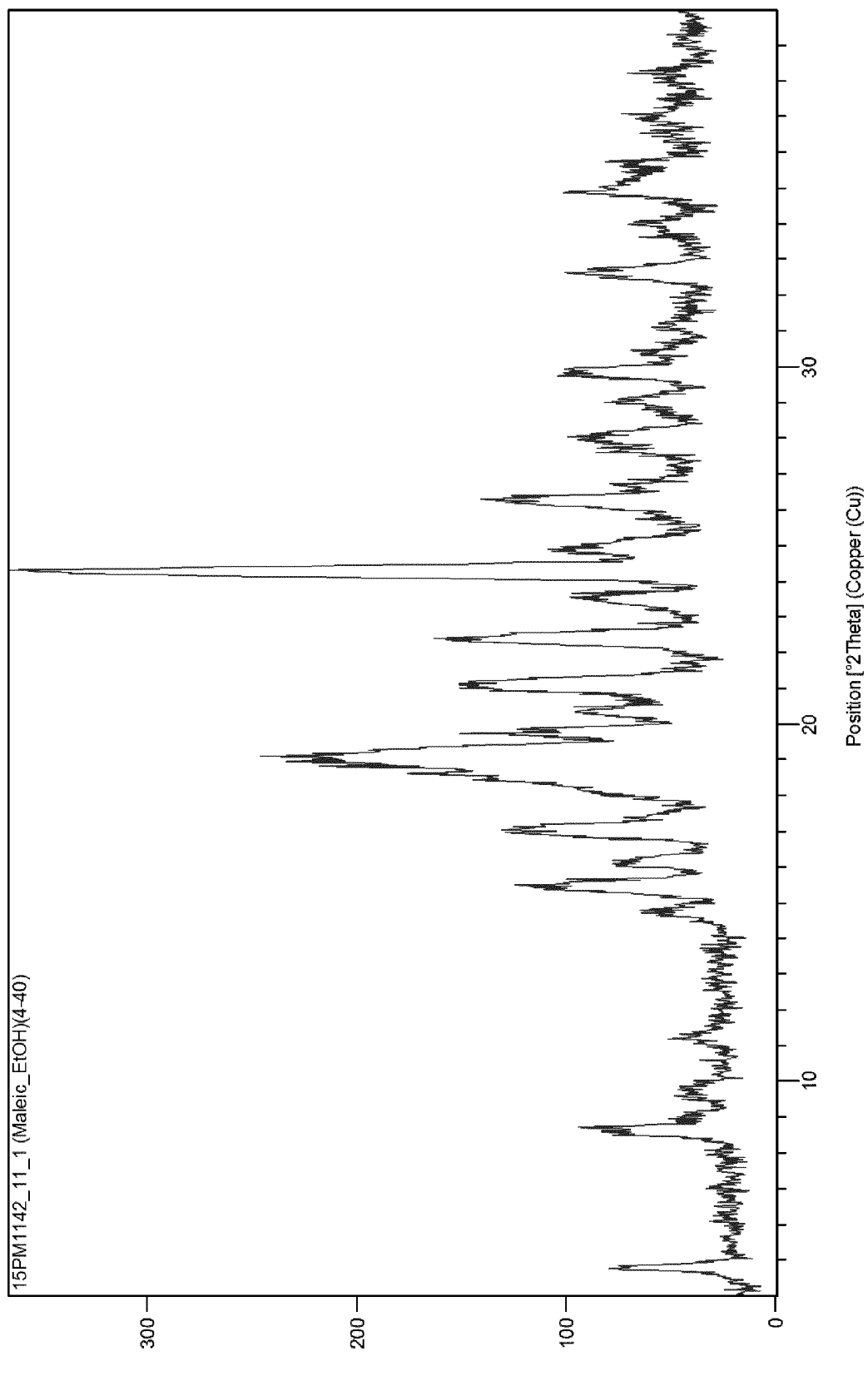
Figure 16: Characteristic X-ray powder diffraction pattern of crystalline Example 69 maleate salt obtained from EtOH

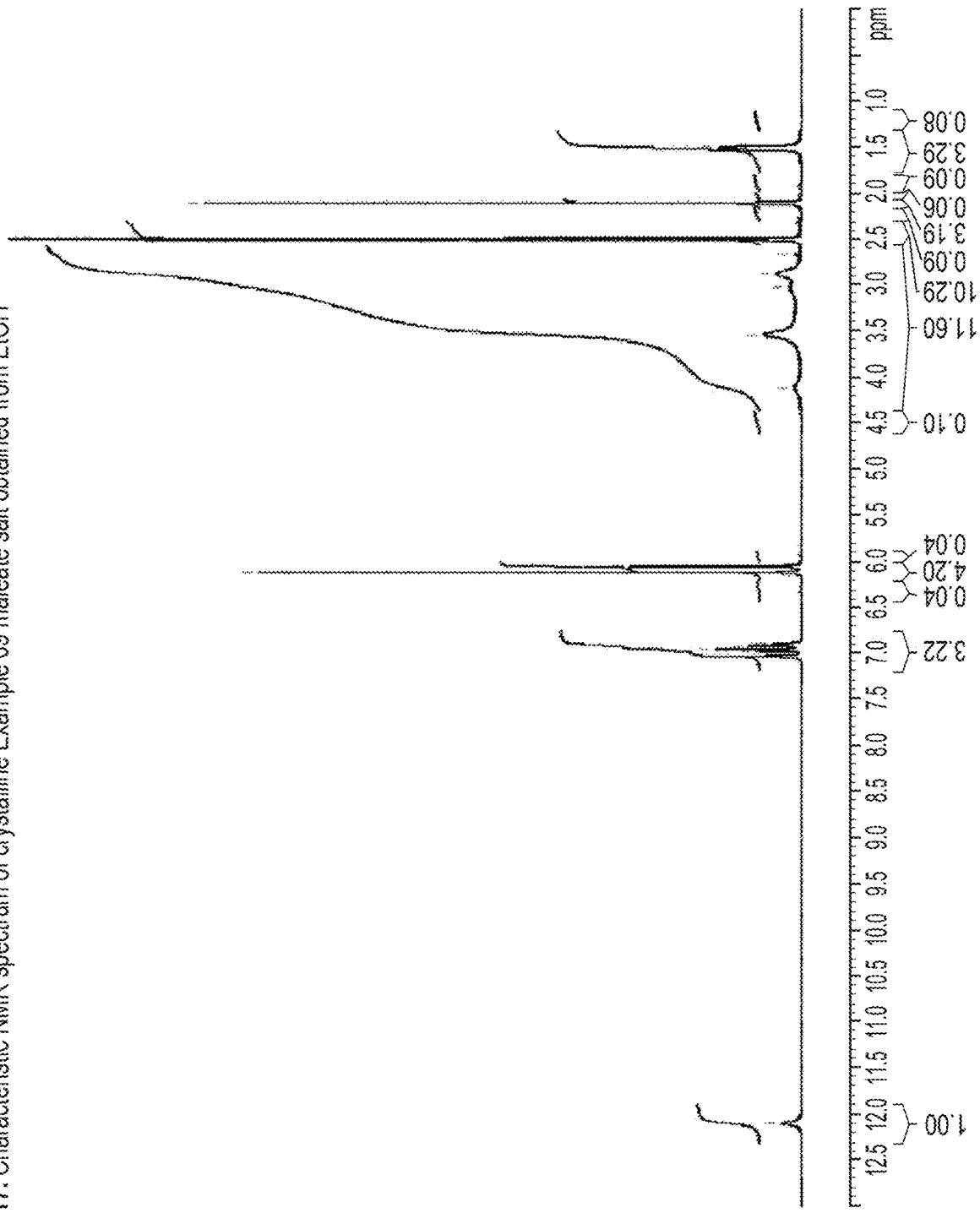
Figure 17: Characteristic NMR spectrum of crystalline Example 69 maleate salt obtained from EtOH

Figure 18: Characteristic STA thermogram of crystalline Example 69 maleate salt obtained from EtOH

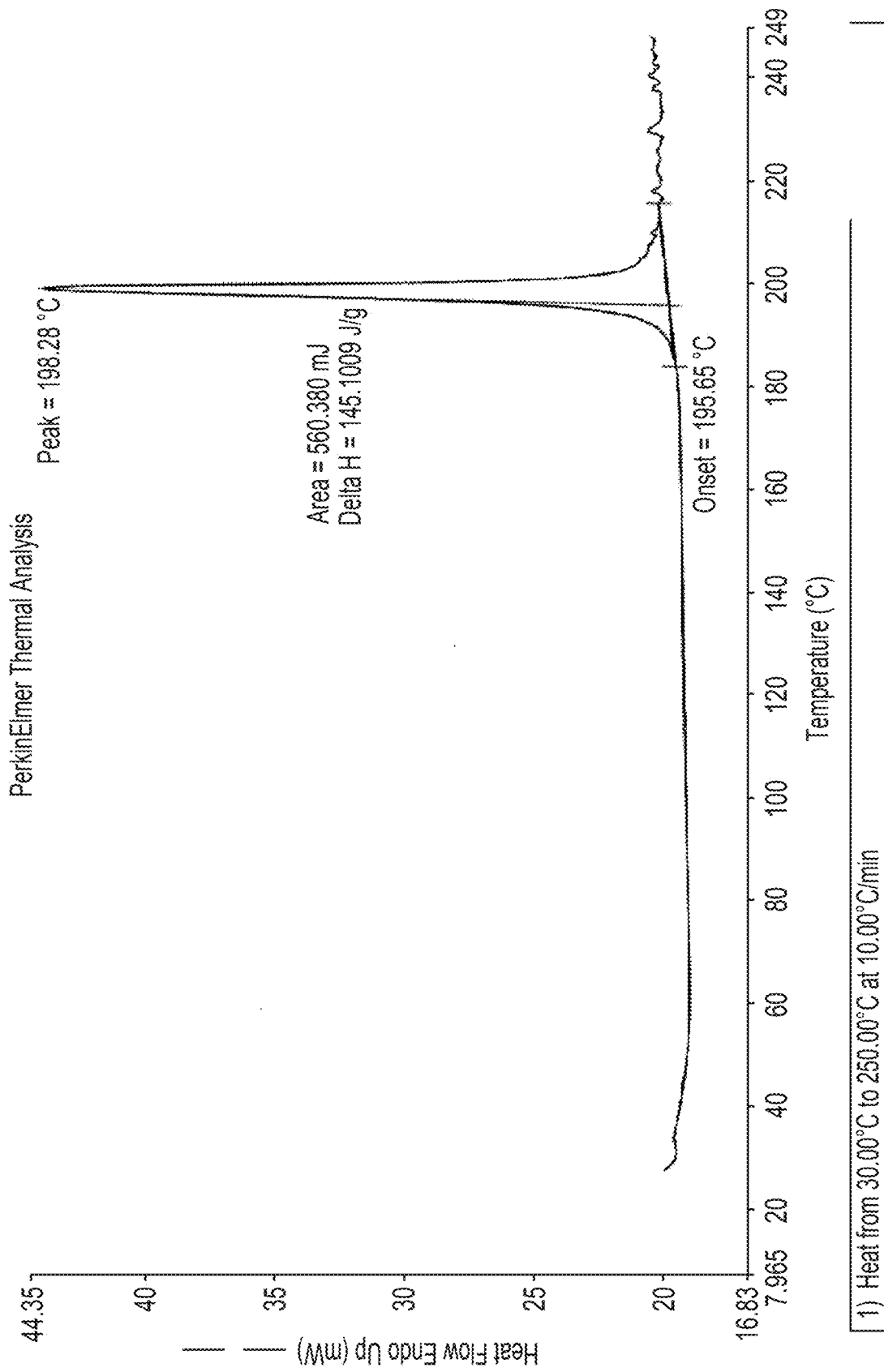
Figure 19. Characteristic DSC thermogram of crystalline Example 69 maleate salt obtained from EtOH

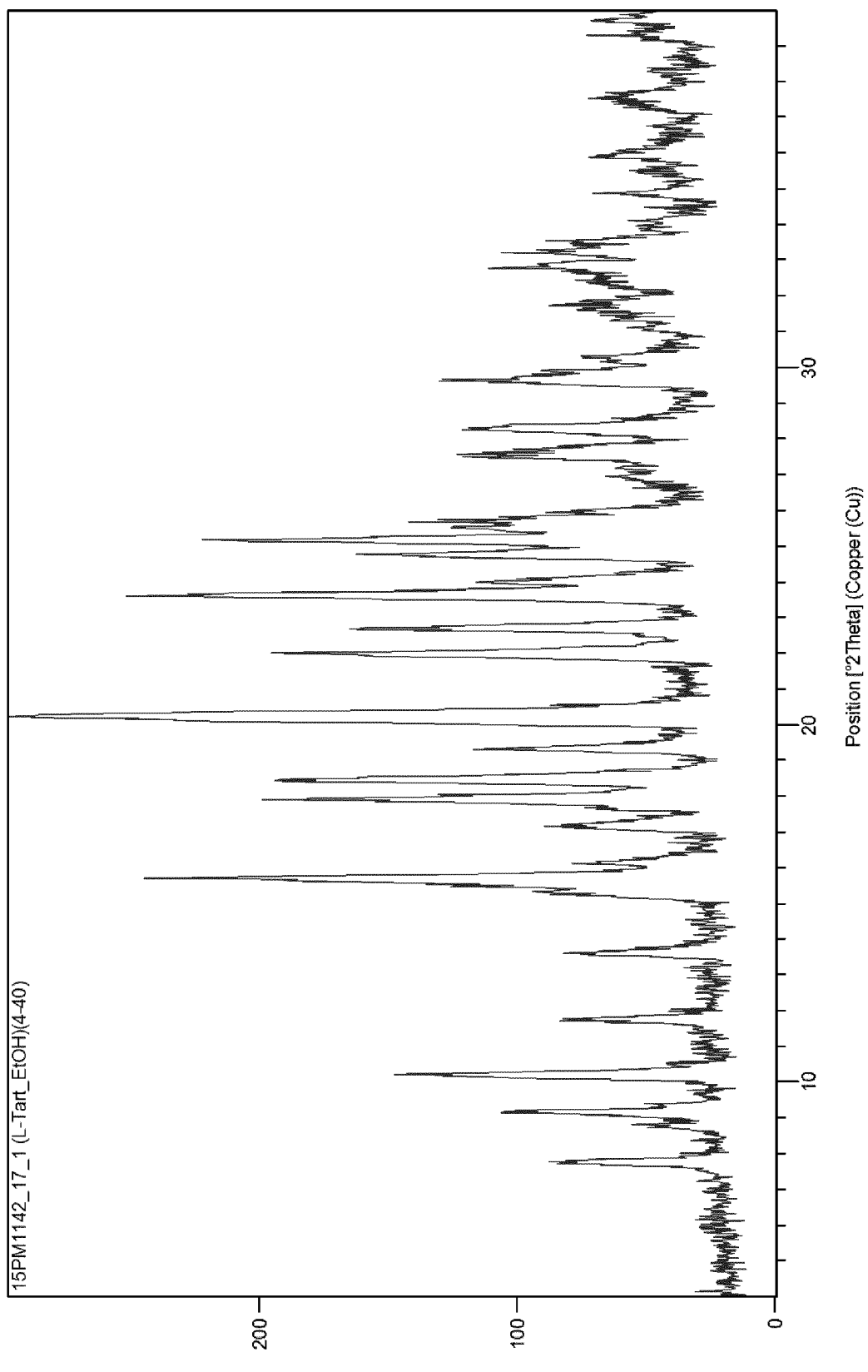
Figure 20: Characteristic X-ray powder diffraction pattern of crystalline Example 69 L-tartrate salt

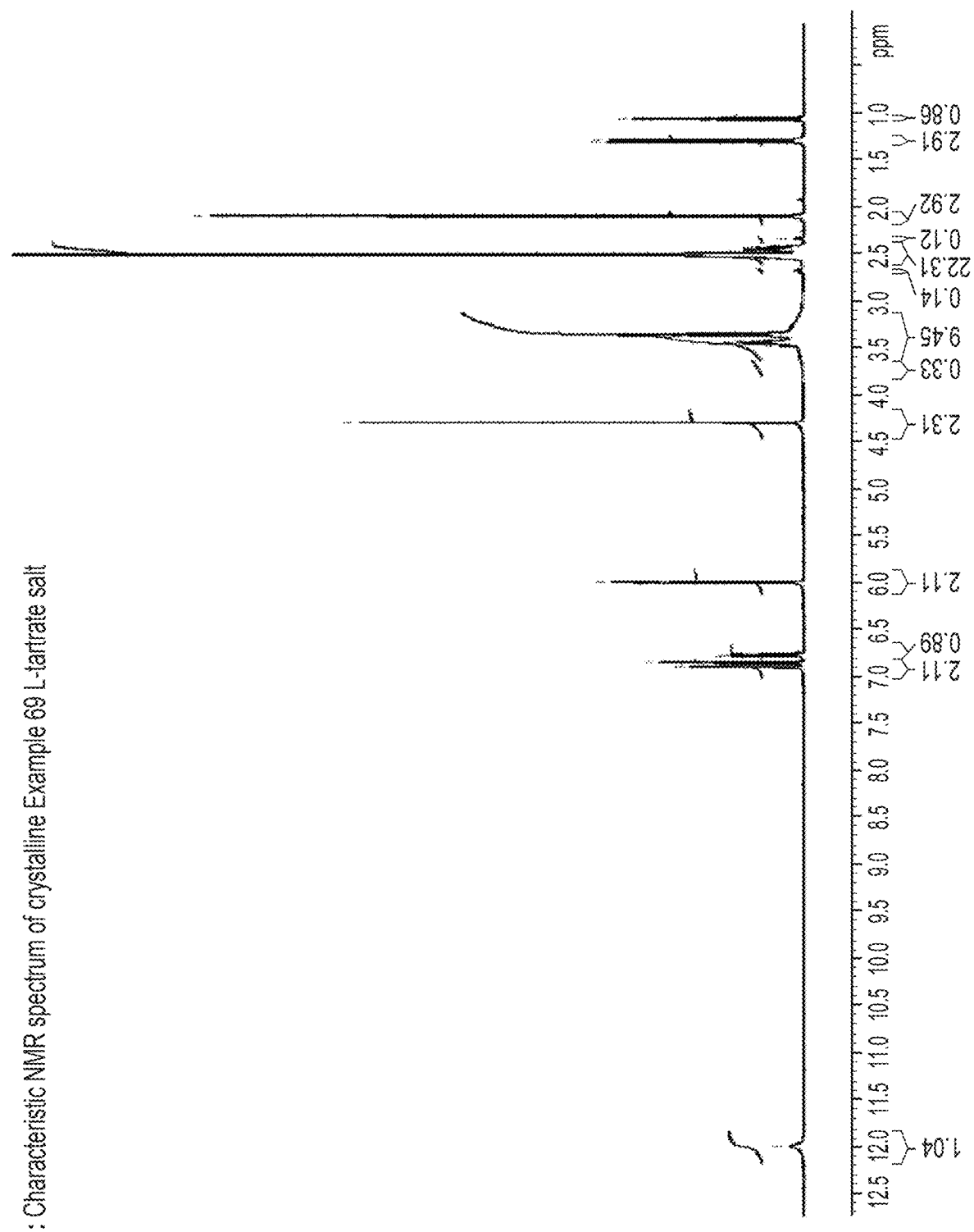
Figure 21: Characteristic NMR spectrum of crystalline Example 69 L-tartrate salt

ACID ADDITION SALTS OF PIPERAZINE DERIVATIVES

RELATED APPLICATIONS

This application is a division of U.S. patent application Ser. No. 16/877,284, filed May 18, 2020, now U.S. Pat. No. 11,591,327, which is a division of Ser. No. 16/079,162, now U.S. Pat. No. 10,696,668, and having a 35 U.S.C. 371(c) date of Aug. 23, 2018, which is a U.S. National Phase application, filed under 35 U.S.C. § 371(c), of International Application No. PCT/EP2017/054278, filed Feb. 24, 2017, which claims priority to, and the benefit of, Indian Patent Application number 201621006638, filed Feb. 25, 2016, each of which is incorporated by reference herein in its entirety for all purposes.

FIELD OF THE INVENTION

The invention relates to acid addition salts of hydrochloric acid, maleic acid or tartraic acid or other acids with piperazine derivatives, as well as solid forms, such as polymorphic forms, thereof, which are useful as pharmaceutical ingredients and in particular as glycosidase inhibitors.

BACKGROUND OF THE INVENTION

Piperazine Derivatives of Formula I

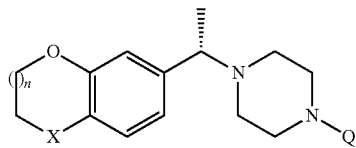

(I)

wherein X, n and Q are as defined further below, are as pharmaceutical ingredients and show high activity as glycosidase inhibitors. For example, PCT/EP2015/069598 describes e.g. N-(5-{4-[(1S)-1-(2,3-dihydro-1-benzofuran-6-yl)ethyl]piperazin-1-yl}-1,3,4-thiadiazol-2-yl)acetamide and N-(2-{4-[(1S)-1-(2H-1,3-benzodioxol-5-yl)ethyl]piperazin-1-yl}pyrimidin-5-yl)acetamide as active glycosidase inhibitors having high inhibitory activities.

Although the compounds of formula I have very useful pharmaceutical activities as free piperazine bases, they are not ideal for pharmaceutical manufacturing and as such may not be suitable for certain dosage forms, especially oral dosage forms, due to their unfavorable dissolution behaviour and stability or reactivity and other properties in the solid state.

Thus, there is a need to provide improved solid forms comprising the compounds of formula I, which exhibit improved properties, can be easily manufactured into solid dosage forms or other pharmaceutical dosage forms, and show an improved dissolution behaviour and stability and/or are less reactive in the solid state.

SUMMARY OF THE INVENTION

It has now been found that compounds of formula I

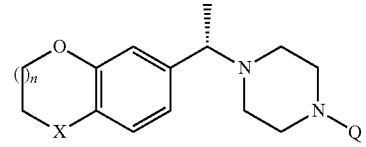

(I)

wherein X, n and Q are as defined further below show improved solid state properties, after they have been transformed in acid additions salts of hydrochloride acid, maleic acid or tartaric acid or other acids. In particular, the acid addition salts can be easily manufactured into solid dosage forms or other pharmaceutical dosage forms, and show an improved dissolution behavior and stability and/or are less reactive in the solid state. The acid addition salts of the present invention often exhibit low hygroscopicity.

It has also been found that certain polymorphic forms of the acid addition salts show even further improved properties, making them ideal for pharmaceutical manufacturing, in particular for solid oral dosage forms. Moreover, acid addition salts of the present invention that have a molar ratio of the compounds of formula I to the respective acid of 1 to 1 are especially stable, soluble and/or show other improved properties.

DETAILED DESCRIPTION OF THE INVENTION

The invention relates to acid addition salts of hydrochloric acid, maleic acid or tartraic acid or other acids with compounds of formula I

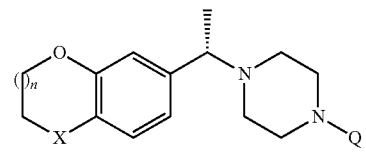

(I)

wherein
X denotes O or $CH_2$,
n denotes 0 or 1,
and
Q denotes one of the following groups:

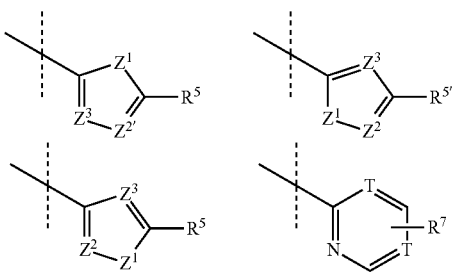

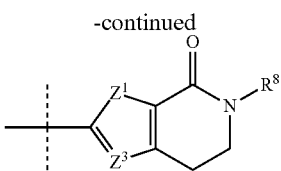

$Z^1$ is S, O, $NR^3$;

$Z^2$, $Z^{2'}$, $Z^3$ independently denote $CR^5$, $CR^6$ or N;

$R^3$, $R^4$ denote each independently H or a straight chain or branched alkyl group having 1 to 12 carbon atoms;

$R^5$, $R^{5'}$, $R^6$, $R^7$ independently denote H, Hal, $NR^3R^4$, $NO_2$, straight chain or branched alkyl having 1 to 12 carbon atoms, wherein 1 to 3 $CH_2$-groups may be replaced by a group selected from O, $NR^3$, S, SO, $SO_2$, CO, COO, OCO, $CONR^3$, $NR^3CO$ and wherein 1 to 5 hydrogen atoms may be replaced by Hal, $NR^3R^4$, $NO_2$, $OR^3$, Het, Ar, Cyc, or denote Ar, Het or Cyc;

$R^8$ denotes H, methyl or straight chain or branched alkyl having 2 to 12 carbon atoms, wherein 1 to 3 $CH_2$-groups may be replaced by a group selected from O, $NR^3$, S, SO, $SO_2$, CO, COO, OCO, $CONR^3$, $NR^3CO$ and wherein 1 to 5 hydrogen atoms may be replaced by Hal, $NR^3R^4$ or $NO_2$;

Hal denotes F, Cl, Br or I;

Het denotes a saturated, unsaturated or aromatic ring, being monocyclic or bicyclic or fused-bicyclic and having 3- to 8-members and containing 1 to 4 heteroatoms selected from N, O and S, which may be substituted by 1 to 3 substituents selected from $R^5$, Hal and $OR^3$;

Ar denotes a 6-membered carbocyclic aromatic ring or a fused or non fused bicyclic aromatic ring system, which is optionally substituted by 1 to 3 substituents independently selected from $R^5$, $OR^3$ and Hal;

Cyc denotes a saturated or an unsaturated carbocyclic ring having from 3 to 8 carbon atoms which is optionally substituted by 1 to 3 substituents independently selected from $R^5$ or Hal or OH, as well as solid forms, such as solvates and polymorphic forms thereof.

Polymorphism describes the occurrence of different solid or crystalline forms of a single compound and it is a property of certain compounds and complexes. Thus, polymorphs or polymorphic forms are distinct solids sharing the same molecular formula, yet each polymorph or polymorphic form may have distinct physical properties. Therefore, a single compound may give rise to a variety of polymorphic forms where each form has different and distinct physical properties, such as different solubility profiles, different melting point temperatures and/or different x-ray diffraction peaks.

The occurrence of a polymorphic form may determined by the crystallization conditions such as choice of solvent(s), rate of solvent addition, temperature, stirring rate, level of super-saturation, and level of impurities. Hence, different crystallization processes may give rise to different polymorphs. Polymorphs also have different stabilities and may spontaneously convert from one form to another.

The unpredictability of polymorphism, both as regards the uncertainty that any forms could be found, and the lack of any standard methods for preparing a new form has e.g. been discussed in A. Goho, "Tricky Business," Science News, Vol. 166(8), Aug. 21, 2004, and A. M. Rouhi, "The Right Stuff," Chemical and Engineering News, Feb. 24, 2003, pages 32-35.

Polymorphs can be distinguished from each other by a variety of analytical techniques. Polymorphs exhibit distinct spectroscopic properties and can be identified using infrared spectroscopy, raman spectroscopy, and 13C-NMR spectroscopy. Due to the fact that each crystal form diffracts X-rays in different ways, X-ray powder diffractometry (XRPD) can also be used for identification. Furthermore, thermal methods such as differential scanning calorimetry (DSC) and thermogravimetric 5 analysis (TGA) can provide information unique to a particular polymorph. The polymorphic forms of a compound can be also be distinguished by other methods such as, infrared spectrometry. For a general review of polymorphs and the pharmaceutical applications of polymorphs, See G. M. Wall, Pharm Manuf. 3, 33 (1986); J. Haleblian and W. McCrone, J. Pharm. Sci., 58, 91 1 (1969); and J. Haleblian, J. Pharm. Sci., 64, 1269 (1975).

The physicochemical properties may vary strongly between individual polymorphic forms. For example, solubility and dissolution rate may vary between polymorphs, leading to potential differences in bioavailability. Furthermore, mechanical properties such as flowability and compactability, which affect the processing properties of a compound, may be different. Stability, vapor impermeability and shelf life of a compound may also depend on the chosen polymorph.

The polymorphic forms, including solvates of the present invention provide materials having desirable processing properties, such as ease of handling, ease of processing, storage stability, and ease of purification, or as desirable intermediate crystal forms that facilitate conversion to other polymorphic forms with improved properties. Moreover the invention provides and stable forms of drug substances, which preferably exhibit thermodynamic stability, enhanced solubility, rapid onset of action and an enhanced bioavailability. The acid addition salts of the present invention are improved at least in one of the aforementioned properties.

In a preferred embodiment, the invention relates to the acid addition salts of compounds of formula Ia

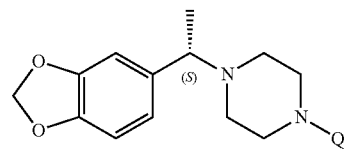

(Ia)

wherein Q has the meaning given above and solid forms, such as solvates and polymorphic forms, thereof.

More preferably the invention relates to acid addition salts of compounds of formula Ia, wherein Q is selected from the group

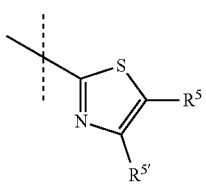 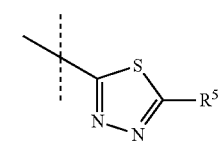

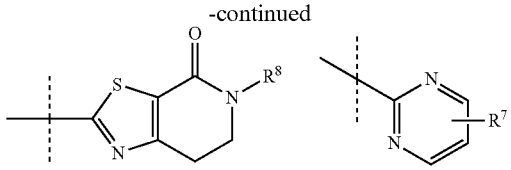

wherein $R^5$, $R^{5'}$, $R^7$ and $R^8$ have the meaning given above.

In a preferred embodiment, the invention relates to acid addition salts of compounds of formula I or Ia, wherein $R^5$, $R^{5'}$, $R^6$, $R^7$ are independently H, Hal, $NR_3R_4$, $NH_2$, $N(CH_3)_2$, phenyl, 2-, 3- or 4-hydroxy or methoxyphenyl, alkyl, $CF_3$, alkoxy (Oalkyl), hydroxyalkylen, alkoxyalkylen, COOH, COOalkyl, CONHalkyl, $CONH_2$, $CON(CH_3)_2$, NHCOalkyl, NHalkyl, CO—N-morpholinyl, $CON(CH_3)$ $CH_2CH_2N(CH_3)_2$, CO-1-piperidinyl, CO-4-hydroxy-1-piperidinyl, CO-1-piperazinyl, CO-4-methyl-1-piperazinyl, $CH_2$—N-morpholinyl, $CH_2N(H)COCH_3$, $CH_2N(CH_3)COCH_3$, substituted or unsubstituted Cyc or Het, as well as solid forms, such as polymorphic forms, thereof.

Very preferred are the acid additions salts, as well as solid forms, such as polymorphic forms thereof, of compounds of formula I, wherein Q is selected from the group:

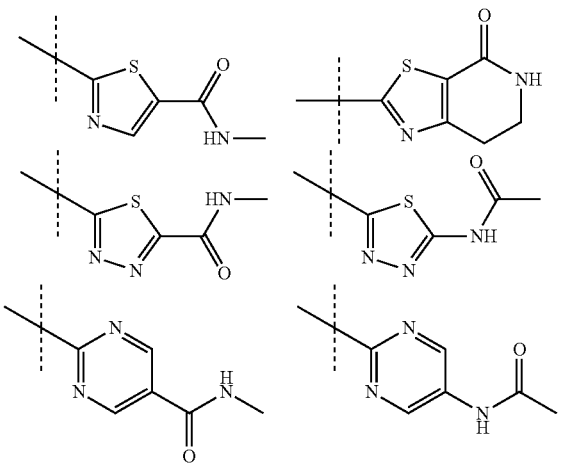

Very preferred are also the acid additions salts, as well as solid forms, such as polymorphic forms thereof, of the following compounds:

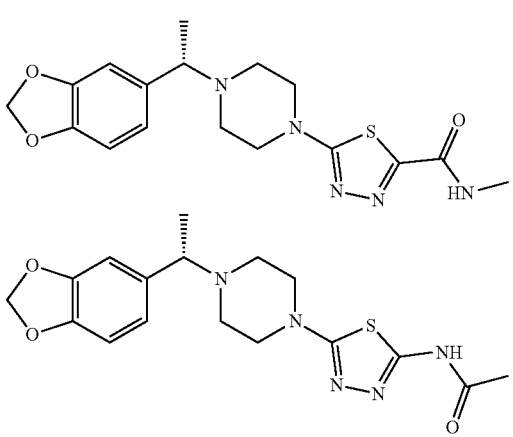

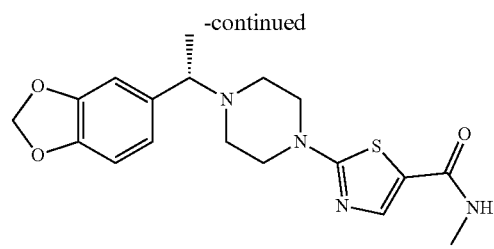

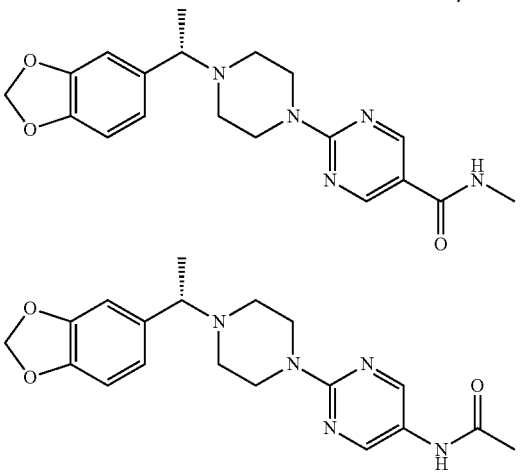

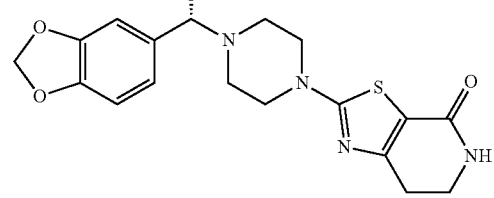

The compounds of formula I are usually employed in an enantiomeric excess, as measured by methods well known by one skilled in the art, of 10% or more, preferably 50% or more, and more preferably more than 95%, 96%, 98% or 99%.

The nomenclature as used herein for defining compounds, especially the compounds according to the invention, is in general based on the rules of the IUPAC-organization for chemical compounds and especially organic compounds. The compounds of invention have been named according to the standards used in the program AutoNom 2000 or ACD Lab Version 12.01. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent the expression of such substituent may differ from each other (e.g. methyl and ethyl). It shall be understood accordingly that a multiple substitution by any radical of the invention may involve identical or different radicals. Hence, if individual radicals occur several times within a compound, the radicals adopt the meanings indicated, independently of one another.

The term "alkyl" or "alkyl group" refers to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In an embodiment of the invention, alkyl denotes unbranched or branched alkyl having 1-10 C atoms, in which 1-7 H atoms may be replaced independently from one another by Hal. A preferred embodiment of alkyl denotes unbranched or branched alkyl having 1-6 C atoms, in which 1-4 atoms may be replaced independently from one another by Hal. In a more preferred embodiment of the invention, alkyl denotes unbranched or branched alkyl having 1-4 C atoms, in which 1-3 H atoms can be replaced independently from one another by Hal, particularly by F and/or Cl. It is most preferred that alkyl denotes unbranched or branched alkyl having 1-6 C atoms. Highly preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of alkyl is independently of one another in any radical of the invention.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In an embodiment of the invention, Cyc denotes cycloalkyl having 3-7 C atoms, in which 1-4 H atoms may be replaced independently of one another by Hal. Preferred is $C_3$-$C_7$-cycloalkyl. More preferred is $C_4$-$C_7$-cycloalkyl. Most preferred is $C_5$-$C_7$-cycloalkyl, i.e. cyclopentyl, cyclohexyl or cycloheptyl, highly preferably cyclohexyl. It shall be understood that the respective denotation of Cyc is independently of one another in any radical of the invention.

The term "Ar" "aryl" or "carboaryl" for the purposes of this invention refers to a mono- or polycyclic aromatic hydrocarbon systems having 3 to 14, preferably 3-12, more preferably 4 to 12, most preferably 5 to 10, highly preferably 6 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suited aryl radicals are phenyl, biphenyl, naphthyl, 1-naphthyl, 2-naphthyl and anthracenyl, but likewise indanyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

Aryl is preferably selected from the following group: phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)-phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Irrespective of further substitutions, Het denotes preferably 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazoM-, -4- or -5-yl, 1,2,4-triazo-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-iso-5i-ndolyl, indazolyl, 1-, 2-, 4- or 5-benzimidazolyl, 1-, 3-, 4-, 5-, 6- or 7-benzo-pyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo-[3.2.1]octyl or dibenzofuranyl. The heterocyclic radicals may also be partially or fully hydrogenated.

Irrespective of further substitutions, Het can thus also denote, preferably, 2,3-dihydro-2-, -3-, -4- or -5-furyl, 2,5-dihydro-2-, -3-, -4- or 5-furyl, tetra-hydro-2- or -3-furyl, 1,3-dioxolan-4-yl, tetrahydro-2- or -3-thienyl, 2,3-di-hydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-(-2-, -3-, -4-, -5-, -6-, -7- or -8-quinolyl, 1,2,3,4-tetra-hydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydro-benzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxo-furanyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2, 3-dihydrobenzimidazolyl.

Het preferably denotes piperidinyl, 4-hydroxypiperidinyl, piperazinyl, 4-methylpiperazinyl, pyrrolidinyl, morpholinyl, dihydro-pyrazolyl, dihydro-pyridyl, dihydropyranyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, particularly when the halogens are substituted on an alkyl (haloalkyl) or alkoxy group (e.g. $CF_3$ and $CF_3O$). It shall be understood that the respective denotation of Hal is independently of one another in any radical of the invention.

Preferred acids for the preparation of the acid addition salts are hydrochloric acid, maleic acid or tartraic acid, especially hydrochloric acid. Other pharmaceutically suitable acids, especially strong acids, such as sulfuric acid or p-toluene sulphonic acid may also be used according to the invention.

Acid addition salts of the present invention can be obtained in different molar ratios. Due to the presence of at least the two nitrogen atoms in the piperazine moiety of the compound of formula I, the acid addition salts can be prepared in a 1 to 1 molar ratio or in a 1 to 2 molar ratio for the compounds of formula I to an acid having a one acidic proton. This usually also holds true in cases where the acid has more than one acidic proton, as the second or further protons are significantly less acid than the one of the first deprotonation step. It has been found that the acid addition salts of the present invention that have a molar ratio of the compounds of formula I to the respective acid of 1 to 1 are especially preferred and stable, soluble and/or show other improved properties.

The acid addition salts of hydrochloric acid with compounds of formula I and solid forms, such as solvates and polymorphic forms thereof, are very preferred. Most preferred are acid addition salts of hydrochloric acid with compounds of formula I and solid forms, such as solvates and polymorphic forms thereof, wherein the molar ratio of the compound of formula I to hydrochloric acid is 1 to 1.

A preferred method of preparation of the acid addition salts of compounds of formula I according to the invention comprises the following steps:
  a) suspending or dissolving the compound of formula I and the selected acid in a suitable solvent or solvent mixture;
  b) heating the mixture obtained in step a) to a temperature of between about 30° C. to about the boiling point of the selected solvent, preferably between about 50° C. and about 100° C. and most preferably to about 60° C., to about 70° C. or to about 80° C. and allowing the mixture to cool to room temperature;
  c) optionally repeating step b) several times;
  d) separating and drying the solid thus obtained.

Suitable solvents for the method of preparation of the acid addition salts of the present invention are preferably alcohols such as water, methanol (MeOH, ethanol, 1-propanol, 2-propanol (IPA), 1-butanol, 2-butanol, 2-methyl-1-propanol, 2-methyl-2-propanol, 1-pentanol, 3-methyl-1-butanol, 2,2-dimethyl-1-propanol, cyclopentanol, 1-hexanol, cyclohexanol, 1-heptanol, 1-octanol, 1-nonanol, 1-decanol, 2-propen-1-ol, ketones, such as acetone, esters, such as ethyl acetate, acetonitrile, ethers such as tetrahydrofurane (THF), aromatic hydrocarbones, such as toluene and homogeneous mixtures of the above solvents, such as MeOH/water e.g. as 50/50 (v/v) mixture or IPA/water, e.g. as 90/10 (v/v) mixture.

Pharmaceutical formulations can be administered in the form of dosage units, which comprise a predetermined amount of active ingredient per dosage unit. The concentration of the prophylactically or therapeutically active ingredient in the formulation may vary from about 0.1 to 100 wt %. Preferably, the acid addition salts of the compounds of formula I or the pharmaceutically are administered in doses of approximately 0.5 to 1000 mg, more preferably between 1 and 700 mg, most preferably 5 and 100 mg per dose unit, calculated on the respective base. Generally, such a dose range is appropriate for total daily incorporation. In other terms, the daily dose is preferably between approximately 0.02 and 100 mg/kg of body weight.

Preferably the daily dose, i.e. the sum of all doses given to a patient during a given day, of a compound of formula N-(5-{4-[(1S)-1-(2,3-dihydro-1-benzofuran-6-yl)ethyl]piperazin-1-yl}-1,3,4-thiadiazol-2-yl)acetamide, N-(5-{4-[(1S)-1-(2H-1,3-benzodioxol-5-yl)ethyl]piperazin-1-yl}-1,3,4-thiadiazol-2-yl)acetamide, 2-{4-[(1S)-1-(2H-1,3-benzodioxol-5-yl)ethyl]piperazin-1-yl}-N-methyl-1,3-thiazole-5-carboxamide, 2-{4-[(1S)-1-(2H-1,3-benzodioxol-5-yl)ethyl]piperazin-1-yl}-N-methylpyrimidine-5-carboxamide, N-(2-{4-[(1S)-1-(2H-1,3-benzodioxol-5-yl)ethyl]piperazin-1-yl}pyrimidin-5-yl)acetamide, 2-{4-[(1S)-1-(2,3-dihydro-1-benzofuran-6-yl)ethyl]piperazin-1-yl}-4H,5H,6H,7H-[1,3]thiazolo[5,4-c]pyridin-4-one is between about 20 and about 100 mg, more preferably between about 30 mg and 70 mg calculated on the respective base, such as about 30, 35 or 40 mg given twice daily, preferably orally adminstered. The compounds are preferably administered in form of their hydrochloride salt, especially that having a molar ratio of the respective compound to hydrochloric acid of 1 to 1. The acid addition salts of the present invention are preferably orally administered.

The following embodiments are related to the use of the acid addition salts of the invention:
  1. Acid addition salts according to the invention for use in a treatment of a condition selected from neurodegenerative diseases, diabetes, cancer, cardiovascular diseases and stroke.
  2. Acid addition salts according to embodiment 1 for use in a treatment of a condition according to claim 10, wherein the condition is selected from the group of one or more tauopathies and Alzheimer's disease, Dementia, Amyotrophic lateral sclerosis (ALS), Amyotrophic lateral sclerosis with cognitive impairment (ALSci), Argyrophilic grain disease, Behavioural variant frontomeporal dementia (BvFTD), Bluit disease, Chronic traumatic encephalopathy, Corticobasal degeneration (CBP), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Frontotemporal lobar degeneration (FTLD), Ganglioglioma, Gangliocytoma, Gerstmann-Straussler-Scheinker disease, Globular glia tauopathy, Guadeloupean parkinsonism, Hallevorden-Spatz disease (neurodegeneration with brain iron accumulation type 1), Lead encephalopathy, Lipofuscinosis, Meningioangiomatosis, Multiple system atrophy, Myotonic dystrophy, Niemann-Pick disease (type C), Pallido-ponto-nigral degeneration, Parkinsonism-dementia complex of Guam, Pick's disease (PiD), Parkinson's disease dementia, Postencephalitic parkinsonism (PEP), Primary progressive aphasia, Prion diseases (including Creutzfeldt-Jakob Disease (GJD), Progressive nonfluent aphasia, Variant Creutzfeldt-Jakob Disease (vCJD), Fatal Familial Insomnia, Kuru, Progressive supercortical gliosis, Progressive supranuclear palsy (PSP), Semantic dementia, Steele-Richardson-Olszewski syndrome, Subacute sclerosing panencephalitis, Tangle-only dementia, Tuberous sclerosis, Huntington's disease and Parkinson's disease, preferably one or more tauopathies and Alzheimer's disease.

3. A method for treating a tauopathy, wherein an acid addition salt according to the invention is administered to a mammal in need of such treatment.

4. A method for inhibiting a glycosidase, wherein a system expressing the glycosidase is contacted with an acid addition salt of hydrochloric acid, maleic acid or tartraic acid with acid addition salt according the invention under in-vitro conditions such that the glycosidase is inhibited.

Preparation of Compounds of Formula I

Preferred forms of the acid addition salts of the present invention demonstrate adequate properties for use as a drug. In particular such preferred compounds show a high solid state stability, high stability in the presence of liver microsome, high oxidation stability and suitable permeability. Further preferred compounds of the present invention demonstrate their suitability as drugs by potent biological activity, such as the level of O-GlcNAcylation of total proteins measured in brain extracts. Relevant tests for determining such parameters are known by the person skilled in the art, e.g. solid state stability (Waterman K. C. (2007) *Pharm Res* 24(4); 780-790), stability in the presence of liver microsome (Obach R. S. (1999) *Drug Metab Dispos* 27(11); 1350-135) and the permeability (e.g. Caco-2 permeability assay, Calcagno A. M. (2006) *Mol Pharm* 3(1); 87-93); alternatively, they are described in Examples below, such as Example B02 describing the determination of O-GlcNAcylation level of total proteins measured in brain extracts. Compounds of the present invention that show a high potency in OGA inhibition assays and one or more of the above properties are especially suitable as a drug for the indications mentioned in the present specification.

The compounds according to formula (I) and the starting materials for its preparation, respectively, are produced by methods known per se, as described in the literature, i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The following abbreviations refer respectively to the definitions below:

Ac (acetyl), aq (aqueous), h (hour), g (gram), L (liter), mg (milligram), MHz (Megahertz), µM (micromolar), min (minute), mm (millimeter), mmol (millimole), mM (millimolar), m.p. (melting point), equiv (equivalent), mL (milliliter), µL (microliter), ACN (acetonitrile), AcOH (acetic acid), BINAP (2,2'-bis(disphenylphosphino)-1,1'-binaphthalene, BOC (tert-butoxy-carbonyl), CBZ (carbobenzoxy), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), dppf (1,1'-bis(diphenylphosphino)ferrocene), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (Ethyl acetate), $Et_2O$ (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MD Autoprep (Mass directed Autoprep), MeOH (methanol), $MgSO_4$ (magnesium sulfate), MS (mass spectrometry), MTBE (Methyl tert-butyl ether), Mtr. (4-Methoxy-2, 3, 6-trimethylbenzensulfonyl), MW (microwave), NBS (N-bromo succinimide), $NaHCO_3$ (sodium bicarbonate), $NaBH_4$ (sodium borohydride), NMM (N-methyl morpholine), NMR (Nuclear Magnetic Resonance), POA (phenoxyacetate), Py (pyridine), PyBOP® (benzotriazole-1-yl-oxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluromium tetrafluoroborate), TEA (triethylamine), TFA (trifluoroacetic acid), THF (tetrahydrofurane), TLC (Thin Layer Chromatography), UV (Ultraviolet).

In general, the compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those having ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by a person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

A "leaving group" LG denotes a chemical moiety which can be removed or replaced by another chemical group. Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p-tolylsulfonyloxy). When a leaving group LG is attached to an aromatic or heteroaromatic ring, LG can denote in addition $SO_2$-alkyl or F. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example through addition of HOBt, N-hydroxysuccinimide or HATU.

Depending on the nature of the groups such as Q, different synthetic strategies may be selected for the synthesis of compounds of Formula (I). In the process illustrated in the following schemes, X, n and Q are as above-defined in the description unless otherwise mentioned.

Compounds of Formula (I), wherein X, n and Q are defined as above, can be prepared from alternative compounds of Formula (I), using suitable interconversion procedures such as those described hereinafter in the examples, or conventional interconversion procedures well known by one skilled in the art.

Compound of formula (I) can be separated its corresponding other enantiomer by chiral chromatography or by chiral resolution, re-crystallization with use of an optically active acid.

Preferred chiral acids used for the chiral resolution of compounds of formula I and Ia are selected from but not limited to (S)-Me-mandelic acid, (S)-4-bromo-mandelic acid, (S)-4-chloro-mandelic acid, (S)-phenylsuccinic acid. These acids are preferably employed, as the S-enatiomer of the respective compound of formula I is desired and the diastereomeric salts are crystallizing. Preferably, between about 0.5 and about 2 equivalents of chiral acid are used for the selective crystallization. Solvents and solvent mixtures that are preferably used for the chiral resolution with chiral acids, are $H_2O$, MeCN (Acetonitril), about 2 to about 50% $H_2O$ in EtOH (Ethanol), EtOH, 2 to 50% $H_2O$ in MeOH (methanol), MeOH, 2 to 50% $H_2O$ in IPA (isopropyl alcohol), IPA, 2 to 50% MeOH in MEK (methyl ethyl ketone, 2-butanone), MEK, 2 to 50% MeOH in iPrOAc (isopropyl acetate), iPrOAc, dioxane. All percentages for solvent mixtures are given in volume percent, if not indicated otherwise.

Preferably, methods known by one skilled in the art are used in the preparation. Further methods of preparation are as described below in the examples.

Compounds of formula (Ic), wherein A is

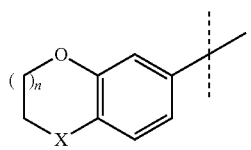

R is methyl and Q are defined as above, can be prepared by the addition of an amine of formula (II) to a heterocycle of formula (III), where LG is a leaving group as defined above. This addition can be performed under thermic conditions, heating both compounds at a temperature between 50° C. and 200° C., using regular heating or microwave irradiation, in the presence of a base, such as but not limited to TEA, DIEA, $K_2CO_3$ or $Cs_2CO_3$, in a polar solvent, e.g. DMF, DMA or NMP. Alternatively, this addition can be catalysed by a metal complex, such as but not limited to $PdCl_2$, $Pd(OAc)_2$, $Pd_2(dba)_3$ in the presence of a ligand, e.g. BINAP, o-Tol$_3$P, X-Phos, and a base, e.g. NaOtBu, $Cs_2CO_3$ or $K_2CO_3$, in a suitable solvent or solvent mixture, for example dioxane, Toluene/MeOH, at a temperature between RT to 150° C., preferably at RT, for a few hours, e.g. one hour to 24 h (Scheme 1). Amine of formula (II) is obtained after deprotection of compound (IVa). PG is a suitable protecting group, which is compatible with the chemistry described below, such as but not limited to BOC. It can be removed under acidic conditions, such as but not limited to HCl in MeOH or dioxane or TFA in DCM, yielding isolation of amine (II).

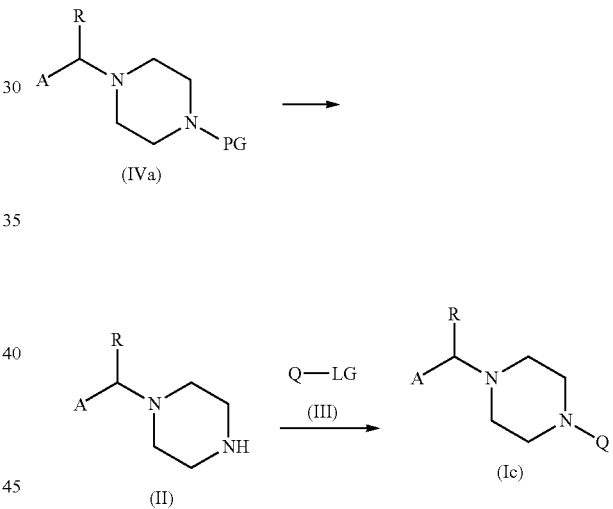

Scheme 1

Compound of formula (IV), wherein A, R and Q are defined as above and Y$^1$ is a protecting group PG, can be prepared from the corresponding ketone (IX) by reductive amination with amine (VI), using conditions known to the one skilled in the art, such as but not limited to the use of NaBH(OAc)$_3$ as reducing agent, in the presence of one equivalent of AcOH in DCE. Alternatively, reductive amination can be performed in two steps, with first imine formation, that can be catalysed by Ti(OiPr)$_4$, followed by reduction with suitable reducing agent, such as but not limited to NaBH$_4$ in MeOH (Abdel-Magid, A. F. at al. *J. Org. Chem.* 1996, 61, 3849-3862). Alternatively, ketone (IX) can be reduced into the corresponding alcohol (VIII) using usual reductive agents such as NaBH$_4$ in an alcoholic solvent, such as MeOH. Alcohol functionality can be then transformed into a suitable leaving group, such as but not limited to Cl or OMs, using conditions known to a person skilled in the art. The addition of amine (VI) to intermediate (VII) would yield the formation of compound (IV) (Scheme 2).

Scheme 2

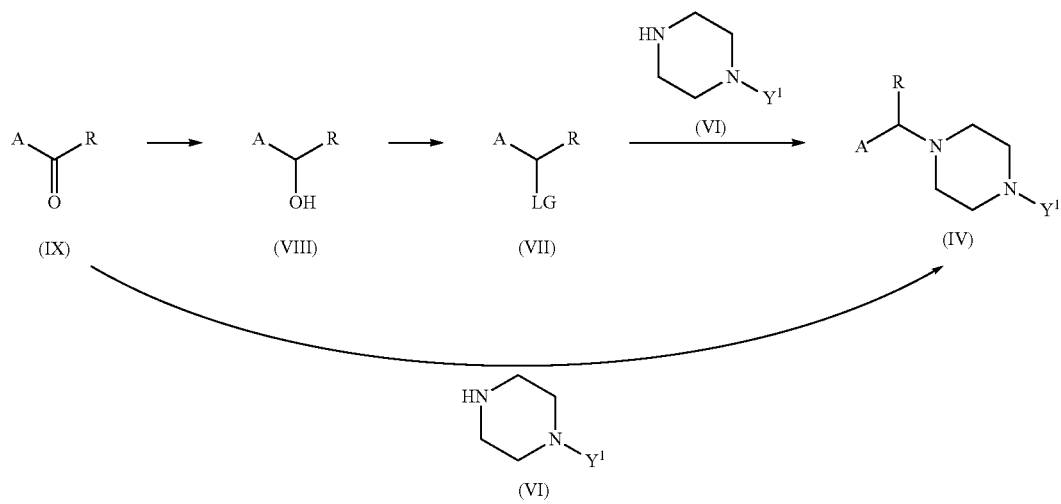

Alternatively, compound of formula (X), wherein Q are defined as above and PG is a suitable protecting group, such as but not limited to BOC, can be prepared from amine (XI) (Scheme 3).

Compound of formula (X) can be prepared by the addition of an amine of formula (XI) to a heterocycle of formula (III), where LG is a leaving group as defined above. This addition can be performed under thermic conditions or can be catalysed by a metal complex, using conditions known by a person skilled in the art and as described below in the examples.

PG is a suitable protecting group, which is compatible with the chemistry described above, such as but not limited to BOC. It can be removed under acidic conditions, such as but not limited to HCl in MeOH or dioxane or TFA in DCM, yielding isolation of amine (XIV). It can be further transformed into compound of formula (I) by reductive alkylation with ketone of formula (IX), following conditions well known by a person skilled in the art, as described in the examples (Abdel-Magid, A. F. at al. *J. Org. Chem.* 1996, 61, 3849-3862). Alternatively, amine (XIV) addition to compound (VII), prepared as described above and in the examples, would yield the formation of compound of formula (I) after chiral resolution.

Scheme 3

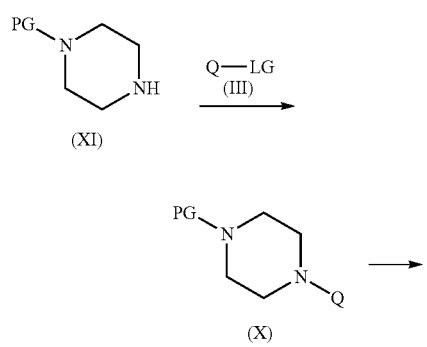

-continued

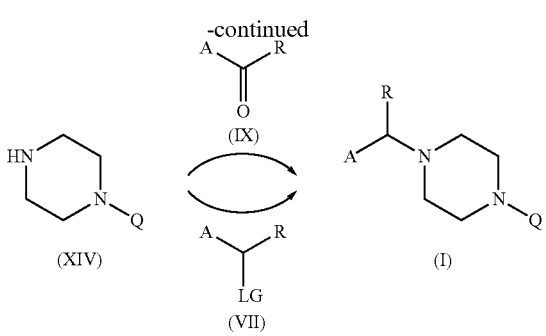

Amine of formula (II) can be separated into amines of formula (IIa) and (IIb) by chiral chromatography or chiral resolution by re-crystallization with an optically active acid, using methods known by one skilled in the art and as described below in the examples (Scheme 5).

Scheme 5

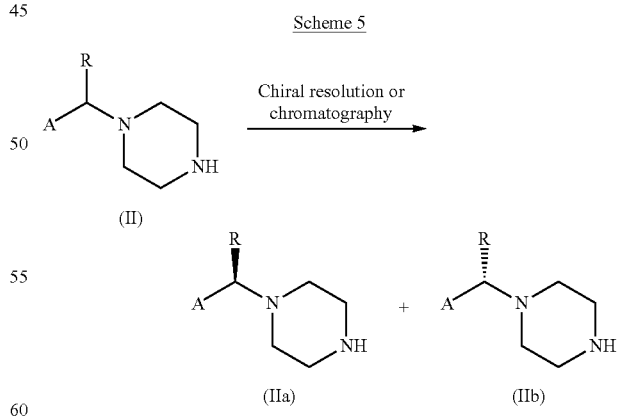

Alternatively, amines of formula (IIa) and (IIb) can be synthesized from chiral amines (XVIa) and (XVIb) respectively according to Scheme 6. Addition of amines (XVIa) and (XVIb) to reagent (XV), wherein PG is a protecting group, e.g. BOC or $SO_2$Tol and LG is a leaving group, e.g. Cl, would yield the formation of protected amines (IVe) and (IVf) respectively (Thiel, O. R. et al. *J. Org. Chem.* 2008, 73, 3508-3515). Deprotection conditions need to be selected based on the nature of the PG, such as HCl in dioxane or MeOH or TFA in DCM for BOC protecting group. Alternatively a mixture of HBr, AcOH and 4-hydroxybenzoic acid or a mixture of $H_2SO_4$ and trifluoroacetic acid at temperatures ranging from RT to 100° C. would be used to cleave a sulfonamide protecting group, such as para-toluene sulfonamide.

Scheme 6

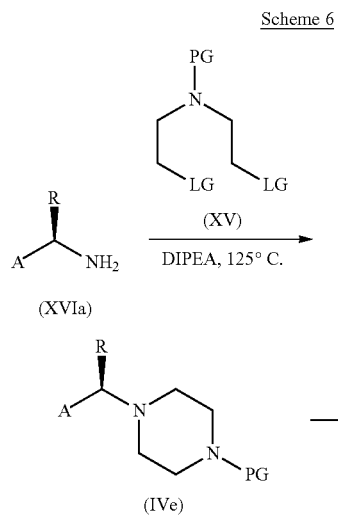

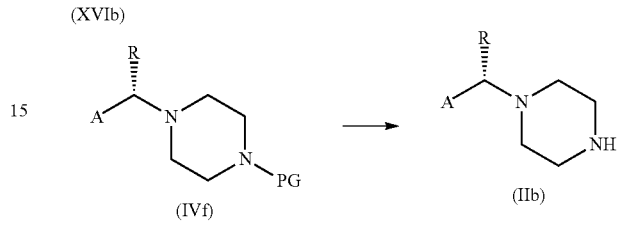

For the preparation of amines of formula (XVIa) and (XVIb), ketone of formula (IX) can be transformed into chiral imine (XVIII) according to Scheme 7, reacting with a chiral auxiliary, such as but not limited to tert-butanesulfinamide group in the presence of titanium ethoxide (Ellman J. A. et al. *Acc. Chem. Res.* 2002, 35, 984-995). It can be further transformed into sulfinamide (XVIIa) or (XVIIb), depending on the conditions used for the reduction step, as described in the reference from Ellman J. A. et al. *J. Org. Chem.* 2007, 72, 626-629.

Scheme 7

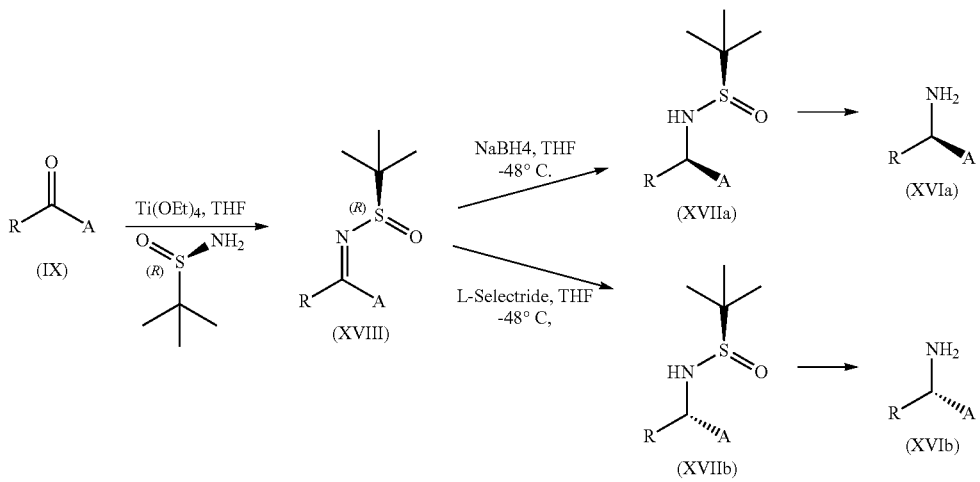

Alternatively aldehyde of formula (XIX) can be transformed into alcohol of formula (VIII) with addition of a suitable nucleophile, such as but not limited to a Grignard reagent (Scheme 8)

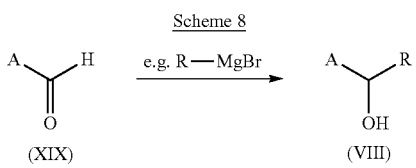

In another process, ketone of formula (IXa) can be obtained by Stille cross coupling reaction between aryl halide (XX) and tributyl(1-ethoxyvinyl)tin in the presence of a catalyst, such as but not limited to Pd(PPh$_3$)$_2$Cl$_2$ in toluene at temperatures ranging from RT to 110° C. (Scheme 9).

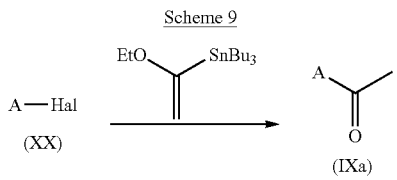

When a reaction is preferably performed under basic conditions, a suitable base might be selected from metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia), alkaline metal carbonates (e.g., sodium bicarbonate) and several organic bases (e.g., N,N-diisopropylethylamine, piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to TFA, DMF, dichloromethane, THF, H$_2$O, methanol, tert. butanol, tert. amylalcohol, triethylamine or dioxane.

Depending on the conditions used, the reaction time is between a few minutes and 14 days, the reaction temperature is between about −80° C. and 140° C., normally between −50° C. and 120° C., preferably between −20° C. and 100° C.

BRIEF DESCRIPTION OF THE DRAWINGS

The present invention is further illustrated by reference to the accompanying figures:

FIG. 1: Characteristic X-ray powder diffraction pattern of crystalline Example 69 sulphate salt obtained in THF FIG. 2: Characteristic X-ray powder diffraction pattern of crystalline Example 69 maleate salts obtained in ethanol, acetone, ethyl acetate FIG. 3: Characteristic X-ray powder diffraction pattern of crystalline Example 69 maleate salt obtained in MeCN FIG. 4: Characteristic X-ray powder diffraction pattern of crystalline Example 69 fumarate salt obtained in alcohol/water mixtures FIG. 5: Characteristic X-ray powder diffraction pattern of crystalline Example 69 L-tartrate salts obtained in ethanol, acetone, MeCN, THF, methanol/water FIG. 6: Characteristic X-ray powder diffraction pattern of crystalline Example 69 Tosylate salts obtained in acetone, MeCN FIG. 7: Characteristic X-ray powder diffraction pattern of crystalline Example 69 free base FIG. 8: Characteristic Raman spectrum of crystalline Example 69 free base FIG. 9: Characteristic STA thermogram of crystalline Example 69 free base FIG. 10: Characteristic DSC thermogram of crystalline Example 69 free base FIG. 11: Characteristic X-ray powder diffraction pattern of crystalline Example 69 hydrochloride salt FIG. 12: Characteristic Raman spectrum of crystalline Example 69 hydrochloride salt FIG. 13: Characteristic NMR spectrum of crystalline Example 69 hydrochloride salt FIG. 14: Characteristic STA thermogram of crystalline Example 69 hydrochloride salt FIG. 15: Characteristic DSC thermogram of crystalline Example 69 hydrochloride salt FIG. 16: Characteristic X-ray powder diffraction pattern of crystalline Example 69 maleate salt obtained from EtOH FIG. 17: Characteristic NMR spectrum of crystalline Example 69 maleate salt obtained from EtOH FIG. 18: Characteristic STA thermogram of crystalline Example 69 maleate salt obtained from EtOH FIG. 19: Characteristic DSC thermogram of crystalline Example 69 maleate salt obtained from EtOH FIG. 20: Characteristic X-ray powder diffraction pattern of crystalline Example 69 L-tartrate salt FIG. 21: Characteristic NMR spectrum of crystalline Example 69 L-tartrate salt

EXAMPLES

The compounds according to Formula (I) can be prepared from readily available starting materials by several synthetic approaches, using both solution-phase and solid-phase chemistry protocols or mixed solution and solid phase protocols. Examples of synthetic pathways are described below in the examples. All reported yields are non optimized yields. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich, Sigma, ACROS, ABCR, Combi-Blocks, Matrix, Apollo scientific, Alfa Aesar, etc. unless otherwise reported.

The HPLC, MS and NMR data provided in the examples described below are obtained as followed:

$^1$H NMR analyses were carried out using BRUKER NMR, model AV-II and AV-III 400 MHz FT-NMR. Residual signal of deuterated solvent was used as internal reference. Chemical shifts (δ) are reported in ppm in relative to the residual solvent signal (δ=2.50 for $^1$H NMR in DMSO-$d_6$, and 7.26 in $CDCl_3$). s (singlet), d (doublet), t (triplet), q (quadruplet), br (broad), quint (quintuplet).

The MS data provided in the examples described below were obtained as followed: Mass spectrum: LC/MS Agilent (ESI/APCI), Chemstration, 1200 Series.

LCMS Methods:
Method A
  Method: A-0.1% TFA in $H_2O$, B-0.1% TFA in ACN: Flow-2.0 mL/min.
  Column: XBridge C8 (50×4.6 mm, 3.5 µm, +ve mode
Method B
  Method: A-10 mM $NH_4HCO_3$ in $H_2O$, B-ACN: Flow-1.0 mL/min.
  Column: XBridge C8 (50×4.6 mm, 3.5 µm), +ve mode
Method C
  Method: A-10 mM $NH_4HCO_3$ in $H_2O$, B-ACN: Flow-1.0 mL/min.
  Column: XBridge C8 (50×4.6 mm, 3.5 µm), −ve mode HPLC analyses were obtained using Agilent 1200 Series instruments as followed using % with UV detection (maxplot).
Method A
  Method: A-0.1% TFA in $H_2O$, B-0.1% TFA in ACN: Flow-2.0 mL/min.
  Column: XBridge C8 (50×4.6 mm, 3.5 µm).
Method B
  Method: A-10 mM $NH_4HCO_3$ in $H_2O$, B-ACN: Flow-1.0 mL/min.
  Column: XBridge C8 (50×4.6 mm, 3.5 µm).
Method C
  Method: Gradient from 70% $H_2O$ (10 mM $K_2HPO_4$): 30% MeCN to 70% MeCN over 15 minutes, Flow: 1 mL/min. Column: XTERRA RP18 (250×4.6) mm, 5 µm Chiral HPLC
Method A
  Mobile Phase: 0.1% DEA in n-HEXANE:IPA: 60:40; COLUMN: CHIRALPAK AD-H (250×4.6) mm, 5 µm, FLOW: 1.0 mL/min
Method B:
  Mobile Phase: n-HEXANE:EtOH: 90:10: FLOW: 1.0 mL\min; COLUMN: CHIRALPAK IC (250×4.6) mm, 5 µm
Method C:
  Mobile Phase: 0.1% TFA in n-HEXANE:IPA: 60:40; COLUMN: CHIRALcell OD-H (250×4.6) mm, 5 µm, FLOW: 1.0 mL/min
Method D:
  Mobile Phase: 0.1% DEA in Hexane:EtOH: 80:20; FLOW: 1.0 mL\min; COLUMN: Chiralcell OJ-H column (250×4.6) mm, 5 µm
Method E:
  Mobile Phase: 0.1% DEA in Hexane:EtOH: 80:20; FLOW: 1.0 mL\min; COLUMN: Chiralcell AY-H column (250×4.6) mm, 5 µm
Method F:
  Mobile Phase: 0.1% DEA in Hexane:EtOH: 70:30; FLOW: 1.0 mL\min; COLUMN: Chiralpak IA (250×4.6) mm, 5 µm
Method G:
  Mobile Phase: 0.1% DEA in Hexane:EtOH: 60:40; FLOW: 1.0 mL\min; COLUMN: Chiralcel OD-H (250×4.6) mm, 5 µm
Method H:
  Mobile Phase: 0.1% DEA in n-Hexane:EtOH: 80:20; FLOW: 1.0 mL\min; COLUMN: CHIRALPAK IC (250×4.6) mm, 5 µm General flash chromatography conditions used for the purification of intermediates or compounds of Formula I: silica gel 230-400 mesh; gradients used as eluent: 10 to 80% EtOAc in Petroleum ether or 1 to 15% MeOH in DCM MD Autoprep Conditions
The mass directed preparative HPLC purifications were performed with a mass directed autopurification Fractionlynx from Waters.
Method A
  0.1% HCOOH in $H_2O$, B-MeOH or ACN, Column: Symmetry C8 (300 mm×19 mm), 7 µm
Method B
  0.1% TFA in $H_2O$, B-MeOH or ACN, Column: Symmetry C8 (300 mm×19 mm), 7 µm
Method C
  10 mM $NH_4HCO_3$ in $H_2O$, B-MeOH or ACN, Column: Symmetry C8 (300 mm×19 mm), 7 µm
Method D
  10 mM $NH_4OAC$ in $H_2O$, B-MeOH or ACN, Column: Symmetry C8 (300 mm×19 mm), 7 µm Preparative HPLC Conditions
Method PA
  0.1% TFA in $H_2O$, B-MeOH or ACN. Column: Sunfire C8 (19 mm×250 mm) 5 µm or Sunfire C18 (30 mm×250 mm) 10 µm.
Method PB
  10 mM $NH_4HCO_3$ in $H_2O$, B-MeOH or ACN, Column: Sunfire C8 (19 mm×250 mm) 5 µm or Sunfire C18 (30 mm×250 mm) 10 µm.

Chiral Preparative Method PC
  Mobile phase: n-Hexane, IPA; Column: Chiral pak AD-H (20×250) mm, 5 micron, Flow: 12 mL/min
Chiral Preparative Method PD:
  Mobile phase: n-Hexane, IPA; Column: Chiral pak AD-H (20×250) mm, 5 micron, Flow: 12 mL/min
Chiral Preparative Method PE:
  Mobile phase: n-Hexane, IPA; Column: Chiralcell OD-H (20×250) mm, 5 micron, Flow: 12 mL/min
Chiral Preparative Method PF:
  Mobile Phase: 0.1% DEA in Hexane:EtOH: 80:20; FLOW: 12.0 mL/min; COLUMN: Chiralcell OJ-H column (250×20) mm, 5 µm
Chiral Preparative Method PG:
  Mobile Phase: 0.1% DEA in Hexane:EtOH: 80:20; FLOW: 20.0 mL/min; COLUMN: Chiralcell AY-H column (250×30) mm, 5 µm
Chiral Preparative Method PH:
  Mobile Phase: n-HEXANE:ETOH: 90:10: FLOW: 20.0 mL\min; COLUMN: CHIRALPAK IC (250×30) mm, 5 µm
Chiral Preparative Method PI:
  Mobile Phase: 0.1% DEA in Hexane:EtOH: 80:20; FLOW: 12.0 mL\min; COLUMN: Lux Cellulose C4 (250× 21.2) mm, 5 µm
Chiral Preparative Method PJ:
  Mobile Phase: 0.1% DEA in Hexane:EtOH: 70:30; FLOW: 12.0 mL\min; COLUMN: Chiralpak IA (250×20) mm, 5 µm Chiral Preparative Method PK:
Mobile Phase: 0.1% DEA In Hexane:EtOH: 50:50; FLOW: 10.0 mL/min; COLUMN: Chiralpac IC (250×21) mm, 5 μm
The SFC purifications were performed with a Prep SFC, THAR-SFC 80 and THAR-SFC 200.
SFC Analytical Chiral Method AA:
COLUMN: YMC Cellulose SB (250×4.6) mm, 5 μm; CO-SOLVENTS: 0.5% DEA in Methanol 40%; FLOW: 4 mL/min;
SFC Preparative Chiral Method PA:
COLUMN: YMC Cellulose SB (250×30) mm, 5 μm; CO-SOLVENTS: 0.5% DEA in Methanol 40%; FLOW: 60 mL/min;
The microwave chemistry was performed on a single mode microwave reactor Initiator™ Sixty from Biotage.
General Procedure for Ester Reduction of Heterocycles: Procedure A
To a stirred solution of ester (1 equiv) in dry THF (20 to 35 mL), lithium triethylborohydride (1 M solution in THF, 1.7 equiv) was added slowly at 0° C. The reaction mixture was stirred at room temperature for 2 h. The completion of the reaction was monitored by TLC. Reaction mixture was cooled to 0° C. and quenched using 10% ammonium chloride solution. Solvent was removed under vacuum and resulting residue was purified by flash column chromatography to afford the desired product.
General Procedure for Chlorination of Hetrocyclic Alcohol: Procedure B
To a stirred solution of alcohol (1 equiv) in dry DCM (10 to 20 mL), thionyl chloride (1.7 to 3 equiv) was added slowly at 0° C. The reaction mixture was warmed to rt and was refluxed for 1 h. The reaction mixture was concentrated under vacuum and the resulting residue was diluted with DCM (20 to 50 mL). The DCM layer was washed with water (5 to 10 mL), brine solution (5 to 10 mL), dried over anhydrous $Na_2SO_4$ and concentrated under vacuum to give chloro compound.
General Procedure for Reductive Amination: Procedure C
To a solution of aldehyde (1 equiv) in dry THF (4 to 10 mL), amine (0.8 to 1.1 equiv), acetic acid (7 equiv) was added at room temperature and stirred for 30 min. Then the reaction mixture was cooled to 0° C. and sodium triacetoxy borohydride (1.2 equiv) was added slowly. The resulting reaction mixture was stirred at room temperature for 16 h. The reaction mixture was concentrated, the crude product was diluted with (10 to 20 mL) EtOAc and the organic layer was washed with (10-20 mL) of brine. The organic layer was separated, dried over anhydrous $Na_2SO_4$ and concentrated under vacuum. The crude products were purified by flash column chromatography to afford the desired product.
General Procedure for N-Alkylation: Procedure D
To a stirred solution of amine (1 mmol/0.8 to 1 equiv) in dry DMF (5 to 10 mL), chloro compound (1.0 to 1.2 equiv) and potassium carbonate (2 equiv) were added at rt. The resulting mixture was heated at 90° C. for 16 h. It was concentrated under vacuum and the resulting residue was diluted with DCM (20 to 50 mL). The DCM layer was washed with water (5 to 10 mL), brine solution (5 to 10 mL), dried over anhydrous $Na_2SO_4$ and concentrated under vacuum. The crude products were purified by flash chromatography to afford the desired product.
General Procedure for N-Alkylation: Procedure E
To a stirred solution of amine (1 mmol/1 equiv) in acetonitrile (5 to 10 mL), chloro compound (1.5 to 2 equiv), triethyl amine (2 equiv) were added at rt. The resulting mixture was stirred at rt to 60° C. for 16 h. It was diluted with water (15 mL) and extracted with EtOAc (2×20 mL). The organic layer was dried over anhydrous $Na_2SO_4$ and concentrated under reduced pressure. The resulting crude product was purified by flash chromatography to afford the desired product.

INTERMEDIATES SYNTHESIS

Intermediate 1: 5-(1-Chloroethyl)benzo[d][1,3]dioxole

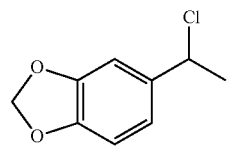

Step 1: 1-(Benzo[d][1,3]dioxol-5-yl)ethan-1-ol

To a stirred solution of 3, 4-methylenedioxy acetophenone (4.5 g, 27 mmol, Alfa aesar) in dry MeOH (50 mL), $NaBH_4$ (1.08 g, 42 mmol, Loba chemie) was added slowly at 0° C. The reaction mixture was stirred at room temperature for 1 h. Then the reaction mixture was concentrated under vacuum and diluted with DCM. The DCM layer was washed with water, brine and dried over anhydrous $Na_2SO_4$. The solvent was removed under reduced pressure and resulting crude alcohol was used as such in the next step. Yield: 90% (4.0 g, colorless liquid). $^1$H NMR (400 MHz, $CDCl_3$): δ 6.89 (s, 1H), 6.89-6.75 (m, 2H), 5.95 (s, 2H), 4.81 (t, J=8.0 Hz, 1H), 1.46 (d, J=8.0 Hz, 3H). LCMS: (Method B) 149.0 (Hydroxy elimination mass), Rt. 2.51 min, 98.6% (Max). HPLC: (Method A) Rt. 2.499 min, 99.5% (Max).

Step 2: 5-(1-Chloroethyl)benzo[d][1,3]dioxole

The title compound was synthesized by following general procedure B. It was used for next step without further purification. Yield: 72% (1.2 g, colorless liquid). $^1$H NMR (400 MHz, DMSO-$d_6$): δ 7.06 (d, J=4.0 Hz, 1H), 6.93 (d, J=8.0 Hz. 1H), 6.86 (d, J=8.0 Hz, 1H), 6.01 (s, 2H), 2.49 (q, J=8.0 Hz, 1H), 1.74 (d, J=8.0 Hz, 3H). LCMS: (Method B) 149.0 (Cl-Elimination mass), Rt. 3.71 min, 80.15% (Max).

Intermediate 2: 1-(1-(Benzo[d][1,3]dioxol-5-yl) ethyl)piperazine hydrochloride

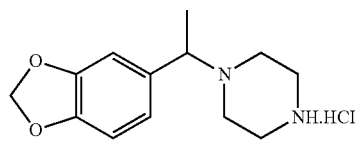

Step 1: tert-butyl 4-(1-(benzo[d][1,3]dioxol-5-yl) ethyl)piperazine-1-carboxylate The title compound was synthesized following general procedure D, starting with Intermediate 1 and N-boc piperazine. The crude product was purified by flash chromatography, affording the title compound (yellow solid). $^1$H NMR (400 MHz, DMSO-$d_6$): δ 6.85-6.82 (m, 2H), 6.74-6.71 (m, 1H), 5.98 (m, 2H), 3.37-3.36 (m, 1H), 3.27 (br. s, 4H), 2.28-2.21 (m, 4H), 1.37 (s, 9H), 1.25 (d, 3H, J=6.8 Hz). LCMS: (Method A) 335.2 (M+H), Rt. 3.10 min, 93.15% (Max). HPLC: (Method A) Rt. 3.12 min, 95.01% (Max).

Step 2: 1-(1-(Benzo[d][1,3]dioxol-5-yl)ethyl)piperazine hydrochloride

To a stirred solution of tert-butyl 4-(1-(benzo[d][1,3]dioxol-5-yl)ethyl)piperazine-1-carboxylate (1.8 g, 5.38 mmol) in dry dioxane (10 mL), HCl in dioxane (10 mL, 4 M, Spectrochem) was added at rt and stirred for 2 h at same temperature. The reaction mixture was concentrated under vacuum and the resulting crude product was washed with diethyl ether to afford the title product as hydrochloride salt. Yield: 82% (1.2 g, off white solid). $^1$H NMR (400 MHz, DMSO-$d_6$): δ 12.29 (s, 1H), 7.34 (s, 1H), 7.08 (d, 1H, J=7.7 Hz), 7.00 (d, 1H, J=7.9 Hz), 6.07 (s, 2H), 4.54 (br. s, 1H), 3.81 (br. s, 1H), 3.49-3.42 (m, 3H), 3.33 (br. s, 2H), 3.12 (br. s, 1H), 2.99 (br. s, 1H), 1.67 (d, 3H, J=5.7 Hz). LCMS: (Method A) 235.0 (M+H), Rt. 1.65 min, 98.08% (Max). HPLC: (Method A) Rt. 1.56 min, 99.86% (Max).

Intermediate 3: 6-(1-chloroethyl)-2,3-dihydrobenzo[b][1,4]dioxine

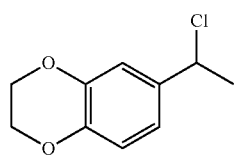

Step 1: 1-(2,3-dihydrobenzo[b][1,4]dioxin-6-yl)ethan-1-ol

The title compound was synthesized with same protocol as described for Intermediate 1, Step 1, using 1-(2,3-dihydrobenzo[b][1,4]dioxin-6-yl)ethan-1-one (2.0 g, 11.2 mmol) and NaBH$_4$ (0.49 g, 13 mmol). The resulting crude alcohol was used as such in the next step. Yield: 99% (2.0 g, colorless liquid). $^1$H NMR (400 MHz, DMSO-$d_6$): δ 6.80 (s, 1H), 6.79-6.76 (m, 2H), 4.59 (q, J=5.6 Hz, 1H), 4.20 (s, 4H), 1.26 (d, J=5.6 Hz, 3H). LCMS: (Method B) 163.0 (Hydroxy elimination mass), Rt. 2.51 min, 99.4% (Max).

Step 2: 6-(1-chloroethyl)-2,3-dihydrobenzo[b][1,4]dioxine

The title compound was synthesized according to the general procedure B. It was used in the next step without further purification. Yield: 90% (2.2 g, brown liquid). $^1$H NMR (400 MHz, DMSO-$d_6$): δ 6.97 (s, 1H), 6.96-6.92 (m, 1H), 6.84-6.82 (m, 1H), 5.26 (t, J=6.7 Hz, 1H), 4.23 (s, 4H), 1.75 (d, J=6.7 Hz, 3H). LCMS: (Method A) 163.0 (Cl-Elimination mass), Rt. 3.66 min, 95.3% (Max).

Intermediate 4: 1-(1-(2,3-dihydrobenzo[b][1,4]dioxin-6-yl)ethyl)piperazine hydrochloride

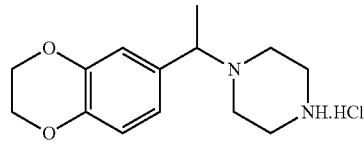

Step 1: t-Butyl 4-(1-(2,3-dihydrobenzo[b][1,4]dioxin-6-yl)ethyl)piperazine-1-carboxylate The title compound was synthesized according to the general procedure D, starting with Intermediate 3 (5 g, 25.2 mmol) and N-boc piperazine (3.96 g, 21.2 mmol). The crude product was purified by flash chromatography, affording the title compound. Yield: 52% (4.6 g, brown liquid). $^1$H NMR (400 MHz, DMSO-$d_6$): δ 6.80-6.71 (m, 3H), 4.21 (s, 5H), 3.34-3.26 (m, 4H), 2.27-2.24 (m, 4H), 1.37 (s, 9H), 1.23 (d, J=6.7 Hz, 3H). LCMS: (Method A) 349.2 (M+H), Rt. 3.19 min, 80.9% (Max).

Step 2: 1-(1-(2,3-dihydrobenzo[b][1,4]dioxin-6-yl)ethyl)piperazine hydrochloride To a stirred solution of tert-butyl 4-(1-(2,3-dihydrobenzo[b][1,4]dioxin-6-yl)ethyl)piperazine-1-carboxylate (4.6 g, 13.20 mmol) in dry dioxane (5.0 mL), HCl in dioxane (10.0 mL, 4 M, Spectrochem) was added at 0° C. The reaction mixture was stirred at rt for 2 h. The completion of the reaction was monitored by TLC. The reaction mixture was concentrated. Diethyl ether was added and was evaporated again, affording the title compound. Yield: 89% (3.8 g, off white solid). $^1$H NMR (400 MHz, DMSO-$d_6$): δ 12.08 (br. s, 1H), 9.48-9.18 (m, 2H), 7.18 (s, 1H), 7.03 (s, 1H), 6.92 (d, J=10.6 Hz, 1H), 4.49 (s, 1H), 4.24 (s, 4H), 3.41-3.15 (m, 4H), 2.91-2.71 (m, 4H), 1.64 (s, 3H). LCMS: (Method A) 249.2 (M+H), Rt. 1.64 min, 92.6% (Max).

Intermediate 7: N-(5-(piperazin-1-yl)-1,3,4-thiadiazol-2-yl)acetamide hydrochloride

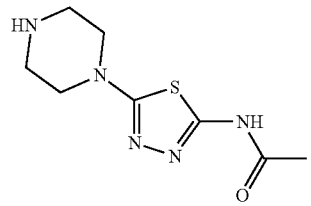

Step 1: tert-Butyl 4-(5-amino-1,3,4-thiadiazol-2-yl)piperazine-1-carboxylate To a stirred solution of 2-amino 5-bromo-1, 3, 4-thiadiazole (10.0 g, 55.5 mmol) in dry DMF (100 mL), K$_2$CO$_3$ (15.3 g, 111.1 mmol) and 1-boc piperazine (12.4 g, 66.65 mmol) were added at 0° C. The reaction mixture was stirred overnight at 80° C. The reaction mixture was concentrated under vacuum. To the resulting crude solids, DCM (200 mL)

was added. The DCM layer was washed with water (100 mL), brine (100 mL) and, dried over anhydrous $Na_2SO_4$ and concentrated. The crude product was purified by silica gel column chromatography to afford the title compound. Yield: 76% (12 g, pale brown solid). $^1$H NMR (400 MHz, DMSO-$d_6$): δ 6.51 (s, 2H), 3.39 (d, J=6.9 Hz, 4H), 3.19 (d, J=7.7 Hz, 4H), 1.39 (s, 9H). LCMS: (Method A) 286.1 (M+H), Rt. 2.71 min, 97.6% (Max).

Step 2: tert-Butyl 4-(5-acetamido-1,3,4-thiadiazol-2-yl)piperazine-1-carboxylate To a stirred solution of tert-butyl 4-(5-amino-1,3,4-thiadiazol-2-yl)piperazine-1-carboxylate (12.0 g, 42.09 mmol) in pyridine (120 mL), acetic anhydride (5.1 g, 50.5 mmol) was added at 0° C. The reaction mixture was stirred overnight at 50° C. The reaction mixture was concentrated under vacuum and triturated with diethyl ether (100 mL). The solid obtained was filtered, washed with diethyl ether (20 mL), dried and taken for next step without any further purification. Yield: 87% (12 g, off white solid). $^1$H NMR (400 MHz, DMSO-$d_6$): δ 12.07 (br. s, 1H), 3.45-3.34 (m, 8H), 2.11 (s, 3H), 1.42 (s, 9H). LCMS: (Method A) 328.0 (M+H), Rt. 3.11 min, 86.3% (Max).

Step 3: N-(5-(Piperazin-1-yl)-1,3,4-thiadiazol-2-yl)acetamide hydrochloride

To a stirred solution of tert-butyl 4-(5-acetamido-1,3,4-thiadiazol-2-yl)piperazine-1-carboxylate (12.0 g) in dry dioxane (100 mL), HCl in dioxane (100 mL, 4 N) was added and the reaction mixture was stirred at rt for 3 h. The reaction mixture was concentrated under vacuum and the resulting crude product was suspended diethyl ether (50 mL). The title compound was obtained after evaporation of the solvent. Yield: 93% (9 g, white solid). $^1$H NMR (400 MHz, DMSO-$d_6$): δ 12.07 (br. s, 1H), 3.67 (s, 4H), 3.21 (s, 4H), 2.13 (s, 3H). LCMS: (Method A) 228.0 (M+H), Rt. 0.71 min, 85.3% (Max).

Intermediate 8: Ethyl 2-(piperazin-1-yl)thiazole-5-carboxylate hydrochloride

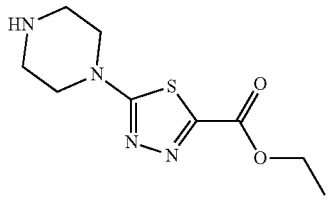 [SMILES: CCOC(=O)c1nnc(N2CCNCC2)s1]

Step 1: Ethyl 2-(4-(tert-butoxycarbonyl)piperazin-1-yl)thiazole-5-carboxylate

To a stirred solution of ethyl 2-bromothiazole-5-carboxylate (4.0 g, 17.0 mmol) in dry DMF (40 mL), triethylamine (7.3 mL, 51.0 mmol, Spectrochem), followed by N-Boc piperazine (3.6 g, 19.0 mmol, GLRscientific) were added. The resulting mixture was heated at 90° C. for 12 h. It was then concentrated, diluted with DCM (200 mL), washed with water (100 mL) and dried over $Na_2SO_4$. After evaporation of the solvents, the crude product was purified by flash chromatography (3% methanol in DCM) to afford the title compound. Yield: 77% (4.5 g, white solid). LCMS: (Method A) 342.0 (M+H), Rt. 4.42 min, 99.5% (Max). $^1$H NMR (400 MHz, CDCl$_3$): δ 7.88 (s, 1H), 4.30 (q, J=7.2 Hz, 2H), 3.57 (s, 8H), 1.49 (s, 9H), 1.35 (t, J=7.2 Hz, 3H).

Step 2: Ethyl 2-(piperazin-1-yl)thiazole-5-carboxylate hydrochloride

To a stirred solution of ethyl 2-(4-(tert-butoxycarbonyl)piperazin-1-yl)thiazole-5-carboxylate (4.5 g, 13.0 mmol) in dry dioxane (20 mL), HCl in dioxane (4 N, 50 mL) was added at 0° C. and the reaction mixture was stirred at rt for 2 h. The reaction mixture was concentrated and the resulting solid was washed with diethyl ether and dried under vacuum. Yield: 90% (5.4 g, off white solid). $^1$H NMR (400 MHz, DMSO-$d_6$): δ 9.32 (s, 2H), 7.88 (s, 1H), 4.21 (q, J=9.4 Hz, 2H), 3.96-3.73 (m, 4H), 3.55-2.41 (m, 4H), 1.24 (t, J=7.0 Hz, 3H). LCMS: (Method B) 242.0 (M+H), Rt. 2.11 min, 99.8% (Max).

Intermediate 10: N-(2-(piperazin-1-yl)pyrimidin-5-yl)acetamide, hydrochloride

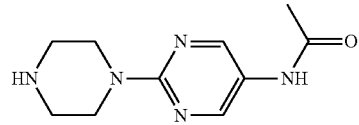

Step 1: Tert-butyl 4-(5-nitropyrimidin-2-yl)piperazine-1-carboxylate

To a stirred solution of 2-chloro-5-nitro-pyrimidine (2.2 g, 13.7 mmol) in dry DMF (25 mL), triethylamine (5.7 mL, 41.3 mmol, Spectrochem) followed by N-Boc piperazine (2.8 g, 15.7 mmol) were added and the resulting mixture was heated at 90° C. for 12 h. It was concentrated and the residue was diluted with DCM (50 mL), washed with water (15 mL) and dried over $Na_2SO_4$. After evaporation of the solvents, the crude product was washed with ACN with 5% methanol to afford the title compound (brown solid). $^1$H NMR (400 MHz, DMSO-$d_6$): δ 9.12 (s, 2H), 3.92-3.88 (m, 4H), 3.45-3.42 (m, 4H), 1.4 (s, 9H). LCMS: (Method A) 254.0 (M-(t-butyl)+H), Rt. 4.43 min, 98.03% (Max).

Step 2: Tert-butyl 4-(5-aminopyrimidin-2-yl)piperazine-1-carboxylate

To a stirred solution of tert-butyl 4-(5-nitropyrimidin-2-yl)piperazine-1-carboxylate (2.1 g, 6.79 mmol) in methanol (25 mL), Pd/C (10%, 0.210 g, Aldrich) was added and the reaction mixture was stirred under H$_2$ atmosphere for 3 h. The reaction completion was monitored by TLC. The reaction mixture was filtered through celite and evaporated under vacuum. The crude product was used without further purification. Yield: 95% (1.8 g, pale brown solid). $^1$H NMR (400 MHz, DMSO-$d_6$): δ 7.88 (s, 2H), 4.62 (s, 2H), 3.48-3.45 (m, 4H), 3.35-3.28 (m, 4H), 1.33 (s, 9H). LCMS: (Method A) 280 (M+H), Rt. 2.66 min, 98.82% (Max).

Step 3: Tert-butyl 4-(5-acetamidopyrimidin-2-yl)piperazine-1-carboxylate

To a stirred solution of tert-butyl 4-(5-aminopyrimidin-2-yl)piperazine-1-carboxylate (1.8 g, 6.44 mmol) in dry DCM (18 mL), pyridine (0.7 mL, 9.67 mmol, spectrochem), acetic anhydride (0.9 mL, 9.67 mmol, spectrochem) and dimethyl aminopyridine (0.036 g, 2%, spectrochem) were added. The resulting mixture was stirred at rt for 12 h. The reaction mixture was concentrated under reduced pressure and the resulting solid was suspended in HCl (1.5 N in water, 15 mL). The solid was filtered and washed with water (200 mL) to afford the title compound. Yield: 87% (1.8 g, off white solid). $^1$H NMR (400 MHz, DMSO-$d_6$): δ 9.85 (s, 1H), 8.51 (s, 2H), 3.66-3.61 (m, 4H), 3.33-3.31 (m, 4H), 2.00 (s, 3H), 1.41 (s, 9H). LCMS: (Method A) 322 (M+H), Rt. 3.1 min, 98.4% (Max).

Step 4: N-(2-(piperazin-1-yl)pyrimidin-5-yl)acetamide

To a stirred solution of tert-butyl 4-(5-acetamidopyrimidin-2-yl)piperazine-1-carboxylate (1.8 g, 5.6 mmol) in dry dioxane (5 mL) at 0° C., a solution of HCl in dioxane (4 N, 15 mL) was added and the reaction mixture was stirred 3 h at rt. It was concentrated and the resulting product washed with diethyl ether, affording the title compound. Yield: 83% (1.8 g, off white solid). $^1$H NMR (400 MHz, DMSO-$d_6$): δ 10.9 (s, 1H), 9.92 (s, 1H), 8.86 (s, 2H), 3.22-3.17 (m, 4H), 3.02-2.78 (m, 4H), 2.06 (s, 3H). LCMS: (Method B) 222.0 (M+H), Rt. 2.36 min, 95.34% (Max)

Intermediate 16: (S)-1-(1-(benzo[d][1,3]dioxol-5-yl)ethyl)piperazine hydrochloride

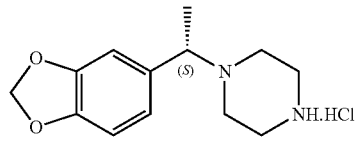

Step 1: (R)—N-(1-(benzo[d][1,3]dioxol-5-yl)ethylidene)-2-methylpropane-2-sulfinamide To a mixture of 1-(benzo[d][1,3]dioxol-5-yl)ethan-1-one (105.7 g, 644.6 mmol), (R)-(+)-2-methyl-2-propanesulfinamide (85.79 g, 709 mmol) in THF (1.0 L), titanium(IV) ethoxide (294.06 g, 1289.2 mmol) was added at rt over 30 min and refluxed for 35 h. The reaction was monitored by HPLC. The reaction mixture was cooled to rt and slowly quenched with water (500 mL). The precipitate observed was filtered through celite bed (100 g) and washed with EtOAc (2.0 L). The organic layer was washed with water (500 mL), brine solution (300 mL) and dried over Na$_2$SO$_4$ (100 g) and evaporated under vacuum at 50° C. The resulting crude product was codistilled with toluene (2×500 mL) and used as such for next step without any further purification (164 g, brown liquid).

LCMS: (Method A) 268.0 (M+H), Rt. 3.87 min, 83.05% (Max).

HPLC: (Method A) Rt. 3.81 min, 57.62% (Max).

Step 2: (R)—N—((S)-1-(benzo[d][1,3]dioxol-5-yl)ethyl)-2-methylpropane-2-sulfinamide To a stirred solution of (R)—N-(1-(benzo[d][1,3]dioxol-5-yl)ethylidene)-2-methylpropane-2-sulfinamide (96 g, 359 mmol) in THF (960 mL), L-Selectride (539 mL, 539 mmol, 1 M solution in THF) was added under nitrogen atmosphere at −50° C. over 30 min and stirred for 1 h. The completion of the reaction was confirmed by TLC. The reaction mixture was quenched with methanol (150 mL), water (750 mL) and stirred overnight at rt. The aqueous layer was extracted with EtOAc (2×300 mL). The combined organic layer was washed with sat. NH$_4$Cl (2×250 mL), brine (250 mL), dried over Na$_2$SO$_4$ and evaporated under vacuum at 50° C. The resulting crude product (as light brown thick oil) was diluted with pet ether (250 mL) and stirred at −20° C. for 30 min. The resulting precipitate was filtered and washed with pet ether (2×100 mL). It was dried under vacuum to give the title compound. Yield: 70.2% (68 g, Off white solid). $^1$H NMR (400 MHz, DMSO-$d_6$): δ 6.89 (s, 1H), 6.83-6.77 (m, 2H), 5.99-5.95 (m, 2H), 5.25 (d, J=5.2 Hz, 1H), 4.30 (q, J=6.0 Hz, 1H), 1.39 (d, J=1.6 Hz, 3H), 1.11-1.06 (m, 9H). LCMS: (Method A) 270.0 (M+H), Rt. 3.66 min, 99.65% (Max). HPLC: (Method A) Rt. 3.62 min, 99.69% (Max). Chiral HPLC: (Method C) Rt. 9.71 min, 100%.

Step 3: (S)-1-(benzo[d][1,3]dioxol-5-yl)ethan-1-amine

To a stirred solution of (R$_S$)—N—((S)-1-(benzo[d][1,3]dioxol-5-yl)ethyl)-2-methylpropane-2-sulfinamide (68 g, 252 mmol) in MeOH (680 mL), thionyl chloride (74.3 g, 630 mmol) was added at 0° C. over 15 min and the resulting mixture was stirred at rt for 1 h. The completion of the reaction was confirmed by TLC. The reaction mixture was concentrated under vacuum at 50° C. The resulting residue was suspended in EtOAc (300 mL), filtered and washed with EtOAc (150 mL). The product was basified with 30% aqueous ammonia solution (300 mL) and extracted with EtOAc (2×250 mL). The combined organic layer was washed with brine solution (1×150 mL) and dried over Na$_2$SO$_4$. The solvent was evaporated at under vacuum to give the title compound. Yield: 92.84% (38.3 g, brown liquid). $^1$H NMR (400 MHz, DMSO-$d_6$): δ 6.95 (s, 1H), 6.81-6.77 (m, 2H), 5.95 (s, 2H), 3.90 (q, J=6.56 Hz, 1H), 1.85 (s, 2H), 1.19 (m, J=6.56 Hz, 3H). LCMS: (Method A) 149.0 (M-16), Rt. 1.65 min, 99.56% (Max). HPLC: (Method A) Rt. 1.60 min, 99.61% (Max). Chiral HPLC: (Method B) Rt 11.11 min, 100%.

Step 4: (S)-1-(1-(benzo[d][1,3]dioxol-5-yl)ethyl)-4-tosylpiperazine

To a stirred solution of (S)-1-(benzo[d][1,3]dioxol-5-yl)ethan-1-amine (41 g, 248 mmol) in DIPEA (86.6 mL, 496 mmol), N,N-bis(2-chloroethyl)-p-toluene sulfonamide (80.74 g, 273 mmol) was added at rt and the resulting mixture was heated at 105° C. overnight. The completion of the reaction was confirmed by TLC and the reaction mixture was diluted with water (1000 mL) and extracted with EtOAc (2×500 mL). The combined organic layer was washed with water (200 mL), brine solution (200 mL) and dried over Na$_2$SO$_4$. After evaporation of the solvent, the resulting crude solid was suspended in pet ether (350 mL) and stirred for 10 min at rt. The suspension was filtered and was washed with Et$_2$O (2×200 mL) and dried under vacuum to give the title compound. Yield: 63.2% (61 g, Off white solid). $^1$H NMR (400 MHz, DMSO-d$_6$): δ 7.59 (d, J=8.2 Hz, 2H), 7.45 (d, J=8.2 Hz, 2H), 6.81-6.77 (m, 1H), 6.69 (d, J=7.4 Hz, 1H), 5.96 (s, 2H), 3.32 (q, J=7.76 Hz, 1H), 2.81-2.80 (m, 4H), 2.42 (s, 3H), 2.36-2.32 (m, 4H), 1.18 (d, J=6.4 Hz, 3H). LCMS: (Method A) 389.2 (M+H), Rt. 3.40 min, 98.09% (Max). HPLC: (Method A) Rt. 3.30 min, 98.69% (Max). Chiral HPLC: (Method D) Rt. 15.79 min, 100.00%

Step 5: (S)-1-(1-(benzo[d][1,3]dioxol-5-yl)ethyl)piperazine hydrochloride

To a mixture of (S)-1-(1-(benzo[d][1,3]dioxol-5-yl)ethyl)-4-tosylpiperazine (61 g, 157 mmol) and 4-hydroxy benzoic acid (65.01 g, 471 mmol), HBr in acetic acid (244 mL) was added at 0° C. and the reaction mixture was stirred at rt overnight. The completion of the reaction was confirmed by TLC. The reaction mixture was diluted with water (400 mL). The precipitate was filtered through celite bed and washed with water (200 mL). The aqueous filterate was washed with EtOAc (4×300 mL) and basified up to pH 11 with NaOH pellet (30 g) at 0° C. (during basification the colour of aqeuous was converted to light back). The product was extracted with EtOAc (4×300 mL). The combined organic layer was dried over Na$_2$SO$_4$ and evaporated under vacuum. The resulting light black oil was diluted in 1,4 Dioxane (50 mL) and cooled to 0° C. and 4.5 N HCl solution in dioxane (100 mL) was added and stirred for 15 min at rt. The solvent was evaporated at 45° C. under reduced pressure to get the title compound (pale brown solid). $^1$H NMR (400 MHz, DMSO-d$_6$): δ 12.11 (s, 1H), 7.32 (s, 1H), 7.06-6.99 (m, 2H), 6.07 (s, 2H), 4.55-4.52 (m, 1H), 3.80-3.61 (m, 2H), 3.05-2.95 (m, 2H), 2.51-2.50 (m 4H), 1.68 (s, 3H). LCMS: (Method A) 235.3 (M+H), Rt. 1.53 min, 95.85% (Max). HPLC: (Method A) Rt. 1.52 min, 95.06% (Max). Chiral HPLC: (Method A) Rt. 8.11 min, 100%.

Intermediate 21: 6-(1-chloroethyl)-2,3-dihydrobenzofuran

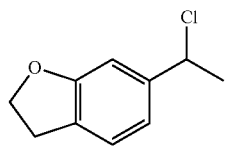

Step 1: 1-(2,3-dihydrobenzofuran-6-yl)ethan-1-one

The title compound was prepared according to the procedure described for Intermediate 6, Step 1, using 6-bromo-2,3-dihydro-1-benzofuran (1 g, 5.03 mmol) as starting material. The crude product was purified by flash chromatography to give the title compound. Yield: 73.7% (0.6 g, pale yellow solid). $^1$H NMR (400 MHz, DMSO-d$_6$): δ 7.48 (d, J=7.64 Hz, 1H), 7.37-7.35 (d, J=7.68 Hz, 1H), 7.26 (s, 1H), 4.58 (t, J=8.76 Hz, 2H), 3.24 (t, J=8.76 Hz, 2H), 2.53 (s, 3H). LCMS: (Method A) 163.2 (M+H), Rt. 3.01 min, 97.60% (Max).

Step 2: 1-(2,3-dihydrobenzofuran-6-yl)ethan-1-ol

The title compound was prepared according to the procedure described for Intermediate 17, Step 2, using 1-(2,3-dihydrobenzofuran-6-yl)ethan-1-one (0.6 g, 3.7 mmol) as starting material. After evaporation of the solvent, the title compound was isolated and used without further purification. Yield: 88.30% (0.53 g, colourless liquid). $^1$H NMR (400 MHz, DMSO-d$_6$): δ 7.11 (d, J=7.6 Hz, 1H), 6.77-6.75 (m, 1H), 6.71 (s, 1H), 5.04 (d, J=4.4 Hz, 1H), 4.63-4.61 (m, 1H), 4.48 (t, J=8.8 Hz, 2H), 3.11 (t, J=8.8 Hz, 2H), 1.25 (d, J=6.4 Hz, 3H). LCMS: (Method A) 147.0 (M−17H), Rt. 2.64 min, 89.95% (Max).

Step 3: 6-(1-chloroethyl)-2,3-dihydrobenzofuran

The title compound was synthesized from 1-(2,3-dihydrobenzofuran-6-yl)ethan-1-ol (0.53 g, 3.23 mmol), according to the general procedure B. The crude product was used in the next step without further purification. Yield: quantitative (0.58 g, brown oil). $^1$H NMR (400 MHz, DMSO-d$_6$): δ 7.20 (d, J=7.56 Hz, 1H), 6.93-6.91 (m, 1H), 6.87 (s, 1H), 5.29-5.24 (m, 1H), 4.53 (t, J=8.72 Hz, 2H), 3.15 (t, J=8.76 Hz, 2H), 1.75 (d, J=6.76 Hz, 3H). LCMS: (Method A) 147.0 (M−35H), Rt. 3.76 min, 83.62% (Max).

Intermediate 25: 2-(piperazin-1-yl)-6,7-dihydrothiazolo[5,4-c]pyridin-4(5H)-one dihydrochloride

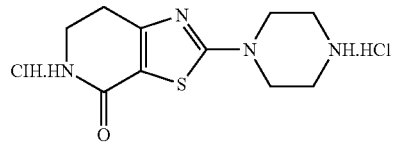

Step 1: tert-butyl 3-bromo-2,4-dioxopiperidine-1-carboxylate

To a stirred solution of tert-butyl 2,4-dioxopiperidine-1-carboxylate (1 g, 4.69 mmol) in dry CCl$_4$ (10 mL), N-bromosuccinimide (0.83 g, 4.69 mmol) was added at 10° C. The reaction mixture was stirred at 10-15° C. for 2 h. It was then evaporated under reduced pressure. Water (10 mL) was added and the desired product was extracted with EtOAc (2×30 mL). The combined organic layer was dried over Na$_2$SO$_4$ and concentrated. The resulting crude product was purified by flash column chromatography, affording the title product. Yield: 99% (1.4 g, off white solid). $^1$H NMR (400 MHz, DMSO-d$_6$): δ 5.50 (s, 1H), 3.74-3.71 (m, 2H), 2.69-2.66 (m, 2H), 1.46 (s, 9H). LCMS: (Method A) 193.8 (M-Boc+H), Rt. 2.93 min, 81.51% (Max).

Step 2: tert-butyl-2-(4-(tert-butoxycarbonyl)piperazin-1-yl)-4-oxo-6,7-dihydrothiazolo[5,4-c]pyridine-5(4H)-carboxylate To a stirred solution of tert-butyl 4-carbamothioylpiperazine-1-carboxylate (synthesized according to Example 5, Step 1, 1.31 g, 5.36 mmol) in isopropanol (15 mL), tert-butyl 3-bromo-2,4-dioxopiperidine-1-carboxylate obtained in the first step (1.3 g, 4.46 mmol) was added at rt. The reaction mixture was stirred overnight at 90° C. It was cooled down to rt and evaporated under reduced pressure. Water (10 mL) was added and the desired product was extracted with diethyl ether (2×30 mL), dried over Na$_2$SO$_4$ and concentrated, affording the title product. Yield: 74% (1.42 g, yellow solid). LCMS: (Method A) 239.0 (M-Boc+H), Rt. 0.70 min, 48.39% (Max).

Step 3: 2-(piperazin-1-yl)-6,7-dihydrothiazolo[5,4-c]pyridin-4(5H)-one dihydrochloride To a stirred solution of tert-butyl-2-(4-(tert-butoxycarbonyl)piperazin-1-yl)-4-oxo-6,7-dihydrothiazolo[5,4-c]pyridine-5(4H)-carboxylate obtained in previous step (1.3 g, 2.96 mmol) in 1,4-dioxane (10 mL), HCl in dioxane (4 M solution, 13 mL, 10 V) was added at 0° C. The reaction mixture was stirred for 2 h at rt. It was evaporated and DCM (15 mL) was added and evaporated. This procedure was repeated twice, affording the title product which was used without any further purification. Yield: 99% (0.82 g, off white solid).

Intermediate 29: 1-(3-(Trifluoromethyl)pyridin-2-yl)piperazine

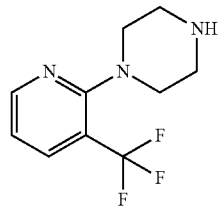 [SMILES: FC(F)(F)c1cccnc1N1CCNCC1]

To a stirred solution of 2-chloro-3-(trifluoromethyl)pyridine (1 g, 5.50 mmol) in n-Butanol (10 mL), 1-piperazine (6.63 g, 77.12 mmol) was added and the reaction mixture was stirred at 100° C. for 24 h. The reaction completion was confirmed by TLC. The reaction mixture was cooled to room temperature and concentrated under reduced pressure. The resulting mixture was diluted with ethyl acetate (30 mL) and neutralized with saturated sodium bicarbonate solution (4 mL), and extracted with EtOAc (2×50 mL). The combined organic layer was dried over anhydrous $Na_2SO_4$ and concentrated under reduced pressure. The crude was purified by column chromatography to afford the title compound. Yield: 63% (0.8 g, colorless gum). $^1$HNMR (400 MHz, DMSO-d$_6$): δ 8.50 (d, J=3.6 Hz, 1H), 8.03 (dd, J=7.8, 2.0 Hz, 1H), 7.16-7.13 (m, 1H), 3.11-3.08 (m, 4H), 2.81-2.79 (m, 4H). LCMS: (Method F) 232.0 (M+H), Rt. 2.10 min, 96.01% (Max).

Intermediate 30: 1-(1-(2,3-dihydrobenzofuran-6-yl)ethyl)piperazine, hydrochloride

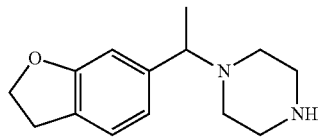 [SMILES: CC(c1ccc2c(c1)OCC2)N1CCNCC1]

Step 1: tert-butyl 4-(1-(2,3-dihydrobenzofuran-6-yl)ethyl)piperazine-1-carboxylate To a stirred solution of N-boc piperazine (5.5 g, 29.5 mmol), TEA (11.9 g, 11.8 mmol) in DMF (55 mL), Intermediate 21 (7.5 g, 41.3 mmol) was added at RT and the resulting mixture was heated at 70° C. overnight. Completion of the reaction was monitored by TLC. The reaction mixture was concentrated under reduced pressure and the resulting crude mixture was dissolved in EtOAc (100 mL). The organic layer was washed with water (50 mL), brine (50 mL), dried over $Na_2SO_4$ and concentrated. The crude product was purified by flash chromatography (12% EtOAc in pet ether as eluent) to give the title compound. Yield: 52% (58% purity) (5.1 g, brown gum). $^1$H NMR (400 MHz, CDCl$_3$): δ 7.19-7.12 (m, 1H), 6.88-6.77 (m, 2H), 4.62-4.59 (m, 2H), 3.42-3.39 (m, 4H), 3.36-3.31 (m, 1H), 3.23-3.18 (m, 2H), 2.44-2.34 (m, 4H), 1.46 (s, 9H), 1.35 (d, J=6.4 Hz, 3H). LCMS: (Method A) 333.3 (M+H), Rt. 3.12 min, 58.09% (Max).

Step 2: 1-(1-(2,3-dihydrobenzofuran-6-yl)ethyl)piperazine, hydrochloride

To a stirred solution of tert-butyl 4-(1-(2,3-dihydrobenzofuran-6-yl)ethyl)piperazine-1-carboxylate (5.1 g, 15.3 mmol) in 1,4 dioxane (25 mL), HCl solution in dioxane (4 M, 25 mL) was added at 0° C. The resulting mixture was stirred at rt for 2 h. Completion of the reaction was monitored by TLC. The reaction mixture was evaporated at 40° C. under reduced pressure. The resulting product was triturated with n-hexanes (2×100 mL) and decanted two times. It was then dried at 40° C. under reduced pressure to give the title compound. Yield: 66.2% (3.1 g, Off white solid). $^1$H NMR (400 MHz, DMSO-d6): δ 7.15 (d, J=7.2 Hz, 1H), 6.76-6.71 (m, 2H), 4.36-4.30 (m, 2H), 3.55-3.53 (m, 4H), 3.43-3.41 (m, 1H), 3.15-3.11 (m, 2H), 2.53-2.43 (m, 4H), 1.31-1.29 (m, 3H). LCMS: (Method A) 233.2 (M+H), Rt. 1.67 min, 90.31% (Max).

Example 5: 2-(4-(1-(Benzo[d][1,3]dioxol-5-yl)ethyl)piperazin-1-yl)-4-phenylthiazole

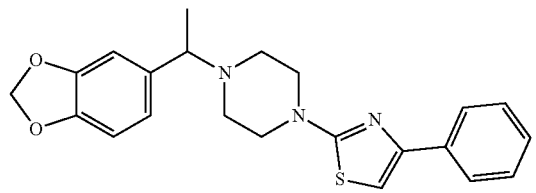 [SMILES: CC(c1ccc2c(c1)OCO2)N1CCN(c2nc(-c3ccccc3)cs2)CC1]

Step 1: tert-butyl 4-carbamothioylpiperazine-1-carboxylate

To a solution of 1-boc piperazine (5.0 g, 26.88 mmol) in dry THF (50 mL), 1,1-thio carbonylimidazole (5.48 g, 29.56 mmol) was added at room temperature and stirred for 2 h. The reaction mixture was heated at 50° C. for 1 h. It was cooled down to 0° C. and methanolic ammonia solution (50 mL, 7 N) was added. The mixture was stirred at 60° C. for 20 h. It was then diluted with water and extracted with EtOAc. The organic layer was dried over anhydrous $Na_2SO_4$ and concentrated under vacuum. The crude product was purified by flash chromatography to give the title compound. Yield: 92% (4.0 g, white solid). $^1$H NMR (400 MHz, DMSO-d$_6$): δ 9.2 (m, 2H), 3.16-3.14 (m, 2H), 2.49-2.48 (m, 6H), 1.30 (s, 9H). LCMS: (Method A) 246.2 (M+H), Rt. 2.93 min, 95.3% (Max).

Step 2: tert-Butyl 4-(4-phenylthiazol-2-yl)piperazine-1-carboxylate

To a stirred solution of tert-butyl 4-carbamothioylpiperazine-1-carboxylate (0.5 g, 2.08 mmol) in dioxane (10 mL), triethyl amine (0.22 mL, 2.6 mmol) and 2-bromo-1-phenylethan-1-one (0.52 g, 2.6 mmol) were added at rt. The resulting mixture was stirred at 90° C. for 20 h. The completion of the reaction was monitored by TLC. It was diluted with water and extracted with EtOAc. The organic layer was separated, dried over anhydrous $Na_2SO_4$ concentrated under vacuum. The resulting crude product was taken as such for the next step. Yield: 86% (0.5 g, colorless liquid).

Step 3: 4-Phenyl-2-(piperazin-1-yl)thiazole hydrochloride

To a stirred solution of tert-butyl 4-(4-phenylthiazol-2-yl) piperazine-1-carboxylate (0.5 g) in dry dioxane (2 mL), HCl in dioxane (10 mL, 4 N) was added at room temperature and stirred for 3 h at same temperature. The reaction mixture was concentrated under reduced pressure and the resulting crude product was suspended in diethyl ether (10 mL). It was filtered and dried under vacuum to afford the title compound. Yield: 75% (350 mg, yellow solid). LCMS: (Method A) 246.2 (M+H), Rt. 2.85 min, 71.5% (Max).

Step 4: 2-(4-(1-(Benzo[d][1,3]dioxol-5-yl)ethyl) piperazin-1-yl)-4-phenylthiazole The title compound was synthesized by following general procedure E, using 4-phenyl-2-(piperazin-1-yl)thiazole hydrochloride (0.2 g, 0.8 mmol) and Intermediate 1 (0.3 g, 1.6 mmol). The reaction mixture was stirred at rt for 16 h. The crude product was purified by flash chromatography, affording the title compound (yellow solid). $^1$H NMR (400 MHz, DMSO-$d_6$): δ 7.84-7.82 (m, 2H), 7.40-7.36 (m, 3H), 7.30-7.26 (m, 1H), 7.14-6.99 (m, 3H), 6.06 (s, 2H), 4.61-4.48 (m, 1H), 4.18-3.98 (m, 2H), 3.43-3.33 (m, 2H) 3.12-2.98 (m, 2H), 2.59-2.49 (m, 2H), 1.63 (br. s, 3H). LCMS: (Method A) 394.0 (M+H), Rt. 3.87 min, 98.3% (Max). HPLC: (Method A) Rt. 3.89 min, 99.3% (Max).

Example 6: 2-(4-(1-(Benzo[d][1,3]dioxol-5-yl)ethyl) piperazin-1-yl)-4-(4-methoxyphenyl)thiazole

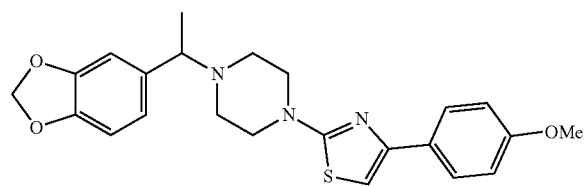 [SMILES: COc1ccc(-c2csc(N3CCN(C(C)c4ccc5c(c4)OCO5)CC3)n2)cc1]

Step 1: tert-butyl 4-(4-(4-methoxyphenyl)thiazol-2-yl)piperazine-1-carboxylate To a stirred solution of tert-butyl 4-carbamothioylpiperazine-1-carboxylate (synthesized according to Example 5, Step 1, 1.0 g, 4.0 mmol) in dioxane (20 mL), triethyl amine (0.6 mL, 8.3 mmol) and 2-bromo-1-(4-methoxyphenyl) ethan-1-one (1.2 g, 5.3 mmol) was added at rt and stirred at 90° C. for 20 h. The completion of the reaction was monitored by TLC. The reaction mixture was diluted with water (10 mL) and extracted with EtOAc (2×25 mL). The organic layer was separated, dried over anhydrous $Na_2SO_4$. After evaporation of the solvents, the resulting crude product was taken as such for the next step. Yield: 53% (0.8 g, pale yellow liquid).

Step 2: 4-(4-Methoxyphenyl)-2-(piperazin-1-yl)thiazole hydrochloride

To a stirred solution of tert-butyl 4-(4-(4-methoxyphenyl) thiazol-2-yl)piperazine-1-carboxylate (0.8 g) in dry dioxane (5 mL), HCl in dioxane (4 M, 10 mL) was added at rt and stirred for 3 h. The reaction mixture was concentrated under vacuum. The resulting crude product was triturated in diethyl ether (10 mL), filtrated and dried under vacuum to afford the title compound. Yield: 68% (400 mg, yellow solid). LCMS: (Method A) 276.0 (M+H), Rt. 2.82 min, 69.9% (Max).

Step 3: 2-(4-(1-(Benzo[d][1,3]dioxol-5-yl)ethyl) piperazin-1-yl)-4-(4-methoxyphenyl)thiazole The title compound was synthesized by following general procedure E, using 4-(4-methoxyphenyl)-2-(piperazin-1-yl) thiazole hydrochloride (0.5 g, 2.7 mmol) and Intermediate 1 (0.9 g, 5.4 mmol). The reaction mixture was stirred at rt for 16 h. The crude product was purified by flash chromatography, affording the title compound (pale yellow solid). $^1$H NMR (400 MHz, DMSO-$d_6$): δ 7.76 (d, J=8.4 Hz, 2H), 7.07 (s, 1H), 6.94-6.91 (m, 3H), 6.86-6.84 (m, 1H), 6.78-6.76 (m, 1H), 5.99 (m, 2H), 3.76 (s, 3H), 3.43-3.42 (m, 5H), 2.50 (m, 2H) 2.42-2.41 (m, 2H), 1.30 (d, J=6.8 Hz, 3H). LCMS: (Method A) 424.0 (M+H), Rt. 3.86 min, 98.7% (Max). HPLC: (Method A) Rt. 3.85 min, 99.3% (Max).

Example 7: 2-(4-(1-(Benzo[d][1,3]dioxol-5-yl)ethyl) piperazin-1-yl)thiazole

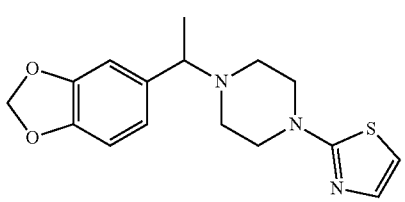 [SMILES: CC(c1ccc2c(c1)OCO2)N1CCN(c2nccs2)CC1]

To a stirred solution of Intermediate 2 (0.1 g, 0.37 mmol) in dry DMSO (5 mL), $K_2CO_3$ (0.15 g, 11.11 mmol) and 2-bromo thiazole (0.066 g, 0.407 mmol) were added. The reaction mixture was heated in a microwave at 150° C. for 3 h. The reaction mixture was cooled and concentrated under vacuum. The resulting crude product was purified by MD Autoprep (Method B) to afford the title compound (off white solid). $^1$H NMR (400 MHz, CDCl$_3$): δ 7.20 (d, J=4.0 Hz, 1H), 6.90 (s, 1H), 6.77 (s, 2H), 6.57 (s, 1H), 5.97 (s, 2H), 3.48 (s, 4H), 3.36 (s, 1H), 2.60-2.53 (m, 4H), 1.37 (s, 3H). LCMS: (Method A) 318.0 (M+H), Rt. 2.04 min, 94.4% (Max). HPLC: (Method A) Rt. 2.04 min, 98.6% (Max).

Example 9: 2-(4-(1-(Benzo[d][1,3]dioxol-5-yl)ethyl) piperazin-1-yl)-4-methylpyrimidine

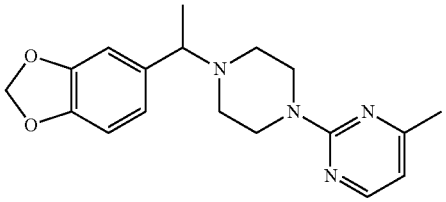 [SMILES: Cc1ccnc(N2CCN(C(C)c3ccc4c(c3)OCO4)CC2)n1]

To a stirred solution of Intermediate 2 (0.1 g, 0.37 mmol) in dry DMF (5 mL), DIPEA (0.22 g, 1.7 mmol) and 2-chloro-4-methyl pyrimidine (0.109 g, 0.8 mmol) were added at rt and the reaction mixture was stirred at 120° C. for 12 h. It was cooled down to rt and concentrated under vacuum. The resulting crude product was purified by flash chromatography to afford the title compound (brown oil). $^{1}$H NMR (400 MHz, DMSO-d$_{6}$): δ 8.17 (d, J=4.8 Hz, 1H), 6.89 (s, 1H), 6.84 (d, J=8.0 Hz, 1H), 6.76-6.74 (m, 1H), 6.48 (d, J=4.8 Hz, 1H), 5.99 (m, 2H), 3.70-3.66 (m, 4H), 3.40-3.34 (m, 1H), 2.43-2.39 (m, 2H), 2.34-2.31 (m, 2H) 2.24 (s, 3H), 1.28 (d, J=6.4 Hz, 3H). LCMS: (Method A) 327.0 (M+H), Rt. 2.57 min, 98.1% (Max). HPLC: (Method A) Rt. 2.59 min, 98.6% (Max).

Example 10: 1-(1-(Benzo[d][1,3]dioxol-5-yl)ethyl)-4-(pyridin-2-yl)piperazine

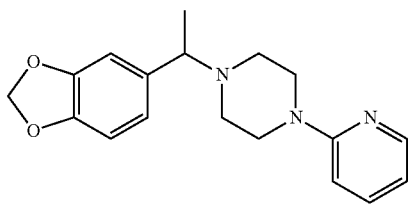 [SMILES: CC(c1ccc2c(c1)OCO2)N1CCN(c2ccccn2)CC1]

The title compound was synthesized by following general procedure D, using 1-pyridyl-2-piperazine (0.2 g, 1.3 mmol) and Intermediate 1 (0.3 g, 1.63 mmol). The resulting crude product was purified by silicagel column, affording the title compound (colorless oil). $^{1}$H NMR (400 MHz, DMSO-d$_{6}$): δ 8.07 (dd, J=2.0, 4.8 Hz, 1H), 7.51-7.46 (m, 1H), 6.88 (s, 1H), 6.84-6.82 (m, 1H), 6.76-6.74 (m, 2H), 6.61-6.58 (m, 1H), 5.98 (m, 2H), 3.43-3.40 (m, 4H), 3.34-3.33 (m, 1H), 2.47-2.44 (m, 2H), 2.39-2.35 (m, 2H), 1.28 (d, J=6.8 Hz, 3H). LCMS: (Method A) 312.0 (M+H), Rt. 1.83 min, 98.0% (Max). HPLC: (Method A) Rt. 1.82 min, 98.4% (Max).

Example 11: 2-(4-(1-(Benzo[d][1,3]dioxol-5-yl) ethyl)piperazin-1-yl)pyrimidine

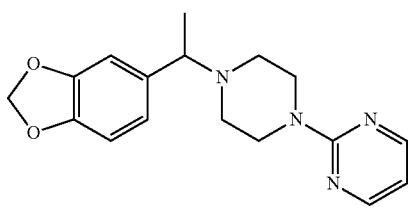

The title compound was synthesized by following general procedure D, using 2-(piperazin-1-yl)pyrimidine (0.2 g, 1.21 mmol) and Intermediate 1 (0.366 g, 1.82 mmol). The resulting crude product was purified by MD Autoprep (Method B), affording the title compound (colourless oil). $^{1}$H NMR (400 MHz, MeOH-d$_{4}$): δ 8.36 (d, J=4.8 Hz, 2H), 6.96 (s, 1H), 6.90-6.84 (m, 2H), 6.66 (t, J=4.8 Hz, 1H), 5.99 (s, 2H), 3.92-3.90 (m, 4H), 3.33 (m, 1H), 2.83 (m, 4H), 1.59 (d, J=6.0 Hz, 3H). LCMS: (Method A) 313.2 (M+H), Rt. 2.45 min, 99.4% (Max). HPLC: (Method A) Rt. 2.44 min, 99.8% (Max).

Example 12: 2-(4-(1-(Benzo[d][1,3]dioxol-5-yl) ethyl)piperazin-1-yl)-4-isopropylthiazole

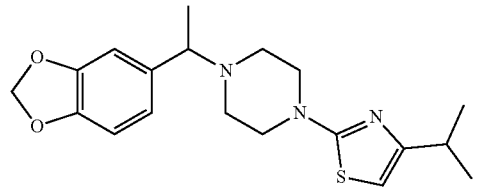 [SMILES: CC(C)c1csc(N2CCN(C(C)c3ccc4c(c3)OCO4)CC2)n1]

Step 1: t-Butyl 4-(4-isopropylthiazol-2-yl)piperazine-1-carboxylate

To a stirred solution of tert-butyl 4-carbamothioylpiperazine-1-carboxylate (synthesized according to Example 5, Step 1, 1.2 g, 4.01 mmol) in THF (10 mL), triethyl amine (0.5 mL, 5.3 mmol) and 1-bromo-3-methylbutan-2-one (1.0 mL, 5.3 mmol) were added at rt. The resulting mixture was stirred for 16 h at 90° C. The completion of the reaction was monitored by TLC. The reaction mixture was quenched with water and extracted with EtOAc. The organic layer was dried over anhydrous Na$_{2}$SO$_{4}$ concentrated under vacuum and the resulting crude product was taken as such for next step. Yield: 80% (0.8 g, pale yellow oil). LCMS: (Method A) 312.0 (M+H), Rt. 3.24 min, 95.2% (Max).

Step 2: 4-Isopropyl-2-(piperazin-1-yl)thiazole hydrochloride

To a stirred solution of tert-butyl 4-(4-isopropylthiazol-2-yl)piperazine-1-carboxylate (0.8 g, 2.4 mmol) in dry dioxane (2 mL), HCl in dioxane (4 N, 10 mL) was added at rt and stirred for 2 h at same temperature. The reaction mixture was concentrated under vacuum and the crude product was washed with diethyl ether to afford the title compound. Yield: 93% (1.2 g, pale yellow oil).

Step 3: 2-(4-(1-(Benzo[d][1,3]dioxol-5-yl)ethyl) piperazin-1-yl)-4-isopropylthiazole The title compound was synthesized by following general procedure D, using 4-isopropyl-2-(piperazin-1-yl)thiazole hydrochloride (0.57 g, 2.3 mmol) and Intermediate 1 (0.5 g, 2.3 mmol). The resulting crude product was purified by MD Autoprep (Method C), affording the title compound (pale yellow oil). $^{1}$H NMR (400 MHz, DMSO-d$_{6}$): δ 6.89 (s, 1H), 6.84 (d, J=8.0 Hz, 1H), 6.76 (d, J=8.0 Hz, 1H), 6.33 (s, 1H), 5.98 (m, 2H), 3.41-3.11 (m, 5H), 2.74-2.72 (m, 1H), 2.46-2.38 (m, 4H), 1.27 (d, J=6.8 Hz, 3H), 1.15 (d, J=6.8 Hz, 3H). LCMS: (Method A) 360.0 (M+H), Rt. 2.71 min, 94.5% (Max). HPLC: (Method A) Rt. 2.69 min, 98.8% (Max).

Example 13: 2-(4-(1-(Benzo[d][1,3]dioxol-5-yl)ethyl)piperazin-1-yl)-4-(trifluoromethyl)thiazole

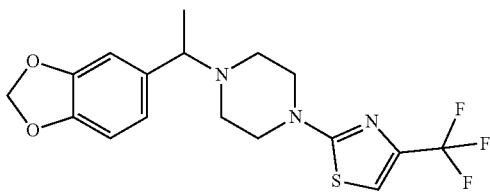 [SMILES: CC(c1ccc2c(c1)OCO2)N1CCN(c2nc(C(F)(F)F)cs2)CC1]

Step 1: tert-Butyl 4-(4-(trifluoromethyl)thiazol-2-yl)piperazine-1-carboxylate To a stirred solution of tert-butyl 4-carbamothioylpiperazine-1-carboxylate (synthesized according to Example 5, Step 1, 2 g, 13.75 mmol) in dioxane (20 mL), triethyl amine (1.7 mL, 12.24 mmol) and 1-bromo-3,3,3-trifluoro acetone (3.2 g, 16.5 mmol) were added and stirred at 90° C. for 3 h. The completion of the reaction was monitored by TLC. The reaction mixture was quenched with water (10 mL) and extracted with ethyl acetate (2×25 mL). The organic layer was separated, dried over anhydrous $Na_2SO_4$, concentrated under vacuum and was used as such for next step. Yield: 75% (1.0 g, white solid). $^1$H NMR (300 MHz, DMSO-$d_6$): δ 7.57 (s, 1H), 3.42 (m, 8H), 1.40 (s, 9H). LCMS: (Method A) 338.0 (M+H), Rt. 5.37 min, 99.0% (Max).

Step 2: 2-(Piperazin-1-yl)-4-(trifluoromethyl)thiazole hydrochloride

To a stirred solution of tert-butyl 4-(4-(trifluoromethyl)thiazol-2-yl)piperazine-1-carboxylate (1.0 g, 2.93 mmol) in dry dioxane, HCl in dioxane (4 N, 15 mL) was added and the reaction mixture was stirred at rt for 1 h. The reaction mixture was concentrated under vacuum and the resulting crude product was triturated in diethyl ether, filtrated and dried under vacuum to afford the title compound. Yield: 99% (700 mg, white solid). $^1$H NMR (400 MHz, DMSO-$d_6$): δ 9.22 (br. s, 2H), 7.66 (s, 1H), 3.68-3.64 (m, 4H), 3.21 (m, 4H). LCMS: (Method A) 238.0 (M+H), Rt. 2.33 min, 99.7% (Max).

Step 3: 2-(4-(1-(Benzo[d][1,3]dioxol-5-yl)ethyl)piperazin-1-yl)-4-(trifluoromethyl)thiazole To a stirred solution of 2-(piperazin-1-yl)-4-(trifluoromethyl)thiazole hydrochloride (0.26 g, 1.07 mmol) in dry DMF (3 mL), Intermediate 1 (0.19 g, 1.07 mmol) and triethyl amine (0.272 g, 2.69 mmol) were added and the reaction mixture was stirred at 80° C. for 16 h. The reaction mixture was concentrated, the crude product was diluted with ethyl acetate (10 mL) and the organic layer was washed with brine (10 mL). The organic layer was separated, dried over anhydrous $Na_2SO_4$ and concentrated to afford the title compound (colorless oil). $^1$H NMR (400 MHz, DMSO-$d_6$): δ 6.96 (s, 1H), 6.88 (s, 1H), 6.76-7.75 (m, 2H), 5.91 (s, 2H), 3.55-3.45 (m, 4H), 3.38 (q, J=6.4 Hz, 1H), 2.62-2.49 (m, 4H), 2.56-2.51 (m, 4H), 1.36 (d, J=6.4 Hz, 3H). LCMS: (Method A) 386.0 (M+H), Rt. 3.55 min, 97.4% (Max). HPLC: (Method A) Rt. 3.54 min, 98.7% (Max).

Example 14: 1-(1-(Benzo[d][1,3]dioxol-5-yl)ethyl)-4-(5-methylpyridin-2-yl)piperazine

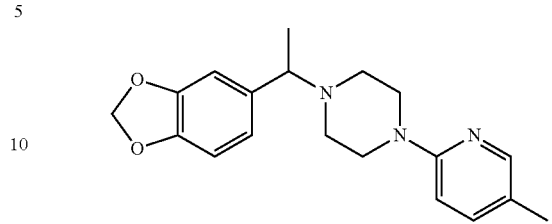

The title compound was synthesized according the general procedure D, using Intermediate 2 and 2-fluoro-5-methyl pyridine. The crude product was purified by flash chromatography to afford the title compound (off white solid). $^1$H NMR (400 MHz, DMSO-$d_6$): δ 7.92 (s, 1H), 7.36-7.33 (m, 1H), 6.89 (s, 1H), 6.84 (d, J=8.0 Hz, 1H), 6.76 (d, J=7.6 Hz, 1H), 6.70 (d, J=8.4 Hz, 1H), 5.99 (m, 2H), 3.37-3.35 (m, 5H), 2.47-2.44 (m, 2H), 2.38-2.36 (m, 2H), 2.12 (s, 3H), 1.28 (d, J=6.8 Hz, 3H). LCMS: (Method A) 326.2 (M+H), Rt. 1.96 min, 97.6% (Max). HPLC: (Method A) Rt. 1.96 min, 98.1% (Max).

Example 15: (R)-2-(4-(1-(benzo[d][1,3]dioxol-5-yl)ethyl)piperazin-1-yl)-4-methylthiazole or (S)-2-(4-(1-(benzo[d][1,3]dioxol-5-yl)ethyl)piperazin-1-yl)-4-methylthiazole

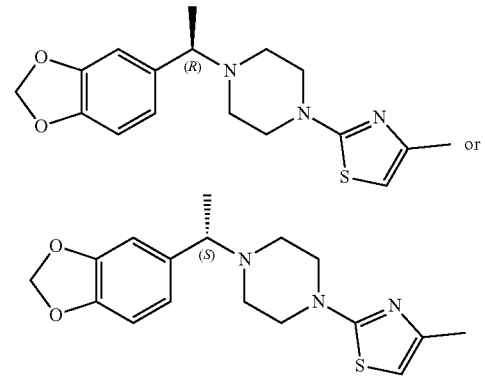

The two enantiomers of Example A were separated by chiral preparative HPLC (Method PE). The first eluting compound has Rt. 5.76 min (Method C) (colorless oil). $^1$H NMR (400 MHz, DMSO-$d_6$): δ 6.89 (s, 1H), 6.84 (d, J=8.0 Hz, 1H), 6.76 (d, J=8.0 Hz, 1H), 6.35 (s, 1H), 5.99-5.98 (m, 2H), 3.40-3.36 (m, 1H), 3.32-3.29 (m, 4H), 2.47-2.44 (m, 2H), 2.41-2.37 (m, 2H), 2.11 (s, 3H), 1.26 (d, J=6.4 Hz, 3H). LCMS: (Method A) 332.0 (M+H), Rt. 2.06 min, 96.3% (Max). HPLC: (Method A) Rt 2.05 min, 99.5% (Max), 99.4% (254 nm). HPLC chiral purity: (Method C) Rt. 5.76 min, 100% (Max). Example 15 is the second eluting compound with Rt. 7.44 min (Method C) (colorless oil). $^1$H NMR (400 MHz, DMSO-$d_6$): δ 6.89 (s, 1H), 6.84 (d, J=8.0 Hz, 1H), 6.76 (d, J=8.0 Hz, 1H), 6.35 (s, 1H), 5.99 (s, 2H), 3.42-3.37 (m, 1H), 3.32-3.30 (m, 4H), 2.47-2.44 (m, 2H), 2.40-2.36 (m, 2H), 2.11 (s, 3H), 1.26 (d, J=6.8 Hz, 3H). LCMS: (Method A) 332.0 (M+H), Rt. 2.04 min, 99.2%

(Max). HPLC: (Method A) Rt. 2.05 min, 99.2% (Max). HPLC chiral purity: (Method C) Rt. 7.44 min, 99.83% (Max).

Example 16: 2-(4-(1-(benzo[d][1,3]dioxol-5-yl)ethyl)piperazin-1-yl)-4-(tert-butyl)thiazole

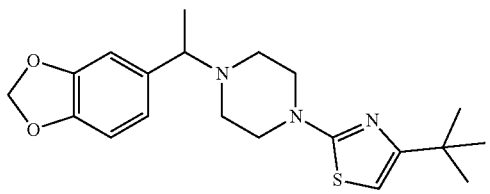 [SMILES: CC(c1ccc2c(c1)OCO2)N1CCN(c2nc(C(C)(C)C)cs2)CC1]

Step 1: tert-butyl 4-(4-(tert-butyl)thiazol-2-yl)piperazine-1-carboxylate

To a stirred solution of tert-butyl 4-carbamothioylpiperazine-1-carboxylate (synthesized according to Example 5, Step 1, 1.3 g, 5.3 mmol) in dioxane (10 mL), TEA (1 mL, 7 mmol) and 1-bromo-3,3-dimethylbutan-2-one (0.94 mL, 6.8 mmol) were added at rt and stirred for 16 h at 90° C. The completion of the reaction was monitored by TLC. The reaction mixture was quenched with water and extracted with EtOAc. The organic layer was dried over anhydrous Na$_2$SO$_4$ concentrated under vacuum and the resulting crude product was taken as such for next step without further purification. Yield: 88% (1.5 g, black liquid). LCMS: (Method A) 326.2 (M+H), Rt. 3.75 min, 60.4% (Max).

Step 2: 4-(tert-Butyl)-2-(piperazin-1-yl)thiazole hydrochloride

To a stirred solution of tert-butyl 4-(4-(tert-butyl)thiazol-2-yl)piperazine-1-carboxylate (1.5 g, 4.61 mmol) in dry dioxane (2 mL), HCl in dioxane (4 N, 10 mL) was added and the reaction mixture was stirred at rt for 2 h. The reaction mixture was concentrated under vacuum and the resulting crude product was triturated in diethyl ether (100 mL), filtered and dried under vacuum to afford the title compound. Yield: 63% (1.02 g, black solid).

Step 3: 2-(4-(1-(benzo[d][1,3]dioxol-5-yl)ethyl)piperazin-1-yl)-4-(tert-butyl)thiazole The title compound was synthesized following the general procedure D, using 4-(tert-butyl)-2-(piperazin-1-yl)thiazole hydrochloride (0.732 g, 2.8 mmol) and Intermediate 1 (0.28 g, 2.8 mmol) and the crude product was purified by flash chromatography (pale yellow oil). $^1$H NMR (400 MHz, DMSO-d$_6$): δ 6.89 (s, 1H), 6.85 (d, J=7.6 Hz), 6.76 (d, J=7.6 Hz, 1H), 6.33 (s, 1H), 5.99 (m, 2H), 3.40 (m, 1H), 3.37-3.30 (m, 4H), 2.49-2.46 (m, 2H), 2.43-2.40 (m, 2H), 1.28 (d, J=6.8 Hz, 3H), 1.19 (s, 9H). LCMS: (Method A) 374.0 (M+H), Rt. 3.40 min, 98.6% (Max). HPLC: (Method A) Rt. 3.39 min, 99.7% (Max).

Example 17: Ethyl 2-(4-(1-(benzo[d][1,3]dioxol-5-yl)ethyl)piperazin-1-yl)thiazole-4-carboxylate

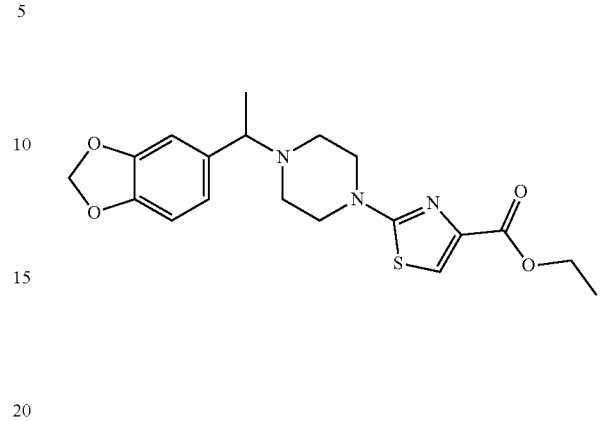

Step 1: Ethyl 2-(4-(tert-butoxycarbonyl)piperazin-1-yl)thiazole-4-carboxylate To a stirred solution of tert-butyl 4-carbamothioylpiperazine-1-carboxylate (synthesized according to Example 5, Step 1, 3.0 g, 12 mmol) in dioxane (10 mL), TEA (2.6 mL, 16 mmol) and 3-bromo-ethyl pyruvate (2.1 mL, 16 mmol) were added at rt and the mixture was stirred at 90° C. for 16 h. The completion of the reaction was monitored by TLC. The reaction mixture was quenched with water and extracted with EtOAc. The organic layer was dried over anhydrous Na$_2$SO$_4$ concentrated under vacuum and the resulting crude product was taken as such for next step. Yield: 95% (4 g, black solid).

Step 2: Ethyl 2-(piperazin-1-yl)thiazole-4-carboxylate hydrochloride

To a stirred solution of ethyl 2-(4-(tert-butoxycarbonyl)piperazin-1-yl)thiazole-4-carboxylate (4.0 g, 11.73 mmol) in dry dioxane (2 mL), HCl in dioxane (4 N, 10 mL) was added at rt and stirred for 2 h. The reaction mixture was concentrated under vacuum and the resulting crude product was triturated in diethyl ether (25 mL), filtered and dried under vacuum to afford the title compound. Yield: 90% (3.2 g, black solid). LCMS: (Method A) 242.0 (M+H), Rt. 1.88 min, 90.7% (Max).

Step 3: Ethyl 2-(4-(1-(benzo[d][1,3]dioxol-5-yl)ethyl)piperazin-1-yl)thiazole-4-carboxylate The title compound was synthesized following the general procedure D, using ethyl 2-(piperazin-1-yl)thiazole-4-carboxylate hydrochloride and Intermediate 1 and the crude product was purified by flash chromatography followed by MD Autoprep (Method B) (yellow solid). $^1$HNMR (400 MHz, DMSO-d$_6$): δ 7.66 (d, J=2.0 Hz, 1H), 6.88 (s, 1H), 6.84 (d, J=8.0 Hz, 1H), 6.75 (d, J=8.0 Hz, 1H), 5.98 (m, 2H), 4.21-4.20 (m, 2H), 3.38-3.32 (m, 5H), 2.49-2.40 (m, 4H), 1.26-1.23 (m, 6H). LCMS: (Method A) 390.0 (M+H), Rt. 2.99 min, 97.8% (Max). HPLC: (Method A) Rt. 2.95 min, 98.9% (Max).

Example 18: 2-(4-(1-(Benzo[d][1,3]dioxol-5-yl)ethyl)piperazin-1-yl)thiazole-4-carboxylic acid

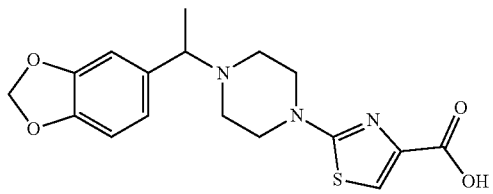 [SMILES: CC(c1ccc2c(c1)OCO2)N1CCN(c2nc(C(=O)O)cs2)CC1]

To a stirred solution of Example 17 (0.2 g) in dry THF (10 mL), 5% NaOH in water (5 mL) was added slowly at rt and the mixture was stirred for 16 h at same temperature. It was then concentrated under vacuum, neutralised to pH=6 with 2N HCl and extracted with DCM (20 mL). The organic layer was washed with brine (10 mL), water (10 mL), dried over anhydrous $Na_2SO_4$ and concentrated under reduced pressure. The crude product was purified by flash chromatography followed by MD Autoprep (Method B) to afford the title compound (off white solid). $^1$H NMR (400 MHz, DMSO-$d_6$): δ 7.58 (s, 1H), 6.90 (s, 1H), 6.88 (d, J=8.0 Hz, 1H). 6.76 (d, J=8.0 Hz, 1H), 6.00-5.99 (m, 2H), 3.35-3.36 (m, 5H), 2.51-2.49 (m, 2H), 2.44-2.40 (m, 2H), 1.29-1.27 (d, J=6.8 Hz, 3H). LCMS: (Method A) 362.0 (M+H), Rt. 2.29 min, 95.5% (Max). HPLC: (Method A) Rt. 2.30 min, 95.9% (Max).

Example 19: 2-(4-(1-(Benzo[d][1,3]dioxol-5-yl)ethyl)piperazin-1-yl)-4-ethylthiazole

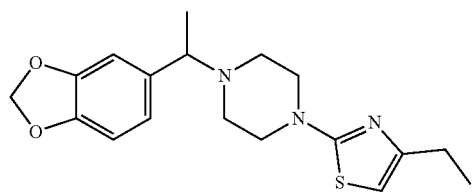 [SMILES: CCc1csc(N2CCN(C(C)c3ccc4c(c3)OCO4)CC2)n1]

Step 1: t-Butyl 4-(4-ethylthiazol-2-yl)piperazine-1-carboxylate

To a stirred solution of tert-butyl 4-carbamothioylpiperazine-1-carboxylate (synthesized according to Example 5, Step 1, 2.0 g, 8.16 mmol) in dioxane (20 mL), TEA (1.7 mL, 10.6 mmol) and 1-bromobutan-2-one (1.2 mL, 10 mmol) were added and stirred at 80° C. for 16 h. The completion of the reaction was monitored by TLC. The reaction mixture was quenched with water (10 mL) and extracted with EtOAc (2×25 mL). The organic layer was separated, dried over anhydrous $Na_2SO_4$, concentrated under vacuum. The resulting product was taken as such for next step. Yield: 86% (2.1 g, pale yellow solid). LCMS: (Method A) 298.0 (M+H), Rt. 2.94 min, 93.1% (Max).

Step 2: 4-Ethyl-2-(piperazin-1-yl)thiazole hydrochloride

To a stirred solution of tert-butyl 4-(4-ethylthiazol-2-yl)piperazine-1-carboxylate (1.9 g, 6.3 mmol) in dry dioxane (2 mL), HCl in dioxane (4 N, 10 mL) was added and the reaction mixture was stirred at rt for 2 h. The reaction mixture was concentrated under vacuum and the crude product was triturated in diethyl ether (15 mL), filtered and dried under vacuum to afford the title compound. Yield: 53% (0.8 g, black solid).

Step 3: 2-(4-(1-(Benzo[d][1,3]dioxol-5-yl)ethyl)piperazin-1-yl)-4-ethylthiazole The title compound was synthesized following the general procedure D, using 4-ethyl-2-(piperazin-1-yl)thiazole hydrochloride (1.1 g, 4.7 mmol) and Intermediate 1 (0.9 g, 4.7 mmol). The crude product was purified by flash chromatography (pale yellow oil). $^1$H NMR (400 MHz, DMSO-$d_6$): δ 6.89 (d, J=1.6 Hz, 1H), 6.84 (d, J=7.6 Hz, 1H), 6.75 (d, J=7.5 Hz, 1H), 6.35 (s, 1H), 5.98 (m, 2H), 3.40-3.37 (m, 1H), 3.37-3.30 (m, 4H), 2.51-2.38 (m, 6H), 1.28 (d, J=6.8 Hz, 3H), 1.23 (t, J=7.6 Hz, 3H). LCMS: (Method A) 346.0 (M+H), Rt. 2.31 min, 98.0% (Max). HPLC: (Method A) Rt. 2.34 min, 99.4% (Max).

Example 20: 1-(1-(Benzo[d][1,3]dioxol-5-yl)ethyl)-4-(6-chloropyridin-3-yl)piperazine

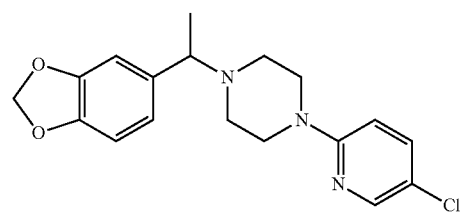 [SMILES: CC(c1ccc2c(c1)OCO2)N1CCN(c2ccc(Cl)cn2)CC1]

The title compound was synthesized following the general procedure D, using Intermediate 1 and 1-(5-chloro-2-pyridyl) piperazine. The crude product was purified by flash chromatography (off white solid). $^1$H NMR (400 MHz, DMSO-$d_6$): δ 8.07 (d, J=2.4 Hz, 1H), 7.57-7.54 (m, 1H), 6.88-6.74 (m, 4H), 5.98 (m, 2H), 3.42 (q, J=6.4 Hz, 1H), 2.46-2.43 (m, 2H), 2.37-2.34 (m, 2H), 1.28 (d, J=6.4 Hz, 3H). LCMS: (Method A) 346.0 (M+H), Rt. 3.27 min, 98.7% (Max). HPLC: (Method A) Rt 3.25 min, 99.2% (Max).

Example 21: 1-(1-(Benzo[d][1,3]dioxol-5-yl)ethyl)-4-(6-methylpyridin-2-yl)piperazine

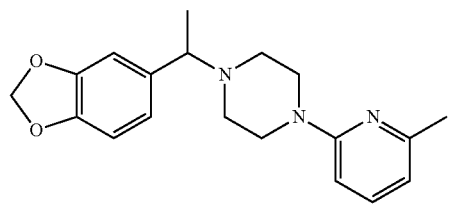 [SMILES: Cc1cccc(N2CCN(C(C)c3ccc4c(c3)OCO4)CC2)n1]

To a stirred solution of Intermediate 2 (0.12 g, 0.5 mmol) in dry DMF (2 mL), 2-fluoro-6-methyl pyridine (0.11 g, 0.99 mmol) and DIPEA (0.26 g, 2.4 mmol) were added at rt and the reaction mixture was stirred at 120° C. for 16 h. The reaction mixture was cooled to rt and concentrated under vacuum. The resulting crude product was purified by flash chromatography followed by preparative HPLC (Method PA) to afford the title compound (brown liquid). $^1$H NMR (400 MHz, DMSO-d$_6$): δ 7.40-7.36 (m, 1H), 6.90 (s, 1H), 6.85 (d, J=7.6 Hz, 1H), 6.77 (d, J=7.6 Hz, 1H), 6.55-6.46 (m, 2H), 5.98 (s, 2H), 3.410-3.415 (m, 5H), 2.38-2.37 (m, 4H), 2.28-2.30 (m, 3H), 1.29 (d, J=7.2 Hz, 3H). LCMS: (Method A) 326.2 (M+H), Rt. 1.89 min, 94.9% (Max). HPLC: (Method A) Rt 1.91 min, 96.6% (Max).

Example 22: 2-(4-(1-(Benzo[d][1,3]dioxol-5-yl)ethyl)piperazin-1-yl)pyrimidin-4-amine

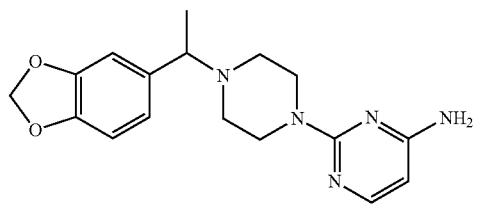 [SMILES: CC(c1ccc2c(c1)OCO2)N1CCN(c2nccc(N)n2)CC1]

The title compound was synthesized by following procedure D, using Intermediate 2 (0.228 g, 0.85 mmol) and 4-amino-2-chloro pyrimidine (0.1 g, 0.77 mmol). The crude product was purified by flash chromatography followed by MD Autoprep (Method B) (white solid). $^1$H NMR (400 MHz, DMSO-d$_6$): δ 7.70 (d, J=5.2 Hz, 1H), 6.88 (s, 1H), 6.83 (d, J=8.0 Hz, 1H), 6.75 (d, J=7.6 Hz, 1H), 6.36 (s, 2H), 5.98 (m, 2H), 5.69 (d, J=5.6 Hz, 1H), 3.6-3.58 (m, 4H), 3.33-3.32 (m, 1H), 2.38-2.34 (m, 2H), 2.31-2.27 (m, 2H), 1.27 (d, J=6.8 Hz, 3H). LCMS: (Method A) 328.0 (M+H), Rt. 1.85 min, 97.2% (Max). HPLC: (Method A) Rt. 1.84 min, 97.1% (Max).

Example 23: N-(2-(4-(1-(Benzo[d][1,3]dioxol-5-yl)ethyl)piperazin-1-yl)pyrimidin-4-yl)acetamide

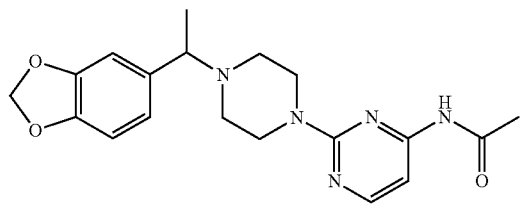 [SMILES: CC(=O)Nc1ccnc(N2CCN(C(C)c3ccc4c(c3)OCO4)CC2)n1]

Step 1: N-(2-Chloropyrimidin-4-yl)acetamide

To a stirred solution of 4-amino-2-chloro pyrimidine (0.6 g, 4.65 mmol) in DCM (5 mL), pyridine (1.8 mL) and acetic anhydride (0.71 g, 6.9 mmol) were added at 0° C. and stirred at 75° C. for 6 h. The reaction mixture was concentrated under vacuum and the resulting crude product was dissolved in EtOAc (15 mL). The organic layer was washed with water (10 mL), brine (10 mL) and dried over anhydrous Na$_2$SO$_4$. After concentration under vacuum, the crude product was taken as such for next step. Yield: 56.9% (0.45 g, pale brown solid). LCMS: (Method A) 172.0 (M+H), Rt. 1.58 min, 80.2% (Max).

Step 2: N-(2-(4-(1-(Benzo[d][1,3]dioxol-5-yl)ethyl)piperazin-1-yl)pyrimidin-4-yl)acetamide The title compound was synthesized following procedure D and using Intermediate 2 (0.25 g, 0.93 mmol) and N-(2-chloropyrimidin-4-yl)acetamide (0.19 g, 1.12 mmol). The crude product was purified by flash chromatography followed by MD Autoprep (Method B) (white solid). $^1$H NMR (400 MHz, DMSO-d$_6$): δ 10.30 (s, 1H), 8.18 (d, J=5.6 Hz, 1H), 7.21 (d, J=5.6 Hz, 1H), 6.89 (d, J=1.6 Hz, 1H), 6.84 (d, J=7.6 Hz, 1H), 6.75 (dd, J=1.6, 8 Hz, 1H), 5.98 (m, 2H), 3.68-3.66 (m, 4H), 3.37-3.36 (m, 1H), 2.42-2.38 (m, 2H), 2.35-2.31 (m, 2H), 2.07 (s, 3H), 1.28 (d, J=6.8 Hz, 3H). LCMS: (Method A) 370.0 (M+H), Rt. 2.26 min, 97.5% (Max). HPLC: (Method A) Rt. 2.21 min, 98.9% (Max).

Example 24: 4-(4-(1-(Benzo[d][1,3]dioxol-5-yl)ethyl)piperazin-1-yl)-6-chloropyrimidine

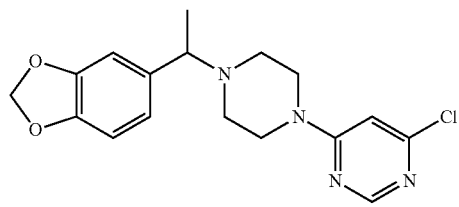 [SMILES: CC(c1ccc2c(c1)OCO2)N1CCN(c2cc(Cl)ncn2)CC1]

To a stirred solution of Intermediate 2 (0.2 g, 0.74 mmol) in DMF (5 mL), TEA (0.5 mL, 3.70 mmol) and 4,6-dichloro pyrimidine (0.11 g, 0.74 mmol) were added and the resulting mixture was stirred at 120° C. for 2 h. It was concentrated under vacuum and the resulting crude product was dissolved in DCM and washed with water, dried over anhydrous Na$_2$SO$_4$ and concentrated under vacuum. The crude product was purified by flash chromatography to afford the title product (brown oil). $^1$H NMR (400 MHz, DMSO-d$_6$): δ 8.30 (s, 1H), 6.91 (s, 1H), 6.89 (s, 1H), 6.84 (d, J=8.0 Hz, 1H), 6.75 (d, J=8.0 Hz, 1H), 5.98 (m, 2H), 3.55-3.52 (m, 4H), 3.39-3.37 (m, 1H), 2.43-2.39 (m, 2H), 2.36-2.32 (m, 2H), 1.27 (d, J=6.8 Hz, 3H). LCMS: (Method A) 347.0 (M+H), Rt. 2.55 min, 98.7% (Max). HPLC: (Method A) Rt. 2.57 min, 99.7% (Max).

Example 26: (R)-2-(4-(1-(Benzo[d][1,3]dioxol-5-yl)ethyl)piperazin-1-yl)pyrimidine or (S)-2-(4-(1-(Benzo[d][1,3]dioxol-5-yl)ethyl)piperazin-1-yl)pyrimidine

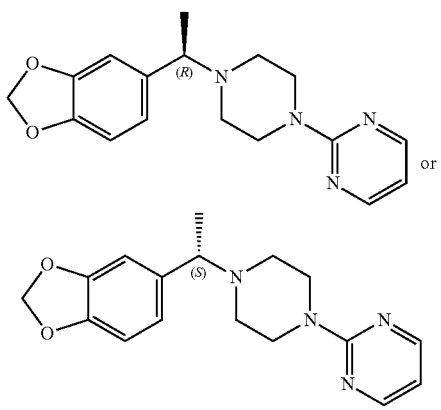

The two enantiomers of Example 11 were separated by chiral preparative HPLC (Method PF). The first eluting compound has Rt. 8.50 min (colorless oil). ¹H NMR (400 MHz, DMSO-d₆): δ 8.32 (d, J=4.8 Hz, 2H), 6.88 (s, 1H), 6.83 (d, J=8.0 Hz, 1H), 6.74 (d, J=8.0 Hz, 1H), 6.58 (t, J=4.4 Hz, 1H), 5.97 (m, 2H), 3.68-3.67 (m, 4H), 3.37-3.35 (m, 1H), 2.49-2.38 (m, 2H), 2.35-2.30 (m, 2H), 1.27 (d, J=6.4 Hz, 3H). LCMS: (Method A) 313.0 (M+H), Rt. 2.45 min, 99.5% (Max). HPLC: (Method A) Rt. 2.47 min, 99.5% (Max). HPLC chiral purity: (Method D) Rt. 8.50 min, 100% (Max). Example 26 is the second eluting compound, with Rt. 13.33 min (colorless oil). ¹H NMR (400 MHz, DMSO-d₆): δ 8.32 (d, J=4.8 Hz, 2H), 6.88 (s, 1H), 6.83 (d, J=8.0 Hz, 1H), 6.74 (d, J=8.0 Hz, 1H), 6.58 (t, J=4.4 Hz, 1H), 5.97 (m, 2H), 3.68-3.67 (m, 4H), 3.36-3.33 (m, 1H), 2.49-2.38 (m, 2H), 2.35-2.30 (m, 2H), 1.27 (d, J=6.4 Hz, 3H). LCMS: (Method A) 313.0 (M+H), Rt. 2.44 min, 99.5% (Max). HPLC: (Method A) Rt. 2.47 min, 99.8% (Max). HPLC chiral purity: (Method D) Rt. 13.33 min, 100% (Max).

Example 27: Ethyl 2-(4-(1-(benzo[d][1,3]dioxol-5-yl)ethyl)piperazin-1-yl)thiazole-5-carboxylate

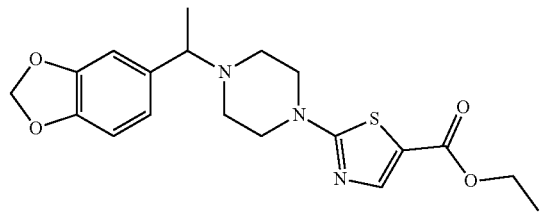 [SMILES: CCOC(=O)c1cnc(N2CCN(C(C)c3ccc4c(c3)OCO4)CC2)s1]

Step 1: Ethyl 2-bromothiazole-5-carboxylate

To a stirred solution of ethyl-2-amino thiazole-5-carboxylate (10.0 g, 46.45 mmol, Combi block) in 48% HBr (75 mL), sodium nitrite (4.80 g, 69.68 mmol) in water (50 mL) was added dropwise at 0° C. and the reaction mixture was stirred at 0° C. for 15 min. Copper (I)bromide (6.66 g, 46.45 mmol) in 48% HBr (75 mL) was added dropwise at 0° C. and the reaction mixture was stirred at rt for 4 h. The reaction mixture was diluted with DCM (200 mL) and washed with water (50 mL), brine (50 mL), dried over Na₂SO₄ and concentrated under reduced pressure. The crude product was purified by flash chromatography (100% CHCl₃) to afford the title compound. Yield: 50.18% (5.5 g, yellow liquid). ¹H NMR (400 MHz, DMSO-d₆): δ 8.16 (s, 1H), 4.38 (q, J=7.16 Hz, 2H), 1.40 (t, J=7.12 Hz, 3H). LCMS: (Method A) 235.9 (M+H), Rt. 3.85 min, 98.6% (Max).

Step 2: Ethyl 2-(4-(1-(benzo[d][1,3]dioxol-5-yl)ethyl)piperazin-1-yl)thiazole-5-carboxylate To a stirred solution of Intermediate 2 (1.5 g, 6.40 mmol) in dry DMF (15 mL), ethyl 2-bromothiazole-5-carboxylate (1.96 g, 8.32 mmol) and TEA (3.5 mL, 25.6 mmol) were added at rt and the reaction mixture was stirred at 120° C. for overnight. The reaction mixture was cooled to rt and was diluted with EtOAc. The organic layer was washed with brine (10 mL), water (10 mL), dried over anhydrous Na₂SO₄ and concentrated under vacuum. The crude product was purified by column chromatography to afford the title compound (off white solid). ¹H NMR (400 MHz, DMSO-d₆): δ 7.83 (s, 1H), 6.89 (s, 1H), 6.89 (d, J=8.0 Hz, 1H). 6.76 (d, J=8.0 Hz, 1H), 5.99 (s, 2H), 4.19 (q, J=6.8 Hz, 2H), 3.50-3.42 (m, 5H), 2.51-2.46 (m, 2H), 2.44-2.33 (m, 2H), 1.30-1.22 (m, 6H). LCMS: (Method A) 247.2 (M+H), Rt. 3.17 min, 78.6% (Max).

Example 28: (2-(4-(1-(Benzo[d][1,3]dioxol-5-yl)ethyl)piperazin-1-yl)thiazol-5-yl)methanol

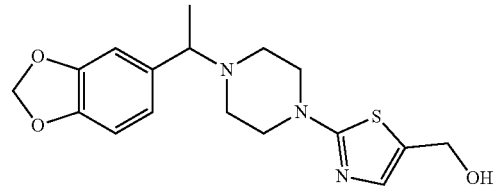 [SMILES: CC(c1ccc2c(c1)OCO2)N1CCN(c2ncc(CO)s2)CC1]

The title compound was synthesized following the general procedure A starting from Example 27. The crude product was purified by flash chromatography followed by MD Autoprep (Method B) (off white solid). ¹H NMR (400 MHz, DMSO-d₆): δ 6.96 (s, 1H), 6.89 (s, 1H), 6.84 (d, J=7.6 Hz, 1H), 6.75 (d, J=7.6 Hz, 1H), 5.98 (m, 2H), 5.21 (t, J=5.6 Hz, 1H), 4.44 (d, J=5.6 Hz, 2H), 3.40-3.37 (m, 1H), 3.34-3.31 (m, 4H), 2.46-2.42 (m, 2H), 2.41-2.38 (m, 2H), 1.28 (d, J=6.4 Hz, 3H). LCMS: (Method A) 348.0 (M+H), Rt. 1.91 min, 96.3% (Max). HPLC: (Method A) Rt. 1.89 min, 95.1% (Max).

Example 29: (2-(4-(1-(Benzo[d][1,3]dioxol-5-yl)ethyl)piperazin-1-yl)thiazol-4-yl)methanol

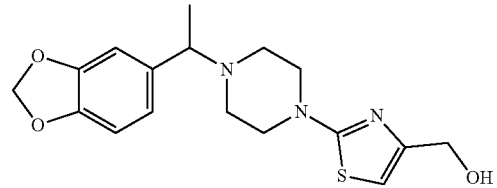 [SMILES: CC(c1ccc2c(c1)OCO2)N1CCN(c2nc(CO)cs2)CC1]

The title compound was synthesized following general procedure A, starting with Example 17 (0.5 g) and the crude product was purified by flash chromatography (pale yellow oil). ¹H NMR (400 MHz, DMSO-d₆): δ 6.89 (s, 1H), 6.85 (d, J=8.0 Hz, 1H), 6.75 (dd, J=1.6, 8.0 Hz, 1H), 6.52 (s, 1H), 5.99 (m, 2H), 5.11-5.09 (t, J=8.0 Hz, 1H), 4.31 (d, J=8.0 Hz, 2H), 3.40-3.34 (m, 5H). 2.51-2.49 (m, 2H), 2.42-2.32 (m, 2H), 1.28 (d, J=6.8 Hz, 3H). LCMS: (Method A) 348.0 (M+H), Rt. 1.98 min, 94.8% (Max). HPLC: (Method A) Rt. 1.99 min, 96.0% (Max).

Example 30: 2-(4-(1-(Benzo[d][1,3]dioxol-5-yl)ethyl)piperazin-1-yl)-N-methylthiazole-4-carboxamide

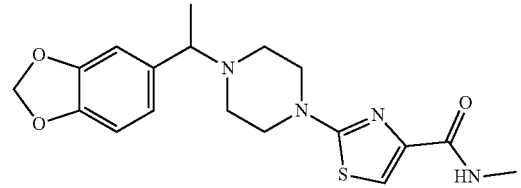 [SMILES: CNC(=O)c1csc(N2CCN(C(C)c3ccc4c(c3)OCO4)CC2)n1]

To a stirred solution of Example 18 (0.3 g, 0.5 mmol) in DCM (10 mL), DIPEA (0.6 mL, 2 mmol) and HATU (0.56 g, 1.48 mmol) were added slowly at 0° C. The reaction mixture was stirred at 0° C. for 20 min. Methyl amine in THF (0.6 mL, 1.48 mmol) was added and the reaction mixture was stirred overnight at room temperature. The reaction mixture was diluted with EtOAc (10 mL) and washed with water (10 mL) and brine (10 mL). The organic layer was dried over anhydrous $Na_2SO_4$ concentrated under vacuum. The crude product was purified by flash chromatography followed by MD Autoprep (Method B) to afford the title compound (off white solid). $^1$H NMR (400 MHz, DMSO-$d_6$): δ 7.96 (d, J=4.8 Hz, 1H), 7.33 (s, 1H), 6.89 (s, 1H). 6.85 (d, J=8.0 Hz, 1H), 6.75 (dd, J=1.6, 8.0 Hz, 1H), 5.98 (m, 2H), 3.43-3.38 (m, 5H), 2.72 (d, J=4.8 Hz, 3H), 2.41-2.39 (m, 4H), 1.27 (d, J=6.4, 3H). LCMS: (Method A) 375.0 (M+H), Rt. 2.34 min, 98.2% (Max). HPLC: (Method A) Rt. 2.32 min, 99.0% (Max).

Example 32: 2-(4-(1-(Benzo[d][1,3]dioxol-5-yl)ethyl)piperazin-1-yl)-N-isopropylthiazole-4-carboxamide

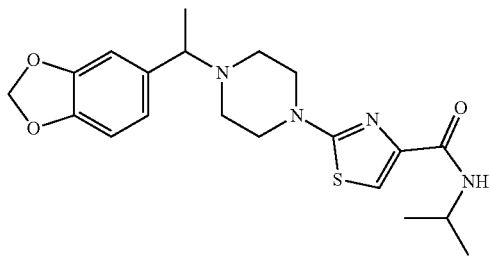 [SMILES: CC(C)NC(=O)c1csc(N2CCN(C(C)c3ccc4c(c3)OCO4)CC2)n1]

The title compound was synthesized by following the same procedure as described for Example 30, using Example 18 (0.3 g, 0.9 mmol) and isopropyl amine (0.09 mL, 1.08 mmol) as starting material (off white solid). $^1$H NMR (400 MHz, DMSO-$d_6$): δ 7.62 (d, J=8.4 Hz, 1H), 7.35 (s, 1H), 6.90 (s, 1H), 6.85 (d, J=8.0 Hz, 1H), 6.77 (d, J=8.0 Hz, 1H), 5.99 (m, 2H), 4.04-3.99 (m, 1H), 3.43-3.34 (m, 5H), 2.50-2.42 (m, 4H), 1.29 (d, J=6.8 Hz, 3H), 1.14-1.07 (m, 6H). LCMS: (Method A) 403.0 (M+H), Rt. 2.90 min, 95.5% (Max). HPLC: (Method A) Rt. 2.91 min, 96.5% (Max).

Example 33: 2-(4-(1-(Benzo[d][1,3]dioxol-5-yl)ethyl)piperazin-1-yl)-N-cyclohexylthiazole-4-carboxamide

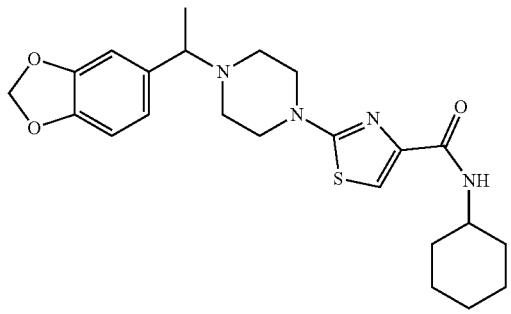 [SMILES: CC(c1ccc2c(c1)OCO2)N1CCN(c2nc(C(=O)NC3CCCCC3)cs2)CC1]

The title compound was synthesized by following the same procedure as described for Example 30, using Example 18 (0.3 g, 0.9 mmol) and cyclohexyl amine (0.12 mL, 1.08 mmol) as starting material (off white solid). $^1$H NMR (400 MHz, DMSO-$d_6$): δ 7.60 (d, J=8.4 Hz, 1H), 7.35 (s, 1H), 6.90 (s, 1H), 6.85 (d, J=7.6 Hz, 1H), 6.77 (d, J=7.6 Hz, 1H), 5.99 (s, 2H), 3.68-3.67 (m, 1H), 3.42 (br. s, 4H), 2.50-2.42 (m, 4H), 1.74-1.70 (m, 4H), 1.59-1.56 (m, 1H), 1.36-1.23 (m, 8H), 1.13-1.09 (m, 1H). LCMS: (Method A) 443.0 (M+H), Rt. 3.57 min, 97.9% (Max). HPLC: (Method A) Rt. 3.62 min, 99.3% (Max).

Example 34: (R)-2-(4-(1-(2,3-Dihydrobenzo[b][1,4]dioxin-6-yl)ethyl)piperazin-1-yl)pyrimidine or (S)-2-(4-(1-(2,3-Dihydrobenzo[b][1,4]dioxin-6-yl)ethyl)piperazin-1-yl)pyrimidine

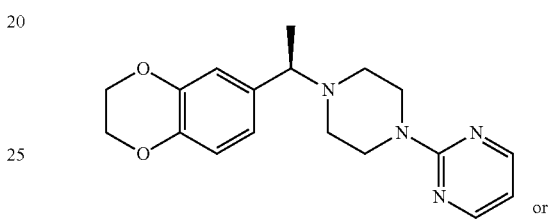

or

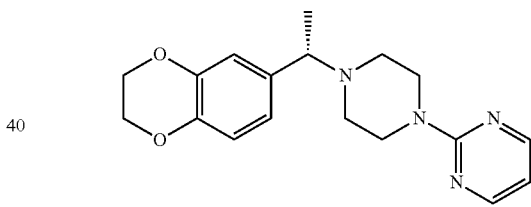

The title compound was synthesized by following procedure D, using Intermediate 3 (2.2 g, 11 mmol) and 1-(2-pyrimidyl) piperazine (1.8 g, 11 mmol). The crude product was purified by flash chromatography followed by preparative chiral HPLC (Method PF) to separate the two enantiomers. The first eluting compound has Rt. 7.90 min (Method D) (off white solid). $^1$H NMR 400 MHz, DMSO-$d_6$): δ 8.32 (d, J=4.4 Hz, 2H), 6.78-6.75 (m, 3H), 6.59 (t, J=9.6 Hz, 1H), 4.21-4.20 (m, 4H), 3.68-3.67 (m, 4H), 3.36-3.26 (m, 1H), 2.49-2.39 (m, 2H), 2.34-2.32 (m, 2H), 1.25 (d, J=6.4 Hz, 3H). LCMS: (Method A) 327.2 (M+H), Rt. 2.51 min, 98.7% (Max). HPLC: (Method A) Rt. 2.54 min, 99.3% (Max). HPLC chiral purity: (Method D) Rt. 7.90 min, 100.0% (Max). Example 34 corresponds to the second eluting compound, with Rt. 13.92 min (Method D) (off white solid). $^1$H NMR (400 MHz, DMSO-$d_6$): δ 8.32 (d, J=4.4 Hz, 2H), 6.80-6.75 (m, 3H), 6.59 (t, J=9.6 Hz, 1H), 4.21-4.20 (m, 4H), 3.69-3.66 (m, 4H), 3.33-3.32 (m, 1H), 2.44-2.38 (m, 2H), 2.36-2.31 (m, 2H), 1.26 (d, J=6.8 Hz, 3H). LCMS: (Method A) 327.0 (M+H), Rt. 2.51 min, 99.1% (Max). HPLC: (Method A) Rt. 2.49 min, 99.2% (Max). HPLC chiral purity: (Method D) Rt. 13.92 min, 99.88% (Max).

Example 35: 2-(4-(1-(Benzo[d][1,3]dioxol-5-yl)ethyl)piperazin-1-yl)thiazole-4-carboxamide

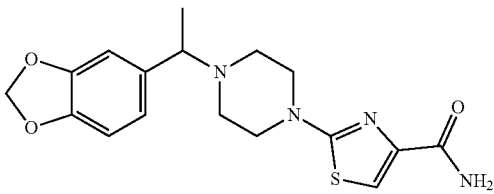 [SMILES: CC(c1ccc2c(c1)OCO2)N1CCN(c2nc(C(N)=O)cs2)CC1]

The title compound was synthesized by following the same procedure as described for Example 30, using Example 18 (0.3 g, 0.9 mmol) and ammonia in THF (4.5 mL, 9 mmol, 2 M in THF) as starting material. The crude mixture was purified by flash chromatography (off white solid). $^1$H NMR (400 MHz, DMSO-$d_6$): δ 7.39 (br s, 2H), 7.37 (s, 1H), 6.90 (s, 1H), 6.85 (d, J=7.6 Hz, 1H), 6.77 (d, J=7.2 Hz, 1H), 5.99 (br s, 2H), 3.41-3.34 (m, 5H), 2.50-2.43 (m, 4H), 1.30 (d, J=6.8 Hz, 3H). LCMS: (Method A) 361.0 (M+H), Rt. 2.19 min, 94.8% (Max). HPLC: (Method A) Rt. 2.17 min, 98.0% (Max).

Example 36: 5-(4-(1-(Benzo[d][1,3]dioxol-5-yl)ethyl)piperazin-1-yl)-2-methylthiazole

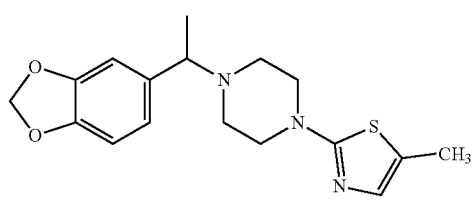 [SMILES: Cc1cnc(N2CCN(C(C)c3ccc4c(c3)OCO4)CC2)s1]

The title compound was synthesized following general procedure D, using 2-bromo-5-methyl thiazole and Intermediate 2. The crude product was purified by flash chromatography (brown solid). $^1$H NMR (DMSO-$d_6$): δ 6.89 (s, 1H), 6.85 (d, J=7.6 Hz, 1H), 6.80 (d, J=7.6 Hz, 1H), 6.76-6.74 (m, 1H), 5.99 (m, 2H), 3.40-3.36 (m, 1H), 3.29-3.26 (m, 4H), 2.46-2.45 (m, 2H), 2.42-2.38 (m, 2H), 2.23 (s, 3H), 1.28-1.27 (m, 3H). LCMS: (Method A) 332.0 (M+H), Rt. 2.13 min, 96.0% (Max). HPLC: (Method A) Rt. 2.11 min, 97.4% (Max).

Example 37: 5-(4-(1-(Benzo[d][1,3]dioxol-5-yl)ethyl)piperazin-1-yl)-2-methylthiazole

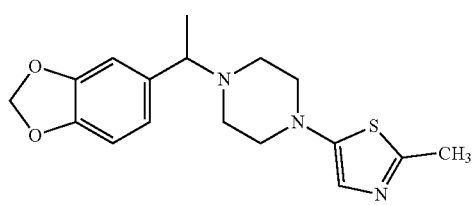 [SMILES: Cc1ncc(N2CCN(C(C)c3ccc4c(c3)OCO4)CC2)s1]

The mixture of 5-bromo-2-methyl thiazole (150 mg, 0.84 mmol), Intermediate 2 (200 mg, 0.84 mmol) and TEA (344 mg, 3.4 mmol) in DMF (4 mL) was heated at 130° C. for overnight. It was concentrated under vacuum and to the resulting crude product was dissolved in EtOAc (10 mL) and washed with water (10 mL). The organic layer was dried over Na$_2$SO$_4$ and concentrated. The crude product was purified by flash column chromatography (brown solid). $^1$H NMR (DMSO-$d_6$): δ 6.90 (s, 1H), 6.85-6.78 (m, 3H), 5.95 (br s, 2H), 3.55-3.51 (m, 1H), 3.12-3.11 (m, 4H), 2.80-2.65 (m, 4H), 2.54 (s, 3H), 1.44 (d, J=5.6 Hz, 3H). LCMS: (Method A) 332.0 (M+H), Rt. 5.71 min, 97.35% (Max). HPLC: (Method B) Rt. 5.64 min, 96.8% (Max).

Example 38: 5-(4-(1-(Benzo[d][1,3]dioxol-5-yl)ethyl)piperazin-1-yl)-2-chloropyrimidine

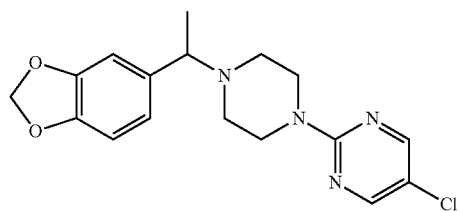

The title compound was synthesized following the general procedure D, using Intermediate 2 and 2,5-dichloropyrimidine. The crude product was purified by flash chromatography (off white solid). $^1$H NMR (400 MHz, DMSO-$d_6$): δ 8.38 (s, 2H), 6.88 (s, 1H), 6.83 (d, J=8.0 Hz, 1H), 6.75 (m, J=8.0 Hz, 1H), 5.98 (m, 2H), 3.68-3.65 (m, 4H), 3.38-3.369 (m, 1H), 2.44-2.39 (m, 1H), 2.36-2.32 (m, 2H), 1.27 (d, J=6.8 Hz, 3H). LCMS: (Method A) 347.0 (M+H), Rt. 3.24 min, 98.3% (Max). HPLC: (Method A) Rt. 3.22 min, 99.6% (Max).

Example 39: 2-(4-(1-(Benzo[d][1,3]dioxol-5-yl)ethyl)piperazin-1-yl)-4-methoxypyrimidine

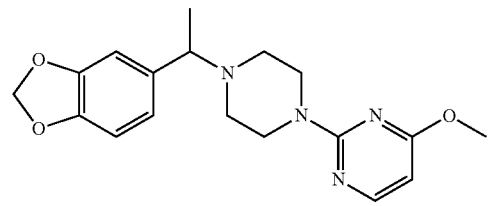 [SMILES: COc1ccnc(N2CCN(C(C)c3ccc4c(c3)OCO4)CC2)n1]

The title compound was synthesized following general procedure D, using Intermediate 2 and 2-chloro-5-methoxy pyrimidine. The crude product was purified by flash chromatography (white solid). $^1$H NMR (400 MHz, DMSO-$d_6$): δ 8.04 (d, J=5.6 Hz, 1H), 6.88-0 (s, 1H), 6.83 (d, J=8.0 Hz, 1H), 6.74 (d, J=8.0 Hz, 1H), 6.02 (d, J=5.6 Hz, 1H), 5.98 (br s, 2H), 3.79 (s, 3H), 3.72-3.66 (m, 4H), 3.37-3.39 (m, 1H), 2.43-2.39 (m, 2H), 2.34-2.30 (m, 2H), 1.28-1.26 (d, J=6.4 Hz, 3H). LCMS: (Method A) 343.0 (M+H), Rt. 2.27 min, 99.6% (Max). HPLC: (Method A) Rt. 2.27 min, 99.4% (Max).

Example 40: 4-(4-(1-(Benzo[d][1,3]dioxol-5-yl)ethyl)piperazin-1-yl)-2-chloropyrimidine

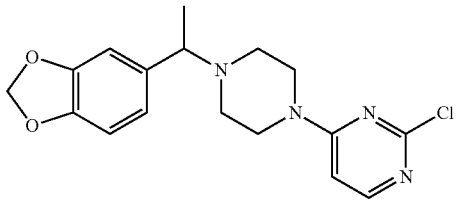 [SMILES: CC(c1ccc2c(c1)OCO2)N1CCN(c2ccnc(Cl)n2)CC1]

The title compound was synthesized following the general procedure D, using Intermediate 2 and 2,4-dichloropyrimidine. The crude product was purified by flash chromatography (yellow oil). $^1$H NMR (400 MHz, DMSO-$d_6$): δ 8.04 (d, J=7.6 Hz, 1H), 6.89 (s, 1H), 6.85 (d, J=8.0 Hz, 1H), 6.80-6.75 (m, 2H), 5.99 (m, 2H), 3.59 (br. s, 4H), 3.39 (q, J=6.4 Hz, 1H), 2.45-2.42 (m, 2H), 2.38-2.33 (m, 2H), 1.29-1.27 (d, J=6.8 Hz, 3H). LCMS: (Method A) 347.0 (M+H), Rt. 2.59 min, 96.4% (Max). HPLC: (Method A) Rt. 2.51 min, 98.2% (Max).

Example 41: 5-(4-(1-(benzo[d][1,3]dioxol-5-yl)ethyl)piperazin-1-yl)-1,3,4-thiadiazol-2-amine

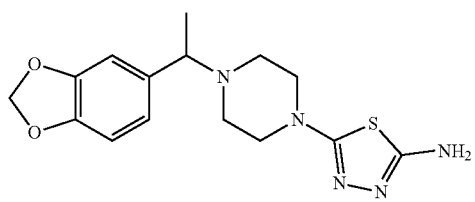 [SMILES: CC(c1ccc2c(c1)OCO2)N1CCN(c2nnc(N)s2)CC1]

The title compound was synthesized following the general procedure D, using Intermediate 2 and 2-amino-5-bromo-1,3,4-thiadiazole. The crude product was purified by recrystallisation. Yield: 81% (2.0 g, off white solid). $^1$H NMR (400 MHz, DMSO-$d_6$): δ 6.88-6.87 (m, 1H), 6.85-6.83 (m, 1H), 6.76-6.73 (m, 1H), 6.47 (s, 2H) 5.99 (s, 2H), 3.40-3.34 (m, 1H), 3.19-3.17 (m, 4H), 2.47-2.43 (m, 2H), 2.40-2.36 (m, 2H), 1.27 (d, J=6.4 Hz, 3H). LCMS: (Method A) 334.0 (M+H), Rt. 1.84 min, 96.5% (Max). HPLC: (Method A) Rt. 1.83 min, 98.2% (Max).

Example 42: 2-(4-(1-(benzo[d][1,3]dioxol-5-yl)ethyl)piperazin-1-yl)-N,N-dimethylthiazole-4-carboxamide

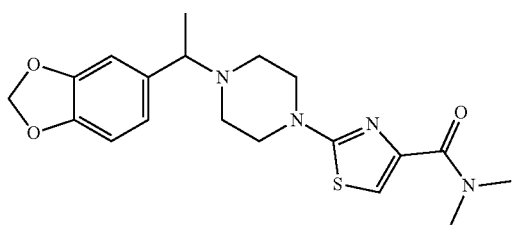 [SMILES: CC(c1ccc2c(c1)OCO2)N1CCN(c2nc(C(=O)N(C)C)cs2)CC1]

The title compound was synthesized following the same procedure as described for Example 30, using Example 18 (0.3 g, 0.9 mmol) and dimethyl amine (0.9 mL, 1.8 mmol, 2 M in THF) as starting material (pale yellow solid). $^1$H NMR (400 MHz, DMSO-$d_6$): δ 7.16 (s, 1H), 6.89 (s, 1H), 6.85 (d, J=7.6 Hz, 1H), 6.76 (d, J=8.0 Hz, 1H), 5.99 (br s, 2H), 3.41-3.34 (m, 5H), 3.30 (s, 3H), 2.90 (s, 3H), 2.43-2.42 (m, 4H), 1.28 (d, J=6.8 Hz, 3H). LCMS: (Method A) 389.0 (M+H), Rt. 2.41 min, 95.1% (Max). HPLC: (Method A) Rt. 2.38 min, 94.3% (Max).

Example 43: 2-(4-(1-(Benzo[d][1,3]dioxol-5-yl)ethyl)piperazin-1-yl)-N-isopropylthiazole-5-carboxamide

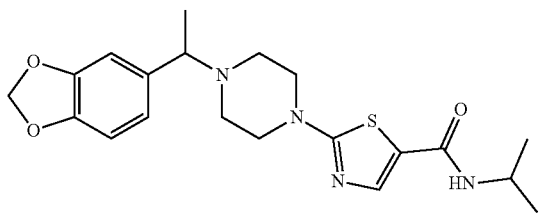 [SMILES: CC(C)NC(=O)c1cnc(N2CCN(C(C)c3ccc4c(c3)OCO4)CC2)s1]

Step 1: 2-(4-(1-(Benzo[d][1,3]dioxol-5-yl)ethyl)piperazin-1-yl)thiazole-5-carboxylic acid To a stirred solution of Example 27 (0.8 g, 2.05 mmol) in dioxane (24 mL), NaOH (2M in water, 3 mL) was added slowly. The reaction mixture was stirred overnight at room temperature. It was then concentrated under vacuum and neutralized with HCl (1.5 N) up to pH=6 and was extracted with DCM (25 mL). The organic layer was washed with water (15 mL), brine (15 mL), dried over anhydrous $Na_2SO_4$ and concentrated under reduced pressure to afford the title compound (off white solid). LCMS: (Method A) 362.0 (M+H), Rt. 2.30 min, 77.6% (Max).

Step 2: 2-(4-(1-(Benzo[d][1,3]dioxol-5-yl)ethyl)piperazin-1-yl)-N-isopropylthiazole-5-carboxamide To a solution of 2-(4-(1-(benzo[d][1,3]dioxol-5-yl)ethyl)piperazin-1-yl)thiazole-5-carboxylic acid (0.1 g, 0.277 mmol) in dry DCM (2 mL), HATU (0.16 g, 0.41 mmol) was added and the resulting mixture was stirred at room temperature for 1 h. Isopropyl amine (0.02 g, 0.36 mmol) and DIPEA (0.14 mL, 0.83 mmol) were added at 0° C. and the mixture was stirred overnight at room temperature. The reaction was quenched with water (10 mL) and extracted with EtOAc (25 mL). The organic layer was dried over anhydrous $Na_2SO_4$ and concentrated under vacuum. The resulting crude product was purified by MD Autoprep (Method B) to afford the title compound (off white solid). $^1$H NMR (400 MHz, DMSO-$d_6$): δ 7.96 (d, J=7.6 Hz, 1H), 7.78 (s, 1H), 6.89 (s, 1H), 6.85 (d, J=7.6 Hz, 1H), 6.75 (d, J=8.0 Hz, 1H), 5.99 (br s, 2H), 3.98-3.96 (m, 1H), 3.42-3.41 (m, 5H), 2.42-2.38 (m, 4H), 1.28 (d, J=6.8 Hz, 3H), 1.11 (d, J=6.8 Hz, 6H). LCMS: (Method A) 403 (M+H), Rt. 2.72 min, 97.81% (Max). HPLC: (Method A) Rt. 2.70 min, 98.62% (Max).

Example 44: N-(5-(4-(1-(Benzo[d][1,3]dioxol-5-yl)ethyl)piperazin-1-yl)-1,3,4-thiadiazol-2-yl)acetamide

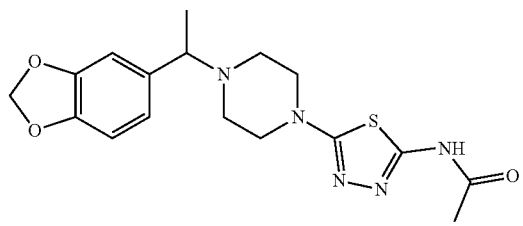 [SMILES: CC(=O)Nc1nnc(N2CCN(C(C)c3ccc4c(c3)OCO4)CC2)s1]

To a stirred solution of Example 41 (0.06 g, 0.7 mmol), diisopropylethylamine (0.4 mL, 0.32 mmol) in dry DCM (4.0 mL), acetic anhydride (0.96 mL, 1.05 mmol) was added at 0° C. and the resulting mixture was stirred for 5 h at rt. The completion of the reaction was monitored by TLC. The reaction mixture was concentrated and the crude products were purified by flash chromatography to afford the title compound (colorless oil). $^1$H NMR (400 MHz, DMSO-$d_6$): δ 12.03 (m, 1H), δ 6.89 (m, 1H), 6.86-6.84 (m, 1H), 6.77-6.75 (m, 1H), 5.99 (m, 2H), 3.41-3.40 (m, 5H), 2.51-2.50 (m, 2H), 2.43-2.40 (m, 2H), 2.10 (s, 3H), 1.28 (d, J=6.8 Hz, 3H). LCMS: (Method A) 376.0 (M+H), Rt. 2.512 min, 96.77% (Max). HPLC: (Method A) Rt. 2.262 min, 98.69% (Max).

Example 45: 2-(4-(1-(Benzo[d][1,3]dioxol-5-yl)ethyl)piperazin-1-yl)-N-propylpyrimidin-4-amine

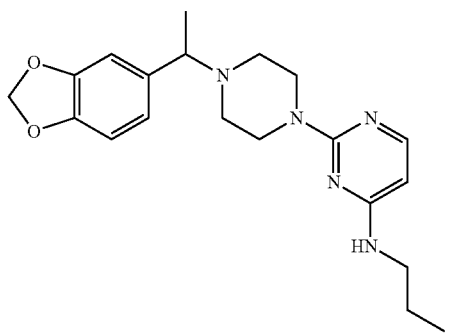 [SMILES: CCCNc1ccnc(N2CCN(C(C)c3ccc4c(c3)OCO4)CC2)n1]

Step 1: 2-chloro-N-propylpyrimidin-4-amine

To a stirred solution of 2,4-dichloro pyrimidine (0.2 g, 1.34 mmol) in dry THF (10 mL), TEA (0.54 g, 5.36 mmol) and propyl amine (0.088 g, 1.34 mmol) were added and the resulting mixture was stirred at room temperature for 10 h. It was diluted with water and extracted with EtOAc. The organic layer was dried over anhydrous $Na_2SO_4$ and concentrated under vacuum to afford the title compound. Yield: 70% (0.18 g, colorless oil). $^1$H NMR (400 MHz, DMSO-$d_6$): δ 7.92-7.85 (m, 2H), 6.49-6.41 (m, 1H), 3.21 (t, J=6.4 Hz 2H), 1.56-1.47 (m, 2H), 0.91-0.87 (t, J=7.36 Hz, 3H). LCMS: (Method A) 172.0 (M+H), Rt. 2.07 min, 99.5% (Max).

Step 2: 2-(4-(1-(Benzo[d][1,3]dioxol-5-yl)ethyl)piperazin-1-yl)-N-propylpyrimidin-4-amine To a stirred solution of Intermediate 2 (0.2 g, 0.9 mmol) in dry DMF (4.0 mL), 2-chloro-N-propylpyrimidin-4-amine (0.18 g, 1.04 mmol) and TEA (0.5 mL, 3.2 mmol) were added at 0° C. The reaction mixture was stirred at 130° C. for overnight. It was then concentrated and the crude product was purified by flash chromatography to afford the title compound (colorless oil). $^1$H NMR (400 MHz, DMSO-$d_6$): δ 7.65 (s, 1H), 6.89-6.75 (m, 3H), 6.12-5.95 (m, 3H), 5.83 (br. s, 1H), 3.62 (m, 4H), 3.20 (s, 3H), 2.51-2.49 (m, 4H), 1.50 (qm, 2H), 1.28-1.24 (m, 3H), 0.88 (t, J=8.0 Hz, 3H). LCMS: (Method A) 370.0 (M+H), Rt. 2.604 min, 97.37% (Max). HPLC: (Method A) Rt. 2.54 min, 99.78% (Max).

Example 46: 4-(4-(1-(Benzo[d][1,3]dioxol-5-yl)ethyl)piperazin-1-yl)pyrimidin-2-amine

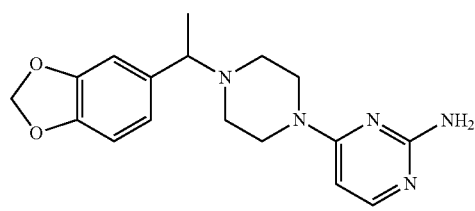 [SMILES: CC(c1ccc2c(c1)OCO2)N1CCN(c2ccnc(N)n2)CC1]

The title compound was synthesized following the general procedure D, using Intermediate 2 and 2-amino-4-chloropyrimidine. The crude product was purified by flash chromatography (off white solid). $^1$H NMR (400 MHz, DMSO-$d_6$): δ 7.72 (d, 1H, J=6.0 Hz), 6.88 (s, 1H), 6.84 (d, J=8.0 Hz, 1H), 6.75 (d, J=8.0 Hz, 1H), 5.98-5.95 (m, 5H), 3.46-3.45 (m, 4H), 3.37-3.35 (m, 1H), 2.40-2.37 (m, 2H), 2.33-2.29 (m, 2H), 1.27 (d, J=6.4 Hz, 3H). LCMS: (Method A) 328.0 (M+H), Rt. 1.86 min, 97.06% (Max). HPLC: (Method A) Rt. 1.81 min, 97.5% (Max).

Example 47: 2-(4-(1-(Benzo[d](1,3)dioxol-5-yl)ethyl)piperazin-1-yl)-N,N-dimethylthiazole-5-carboxamide

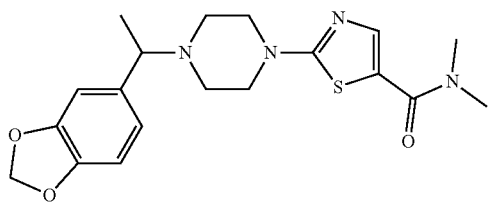 [SMILES: CC(c1ccc2c(c1)OCO2)N1CCN(c2ncc(C(=O)N(C)C)s2)CC1]

To a stirred solution of 2-(4-(1-(benzo[d][1,3]dioxol-5-yl)ethyl)piperazin-1-yl)thiazole-5-carboxylic acid (Example 43, Step 1, 0.155 g, 0.4 mmol) and HATU (0.206 g, 1.2 mmol) in dry DMF (3 mL), DIPEA (0.1 mL, 0.8 mmol) was added and the resulting mixture was stirred for 30 min at room temperature. Dimethylamine in THF (0.5 mL, 8.4 mmol) was then added at 0° C. The reaction mixture was stirred overnight at room temperature. Solvents were evaporated and the resulting crude mixture was diluted with EtOAc, washed with water, 10% sodium bicarbonate solution, brine and dried over $Na_2SO_4$. After evaporation of the solvents, the resulting crude product was purified by MD Autoprep (Method B) to afford the title compound (off white solid). $^1$H NMR (400 MHz, CDCl$_3$): δ 7.47 (s, 1H), 6.87 (s, 1H), 6.77-6.76 (m, 2H), 5.96 (s, 2H), 3.52-3.51 (m, 4H), 3.37-3.36 (m, 1H), 3.17 (s, 6H), 2.57-2.52 (m, 4H), 2.26 (s, 3H). LCMS: (Method B) 389 (M+H), Rt. 5.049 min, 98.02% (Max). HPLC: (Method A) Rt. 2.42 min, 98.49% (Max).

Example 48: 2-(4-(1-(Benzo[d](1,3)dioxol-5-yl)ethyl)piperazin-1-yl)thiazole-5-carboxamide

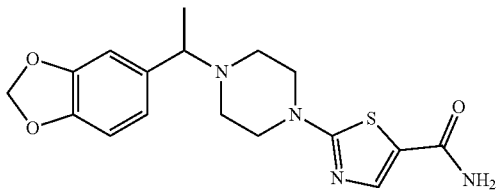 [SMILES: CC(c1ccc2c(c1)OCO2)N1CCN(c2ncc(C(N)=O)s2)CC1]

To a solution of 2-(4-(1-(benzo[d][1,3]dioxol-5-yl)ethyl) piperazin-1-yl)thiazole-5-carboxylic acid (Example 43, Step 1, 0.15 g, 0.4 mmol) in dry DMF (3 mL), HATU (0.206 g, 1.2 mmol) was added and stirred at room temperature for 20 min. Ammonia in THF (5 mL) and DIPEA (0.14 mL, 0.83 mmol) were then added at 0° C. The resulting reaction mixture was stirred at room temperature overnight. It was concentrated under reduced pressure. EtOAc was added to the resulting mixture and was washed with water, 10% sodium bicarbonate solution, brine and dried over $Na_2SO_4$. After evaporation of the solvents, the crude product was purified by MD Autoprep (Method C) to afford the title compound (off white solid). $^1$H NMR (400 MHz, DMSO-$d_6$): δ 7.76 (s, 1H), 7.67 (br s, 1H), 7.11 (br s, 1H), 6.89 (s, 1H), 6.84 (d, J=7.6 Hz, 1H), 6.76 (d, J=7.6 Hz, 1H), 5.99 (br s, 2H), 3.41-3.40 (m, 5H), 2.50-2.39 (m, 4H), 1.28 (d, J=8.0 Hz, 3H). LCMS: (Method A) 361.0 (M+H), Rt. 2.01 min, 99.2% (Max). HPLC: (Method A) Rt. 2.03 min, 98.5% (Max).

Example 49: 2-(4-(1-(2,3-Dihydrobenzo[b][1,4]dioxin-6-yl)ethyl)piperazin-1-yl)thiazole-4-carboxamide

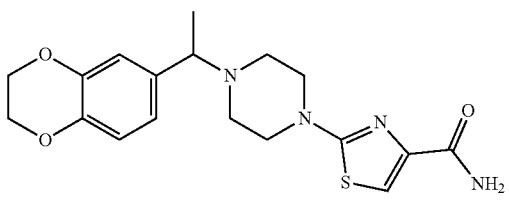 [SMILES: CC(c1ccc2c(c1)OCCO2)N1CCN(c2nc(C(N)=O)cs2)CC1]

Step 1: Ethyl-2-(4-(1-(2,3-dihydrobenzo[b][1,4]dioxin-6-yl)ethyl)piperazin-1-yl)thiazole-4-carboxylate The title compound was synthesized following general procedure D, using ethyl 2-(piperazin-1-yl)thiazole-4-carboxylate hydrochloride (Example 17, Step 2, 5.0 g, 20.4 mmol) and Intermediate 3 (4.97 g, 24 mmol). The crude product was purified by flash chromatography. Yield: 54% (4.5 g, black oil).

Step 2: 2-(4-(1-(2,3-Dihydrobenzo[b][1,4]dioxin-6-yl)ethyl)piperazin-1-yl)thiazole-4-carboxylic acid To a stirred solution of ethyl-2-(4-(1-(2,3-dihydrobenzo[b][1,4]dioxin-6-yl)ethyl)piperazin-1-yl)thiazole-4-carboxylate (4.5 g, 11.1 mmol) in THF (20 mL), 10% NaOH (50 mL) was added slowly. The reaction mixture was stirred at room temperature for overnight. It was concentrated under vacuum, neutralized with HCl (2 N in water) to pH=6 and extracted with DCM (25 mL). The organic layer was washed with water (10 mL), brine (25 mL), dried over anhydrous $Na_2SO_4$ and concentrated under reduced pressure afford the title compound (pale yellow solid). $^1$H NMR (400 MHz, CDCl$_3$): δ 7.44 (s, 1H), 6.94-6.76 (m, 3H), 4.26 (s, 4H), 3.65-3.49 (m, 5H), 2.59-3.54 (m, 4H), 2.49-2.45 (m, 4H), 1.26 (d, J=4.8 Hz, 3H), LCMS: (Method A) 376.0 (M+H), Rt. 2.36 min, 79.7% (Max).

Step 3: 2-(4-(1-(2,3-Dihydrobenzo[b][1,4]dioxin-6-yl)ethyl)piperazin-1-yl)thiazole-4-carboxamide The title compound was synthesized according to the same procedure as described for Example 30, using 2-(4-(1-(2,3-dihydrobenzo[b][1,4]dioxin-6-yl)ethyl)piperazin-1-yl)thiazole-4-carboxylic acid and NH$_3$ in THF. The crude product was purified by flash chromatography (off white solid). $^1$H NMR (400 MHz, DMSO-$d_6$): $^1$H NMR (400 MHz, DMSO-$d_6$): δ 7.39 (br s, 2H), 7.35 (s, 1H), 6.80-6.76 (m, 3H), 4.21 (s, 4H), 3.38-3.38 (m, 5H), 2.49-2.45 (m, 4H), 1.27-1.23 (m, 3H). LCMS: (Method A) 375.0 (M+H), Rt. 2.21 min, 96.1% (Max). HPLC: (Method A) Rt. 2.28 min, 96.6% (Max).

Example 50: 2-(4-(1-(2,3-dihydrobenzo[b][1,4]dioxin-6-yl)ethyl)piperazin-1-yl)-N-methylthiazole-4-carboxamide

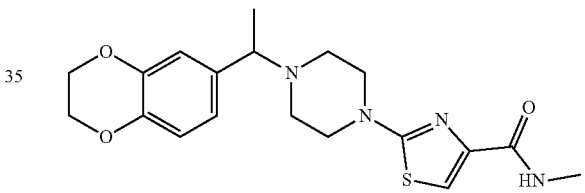

The title compound was synthesized according to the same procedure as described for Example 30, using 2-(4-(1-(2,3-dihydrobenzo[b][1,4]dioxin-6-yl)ethyl)piperazin-1-yl)thiazole-4-carboxylic acid and MeNH$_2$ in THF. The crude product was purified by flash chromatography (yellow oil). $^1$H NMR (400 MHz, DMSO-$d_6$): δ 8.07 (q, J=4.0 Hz, 1H), 7.33 (s, 1H), 6.76-6.39 (m, 3H), 4.21 (s, 4H), 3.38-3.32 (m, 5H), 2.75-2.71 (m, 3H), 2.49-2.48 (m, 4H), 1.26-1.25 (m, 3H). LCMS: (Method A) 389.0 (M+H), Rt. 2.38 min, 95.9% (Max). HPLC: (Method A) Rt. 2.46 min, 97.7% (Max).

Example 51: Ethyl 2-(4-(1-(benzo[d][1,3]dioxol-5-yl)ethyl)piperazin-1-yl)pyrimidine-5-carboxylate

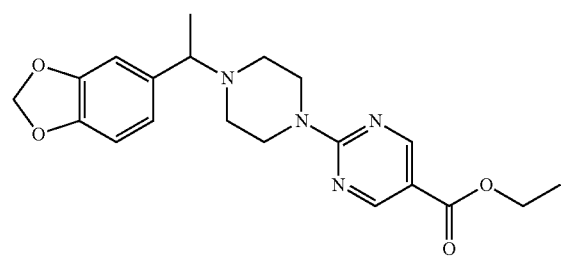 [SMILES: CCOC(=O)c1cnc(N2CCN(C(C)c3ccc4c(c3)OCO4)CC2)nc1]

Step 1: tert-Butyl 4-(5-bromopyrimidin-2-yl)piperazine-1-carboxylate

To a stirred solution of 1-boc-piperazine (6.0 g, 31.5 mmol) in DMF (50 mL), triethyl amine (7 mL, 46.00 mmol) and 5-bromo-2-chloropyrimidine (6.3 g, 37.00 mmol) were added and the reaction mixture was stirred at 90° C. for 8 h. The reaction mixture was concentrated under reduced pressure. Water (50 mL) was added and the desired product was extracted with DCM (150 mL). The organic layer was dried over $Na_2SO_4$ and concentrated under reduced pressure. The crude product was purified by flash chromatography (10% EtOAc in pet ether) to afford the title compound. Yield: 76% (7 g, white). $^1$H NMR (400 MHz, DMSO-$d_6$): δ 8.46 (s, 2H), 3.68-3.67 (m, 4H), 3.39-3.37 (m, 4H), 1.40 (s, 9H). LCMS: (Method A) 289.0 (M+H), Rt. 5.19 min, 99.05% (Max).

Step 2: 2-(4-(t-Butoxycarbonyl)piperazin-1-yl)pyrimidine-5-carboxylic acid

To a stirred solution of tert-butyl 4-(5-bromopyrimidin-2-yl)piperazine-1-carboxylate (5 g, 14.5 mmol) in dry THF (50 mL), n-BuLi (13.5 mL, 21.7 mmol, 1.6 M in THF) was added dropwise at −75° C. and stirred for 2 h at the same temperature. Dry $CO_2$ gas was passed through the reaction mixture for 1 h. The reaction was stirred for 30 min at same temperature and 30 min at rt. It was cooled to 0° C. and quenched by using 10% ammonium chloride solution. The product was extracted with DCM (150 mL). The organic layer was washed with water (50 mL), brine (50 mL) and dried over anhydrous $Na_2SO_4$. After evaporation of the solvents, the title compound was isolated and used in the next step without further purification. Yield: 55% (2.5 g, pale yellow oil). LCMS: (Method A) 308.0 (M+H), Rt. 3.61 min, 55.64% (Max).

Step 3: Ethyl 2-(piperazin-1-yl)pyrimidine-5-carboxylate

To a stirring solution of 2-(4-(tert-butoxycarbonyl)piperazin-1-yl)pyrimidine-5-carboxylic acid (2.0 g, 6.0 mmol) in EtOH (250 mL), $SOCl_2$ (1.7 mL, 16.23 mmol) was added slowly at 0° C. and the mixture was stirred at 90° C. for 15 h. It was concentrated under reduced pressure to afford the title compound (off white solid). LCMS: (Method A) 236 (M+H), Rt. 2.14, 49.8% (Max).

Step 4: Ethyl 2-(4-(1-(benzo[d][1,3]dioxol-5-yl)ethyl)piperazin-1-yl)pyrimidine-5-carboxylate To a stirring solution of ethyl 2-(piperazin-1-yl)pyrimidine-5-carboxylate (2.5 g, 9.0 mmol), diisopropyl ethyl amine (5.9 mL, 27.0 mmol) in dry acetonitrile (50 mL), Intermediate 1 (2.08 g, 11.0 mmol) was added at rt and the reaction mixture was stirred at 80° C. overnight. The reaction mixture was concentrated under vacuum and the resulting crude product was purified by flash chromatography (50% EtOAc in pet ether) to afford the title compound (yellow solid). $^1$H NMR (400 MHz, DMSO-$d_6$): δ 8.75 (s, 2H), 6.90 (s, 1H), 6.85-6.83 (d, J=7.6 Hz, 1H), 6.75 (d, J=7.6 Hz, 1H), 6.05 (d, J=2.8 Hz, 1H), 5.91 (d, J=2.8 Hz, 1H), 4.28-4.23 (q, J=7.2 Hz, 2H), 3.82-3.81 (m, 4H), 3.49 (q, J=6.8 Hz, 1H), 2.55-2.44 (m, 2H), 2.43-2.33 (m, 2H), 1.29-1.24 (m, 6H). LCMS: (Method A) 385 (M+H), Rt. 3.23 min, 94.1% (Max). HPLC: (Method A) Rt. 3.23 min, 99.14% (Max).

Example 52: (2-(4-(1-(benzo[d][1,3]dioxol-5-yl)ethyl)piperazin-1-yl)pyrimidin-5-yl)methanol

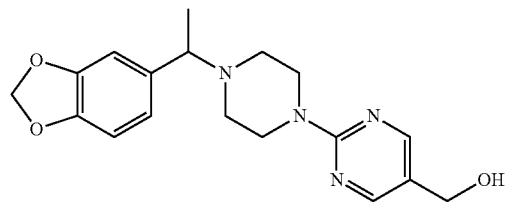 [SMILES: CC(c1ccc2c(c1)OCO2)N1CCN(c2ncc(CO)cn2)CC1]

The title compound was synthesized following general procedure A from Example 51. The crude product was purified by flash chromatography (30% EtOAc in pet ether) to afford the title compound (off white solid). $^1$H NMR (400 MHz, DMSO-$d_6$): δ 8.27 (s, 2H), 6.89 (s, 1H), 6.84 (d, J=8 Hz, 1H), 6.75 (d, J=8.0 Hz, 1H), 5.99 (m, 2H), 5.05 (t, J=5.2 Hz, 1H), 4.30 (d, J=5.2 Hz, 2H), 3.67 (s, 4H), 3.36-3.34 (m, 1H), 2.43-3.32 (m, 4H), 1.27 (d, J=6.8 Hz, 3H). LCMS: (Method A) 343.0 (M+H), Rt. 2.16 min, 95.05% (Max). HPLC: (Method A) Rt. 2.11 min, 97.35% (Max).

Example 53: 2-(4-(1-(2,3-dihydrobenzofuran-5-yl)ethyl)piperazin-1-yl)pyrimidine

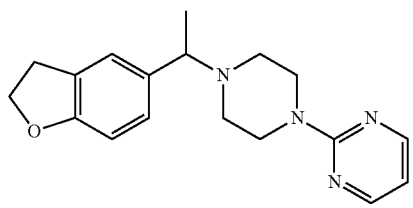 [SMILES: CC(c1ccc2c(c1)CCO2)N1CCN(c2ncccn2)CC1]

To a solution of 2-(piperazin-1-yl)pyrimidine (0.8 g, 4.8 mmol), diisopropylethylamine (3.0 mL, 5.7 mmol) in ACN (20 mL), Intermediate 5 (1.04 g, 5.7 mmol) was added at rt and the resulting mixture was stirred overnight. It was diluted with water (5 mL) and extracted with DCM (2×50 mL). The combined organic layer was dried over $Na_2SO_4$ and concentrated under vacuum. The crude product was purified by MD Autoprep (Method B) to afford the title compound (white solid). $^1$H NMR (400 MHz, DMSO-$d_6$): δ 8.31 (d, J=4.8 Hz, 2H), 7.16 (s, 1H), 6.99 (d, J=8.4 Hz, 1H), 6.67 (d, J=8.0 Hz, 1H), 6.58 (t, J=4.8 Hz, 1H), 4.48 (t, J=8.8 Hz, 2H), 3.67 (m, 4H), 3.34 (t, J=6.8 Hz, 1H), 3.14 (m, 2H), 2.42-2.38 (m, 2H), 2.35-2.31 (m, 2H), 1.28 (d, J=6.8 Hz, 3H). LCMS: (Method A) 311.2 (M+H), Rt. 2.511 min, 98.68% (Max). HPLC: (Method A) Rt. 2.52 min, 99.82% (Max).

Example 54: N-(4-(4-(1-(Benzo[d][1,3]dioxol-5-yl)ethyl)piperazin-1-yl)pyrimidin-2-yl)acetamide

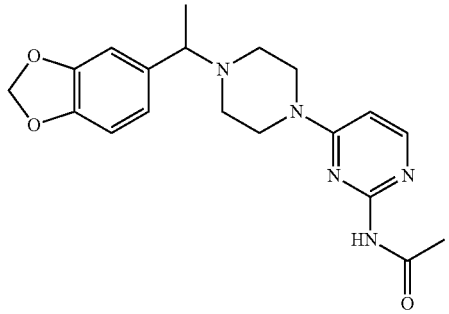 [SMILES: CC(=O)Nc1nccc(N2CCN(C(C)c3ccc4c(c3)OCO4)CC2)n1]

To a stirred solution of Example 46 (0.35 g, 1.0 mmol) in dry DCM (3.5 mL), pyridine (0.2 mL, 2.1 mmol), acetic anhydride (0.12 mL, 1.3 mmol) and DMAP (0.006 g, 0.5 mmol) were added at rt. The resulting mixture was stirred for 5 h at rt and overnight at 50° C. It was diluted with ethyl acetate (100 mL) and washed with HCl (1.5N), water, brine, dried over $Na_2SO_4$ and concentrated under vacuum. The resulting crude product was purified by MD Autoprep (Method C) to afford the title compound (off white solid). $^1$H NMR (400 MHz, MeOH-$d_4$): δ 7.99 (s, 1H), 6.88 (s, 1H), 6.77 (s, 2H), 6.54 (br. s, 1H), 5.93 (s, 2H), 3.71 (s, 4H), 3.40 (q, J=6.8 Hz, 1H), 2.61-2.57 (m, 2H), 2.51-2.47 (m, 2H), 2.24 (s, 3H), 1.38 (d, J=6.8 Hz, 3H). LCMS: (Method A) 370.2 (M+H), Rt. 1.88 min, 95.01% (Max). HPLC: (Method A) Rt. 1.83 min, 98.7% (Max).

Example 55: 1-(1-(benzo[d][1,3]dioxol-5-yl)ethyl)-4-(5-nitropyridin-2-yl)piperazine

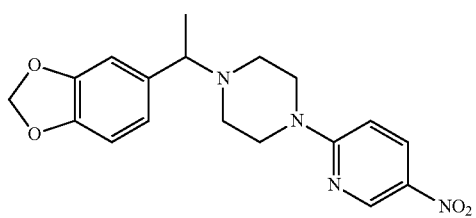

To a stirred solution of Intermediate 2 (0.2 g, 2.1 mmol), $Et_3N$ (1.2 mL, 8.5 mmol) in dry DMF (5 mL), 2-chloro-5-nitropyridine (0.44 g, 2.8 mmol) was added at rt. The resulting mixture was stirred at 120° C. for 20 h. The completion of the reaction was monitored by TLC. The reaction mixture was diluted with water (10 mL) and extracted with EtOAc (25 mL). The organic layer was dried over anhydrous $Na_2SO_4$ and concentrated under vacuum. The resulting crude product was purified by flash chromatography to afford the title compound (yellow solid). $^1$H NMR (400 MHz, DMSO-$d_6$): δ 8.93 (d, J=2.8 Hz, 1H), 8.19 (dd, J=9.6, 2.8 Hz, 1H), 6.91-6.89 (m, 2H), 6.85 (d, J=8.0 Hz, 1H), 6.76 (d, J=8.0 Hz, 1H), 5.99 (br s, 2H), 3.73 (s, 4H), 3.40 (q, J=6.4 Hz, 1H), 2.41-2.38 (m, 4H), 1.29 (d, J=6.4 Hz, 3H). LCMS: (Method A) 357.0 (M+H), Rt. 2.98 min, 96.03% (Max). HPLC: (Method A) Rt. 3.03 min, 95.35% (Max).

Example 56: (R)-2-(4-(1-(Benzo[d][1,3]dioxol-5-yl)ethyl)piperazin-1-yl)-N-methylthiazole-4-carboxamide or (S)-2-(4-(1-(benzo[d][1,3]dioxol-5-yl)ethyl)piperazin-1-yl)-N-methylthiazole-4-carboxamide

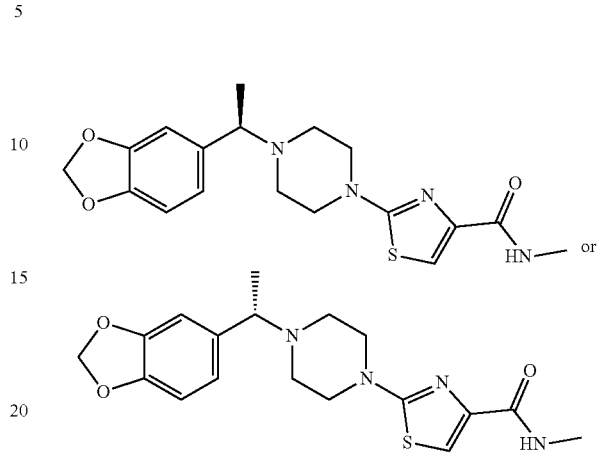

The two enantiomers of Example 30 were separated by chiral preparative HPLC (Method PG). The first eluting compound has a Rt. 15.74 min (white solid). $^1$H NMR (400 MHz, DMSO-$d_6$): δ 7.99 (q, J=4.8 Hz, 1H), 7.34 (s, 1H), 6.90 (d, J=1.2 Hz, 1H), 6.85 (d, J=8.0 Hz, 1H), 6.76 (dd, J=8.0, 1.2 Hz, 1H), 5.99 (s, 2H), 3.50-3.42 (m, 5H), 2.72 (d, J=4.8 Hz, 3H), 2.50-2.49 (m, 4H), 1.29 (d, J=6.8 Hz, 3H). LCMS: (Method A) 375 (M+H), Rt. 2.35 min, 98.15% (Max). HPLC: (Method A) Rt. 2.38 min, 97.08% (Max), 96.58% (254 nm). Chiral HPLC: (Method E) Rt. 15.74 min, 100.00%. Example 56 corresponds to the second eluting compound, with Rt. 28.85 min (white solid). $^1$HNMR (400 MHz, DMSO-$d_6$): δ 7.99 (q, J=4.8 Hz, 1H), 7.34 (s, 1H), 6.90 (d, J=1.2 Hz, 1H), 6.85 (d, J=7.6 Hz, 1H), 6.76 (dd, J=8.0, 1.2 Hz, 1H), 5.99 (s, 2H), 3.50-3.41 (m, 5H), 2.72 (d, J=4.8 Hz, 3H), 2.50-2.43 (m, 4H), 1.29 (d, J=6.8 Hz, 3H). LCMS: (Method A) 375.0 (M+H), Rt. 2.34 min, 99.94% (Max). HPLC: (Method A) Rt. 2.37 min, 99.77% (Max). Chiral HPLC: (Method E) Rt. 28.85 min, 100.00%

Example 57: (R)-2-(4-(1-(2,3-dihydrobenzo[b][1,4]dioxin-6-yl)ethyl)piperazin-1-yl)-N-methylthiazole-4-carboxamide or (S)-2-(4-(1-(2,3-dihydrobenzo[b][1,4]dioxin-6-yl)ethyl)piperazin-1-yl)-N-methylthiazole-4-carboxamide

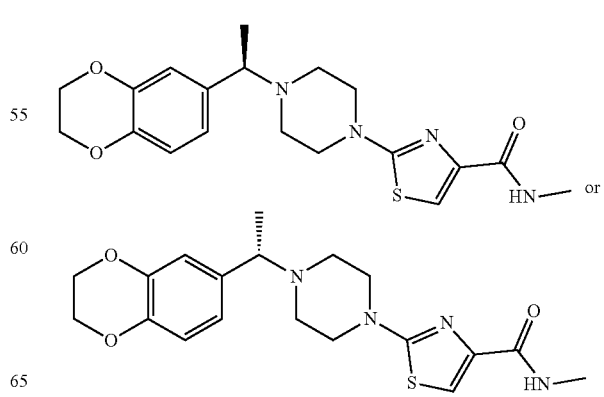

The two enantiomers of Example 50 were separated by chiral preparative HPLC (Method PG). The first eluting compound has a Rt. 16.29 min (yellow solid). ¹H NMR (400 MHz, DMSO-d₆): δ 7.98 (q, J=4.4 Hz, 1H), 7.34 (s, 1H), 6.81-6.74 (m, 3H), 4.22 (s, 4H), 3.42-3.39 (m, 5H), 2.73 (d, J=4.8 Hz, 3H), 2.48-2.41 (m, 4H), 1.27 (t, J=6.4 Hz, 3H). LCMS: (Method A). 389.0 (M+H), Rt. 2.40 min, 99.14% (Max). HPLC: (Method A) Rt. 2.36 min, 99.63% (Max). Chiral HPLC: (Method E) Rt, 16.29 min, 100% (max). Example 57 corresponds to the second eluting compound, with Rt. 33.49 min (yellow solid). ¹H NMR (400 MHz, DMSO-d₆): δ 7.98 (d, J=4.4 Hz, 1H), 7.34 (s, 1H), 6.81-6.74 (m, 3H), 4.21 (s, 4H), 3.42-3.37 (m, 5H), 2.73 (d, J=4.8 Hz, 3H), 2.46-2.41 (m, 4H), 1.26 (t, J=6.4 Hz, 3H). LCMS: (Method A). 389.0 (M+H), Rt. 2.34 min, 98.58% (Max). HPLC: (Method A) Rt. 2.37 min, 99.28% (Max). Chiral HPLC: (Method E) Rt. 33.49 min, 99.66% (max).

Example 58: 6-(4-(1-(Benzo[d][1,3]dioxol-5-yl) ethyl)piperazin-1-yl)pyridin-3-amine

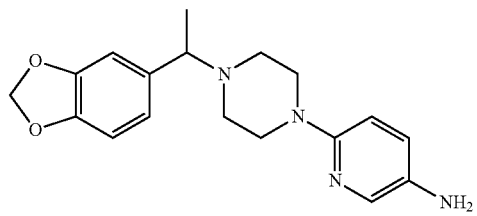

To a stirred solution of Example 55 (0.20 g, 5.6 mmol) in methanol (4.0 mL), Pd/C (0.02 g, 10% w/w) was added at rt and the mixture was stirred overnight under hydrogen atmosphere (5 Kg/cm²) at rt. The reaction mixture was filtered through celite and washed with methanol (10 mL). The organic layer was dried over anhydrous Na₂SO₄ and concentrated under vacuum. The resulted crude product was purified by MD Autoprep (Method C) to afford the title compound (dark oil). ¹H NMR (400 MHz, DMSO-d₆): δ 7.57 (d, J=2.8 Hz, 1H), 6.90-6.88 (m, 2H), 6.84 (d, J=8.0 Hz, 1H), 6.76 (d, J=8.0 Hz, 1H), 6.57 (d, J=8.8 Hz, 1H), 5.98 (m, 2H), 4.55 (s, 2H), 3.33 (br m, 1H), 3.18 (s, 4H), 2.38-2.36 (m, 4H), 1.27 (d, J=6.4 Hz, 3H). LCMS: (Method A) 327.2 (M+H), Rt. 1.85 min, 98.76% (Max). HPLC: (Method A) Rt. 1.81 min, 99.66% (Max).

Example 59 and Example 60: (R)-2-(4-(1-(Benzo[d][1,3]dioxol-5-yl)ethyl)piperazin-1-yl)-N-ethylthiazole-5-carboxamide and (S)-2-(4-(1-(benzo[d][1,3]dioxol-5-yl)ethyl)piperazin-1-yl)-N-ethylthiazole-5-carboxamide

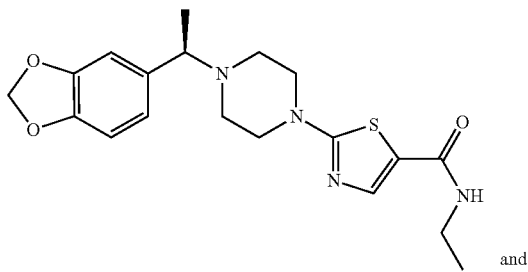
and

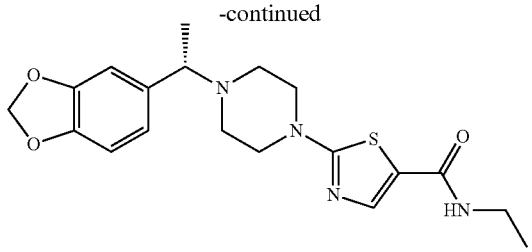

Step 1: Lithium 2-(4-(1-(benzo[d][1,3]dioxol-5-yl) ethyl)piperazin-1-yl)thiazole-5-carboxylate To a stirred solution of Example 27 (1.8 g, 3.86 mmol) in THF (14 mL) MeOH (4 mL) and H₂O (2 mL) was added LiOH·H₂O (395 mg, 9.65 mmol). The reaction mixture was stirred at 50° C. for 3 h. The completion of the reaction was monitored by TLC. The reaction mixture was concentrated under vacuum. The resulting crude product was suspended in toluene and the solvents were evaporated again. It was used in the next step without any further purification. Yield: 89% (1.5 g, off white solid). ¹H NMR (400 MHz, DMSO-d₆): δ 7.73 (s, 1H), 6.88-6.82 (m, 2H), 6.75-6.73 (m, 1H), 5.97 (s, 2H), 3.67-3.32 (m, 5H), 2.87-2.59 (m, 4H), 1.32-1.15 (m, 3H). LCMS: (Method A) 362.0 (M+H), Rt. 2.26 min, 88.6% (Max).

Step 2: (R)-2-(4-(1-(Benzo[d][1,3]dioxol-5-yl)ethyl) piperazin-1-yl)-N-ethylthiazole-5-carboxamide and (S)-2-(4-(1-(benzo[d][1,3]dioxol-5-yl)ethyl)piperazin-1-yl)-N-ethylthiazole-5-carboxamide To a stirred solution of lithium 2-(4-(1-(benzo[d][1,3] dioxol-5-yl)ethyl)piperazin-1-yl)thiazole-5-carboxylate (500 mg, 1.33 mmol) in DMF (10 mL), DIPEA (0.7 mL, 3.99 mmol), ethyl amine (2 M in THF, 1 mL, 2.00 mmol) and HATU (607 mg, 1.60 mmol) were added at 0° C. The reaction mixture was stirred at room temperature overnight. The reaction mixture was concentrated under vacuum and diluted with DCM. It was washed with water, brine and dried over anhydrous Na₂SO₄. The crude product was purified by flash chromatography. Both enantiomers were separated by chiral preparative HPLC (Method PF). Example 59 corresponds to the first eluting compound with a Rt. 17.99 min (white solid). ¹H NMR (400 MHz, DMSO-d₆): δ 8.19 (t, J=5.6 Hz, 1H), 7.74 (s, 1H), 6.90 (s, 1H), 6.85 (d, J=8.0 Hz, 1H), 6.76 (d, J=6.4 Hz, 1H), 5.99 (s, 2H), 3.21-3.17 (m, 2H), 2.48-2.39 (m, 4H), 1.28 (d, J=6.4 Hz, 3H), 1.07 (t, J=7.2 Hz, 3H). LCMS: (Method A) 389.2 (M+H), Rt. 2.47 min, 97.4% (Max). HPLC: (Method A) Rg. 2.43 min, 99.9% (Max). Chiral HPLC: (Method D) Rt. 17.99 min, 100.00%. Example 60 corresponds to the second eluting compound with a Rt. 19.92 min (white solid). ¹H NMR (400 MHz, DMSO-d₆): δ 8.19 (t, J=5.6 Hz, 1H), 7.74 (s, 1H), 6.90 (s, 1H), 6.85 (d, J=8.0 Hz, 1H), 6.76 (d, J=6.8 Hz, 1H), 5.99 (s, 2H), 3.21-3.17 (m, 2H), 2.48-2.33 (m, 4H), 1.28 (d, J=6.8 Hz, 3H), 1.07 (t, J=7.2 Hz, 3H). LCMS: (Method A) 389.0 (M+H), Rt. 2.46 min, 99.3% (Max). HPLC: (Method A) Rt. 2.43 min, 99.9% (Max). Chiral HPLC: (Method D) Rt. 19.92 min, 100.00%.

Example 61: (R)-2-(4-(1-(benzo[d][1,3]dioxol-5-yl)ethyl)piperazin-1-yl)-N,N-dimethylthiazole-5-carboxamide or (S)-2-(4-(1-(benzo[d][1,3]dioxol-5-yl)ethyl)piperazin-1-yl)-N,N-dimethylthiazole-5-carboxamide

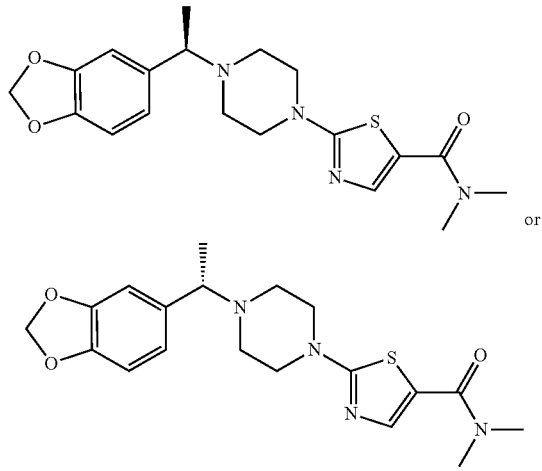

The two enantiomers of Example 47 were separated by chiral preparative HPLC (Method PF). The first eluting compound has a Rt. 14.07 min (white solid). ¹H NMR (400 MHz, DMSO-d₆): δ 7.58 (s, 1H), 6.90 (s, 1H), 6.85 (s, 1H), 6.76 (s, 1H), 5.99 (s, 2H), 3.44-3.42 (m, 5H), 3.07 (br m, 6H), 2.47-2.39 (m, 4H), 1.28 (d, J=6.8 Hz, 3H). LCMS: (Method A) 389.0 (M+H), Rt. 2.39 min, 99.5% (Max). HPLC: (Method A) Rt. 2.37 min, 99.6% (Max). Chiral HPLC: (Method D) Rt. 14.07 min, 100.00%. Example 61 corresponds to the second eluting compound with Rt. 16.06 min (white solid). ¹H NMR (400 MHz, DMSO-d₆): δ 7.58 (s, 1H), 6.90 (s, 1H), 6.85 (s, 1H), 6.76 (s, 1H), 5.99 (s, 2H), 3.44-3.42 (m, 5H), 3.07 (br m, 6H), 2.50-2.39 (m, 4H), 1.28 (d, J=6.4 Hz, 3H). LCMS: (Method A) 389.2 (M+H), Rt. 2.44 min, 95.3% (Max). HPLC: (Method A) Rt. 2.37 min, 99.9% (Max). Chiral HPLC: (Method D) Rt. 16.06 min, 99.7%.

Example 62: (S)-2-(4-(1-(2,3-dihydrobenzo[b][1,4]dioxin-6-yl)ethyl)piperazin-1-yl)-N-ethylthiazole-5-carboxamide or (R)-2-(4-(1-(2,3-dihydrobenzo[b][1,4]dioxin-6-yl)ethyl)piperazin-1-yl)-N-ethylthiazole-5-carboxamide

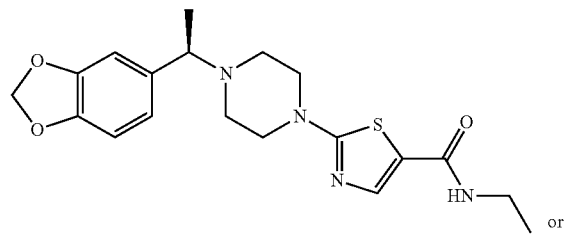

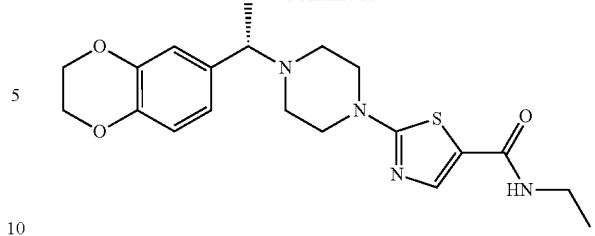

Step 1: Ethyl 2-(4-(1-(2,3-dihydrobenzo[b][1,4]dioxin-6-yl)ethyl)piperazin-1-yl)thiazole-5-carboxylate To a stirred solution of Intermediate 4 (3.4 g, 11.94 mmol) in dry DMF (50 mL), ethyl 2-bromothiazole-5-carboxylate (Example 27, Step 1, 2.8 g, 11.94 mmol) and TEA (5.0 mL, 35.82 mmol) were added at 0° C. The resulting mixture was stirred at 120° C. overnight. It was cooled to rt, diluted with EtOAc, washed with water, brine, dried over anhydrous Na₂SO₄ and concentrated under vacuum. The resulting crude product was purified by flash chromatography to afford the title compound. Yield: 64% (3.1 g, pale brown solid). ¹H NMR (400 MHz, DMSO-d₆): δ 7.81 (s, 1H), 6.79-6.74 (m, 3H), 4.19-4.14 (m, 7H), 3.48-3.32 (m, 4H), 2.42-2.36 (m, 4H), 1.26-1.19 (m, 6H). LCMS: (Method A) 404.0 (M+H), Rt. 3.19 min, 96.5% (Max).

Step 2: Lithium 2-(4-(1-(2,3-dihydrobenzo[b][1,4]dioxin-6-yl)ethyl)piperazin-1-yl)thiazole-5-carboxylate The title compound was synthesized according to the protocol described for Example 60, Step 1, using ethyl 2-(4-(1-(2,3-dihydrobenzo[b][1,4]dioxin-6-yl)ethyl)piperazin-1-yl)thiazole-5-carboxylate as starting material. The resulting product was used in the next step without further purification. Yield: 86% (2.5 g, off white solid). ¹H NMR (400 MHz, DMSO-d₆): δ 7.16 (s, 1H), 6.79-6.72 (m, 3H), 4.20 (s, 4H), 3.34-3.29 (m, 5H), 2.44-2.28 (m, 4H), 1.24 (d, J=8.8 Hz, 3H). LCMS: (Method A) 376.0 (M+H), Rt. 2.34 min, 97.4% (Max).

Step 3: (S)-2-(4-(1-(2,3-dihydrobenzo[b][1,4]dioxin-6-yl)ethyl)piperazin-1-yl)-N-ethylthiazole-5-carboxamide or (R)-2-(4-(1-(2,3-dihydrobenzo[b][1,4]dioxin-6-yl)ethyl)piperazin-1-yl)-N-ethylthiazole-5-carboxamide The title compound was synthesized according to the protocol described for Example 60, Step 2, using lithium 2-(4-(1-(2,3-dihydrobenzo[b][1,4]dioxin-6-yl)ethyl)piperazin-1-yl)thiazole-5-carboxylate as starting material. The crude mixture was purified by flash chromatography followed by chiral preparative HPLC (Method PE) to separate both enantiomers. The first fraction was concentrated to give Example 62 (Rt. 19.00 min) (white solid). ¹H NMR (400 MHz, DMSO-d₆): δ 8.19 (t, J=5.2 Hz, 1H), 7.74 (s, 1H), 6.81-6.74 (m, 3H), 4.22 (s, 4H), 3.42-3.35 (m, 5H), 3.22-3.16 (m, 2H), 2.50-2.33 (m, 4H), 1.27 (d, J=6.8 Hz, 3H), 1.07 (t, J=7.2 Hz, 3H). LCMS: (Method A) 403.0 (M+H), Rt. 2.50 min, 98.4% (Max). HPLC: (Method A) Rt. 2.47 min, 98.2% (Max). Chiral HPLC: (Method A) Rt. 19.00 min, 100%. The second enantiomer had a Rt. 29.37 min (white solid). ¹H NMR (400 MHz, DMSO-d₆): δ 8.19 (t, J=5.6 Hz, 1H), 7.74 (s, 1H), 6.81-6.74 (m, 3H), 4.22 (s, 4H), 3.42-3.37 (m, 5H), 3.22-3.17 (m, 2H), 2.50-2.41 (m, 4H), 1.27 (d, J=6.4 Hz, 3H), 1.07 (t, J=7.2 Hz, 3H). LCMS: (Method A) 403.2 (M+H), Rt. 2.51 min, 99.6% (Max). HPLC: (Method A) Rt. 2.47 min, 98.9% (Max). Chiral HPLC: (Method A) Rt. 29.37 min, 100%.

Example 63 and Example 64: (R)-2-(4-(1-(2,3-di-hydrobenzo[b][1,4]dioxin-6-yl)ethyl)piperazin-1-yl)-N,N-dimethylthiazole-5-carboxamide and (S)-2-(4-(1-(2,3-dihydrobenzo[b][1,4]dioxin-6-yl)ethyl)piperazin-1-yl)-N,N-dimethylthiazole-5-carboxamide

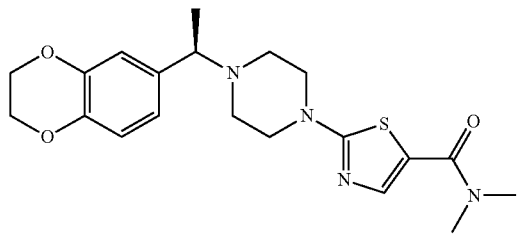

and

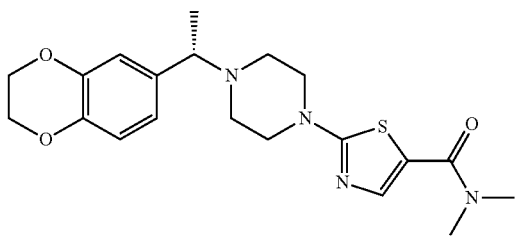

The title compounds were synthesized according to the protocol described for Example 59 and Example 60, Step 2, using lithium 2-(4-(1-(2,3-dihydrobenzo[b][1,4]dioxin-6-yl)ethyl)piperazin-1-yl)thiazole-5-carboxylate (Example 62, Step 2) and dimethyl amine as starting material. The crude mixture was purified by flash chromatography. Both enantiomers were separated by chiral preparative HPLC (Method PF). The first fraction corresponds to Example 63 (Rt. 17.78 min) (white solid). $^1$H NMR (400 MHz, DMSO-$d_6$): δ 7.58 (s, 1H), 6.81-6.75 (m, 3H), 4.22 (s, 4H), 3.44-3.38 (m, 5H), 3.06 (br. s, 6H), 2.47-2.39 (m, 4H), 1.27 (d, J=6.8 Hz, 3H). LCMS: (Method A) 403.0 (M+H), Rt. 2.42 min, 99.3% (Max). HPLC: (Method A) Rt. 2.41 min, 99.6% (Max). Chiral HPLC: (Method D) Rt. 17.78 min, 100.00%. The second fraction corresponds to Example 64 (Rt. 21.09 min) (white solid). $^1$H NMR (400 MHz, DMSO-$d_6$): δ 7.58 (s, 1H), 6.81-6.77 (m, 3H), 4.22 (s, 4H), 3.44-3.38 (m, 5H), 3.12-2.99 (m, 6H), 2.46-2.39 (m, 4H), 1.27 (d, J=6.40 Hz, 3H). LCMS: (Method A) 403.0 (M+H), Rt. 2.43 min, 99.8% (Max). HPLC: (Method A) Rt. 2.40 min, 99.8% (Max). Chiral HPLC: (Method D) Rt. 21.09 min, 97.38%.

Example 65 and Example 66: (R)-2-(4-(1-(benzo[d][1,3]dioxol-5-yl)ethyl)piperazin-1-yl)-N-methylthiazole-5-carboxamide and (S)-2-(4-(1-(benzo[d][1,3]dioxol-5-yl)ethyl)piperazin-1-yl)-N-methylthiazole-5-carboxamide

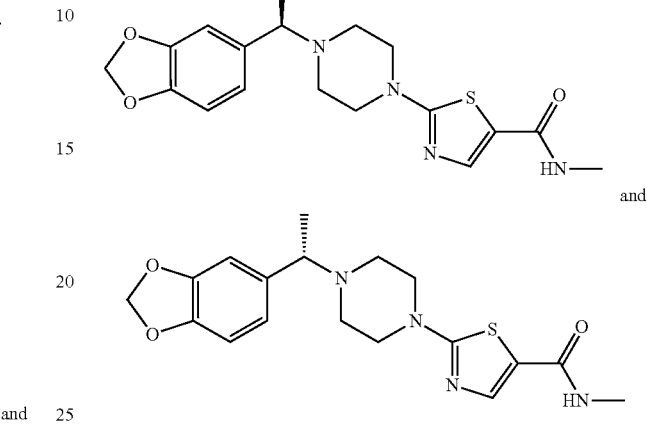

The title compounds were synthesized according to the procedure described for Example 59 and Example 60 using methyl amine (2M in THF) as reagent. The crude mixture was purified by flash chromatography followed by chiral preparative HPLC (Method PF) to separate enantiomers. The first fraction was concentrated to give Example 65 (white solid). $^1$H NMR (400 MHz, DMSO-$d_6$): δ 8.16 (d, J=4.4 Hz, 1H), 7.72 (s, 1H), 6.89 (s, 1H), 6.85 (d, J=7.6 Hz, 1H), 6.76 (d, J=8.0 Hz, 1H), 5.99 (br s, 2H), 3.43-3.42 (m, 5H), 2.69 (d, J=4.4 Hz, 3H), 2.47-2.33 (m, 4H), 1.28 (d, J=6.4 Hz, 3H). LCMS: (Method A) 375.0 (M+H), Rt. 2.23 min, 99.0% (Max). HPLC: (Method A) Rt. 2.19 min, 99.6% (Max). Chiral HPLC: (Method D) Rt. 15.48 min, 98.91%.

The second fraction was concentrated to give Example 66 (white solid). $^1$H NMR (400 MHz, DMSO-$d_6$): δ 8.16 (q, J=4.8 Hz, 1H), 7.72 (s, 1H), 6.90 (s, 1H), 6.85 (d, J=8.0 Hz, 1H), 6.76 (d, J=8.0 Hz, 1H), 5.99 (br s, 2H), 3.43-3.41 (m, 5H), 2.69 (d, J=4.8 Hz, 3H), 2.48-2.39 (m, 4H), 1.28 (d, J=6.8 Hz, 3H). LCMS: (Method A) 375.0 (M+H), Rt. 2.23 min, 97.4% (Max). HPLC: (Method A) Rt. 2.19 min, 96.9% (Max). Chiral HPLC: (Method D) Rt. 18.44 min, 100.00%

Example 67: (2-(4-(1-(Benzo[d][1,3]dioxol-5-yl)ethyl)piperazin-1-yl)thiazol-5-yl)(morpholino)methanone

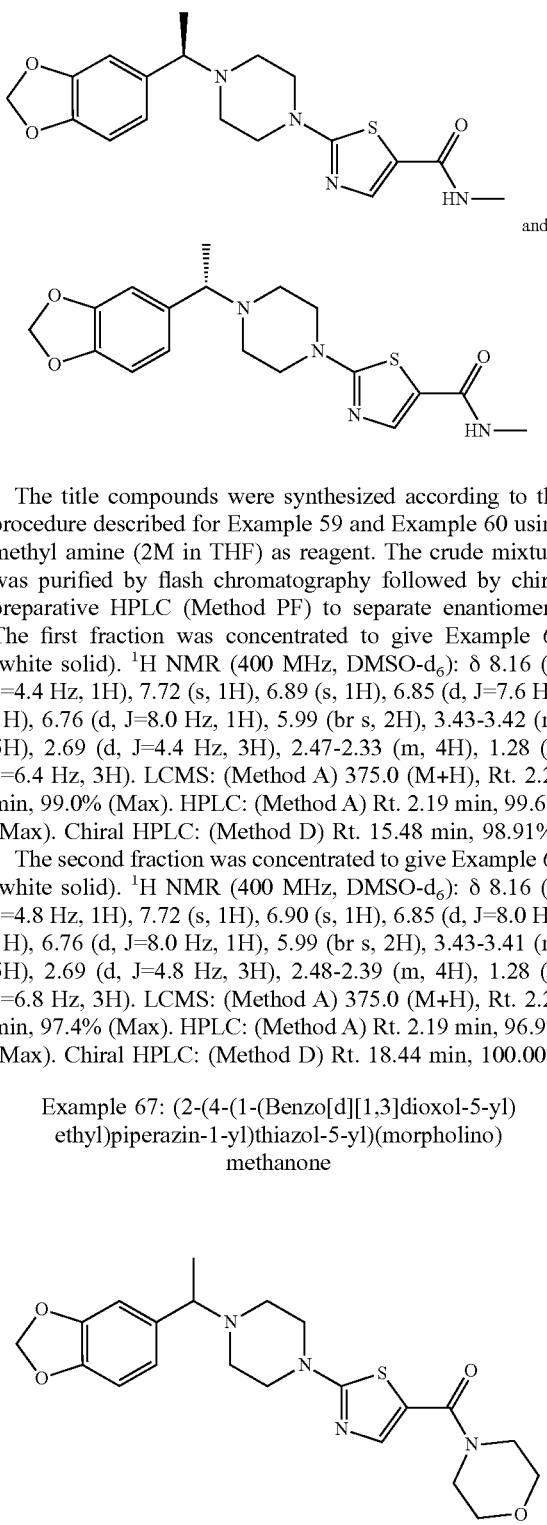

The title compound was synthesized according to the procedure described for Example 59 and Example 60 using morpholine as reagent. Both enantiomers were not separated in this example (pale brown solid). ¹H NMR (400 MHz, DMSO-d₆): δ 7.55 (s, 1H), 6.90 (s, 1H), 6.85 (d, J=8.0 Hz, 1H), 6.76 (d, J=7.6 Hz, 1H), 5.99 (s, 2H), 3.61 (br m, 8H), 3.45-3.42 (m, 5H), 2.47-2.40 (m, 4H), 1.29 (d, J=6.4 Hz, 3H). LCMS: (Method A) 431.0 (M+H), Rt. 2.41 min, 98.6% (Max). HPLC: (Method A) Rt. 2.38 min, 97.1% (Max).

Example 68 and Example 69: (R)—N-(5-(4-(1-(benzo[d][1,3]dioxol-5-yl)ethyl)piperazin-1-yl)-1,3,4-thiadiazol-2-yl)acetamide and (S)—N-(5-(4-(1-(benzo[d][1,3]dioxol-5-yl)ethyl)piperazin-1-yl)-1,3,4-thiadiazol-2-yl)acetamide

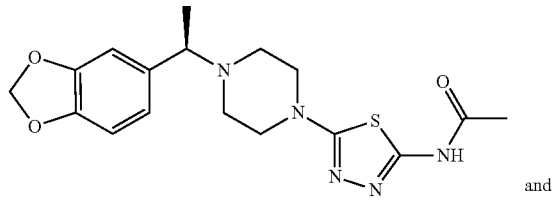

and

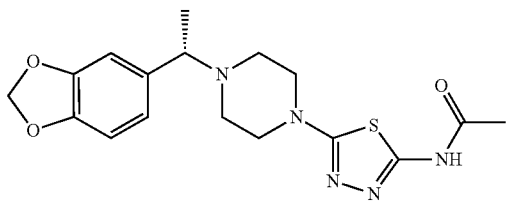

To a stirred solution of Example 41 (0.6 g, 1.8 mmol) in dry DCM (10 mL), acetic anhydride (0.22 mL, 2.3 mmol) and DIPEA (0.615 mL, 3.6 mmol) were added at 0° C. and the reaction mixture was stirred at room temperature for 4 h. It was concentrated under vacuum and the crude product was purified by recrystallization followed by enatiomer separation by SFC. The first fraction was collected as Example 68 (off white solid). ¹H NMR (400 MHz, DMSO-d₆): δ 11.66 (br s, 1H), 6.89 (s, 1H), 6.85 (d, J=8.0 Hz, 1H), 6.76 (d, J=8.0 Hz, 1H), 5.99 (m, 2H), 3.42-3.34 (m, 5H), 2.51-2.50 (m, 2H), 2.43-2.33 (m, 2H), 2.09 (s, 3H), 1.27 (d, J=6.4 Hz, 3H). LCMS: (Method A) 376.0 (M+H), Rt. 2.27 min, 97.4% (Max). HPLC: (Method A) Rt. 2.29 min, 98.2% (Max). HPLC chiral purity: (Method D) Rt. 24.02 min, 99.3% (Max). The second fraction was collected as Example 69 (off white solid). ¹H NMR (400 MHz, DMSO-d₆): δ 11.66 (br s, 1H), 6.89 (s, 1H), 6.85 (d, J=8.0 Hz, 1H), 6.76 (dd, J=8.0, 1.2 Hz, 1H), 5.99 (m, 2H), 3.41-3.34 (m, 5H), 2.55-2.47 (m, 2H), 2.43-2.39 (m, 2H), 2.09 (s, 3H), 1.27 (d, J=6.4 Hz, 3H). LCMS: (Method A) 376.0 (M+H), Rt. 2.28 min, 95.8% (Max). HPLC: (Method A) Rt. 2.29 min, 97.1% (Max). HPLC chiral purity: (Method D) Rt. 26.57 min, 97.5% (Max).

Alternatively, Example 69 can be synthesized according to the following protocol:

Example 69: (S)—N-(5-(4-(1-(benzo[d][1,3]dioxol-5-yl)ethyl)piperazin-1-yl)-1,3,4-thiadiazol-2-yl)acetamide

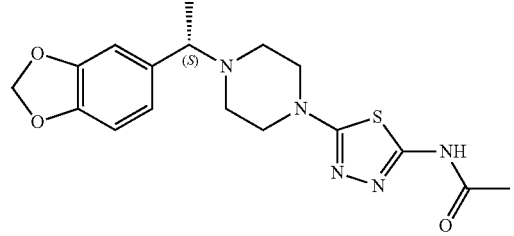

To a stirred solution of Example 132 (102.0 g, 305.9 mmol) in THF (500 mL), pyridine (120.8 g, 1529.9 mmol) and acetic anhydride (33.9 g, 333.0 mmol) were added at 0° C. and the resulting mixture was stirred at rt for 1.0 h. Completion of the reaction was confirmed by TLC. Reaction mixture was evaporated under vacuum at 50° C. Water (200 mL) was added and the resulting suspension was stirred for 15 min at rt and filtered. The filtration cake was washed with water (2×100 mL), hexane (2×200 mL) and Et₂O (2×200 mL). The crude product was heated in Et₂O (500 mL), cooled down to rt and filtered. The filtration cake was washed with Et₂O (100 mL) and dried under vacuum at 40° C. to afford the title compound. Yield: 67% (76.0 g, off white solid). ¹H NMR (400 MHz, DMSO-d₆): δ 12.01 (s, 1H), 6.89 (d, J=1.2 Hz, 1H), 6.83 (d, J=7.9 Hz, 1H), 6.74 (dd, J=7.9, 1.0 Hz, 1H), 5.98-5.97 (m, 2H), 3.38 (q, J=6.7 Hz, 1H), 3.34-3.31 (m, 4H), 2.49-2.40 (m, 4H), 2.01 (s, 3H), 1.26 (d, J=6.7 Hz, 3H). ¹³C NMR (400 MHz, DMSO-d₆): δ168.2, 167.7, 150.6, 147.7, 146.5, 137.5, 121.0, 108.2, 108.0, 101.2, 63.7, 49.6, 49.6, 49.3, 49.3, 22.6, 19.7. LCMS: (Method A) 376.0 (M+H), Rt. 2.37 min, 99.56% (Max), 99.35% (254 nm). HPLC: (Method A) Rt. 2.20 min, 99.65% (Max), 99.34% (254 nm). Chiral HPLC: (Method D) Rt. 26.87 min, 100%. Optical Rotation: [α]²⁸_D −59.78, c 1.0 (CHCl₃). Melting Point: 220.8-221.8° C.

The invention also relates to a compound of formula 69, having a chemical purity of higher than 98%, preferably higher than 99%, even more preferably higher than 99.5% and/or an enantiomeric excess of higher than 98%, preferably higher than 99%, even more preferably higher than 99.5%. The physical data of such compound are presented in FIGS. 7, 8, 9 and 10 of this application.

Example 70: 2-(4-(1-(Benzo[d][1,3]dioxol-5-yl)ethyl)piperazin-1-yl)pyrimidin-5-amine

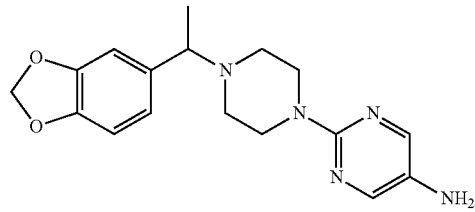 [SMILES: CC(c1ccc2c(c1)OCO2)N1CCN(c2ncc(N)cn2)CC1]

Step 1: 2-(4-(1-(Benzo[d][1,3]dioxol-5-yl)ethyl)piperazin-1-yl)-4-nitropyrimidine To a stirred solution of Intermediate 2 (1 g, 4.2 mmol) in dry DMF (10 mL), Et$_3$N (2.3 mL, 16.8 mmol) and 2-chloro-5-nitropyrimidine (0.74 g, 4.6 mmol) were added at rt and the resulting mixture was stirred at 120° C. for 20 h. It was diluted with water and extracted with EtOAc. The organic layer was dried over anhydrous Na$_2$SO$_4$ and concentrated under vacuum. The resulting crude product was purified by flash chromatography to give the title compound (yellow solid). $^1$H NMR (400 MHz, DMSO-d$_6$): δ 9.08 (s, 2H), 6.92 (s, 1H), 6.85-6.83 (m, 1H), 6.77 (s, 1H), 5.98 (m, 2H), 3.89 (s, 4H), 3.50 (s, 1H), 2.45-2.44 (m, 4H), 1.30 (br s, 3H). LCMS: (Method A) 358.0 (M+H), Rt. 3.00 min, 94.23% (Max).

Step 2: 2-(4-(1-(Benzo[d][1,3]dioxol-5-yl)ethyl)piperazin-1-yl)pyrimidin-5-amine To a stirred solution of 2-(4-(1-(benzo[d][1,3]dioxol-5-yl)ethyl)piperazin-1-yl)-4-nitropyrimidine (0.70 g, 1.9 mmol) in methanol (14 mL), Pd/C (0.07 g, 10% w/w) was added at rt and the resulting mixture was stirred under hydrogen atmosphere (5 kg/cm$^2$) overnight at rt. The reaction mixture was filtered through celite and washed with methanol. The filtrate was dried over anhydrous Na$_2$SO$_4$ and concentrated under vacuum. The crude product was purified by flash chromatography to afford the title compound (yellow solid). $^1$H NMR (400 MHz, DMSO-d$_6$): δ 7.86 (s, 2H), 6.88 (s, 1H), 6.84 (d, J=8.0 Hz, 1H), 6.75 (d, J=7.6 Hz, 1H), 6.46 (s, 2H), 5.98 (m, 2H), 3.48-3.45 (m, 4H), 2.43-2.42 (m, 2H), 2.34-2.31 (m, 2H), 1.27 (d, J=6.8 Hz, 3H). LCMS: (Method A) 328.2 (M+H), Rt. 1.91 min, 96.83% (Max). HPLC: (Method A) Rt. 1.88 min, 95.85% (Max).

Example 71: (R)-2-(4-(1-(2,3-Dihydrobenzo[b][1,4]dioxin-6-yl)ethyl)piperazin-1-yl)-N-(2-(dimethylamino)ethyl)-N-methylthiazole-5-carboxamide or (S)-2-(4-(1-(2,3-dihydrobenzo[b][1,4]dioxin-6-yl)ethyl)piperazin-1-yl)-N-(2-(dimethylamino)ethyl)-N-methylthiazole-5-carboxamide

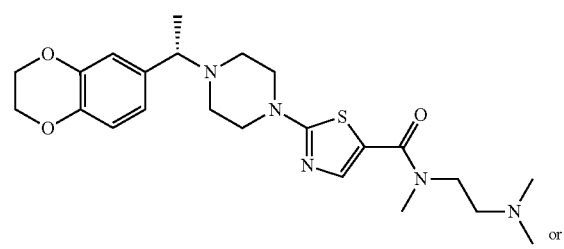

or

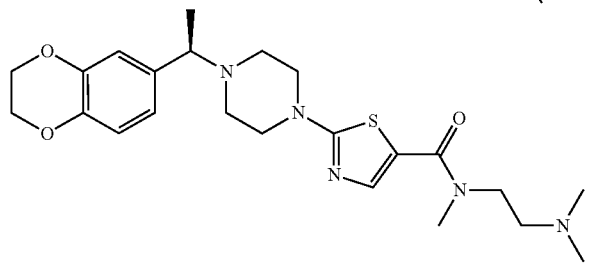

The title compound was synthesized according to the procedure described for Example 62, using N,N,N trimethyl ethylene diamine as reagent. The crude product was purified by flash chromatography, followed by chiral preparative HPLC using (Method PF) to separate both enantiomers. The first eluting compound had Rt. 14.56 min (pale brown oil). $^1$H NMR (400 MHz, DMSO-d$_6$): δ 7.57 (s, 1H), 6.80-6.73 (m, 3H), 4.21 (s, 4H), 3.52 (t, J=6.4 Hz, 2H), 3.50-3.38 (m, 5H), 3.16-3.11 (m, 3H), 2.56-2.50 (m, 1H), 2.49-2.38 (m, 5H), 2.32-2.10 (m, 6H), 1.26 (d, J=6.8 Hz, 3H). LCMS: (Method A) 460.2 (M+H), Rt. 2.12 min, 95.2% (Max). HPLC: (Method A) Rt. 2.02 min, 96.9% (Max). Chiral HPLC: (Method D) Rt. 14.56 min, 97.43%. The second eluting compound corresponds to Example 71 (Rt. 16.81 min) (pale brown oil). $^1$H NMR (400 MHz, DMSO-d$_6$): δ 7.56 (s, 1H), 6.80-6.73 (m, 3H), 4.21 (s, 4H), 3.50 (t, J=6.8 Hz, 2H), 3.48-3.36 (m, 5H), 3.09 (br. s, 3H), 2.55-2.50 (m, 1H), 2.49-2.38 (m, 5H), 2.13 (s, 6H), 1.26 (d, J=6.8 Hz, 3H). LCMS: (Method A) 460.2 (M+H), Rt. 2.13 min, 95.4% (Max). HPLC: (Method A) Rt. 2.03 min, 97.5% (Max). Chiral HPLC: (Method D) Rt. 16.81 min, 98.36%.

Example 72: N-(2-(4-(1-(benzo[d][1,3]dioxol-5-yl)ethyl)piperazin-1-yl)pyrimidin-5-yl)acetamide

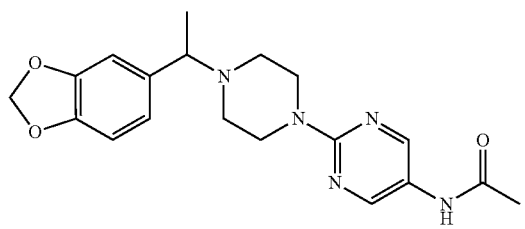 [SMILES: CC(=O)Nc1cnc(N2CCN(C(C)c3ccc4c(c3)OCO4)CC2)nc1]

To a stirred solution of Example 70 (180 mg, 0.54 mmol) in dry pyridine (1.35 mL), acetic anhydride (0.06 mL, 0.65 mmol) was added at room temperature and the resulting mixture was stirred at 50° C. overnight. It was diluted with ethyl acetate (100 mL) and washed with HCl (1.5 N), water, brine and dried over Na$_2$SO$_4$. After evaporation of the solvents, the crude product was purified by flash chromatography to afford the title compound (yellow solid). $^1$H NMR (400 MHz, DMSO-d$_6$): δ 9.82 (s, 1H), 8.46 (d, J=0.4 Hz, 2H), 6.89 (s, 1H), 6.84 (d, J=7.6 Hz, 1H), 6.76 (d, J=7.6 Hz, 1H), 5.98 (m, 2H), 3.64-3.62 (m, 4H), 3.36-3.34 (m, 1H), 2.45-2.32 (m, 4H), 2.00 (s, 3H), 1.25 (d, J=6.8 Hz, 3H). LCMS: (Method A) 370.2 (M+H), Rt. 2.30 min, 94.42% (Max). HPLC: (Method A) Rt. 2.22 min, 95.29% (Max).

Example 73: (2-(4-(1-(2,3-Dihydrobenzo[b][1,4]dioxin-6-yl)ethyl)piperazin-1-yl)thiazol-5-yl)(4-hydroxypiperidin-1-yl)methanone

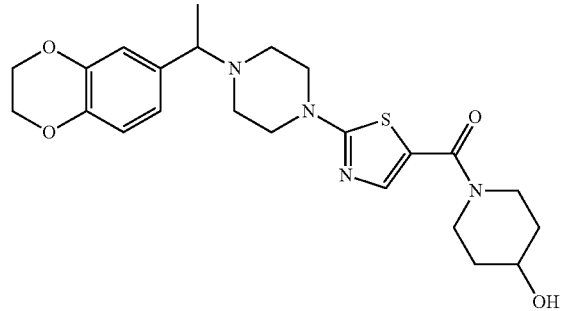 [SMILES: CC(c1ccc2c(c1)OCCO2)N1CCN(c2ncc(C(=O)N3CCC(O)CC3)s2)CC1]

Step 1: 1-(2-(4-(1-(2,3-dihydrobenzo[b][1,4]dioxin-6-yl)ethyl)piperazin-1-yl)thiazole-5-carbonyl)piperidin-4-one The title compound was synthesized according to the same procedure as described for Example 62 using piperidine-4-one, hydrochloride, mono hydrate as starting material (off white solid). $^1$H NMR (400 MHz, DMSO-$d_6$): δ 7.61 (s, 1H), 6.81-6.77 (m, 3H), 4.22 (s, 4H), 3.89 (t, J=6.1 Hz, 4H), 3.71 (t, J=6.1 Hz, 1H), 3.60 (t, J=4.2 Hz, 4H), 2.34-2.33 (m, 8H), 1.27 (d, J=6.7 Hz, 3H). LCMS: (Method A) 457.0 (M+H), Rt. 2.42 min, 90.5% (Max).

Step 2: (2-(4-(1-(2,3-Dihydrobenzo[b][1,4]dioxin-6-yl)ethyl)piperazin-1-yl)thiazol-5-yl)(4-hydroxypiperidin-1-yl)methanone To a stirred solution of 1-(2-(4-(1-(2,3-dihydrobenzo[b][1,4]dioxin-6-yl)ethyl)piperazin-1-yl)thiazole-5-carbonyl)piperidin-4-one (480 mg, 1.0 mmol) in dry MeOH (100 mL), NaBH$_4$ (59 mg, 1.5 mmol) was added slowly at 0° C. The reaction mixture was stirred at room temperature for 2 h. It was then concentrated under vacuum and the resulting crude product was dissolved in DCM, washed with water, brine and dried over anhydrous Na$_2$SO$_4$. The solvent was removed under reduced pressure to get the title compound. Yield: 69% (325 mg, off white solid). $^1$H NMR (400 MHz, DMSO-$d_6$): δ 7.48 (s, 1H), 6.80-6.73 (m, 3H), 4.78 (br. s, 1H), 4.21 (s, 4H), 3.92-3.88 (m, 2H), 3.72 (br s, 1H), 3.42-3.35 (m, 4H), 3.33-3.25 (m, 2H), 2.46-2.38 (m, 4H), 1.75-1.74 (m, 2H), 1.34-1.31 (m, 2H), 1.25 (d, J=6.8 Hz, 3H). LCMS: (Method A) 459.0 (M+H), Rt. 2.32 min, 95.8% (Max). HPLC: (Method A) Rt. 2.33 min, 97.7% (Max).

Example 74 and Example 75: (R)-(2-(4-(1-(2,3-dihydrobenzo[b][1,4]dioxin-6-yl)ethyl)piperazin-1-yl)thiazol-5-yl)(4-methylpiperazin-1-yl)methanone and (S)-(2-(4-(1-(2,3-dihydrobenzo[b][1,4]dioxin-6-yl)ethyl)piperazin-1-yl)thiazol-5-yl)(4-methylpiperazin-1-yl)methanone

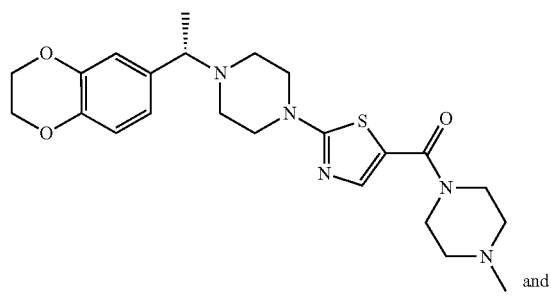
and
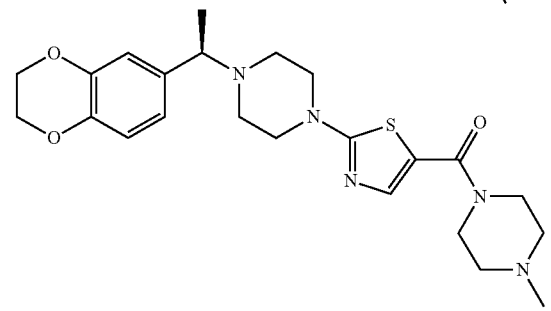

The title compounds were synthesized according to the same procedure as described for Example 62, using N-methyl piperazine as starting material. The crude mixture was purified by column chromatography followed by chiral preparative HPLC using (Method PF) to separate both enantiomers. The first eluting fraction was concentrated to give Example 74 (off white solid). $^1$H NMR (400 MHz, DMSO-$d_6$): δ 7.52 (s, 1H), 6.81-6.77 (m, 3H), 4.22 (s, 4H), 3.60 (br. s, 4H), 3.43-3.38 (m, 5H), 2.45-2.33 (m, 8H), 2.19 (s, 3H), 1.27 (d, J=6.4 Hz, 3H). LCMS: (Method A) 458.2 (M+H), Rt. 2.02 min, 99.2% (Max). HPLC: (Method A) Rt. 2.01 min, 99.7% (Max). Chiral HPLC: (Method D) Rt. 14.95 min, 98.36%. The second eluting fraction was concentrated to give Example 75 (pale brown oil). $^1$H NMR (400 MHz, DMSO-$d_6$): δ 7.52 (s, 1H), 6.81-6.74 (m, 3H), 4.22 (s, 4H), 3.60-3.59 (m, 4H), 3.43-3.37 (m, 5H), 2.50-2.31 (m, 8H), 2.19 (s, 3H), 1.27 (d, J=6.4 Hz, 3H). LCMS: (Method A) 458.2 (M+H), Rt. 2.02 min, 98.3% (Max). HPLC: (Method A) Rt. 2.01 min, 99.2% (Max). Chiral HPLC: (Method D) Rt. 17.10 min, 97.39%.

Example 77 and Example 78: (R)—N-(2-(4-(1-(benzo[d][1,3]dioxol-5-yl)ethyl)piperazin-1-yl)pyrimidin-5-yl)acetamide and (S)—N-(2-(4-(1-(benzo[d][1,3]dioxol-5-yl)ethyl)piperazin-1-yl)pyrimidin-5-yl)acetamide

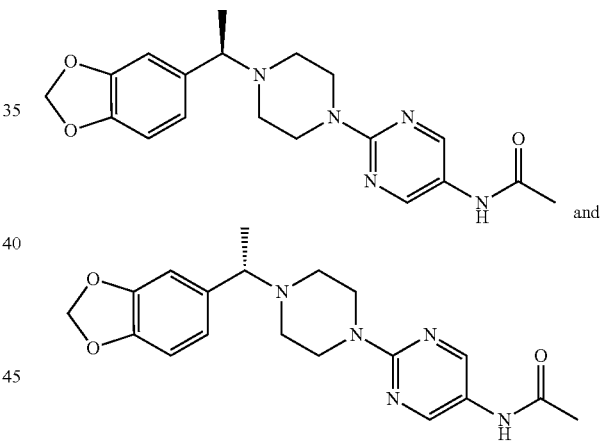

Example 72 was submitted to chiral preparative HPLC (Method PD). The first eluting fraction was concentrated, affording Example 77 (pale yellow solid). $^1$H NMR (400 MHz, DMSO-d6): δ 9.81 (s, 1H), 8.46 (s, 2H), 6.89 (s, 1H), 6.84 (d, J=8.0 Hz, 1H), 6.76 (d, J=8.0 Hz, 1H), 5.98 (m, 2H), 3.63 (t, J=4.8 Hz, 4H), 3.31 (s, 1H), 2.44-2.33 (m, 4H), 2.00 (s, 3H), 1.26 (d, J=6.0 Hz, 3H). LCMS: (Method A) 370.2 (M+H), Rt. 2.33 min, 99.5% (Max). HPLC: (Method A) Rt. 2.24 min, 99.7% (Max). Chiral HPLC: (Method F) Rt. 31.24 min, 99.05%. The second eluting fraction was concentrated, affording Example 78 (pale yellow solid). 1H NMR (400 MHz, DMSO-$d_6$): δ 9.81 (s, 1H), 8.46 (s, 2H), 6.89 (s, 1H), 6.84 (d, J=8.0 Hz, 1H), 6.76 (d, J=8.0 Hz, 1H), 5.98 (m, 2H), 3.63 (t, J=4.8 Hz, 4H), 3.31 (s, 1H), 2.41-2.32 (m, 4H), 2.00 (s, 3H), 1.26 (d, J=6.0 Hz, 3H). LCMS: (Method A) 370.2 (M+H), Rt. 2.31 min, 99.5% (Max). HPLC: (Method A) Rt. 2.25 min, 99.8% (Max). Chiral HPLC: (Method F) Rt. 21.26 min, 100.00%.

Example 79: 4-((2-(4-(1-(Benzo[d][1,3]dioxol-5-yl)ethyl)piperazin-1-yl)thiazol-5-yl)methyl)morpholine

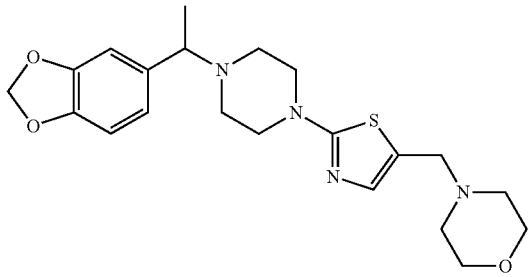 [SMILES: CC(c1ccc2c(c1)OCO2)N1CCN(c2ncc(CN3CCOCC3)s2)CC1]

Step 1: (2-(4-(1-(benzo[d][1,3]dioxol-5-yl)ethyl)piperazin-1-yl)thiazol-5-yl)methanol To a stirred solution of Example 27 (6.0 g, 16.4 mmol) in dry THF (70 mL), Super hydride (65 mL, 65.0 mmol) was added slowly at 0° C. The reaction mixture was stirred at rt for 2 h. The reaction mixture was quenched with saturated NH$_4$Cl and extracted with ethyl acetate. The organic layer was separated, dried over anhydrous Na$_2$SO$_4$, concentrated under vacuum. The crude product was purified by silica gel column chromatography (10% MeOH in DCM) to afford the title compound (white solid). $^1$H NMR (400 MHz, DMSO-d$_6$): δ 6.93 (s, 1H), 6.87-6.84 (d, J=12.8 Hz, 1H), 6.81-6.75 (m, 1H), 6.74-6.72 (d, J=8.8 Hz, 1H), 5.96-5.96 (d, J=1.2 Hz, 2H), 5.18-5.16 (d, J=7.8 Hz, 1H), 3.41-3.28 (m, 3H), 2.52-2.37 (m, 8H), 2.25 (s, 1H). LCMS: (Method A) 348.0 (M+H), Rt. 1.95 min, 97.02% (Max).

Step 2: 2-(4-(1-(benzo[d][1,3]dioxol-5-yl)ethyl)piperazin-1-yl)-5-(chloromethyl)thiazole To a stirred solution of (2-(4-(1-(benzo[d][1,3]dioxol-5-yl)ethyl)piperazin-1-yl)thiazol-5-yl)methanol (4.0 g, 11.5 mmol) in DCM (50 mL), SOCl$_2$ (1.6 mL, 23.0 mmol) was added slowly at 0° C. and the resulting mixture was stirred at rt for 1 h. It was concentrated under vacuum. The resulting crude product was taken for next step reaction without further purification. Yield: 96% (4.8 g, Yellow solid). $^1$H NMR (400 MHz, DMSO-d$_6$): δ 11.69 (s, 1H), 7.36-7.33 (m, 1H), 7.13-6.98 (m, 2H), 6.07 (s, 2H), 4.46 (d, J=12.8 Hz, 2H), 4.04-3.69 (m, 4H), 3.54-3.27 (m, 1H), 3.12-292 (m, 3H), 1.69 (d, J=6.0 Hz, 3H). LCMS: (Method A) 363 (M+H), Rt. 2.49 min, 86.01% (Max).

Step 3: 4-((2-(4-(1-(Benzo[d][1,3]dioxol-5-yl)ethyl)piperazin-1-yl)thiazol-5-yl)methyl)morpholine To a stirred solution of 2-(4-(1-(benzo[d][1,3]dioxol-5-yl)ethyl)piperazin-1-yl)-5-(chloromethyl)thiazole (0.8 g, 2.0 mmol) in dry ACN (20 mL), DIPEA (1.8 mL, 8.0 mmol) and morpholine (0.22 mL, 2.4 mmol) were added and the reaction mixture was stirred at rt overnight. The reaction mixture was diluted with EtOAc and washed with water. It was dried over anhydrous Na$_2$SO$_4$ and concentrated under vacuum. The crude product was purified by flash chromatography (10% MeOH in DCM) to afford the title compound (pale yellow solid). $^1$H NMR (400 MHz, DMSO-d$_6$): δ 6.95 (s, 1H), 6.88 (s, 1H), 6.84 (d, J=8.0 Hz, 1H), 6.75 (d, J=8.0 Hz, 1H), 5.99 (m, 2H), 3.54-3.53 (m, 4H), 3.48 (s, 2H), 3.39 (q, J=6.8 Hz, 1H), 3.25-3.40 (m, 4H), 2.40-2.33 (m, 4H), 1.28-1.27 (d, J=6.4 Hz, 3H). LCMS: (Method A) 418.0 (M+H), Rt. 1.99 min, 97.82% (Max). HPLC: (Method A) Rt. 1.78 min, 95.19% (Max).

Example 80: N-((2-(4-(1-(benzo[d][1,3]dioxol-5-yl)ethyl)piperazin-1-yl)thiazol-5-yl)methyl)-N-methylacetamide

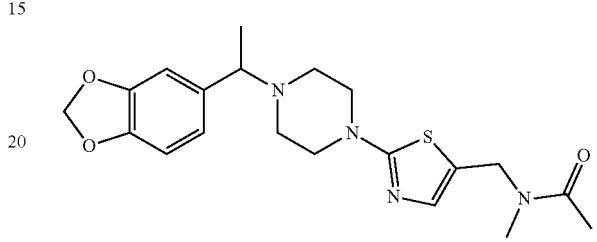

Step 1: 1-(2-(4-(1-(benzo[d][1,3]dioxol-5-yl)ethyl)piperazin-1-yl)thiazol-5-yl)-N-methylmethanamine To a stirred solution of 2-(4-(1-(benzo[d][1,3]dioxol-5-yl)ethyl)piperazin-1-yl)-5-(chloromethyl)thiazole (Example 79, Step 3, 1.2 g, 3.1 mmol) in dry ACN (20 mL), DIPEA (2.3 mL, 12.4 mmol) and methyl amine (5.0 mL, 9.3 mmol, 2 M in THF) were added dropwise. The resulting mixture was stirred at rt overnight. It was diluted with water and extracted with ethyl acetate. The organic layer was separated, dried over anhydrous Na$_2$SO$_4$, concentrated under vacuum. The crude product was purified by flash chromatography (10% MeOH in DCM) to afford the title compound (yellow solid). LCMS: (Method A) 362.0 (M+H), Rt. 1.96 min, 25.6% (Max).

Step 2: N-((2-(4-(1-(benzo[d][1,3]dioxol-5-yl)ethyl)piperazin-1-yl)thiazol-5-yl)methyl)-N-methylacetamide To a stirred solution of 1-(2-(4-(1-(benzo[d][1,3]dioxol-5-yl)ethyl)piperazin-1-yl)thiazol-5-yl)-N-methylmethanamine (0.1 g, 0.27 mmol), DIPEA (0.3 mL, 0.8 mmol) in dry DCM (10 mL), acetic anhydride (0.3 mL, 0.8 mmol) was added portion wise and the reaction mixture was stirred at rt for 12 h. It was quenched with water (10 mL) and extracted with ethyl acetate (25 mL). The organic layer was dried over anhydrous Na$_2$SO$_4$ and concentrated under vacuum. The resulting crude product was purified by flash chromatography (10% MeOH in DCM) to afford the title compound (pale yellow solid). $^1$H NMR (400 MHz, DMSO-d$_6$): δ 7.05 (d, J=9.6 Hz, 1H), 6.88 (s, 1H), 6.84 (d, J=8.0 Hz, 1H), 6.75 (d, J=8.0 Hz, 1H), 5.99-5.98 (m, 2H), 4.40 (s, 2H), 3.39 (q, J=6.0 Hz, 1H), 3.33-3.30 (m, 4H), 2.88 (s, 3H), 2.50-2.37 (m, 4H), 1.97 (s, 3H), 1.27 (d, J=6.8 Hz, 3H). LCMS: (Method A) 403.0 (M+H), Rt. 2.19 min, 97.19% (Max). HPLC: (Method A) Rt. 2.14 min, 98.5% (Max).

Example 81: (R)-(2-(4-(1-(2,3-Dihydrobenzo[b][1,4]dioxin-6-yl)ethyl)piperazin-1-yl)thiazol-5-yl)(4-hydroxypiperidin-1-yl)methanone or (S)-(2-(4-(1-(2,3-Dihydrobenzo[b][1,4]dioxin-6-yl)ethyl)piperazin-1-yl)thiazol-5-yl)(4-hydroxypiperidin-1-yl)methanone

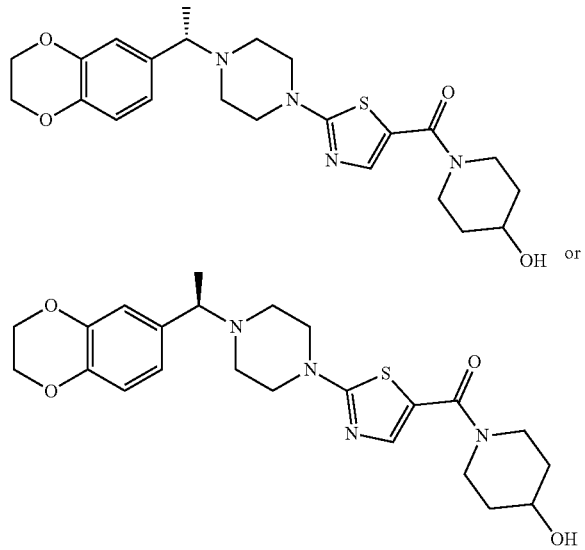

The two enantiomers of Example 73 were separated by chiral preparative HPLC, (Method PH). The first eluting compound had Rt. 32.84 min (pale brown solid). $^1$H NMR (400 MHz, DMSO-d$_6$): δ 7.49 (s, 1H), 6.79-6.77 (m, 3H), 4.78 (br. s, 1H), 4.22 (s, 4H), 3.93-3.90 (m, 2H), 3.73-3.72 (m, 1H), 3.42-3.38 (m, 5H), 3.34-3.28 (m, 2H), 2.50-2.39 (m, 4H), 1.78-1.74 (m, 2H), 1.38-1.26 (m, 5H). LCMS: (Method A) 459.0 (M+H), Rt. 2.32 min, 95.9% (Max). HPLC: (Method A) Rt. 2.21 min, 94.4% (Max). Chiral HPLC: (Method B) Rt. 32.84 min, 100%. The second eluting compound was isolated as Example 81 with Rt. 36.77 min (off white solid). $^1$H NMR (400 MHz, DMSO-d$_6$): δ 7.49 (s, 1H), 6.80-6.74 (m, 3H), 4.78 (br. s, 1H), 4.22 (s, 4H), 3.94-3.88 (m, 2H), 3.74-3.72 (m, 1H), 3.43-3.38 (m, 5H), 3.33-3.26 (m, 2H), 2.50-2.39 (m, 4H), 1.78-1.74 (m, 2H), 1.36-1.32 (m, 2H), 1.27 (d, J=6.4 Hz, 3H). LCMS: (Method A) 459.0 (M+H), Rt. 2.32 min, 98.9% (Max). HPLC: (Method A) Rt. 2.23 min, 99.8% (Max). Chiral HPLC: (Method B) Rt. 36.77 min, 94.52%.

Example 84: (2-(4-(1-(benzo[d][1,3]dioxol-5-yl)ethyl)piperazin-1-yl)thiazol-4-yl)methanamine

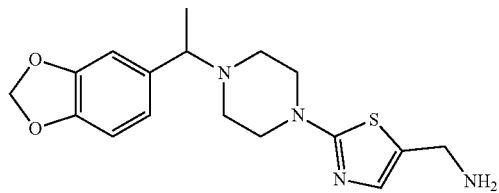 [SMILES: CC(c1ccc2c(c1)OCO2)N1CCN(c2ncc(CN)s2)CC1]

Step 1: 2-(4-(1-(benzo[d][1,3]dioxol-5-yl)ethyl)piperazin-1-yl)-4-(chloromethyl)thiazole To a stirred solution of Example 29 (1 g, 2.88 mmol) in dry DCM at 0° C., thionylchloride (0.4 mL, 8.64 mmol, spectrochem) was added dropwise. The reaction mixture was stirred at rt for 2 h. It was then concentrated and the resulting crude product was used without further purification. Yield: quantitative (1.2 g, pink solid). $^1$H NMR (400 MHz, DMSO-d$_6$): δ 7.73-7.35 (m, 1H), 7.31-6.95 (m, 2H), 6.05 (s, 2H), 5.74 (s, 1H), 5.01-4.96 (m, 1H), 4.46 (s, 1H), 3.97-3.58 (m, 4H), 3.35-3.07 (m, 4H), 1.21 ((d, J=8.8 Hz, 3H). LCMS: (Method A) 362.0 (M–H), Rt. 2.45 min, 77.9% (Max).

Step 2: 4-(azidomethyl)-2-(4-(1-(benzo[d][1,3]dioxol-5-yl)ethyl)piperazin-1-yl)thiazole To a stirred solution of 2-(4-(1-(benzo[d][1,3]dioxol-5-yl)ethyl)piperazin-1-yl)-4-(chloromethyl)thiazole (1.2 g, 3.28 mmol) in dry DCM at 0° C., sodium azide (0.32 g, 4.9 mmol, spectrochem) was added in portion. The resulting mixture was heated at 80° C. for 12 h. It was then concentrated. The residue was dissolved in DCM (50 mL), washed with water (15 mL) and dried over Na$_2$SO$_4$. After evaporation of the solvents, the crude product was used without further purification. Yield: (1.1 g, colorless liquid). LCMS: (Method A) 373.0 (M+H), Rt. 2.96 min, 78.9% (Max).

Step 3: (2-(4-(1-(benzo[d][1,3]dioxol-5-yl)ethyl)piperazin-1-yl)thiazol-4-yl)methanamine To a stirred solution of 4-(azidomethyl)-2-(4-(1-(benzo[d][1,3]dioxol-5-yl)ethyl)piperazin-1-yl)thiazole (1.1 g, 2.95 mmol) in THF (18 mL) and water (2 mL), triphenylphosphine (1.16 g, 4.4 mmol, spectrochem) was added in portion and the resulting mixture was heated at 60° C. for 12 h. The reaction mixture was concentrated in a vacuum. The residue was dissolved in DCM (25 mL), washed with water (10 mL) and dried over Na$_2$SO$_4$. After evaporation of the solvents, the crude product was purified by MD Autoprep (Method B) (off white solid). $^1$H NMR (400 MHz, DMSO-d$_6$): δ 6.88 (t, J=2.4 Hz, 2H), 6.86-6.83 (m, 1H), 6.75 (d, J=8.0 Hz, 1H), 5.98 (m, 2H), 3.70 (s, 2H), 3.40 (t, J=6.8 Hz, 1H), 3.33-3.28 (m, 4H), 2.42-2.37 (m, 4H), 1.90 (s, 2H), 1.26 (d, J=6.8 Hz, 3H). LCMS: (Method A) 347.0 (M+H), Rt. 2.59 min, 98.65% (Max). HPLC: (Method A) Rt. 1.86 min, 98.9% (Max).

Example 85: N-((2-(4-(1-(benzo[d][1,3]dioxol-5-yl)ethyl)piperazin-1-yl)thiazol-4-yl)methyl)acetamide

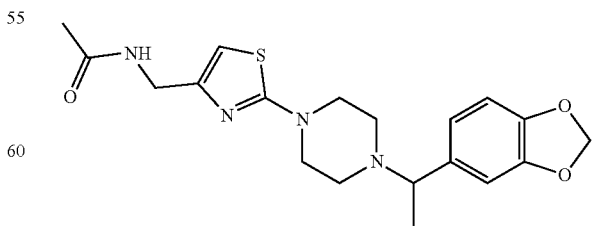

To a solution of Example 84 (0.08 g, 0.23 mmol) in dry dichloromethane (5 mL), pyridine (0.01 mL, 0.11 mmol, spectrochem) and acetic anhydride (0.01 mL, 0.11 mmol, spectrochem) were added and the resulting mixture was stirred at rt for 12 h. It was concentrated. The crude residue was dissolved in DCM (15 mL), washed with water (5 mL) and dried over Na$_2$SO$_4$. After evaporation of the solvents, the crude product was purified by MD Autoprep (Method C) (off white solid). $^1$H NMR (400 MHz, CDCl3): δ 7.00 (s, 1H), 6.90 (s, 1H), 6.77 (s, 2H), 5.97 (s, 2H), 5.77 (s, 1H), 4.43 (d, J=4.6 Hz, 2H), 3.48 (t, J=3.6 Hz, 5H), 2.56 (s, 4H), 2.00 (s, 3H), 1.41 (s, 3H). LCMS: (Method A) 389.2 (M+H), Rt. 2.02 min, 94.37% (Max). HPLC: (Method A) Rt. 1.94 min, 92.8% (Max).

Example 86: N-(5-(4-(1-(benzo[d][1,3]dioxol-5-yl)ethyl)piperazin-1-yl)thiazol-2-yl)acetamide

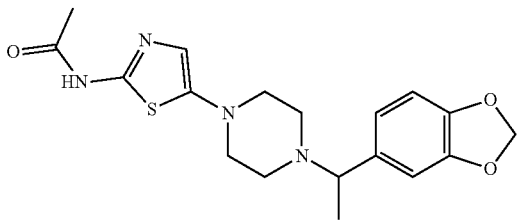 [SMILES: CC(=O)Nc1ncc(N2CCN(C(C)c3ccc4c(c3)OCO4)CC2)s1]

Step 1: 5-(4-(1-(benzo[d][1,3]dioxol-5-yl)ethyl)piperazin-1-yl)thiazol-2-amine

The title compound was synthesized following the general procedure D, using Intermediate 2 and 2-amino-5-bromo thiazole, hydrobromide salt as starting materials. Yield: 66% (0.85 g, black solid). LCMS: (Method A) 333.0 (M+H), Rt. 1.99 min, 57.8% (Max).

Step 2: N-(5-(4-(1-(benzo[d][1,3]dioxol-5-yl)ethyl)piperazin-1-yl)thiazol-2-yl)acetamide The title compound was synthesized via same procedure as described for Example 44, using 5-(4-(1-(benzo[d][1,3]dioxol-5-yl)ethyl)piperazin-1-yl)thiazol-2-amine as starting material (off white solid). $^1$H NMR (400 MHz, DMSO-d$_6$): δ 11.68 (s, 1H), 6.89 (s, 1H), 6.85 (d, J=8.0 Hz, 1H), 6.76 (d, J=7.6 Hz, 1H), 6.57 (s, 1H), 5.99 (s, 2H), 3.38-3.33 (m, 1H), 3.02-2.92 (m, 4H), 2.50-2.43 (m, 4H), 2.06 (s, 3H), 1.27 (d, J=6.4 Hz, 3H). LCMS: (Method A) 375.0 (M+H), Rt. 2.49 min, 97.9% (Max). HPLC: (Method A) Rt. 2.41 min, 97.5% (Max).

Example 96: N-(2-(4-(1-(2,3-Dihydrobenzo[b][1,4]dioxin-6-yl)ethyl)piperazin-1-yl)pyrimidin-5-yl)acetamide

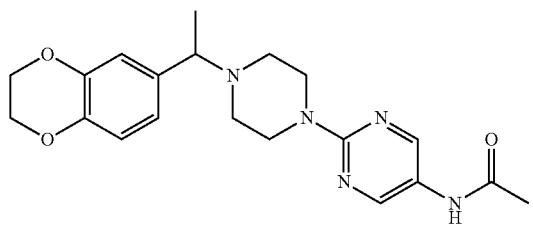 [SMILES: CC(=O)Nc1cnc(N2CCN(C(C)c3ccc4c(c3)OCCO4)CC2)nc1]

To a stirred solution of Intermediate 10 (320 mg, 1.24 mmol) in dry ACN (5 mL), DIPEA (3.66 mL, 20.28 mmol) and Intermediate 3 (270 mg, 1.36 mmol) were added and the reaction mixture was stirred at 80° C. overnight. It was concentrated under vacuum and the crude product was dissolved in EtOAc (30 mL), washed with water (10 mL) and dried over anhydrous Na$_2$SO$_4$. After evaporation of the solvents, the crude product was purified by flash chromatography to afford the title compound (pale yellow solid). $^1$H NMR (400 MHz, DMSO-d$_6$): δ 9.79 (s, 1H), 8.44 (s, 2H), 6.76-6.74 (m, 3H), 4.19 (s, 4H), 3.61 (s, 4H), 2.38-2.31 (m, 4H), 1.98 (s, 3H), 1.24 (d, J=6.4 Hz, 3H). LCMS: (Method A) 384.2 (M+H), Rt. 2.27 min, 99.82% (Max). HPLC: (Method A) Rt. 2.26 min, 98.35% (Max).

Example 97: N-(5-(4-(1-(2,3-Dihydrobenzo[b][1,4]dioxin-6-yl)ethyl)piperazin-1-yl)-1,3,4-thiadiazol-2-yl)acetamide

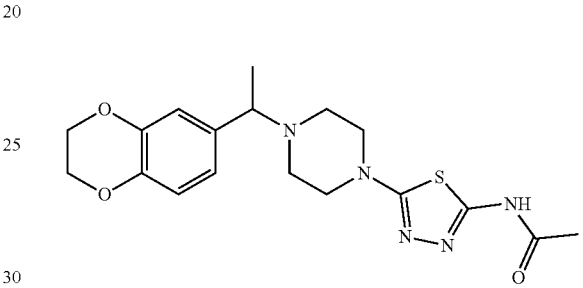

The title compound was synthesized according the same procedure as Example 96, using Intermediate 7 and Intermediate 3 as starting materials. The crude product was purified by flash chromatography followed by MD Autoprep (Method B) to give the title compound (off white solid). $^1$H NMR (400 MHz, DMSO-d$_6$): δ 12.02 (s, 1H), 6.80-6.74 (m, 3H), 4.21 (s, 4H), 3.37-3.33 (m, 5H), 2.43-2.39 (m, 4H), 2.09 (s, 3H), 1.26 (d, J=6.8 Hz, 3H). LCMS: (Method A) 390.0 (M+H), Rt. 2.39 min, 98.62% (Max). HPLC: (Method A) Rt. 2.27 min, 97.05% (Max).

Example 98: 2-(4-(1-(Benzo[d][1,3]dioxol-5-yl)ethyl)piperazin-1-yl)-N-methylpyrimidine-5-carboxamide

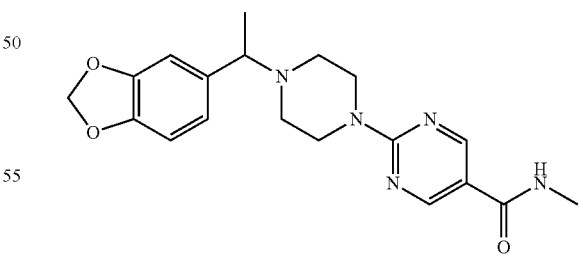

Step 1: Ethyl 2-(methylthio)pyrimidine-5-carboxylate

To a stirred solution of ethyl-4-chloro-(2-methyl thio pyrimidine) 5-carboxylate (10 g, 42.9 mmol) in THF/water (8:2, 100 mL), zinc powder (14.0 g, 0.21 mmol) followed by t-BuOH (2 mL) were added and the resulting mixture was heated at 90° C. for overnight. The reaction completion was monitored by LCMS. The mixture was filtered through celite and evaporated under vacuum. The crude product was dissolved in dichloromethane (100 mL), washed with water (50 mL) and dried over Na$_2$SO$_4$. After evaporation of the solvents, the crude product was purified by MD Autoprep (Method B) (colorless liquid). $^1$H NMR (400 MHz, DMSO-d$_6$): 9.03 (s, 2H), 4.35 (q, J=7.1 Hz, 2H), 2.58 (s, 3H), 1.33 (t, J=7.08 Hz, 3H). LCMS: (Method A) 199.0 (M+H), Rt. 3.50 min, 99.7% (Max).

Step 2: Ethyl 2-(methylsulfonyl)pyrimidine-5-carboxylate

To a stirred solution of ethyl 2-(methylthio)pyrimidine-5-carboxylate (2.8 g, 14.2 mmol) in tetrahydrofuran at 0° C., 3-chloroperbenzoic acid (7.8 g, 60.7 mmol, spectrochem) was added and the resulting solution was stirred at rt for 3 h. It was concentrated. DCM was added and was washed with water (25 mL) and 10% sodium bicarbonate solution (20 mL) and dried over Na$_2$SO$_4$. After evaporation of the solvents, the crude product was purified by flash chromatography to afford the titled product. Yield: 50.7% (1.65 g, off white solid). $^1$H NMR (400 MHz, DMSO-d$_6$): 9.48 (s, 2H), 4.43 (q, J=7.0 Hz, 2H), 3.48 (s, 3H), 1.37 (t, J=7.1 Hz, 3H), LCMS: (Method A) 230.9 (M+H), Rt. 2.33 min, 97.48% (Max).

Step 3: Ethyl 2-(4-(1-(benzo[d][1,3]dioxol-5-yl)ethyl)piperazin-1-yl)pyrimidine-5-carboxylate To a stirred solution of Intermediate 2 (1.87 g, 6.94 mmol) in dry acetonitrile, potassium carbonate (2.87 g, 20.8 mmol, spectrochem) and ethyl 2-(methylsulfonyl)pyrimidine-5-carboxylate were added and the resulting mixture was at rt for 12 h. It was filtered through celite and concentrated. Dichloromethane (25 mL) was added and the solution was washed with water, brine and dried over Na$_2$SO$_4$. After evaporation of the solvents, the crude product was purified by flash column chromatography to afford the title compound (white solid). $^1$H NMR (400 MHz, DMSO-d$_6$): 8.74 (s, 2H), 6.85 (t, J=7.8 Hz, 2H), 6.75 (d, J=7.8 Hz, 1H), 5.98 (s, 2H), 4.25 (q, J=6.8 Hz, 2H), 3.81 (s, 4H), 3.32 (s, 1H), 2.37-2.42 (m, 4H), 1.28 (d, J=6.6 Hz, 6H). LCMS: (Method A) 385.2 (M+H), Rt. 3.22 min, 98.88% (Max).

Step 4: Lithium 2-(4-(1-(benzo[d][1,3]dioxol-5-yl)ethyl)piperazin-1-yl)pyrimidine-5-carboxylate To a stirred solution of ethyl 2-(4-(1-(benzo[d][1,3]dioxol-5-yl)ethyl)piperazin-1-yl)pyrimidine-5-carboxylate (0.9 g, 2.34 mmol) in MeOH (2 mL), THF (7 mL) and water (1 mL) mixture, lithium hydroxide (0.24 g, 5.85 mmol, spectrochem) was added at 0° C. The resulting mixture was stirred at rt for 12 h. It was concentrated and the crude product was used without further purification. Yield: 90% (0.52 g, off white solid). LCMS: (Method A) 357.0 (M+H), Rt. 2.38 min, 99.21% (Max).

Step 5: 2-(4-(1-(Benzo[d][1,3]dioxol-5-yl)ethyl)piperazin-1-yl)-N-methylpyrimidine-5-carboxamide To a stirred solution of lithium 2-(4-(1-(benzo[d][1,3]dioxol-5-yl)ethyl)piperazin-1-yl)pyrimidine-5-carboxylate (300 mg, 0.82 mmol) in dry DMF (5 mL), methyl amine (0.09 mL, 0.988 mmol, 2M in THF), DIPEA (0.45 mL, 2.47 mmol) and HATU (471 mg, 1.29 mmol) were added and the resulting mixture was stirred at rt for 12 h. It was concentrated under vacuum and the crude product was diluted with DCM (20 mL), washed with water (15 mL) and dried over anhydrous Na$_2$SO$_4$. After evaporation of the solvents, the crude product was purified by MD Autoprep (Method B) to give the title compound (off white solid). $^1$H NMR (400 MHz, DMSO-d$_6$): δ 8.71 (s, 2H), 8.29 (q, J=4.4 Hz, 1H), 6.90 (d, J=1.6 Hz, 1H), 6.84 (d, J=7.6 Hz, 1H), 6.75 (dd, J=8.0, 1.2 Hz, 1H), 5.98 (m, 2H), 3.78-3.76 (m, 4H), 3.39 (q, J=6.4 Hz, 1H), 2.74 (d, J=4.8 Hz, 3H), 2.45-2.42 (m, 2H), 2.37-2.32 (m, 2H), 1.28 (d, J=6.4 Hz, 3H). LCMS: (Method A) 370.2 (M+H), Rt. 2.24 min, 97.69% (Max). HPLC: (Method A) Rt. 2.19 min, 99.52% (Max).

Example 99: 2-(4-(1-(benzo[d][1,3]dioxol-5-yl)ethyl)piperazin-1-yl)-N,N-dimethylpyrimidine-5-carboxamide

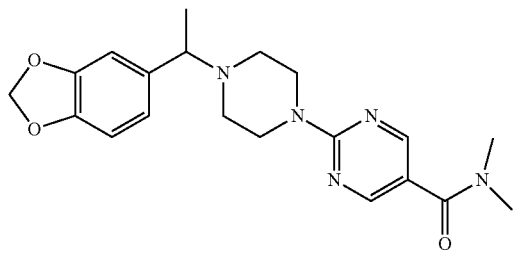 [SMILES: CC(c1ccc2c(c1)OCO2)N1CCN(c2ncc(C(=O)N(C)C)cn2)CC1]

The title compound was synthesized according the same protocol as Example 98, using dimethyl amine (2 M in THF) as reagent. The crude product was purified by MD Autoprep (Method B) to afford the title compound (white solid). $^1$H NMR (400 MHz, DMSO-d$_6$): δ 8.45 (s, 2H), 6.90 (d, J=1.2 Hz, 1H), 6.84 (d, J=7.6 Hz, 1H), 6.75 (dd, J=8.0, 1.2 Hz, 1H), 5.98 (m, 2H), 3.77-3.74 (m, 4H), 3.39 (q, J=6.4 Hz, 1H), 2.97 (s, 6H), 2.47-2.42 (m, 2H), 2.38-2.33 (m, 2H), 1.28 (d, J=6.4 Hz, 3H). LCMS: (Method A) 384.0 (M+H), Rt. 2.51 min, 99.94% (Max). HPLC: (Method A) Rt. 2.35 min, 99.85% (Max).

Example 105: N-(5-(4-(1-(benzo[d][1,3]dioxol-5-yl)ethyl)piperazin-1-yl)-1,3,4-thiadiazol-2-yl)propionamide

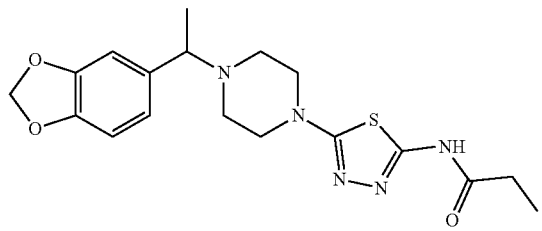 [SMILES: CCC(=O)Nc1nnc(N2CCN(C(C)c3ccc4c(c3)OCO4)CC2)s1]

To a stirred solution of Example 41 (310 mg, 1.2 mmol) in dry DCM (10 mL), TEA (0.4 mL, 2.78 mmol) and propionyl chloride (94 mg, 1.02 mmol) were added at 0° C. and the resulting mixture was stirred at rt overnight. The reaction mixture was concentrated under vacuum and the resulting crude product was purified by flash chromatography to give the title compound (white solid). $^1$H NMR (400 MHz, DMSO-d$_6$): δ 11.96 (s, 1H), 6.83 (s, 1H), 6.83 (d, J=8.0 Hz, 1H), 6.72 (d, J=8.0 Hz, 1H), 5.98 (m, 2H), 3.34-3.32 (m, 5H), 2.51-2.37 (m, 6H), 1.28 (d, J=6.8 Hz, 3H), 1.04 (d, J=7.2 Hz, 3H). LCMS: (Method A) 390.0 (M+H), Rt. 2.57 min, 99.27% (Max). HPLC: (Method A) Rt. 2.48 min, 99.7% (Max).

Example 106: N-(5-(4-(1-(benzo[d][1,3]dioxol-5-yl)ethyl)piperazin-1-yl)-1,3,4-thiadiazol-2-yl)butyramide

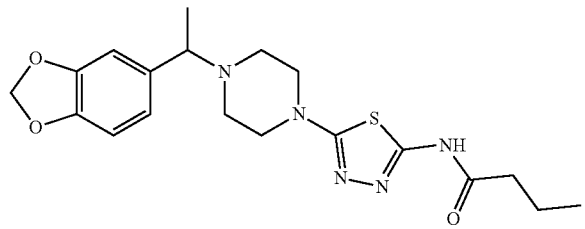 [SMILES: CCCC(=O)Nc1nnc(N2CCN(C(C)c3ccc4c(c3)OCO4)CC2)s1]

The title compound was synthesized according the same protocol as described for the synthesis of Example 105, using butyryl chloride as acylating agent. The resulting crude product was purified by flash column chromatography followed by MD Autoprep (Method B) to give the title compound (off white solid). $^1$H NMR (400 MHz, DMSO-$d_6$): δ 11.98 (s, 1H), 6.89 (d, J=1.6 Hz, 1H), 6.85 (d, J=8.0 Hz, 1H), 6.76 (dd, J=8.0, 1.6 Hz, 1H), 5.98 (m, 2H), 3.39 (q, J=5.6 Hz, 1H), 3.35-3.33 (m, 4H), 2.56-2.40 (m, 4H), 2.36 (t, J=7.6 Hz, 2H), 1.61-1.55 (m, 2H), 1.28 (d, J=6.4 Hz, 3H), 0.86 (t, J=7.2 Hz, 3H). LCMS: (Method A) 404.2 (M+H), Rt. 2.81 min, 97.58% (Max). HPLC: (Method A) Rt. 2.84 min, 99.12% (Max).

Example 107: N-(5-(4-(1-(benzo[d][1,3]dioxol-5-yl)ethyl)piperazin-1-yl)-1,3,4-thiadiazol-2-yl)isobutyramide

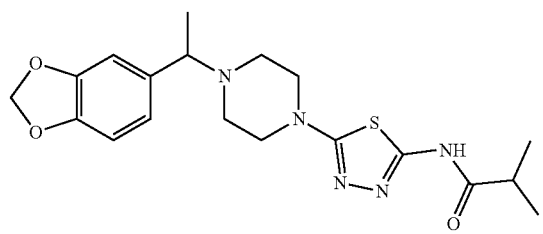 [SMILES: CC(C)C(=O)Nc1nnc(N2CCN(C(C)c3ccc4c(c3)OCO4)CC2)s1]

The title compound was synthesized according the same protocol as described for the synthesis of Example 105, using isobutyryl chloride as acylating agent. The crude product was purified by flash chromatography to give the title compound (white solid). $^1$H NMR (400 MHz, DMSO-$d_6$): δ 11.99 (s, 1H), 6.89 (d, J=1.2 Hz, 1H), 6.85 (d, J=8.0 Hz, 1H), 6.76 (dd, J=8.0, 1.2 Hz, 1H), 5.99 (m, 2H), 3.43 (q, J=6.8 Hz, 1H), 3.80-3.33 (m, 4H), 2.72-2.65 (m, 1H), 2.44-2.32 (m, 4H), 1.28 (d, J=6.8 Hz, 3H), 1.09 (d, J=6.8 Hz, 6H). LCMS: (Method A) 404.2 (M+H), Rt. 2.82 min, 98.33% (Max). HPLC: (Method A) Rt. 2.75 min, 99.73% (Max).

Example 108: N-(5-(4-(1-(benzo[d][1,3]dioxol-5-yl)ethyl)piperazin-1-yl)-1,3,4-thiadiazol-2-yl)cyclopropanecarboxamide

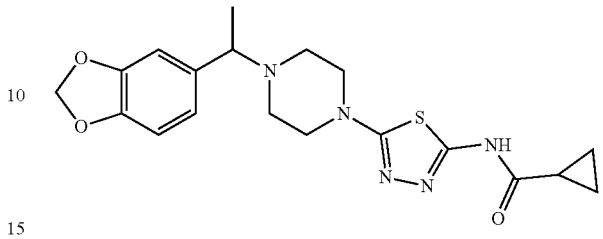

The title compound was synthesized according the same protocol as described for the synthesis of Example 105, using cyclopropane carbonyl chloride as acylating agent. The crude product was purified by flash chromatography followed by MD Autoprep (Method B) to give the title compound (off white solid). $^1$H NMR (400 MHz, DMSO-$d_6$): δ 12.30 (s, 1H), 6.89 (d, J=1.6 Hz, 1H), 6.84 (d, J=8.0 Hz, 1H), 6.76 (dd, J=8.0, 1.6 Hz, 1H), 5.99 (m, 2H), 3.39 (q, J=6.4 Hz, 1H), 3.33-3.28 (m, 4H), 2.56-2.39 (m, 4H), 1.88-1.87 (m, 1H), 1.28 (d, J=6.4 Hz, 3H), 0.90-0.83 (m, 4H). LCMS: (Method A) 402.2 (M+H), Rt. 2.63 min, 99.66% (Max). HPLC: (Method A) Rt. 2.66 min, 99.76% (Max).

Example 109: 2-(4-(1-(2,3-dihydrobenzo[b][1,4]dioxin-6-yl)ethyl)piperazin-1-yl)-N-methylthiazole-5-carboxamide

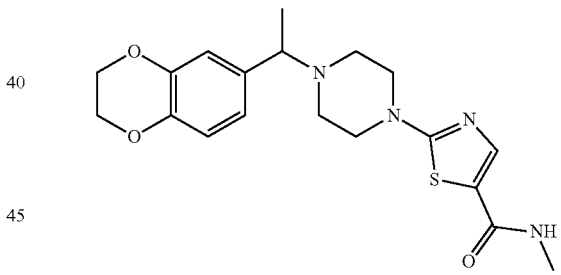

To a stirred solution of lithium 2-(4-(1-(2,3-dihydrobenzo[b][1,4]dioxin-6-yl)ethyl)piperazin-1-yl)thiazole-5-carboxylate (0.7 g, 18.37 mmol, Example 62, Step 2) in dry DMF (7 mL), methyl amine (2M in THF, 1.3 mL, 27.55 mmol), HATU (0.83 g, 22.0 mmol) and DIPEA (0.9 mL, 55.1 mmol) were added and the reaction mixture was stirred overnight at rt. It was cooled to rt and concentrated. Water (15 mL) was added to the resulting mixture and was extracted with EtOAc (2×30 mL). The organic layer was dried over anhydrous $Na_2SO_4$. After evaporation of the solvents, the crude product was purified by MD Autoprep HPLC (Method B) to afford the title compound as off white solid. $^1$H NMR (400 MHz, DMSO-$d_6$): δ 8.14 (q, J=4.0, 1H), 7.70 (s, 1H), 6.77-6.74 (m, 3H), 4.40 (s, 4H), 3.39-3.38 (m, 5H), 2.67 (d, J=4.4 Hz, 3H), 2.49-2.48 (m, 2H), 2.44-2.38 (m, 2H), 1.25 (d, J=6.4 Hz, 3H). LCMS: (Method A) 389.2 (M+H), Rt. 2.26 min, 97.94% (Max). HPLC: (Method A) Rt. 2.23 min, 98.53% (Max).

Example 110: N-(5-(4-(1-(benzo[d][1,3]dioxol-5-yl)ethyl)piperazin-1-yl)-1,3,4-thiadiazol-2-yl)-4-chlorobenzamide

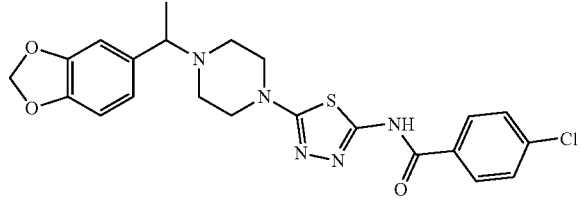 [SMILES: CC(c1ccc2c(c1)OCO2)N1CCN(c2nnc(NC(=O)c3ccc(Cl)cc3)s2)CC1]

To a stirred solution of Example 41 (0.40 g, 1.2 mmol) in dry DCM (10 mL), TEA (0.4 mL, 0.45 mmol) and 4-chlorobenzoyl chloride (0.28 g, 1.65 mmol) were added at 0° C. and the resulting mixture was stirred overnight at rt. It was concentrated under vacuum and the resulting crude product was purified by flash chromatography to give the title compound (off white solid). $^1$H NMR (400 MHz, DMSO-$d_6$): 12.69 (s, 1H), 8.06 (d, J=8.4 Hz, 2H), 7.60 (d, J=8.8 Hz, 2H), 6.75-6.89 (m, 3H), 5.99 (t, J=0.4 Hz, 2H), 3.39-3.42 (m, 5H), 2.42-2.45 (m, 4H), 1.28 (d, J=6.80 Hz, 3H), LCMS: (Method A) 471.1 (M+H), Rt. 3.59 min, 98.8% (Max). HPLC: (Method A) Rt. 3.56 min, 98.7% (Max).

Example 111: 5-(4-(1-(benzo[d][1,3]dioxol-5-yl)ethyl)piperazin-1-yl)-N-(4-chlorobenzyl)-1,3,4-thiadiazol-2-amine

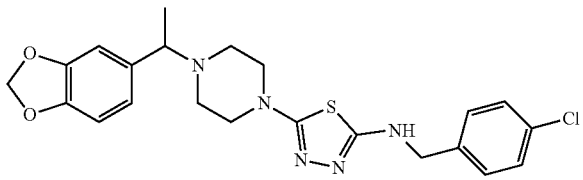 [SMILES: CC(c1ccc2c(c1)OCO2)N1CCN(c2nnc(NCc3ccc(Cl)cc3)s2)CC1]

To a stirred solution of Example 41 (0.3 g, 0.90 mmol) in dry 1,2-dichloroethane (3 mL), titanium isopropoxide (0.8 mL, 2.71 mmol) and 4-chlorobenzaldehyde (0.19 g, 1.35 mmol) were added and the reaction mixture was refluxed for 8 h. It was cooled to 0° C. and sodium borohydride (0.17 g, 4.51 mmol) was added and the mixture was stirred at rt for 2 h. It was concentrated and water (15 mL) was added to the resulting crude product. It was extracted with EtOAc (2×30 mL). The organic layer was dried over anhydrous $Na_2SO_4$. After evaporation of the solvents, the crude product was purified by MD Autoprep HPLC (Method B) to afford the title compound as off white solid. $^1$H NMR (400 MHz, DMSO-$d_6$): δ 7.58 (t, J=6.0 Hz, 1H), 7.39-7.32 (m, 4H), 6.86 (s, 1H), 6.83 (d, J=8.0 Hz, 1H), 6.73 (d, J=8.0 Hz, 1H), 6.97-6.97 (m, 2H), 4.33 (m, 2H), 3.32-3.21 (m, 1H), 3.19-3.16 (m, 4H), 2.43-2.21 (m, 4H), 1.25 (d, J=6.4 Hz, 3H). LCMS: (Method B) 458.0 (M+H), Rt. 6.16 min, 96.93% (Max). HPLC: (Method A) Rt. 3.21 min, 96.02% (Max).

Example 112: 5-(4-(1-(benzo[d][1,3]dioxol-5-yl)ethyl)piperazin-1-yl)-N-ethyl-1,3,4-thiadiazol-2-amine

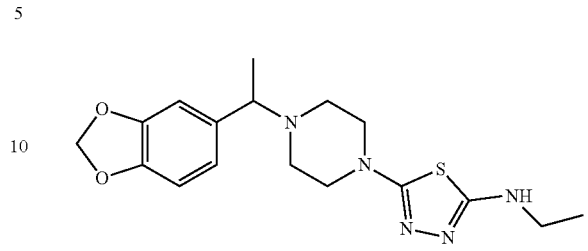

The title compound was synthesized following the same procedure as Example 111, using acetaldehyde (0.17 mL, 1.35 mmol) as starting material. After evaporation of the solvents, the crude product was purified by flash chromatography to afford the title compound as off white solid. $^1$H NMR (400 MHz, DMSO-$d_6$): δ 6.99 (t, J=5.2 Hz, 1H), 6.88 (d, J=1.2 Hz, 1H), 6.84 (d, J=7.6 Hz, 1H), 6.74 (dd, J=7.6, 1.2 Hz, 1H), 5.99-5.98 (m, 2H), 3.37 (d, J=6.4 Hz, 1H), 3.19-3.13 (m, 6H), 2.45-2.32 (m, 4H), 1.25 (d, J=6.4 Hz, 3H), 1.11 (t, d, J=6.8 Hz, 3H). LCMS: (Method A) 362.0 (M+H), Rt. 2.01 min, 96.31% (Max). HPLC: (Method A) Rt. 1.98 min, 94.56% (Max).

Example 128: N-(5-(4-(1-(2,3-dihydrobenzofuran-6-yl)ethyl)piperazin-1-yl)-1,3,4-thiadiazol-2-yl)acetamide

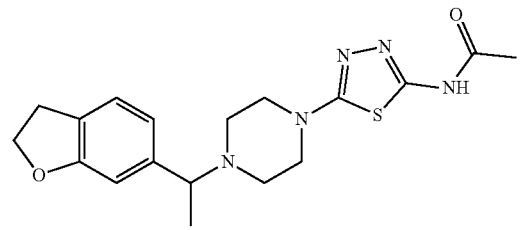 [SMILES: CC(=O)Nc1nnc(N2CCN(C(C)c3ccc4c(c3)OCC4)CC2)s1]

The title compound was synthesized according the protocol used for Example 114, using Intermediate 7 (0.3 g, 1.14 mmol) and Intermediate 21 (0.269 g, 1.48 mmol) as starting materials. The crude product was purified by flash chromatography (7% MeOH in DCM) followed by MD Autoprep HPLC (Method B) to give the title compound (off white solid). $^1$H NMR (400 MHz, DMSO-$d_6$): δ 12.02 (s, 1H), 7.12 (d, J=7.2 Hz, 1H), 6.76 (d, J=87.6 Hz, 1H), 6.71 (s, 1H), 4.51 (t, J=8.4 Hz, 2H), 3.39-3.28 (m, 5H), 3.14 (t, J=8.4 Hz, 2H), 2.42-2.39 (m, 4H), 2.09 (s, 3H), 1.28 (d, J=6.4 Hz, 3H). LCMS: (Method A) 374.2 (M+H), Rt. 2.34 min, 99.62% (Max). HPLC: (Method A) Rt. 2.32 min, 96.03% (Max).

Example 129: N-(2-(4-(1-(2,3-dihydrobenzofuran-6-yl)ethyl)piperazin-1-yl)pyrimidin-5-yl)acetamide

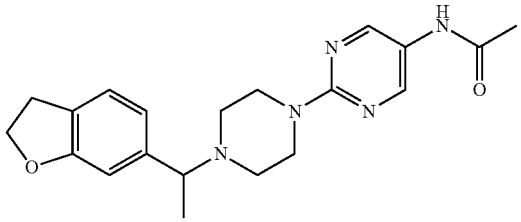 [SMILES: CC(=O)Nc1cnc(N2CCN(C(C)c3ccc4c(c3)OCC4)CC2)nc1]

The title compound was synthesized according the protocol used for Example 114, using Intermediate 10 (0.3 g, 1.16 mmol) and Intermediate 21 (0.274 g, 1.51 mmol) as starting materials. The crude product was purified by flash chromatography (10% MeOH in DCM) followed by MD Autoprep HPLC (Method B) to give the title compound (off white solid). $^1$H NMR (400 MHz, DMSO-d$_6$): δ 9.80 (s, 1H), 8.45 (s, 2H), 7.13 (d, J=7.6 Hz, 1H), 6.75-6.70 (m, 1H), 4.49 (t, J=8.4 Hz, 2H), 3.63-3.61 (m, 4H), 3.12 (t, J=8.4 Hz, 3H), 2.44-2.30 (m, 4H), 1.99 (s, 3H), 1.26 (d, J=6.4 Hz, 3H). LCMS: (Method A) 368.3 (M+H), Rt. 2.34 min, 99.74% (Max). HPLC: (Method A) Rt. 2.33 min, 99.52% (Max).

Example 132: (S)-5-(4-(1-(benzo[d][1,3]dioxol-5-yl)ethyl)piperazin-1-vi)-1,3,4-thiadiazol-2-amine

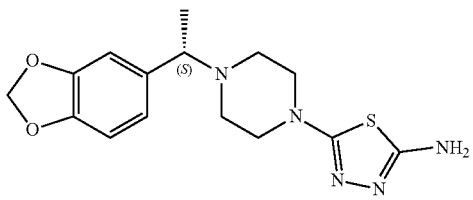

To a stirred solution of Intermediate 16 (35 g, 11.1 mmol) in ACN (30 mL), TEA (3.36 g, 33.3 mmol) and 5-bromo-1,3,4-thiadiazol-2-amine (2.19 g, 12.2 mmol) were added at rt and the mixture was heated at 85° C. overnight. The completion of the reaction was confirmed by TLC. The reaction mixture was evaporated under vacuum and the resulting crude solid was diluted with water (30 mL) and extracted with EtOAc (3×30 mL). The combined organic layer was washed with brine (30 mL), dried over Na$_2$SO$_4$ and evaporated at 45° C. under vacuum. The crude product was purified by flash chromatography (7% MeOH in DCM) to give the title compound (pale brown solid). $^1$H NMR (400 MHz, DMSO-d6): δ 6.88-6.83 (m, 2H), 6.76-6.74 (m, 1H), 6.46 (s, 2H), 5.91 (d, J=1.6 Hz, 2H), 3.39-3.37 (m, 1H), 3.20-3.17 (m, 4H), 2.46-2.30 (m, 4H), 1.25 (d, J=6.5 Hz, 3H). LCMS: (Method A) 334.0 (M+H), Rt. 1.85 min, 96.47% (Max). HPLC: (Method A) Rt. 1.79 min, 96.77% (Max). Chiral HPLC: (Method D) Rt. 20.96 min, 100.00%

Example 134: (S) 2-(4-(1-(benzo[d][1,3]dioxol-5-yl)ethyl)piperazin-1-yl)-N-methylpyrimidine-5-carboxamide

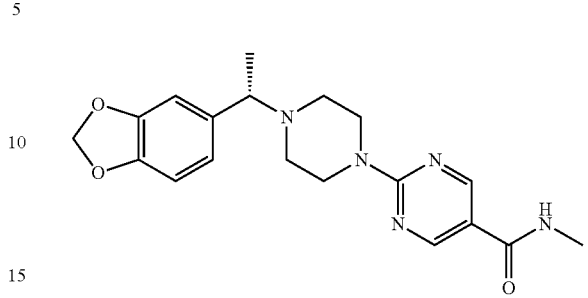

Step 1: Ethyl (S)-2-(4-(1-(benzo[d][1,3]dioxol-5-yl)ethyl)piperazin-1-yl)pyrimidine-5-carboxylate To a stirred solution of Intermediate 16 (1.87 g, 6.94 mmol) in dry acetonitrile (10 mL), potassium carbonate (2.87 g, 20.8 mmol, Spectrochem) and ethyl 2-(methylsulfonyl) pyrimidine-5-carboxylate (1.6 g, 6.94 mmol, synthesis described in Example 98, steps, 1 and 2) were added. The resulting mixture was stirred at rt for 3 h. It was then filtered through celite and concentrated. The crude product was diluted with dichloromethane (25 mL), washed with water and dried over anhydrous Na$_2$SO$_4$. After evaporation of the solvent, the crude product was purified by flash column chromatography to afford the title compound (white solid). $^1$H NMR (400 MHz, DMSO-d$_6$): δ 8.74 (s, 1H), 6.78-6.72 (m, 2H), 5.97 (s, 1H), 4.38-4.36 (m, 1H), 3.81 (s, 2H), 2.37-2.47 (m, 9H), 1.26 (d, J=2.84 Hz, 3H), LCMS: (Method A) 385.2 (M+H), Rt. 3.22 min, 98.6% (Max).

Step 2: Lithium (S)-2-(4-(1-(benzo[d][1,3]dioxol-5-yl)ethyl)piperazin-1-yl)pyrimidine-5-carboxylate To a stirred solution of ethyl (S)-2-(4-(1-(benzo[d][1,3]dioxol-5-yl)ethyl)piperazin-1-yl)pyrimidine-5-carboxylate (1.6 g, 17.5 mmol) in a mixture of MeOH (2 mL), THF (7 mL) and water (1 mL), lithium hydroxide (0.431 g, 5.20 mmol, Spectrochem) was added at 0° C. and the resulting mixture was stirred at rt for 12 h. It was concentrated and the resulting product was taken for next step without any further purification. Yield: 96% (0.61 g, off white solid). $^1$H NMR (400 MHz, DMSO-d$_6$): δ 8.61 (s, 1H), 6.81-6.88 (m, 4H), 5.97 (d, J=1.8 Hz, 2H), 3.68 (d, J=6.2 Hz, 2H), 3.22-3.21 (m, 1H), 2.28-2.35 (m, 6H), 1.26 (d, J=8.9 Hz, 3H), LCMS: (Method A) 357.0 (M+H), Rt. 2.41 min, 97.1% (Max)

Step 3: (S) 2-(4-(1-(benzo[d][1,3]dioxol-5-yl)ethyl) piperazin-1-yl)-N-methylpyrimidine-5-carboxamide To a stirred solution of lithium (S)-2-(4-(1-(benzo[d][1,3]dioxol-5-yl)ethyl)piperazin-1-yl)pyrimidine-5-carboxylate (0.3 g, 0.82 mmol) in dry DCM (10 mL), triethylamine (0.34 mL) and methylamine in THF (2 M, 1.6 mL, 3.32 mmol) were added at 0° C. The reaction mixture was stirred at rt for 1 h. The reaction progression was monitored by TLC. After completion of the reaction, the mixture was diluted with 10% sodium bicarbonate solution (10 mL) and extracted with DCM (20 mL). The organic layer was dried over Na$_2$SO$_4$ and evaporated to dryness. The crude product was purified by flash column chromatography. Yield: 56%

(0.17 g, off white solid). ¹H NMR (400 MHz, DMSO-d₆): δ 8.71 (s, 2H), 8.28 (d, J=4.8 Hz, 1H), 6.90-6.83 (m, 2H), 6.77-6.75 (m, 1H), 5.98 (d, J=2.0 Hz, 2H), 3.77 (t, J=4.8 Hz, 4H), 3.41-3.38 (m, 1H), 2.74 (d, J=4.4 Hz, 3H), 2.38-2.33 (m, 4H), 1.28 (d, J=6.8 Hz, 3H). LCMS: (Method A) 370.2 (M+H), Rt. 2.21 min, 98.9% (Max). HPLC: (Method A) Rt. 2.18 min, 99.3% (Max). Chiral HPLC: (Method G) Rt. 5.51 min, 100.00%

Example 137: (S)-2-(4-(1-(benzo[d][1,3]dioxol-5-yl)ethyl)piperazin-1-yl)-N,N-dimethylpyrimidine-5-carboxamide

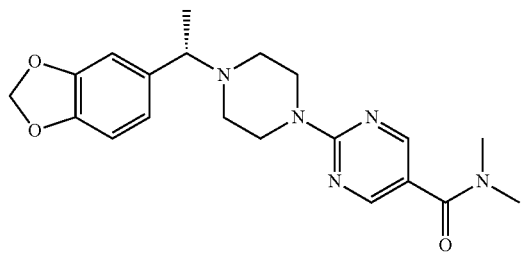

The title compound was synthesized using the same procedure as described for Example 134, using lithium (S)-2-(4-(1-(benzo[d][1,3]dioxol-5-yl)ethyl)piperazin-1-yl)pyrimidine-5-carboxylate and N,N-dimethyl amine as solution in THF as starting materials. The crude product was purified by flash column chromatography (off white solid). ¹H NMR (400 MHz, DMSO-d₆): δ 8.45 (s, 2H), 6.90 (s, 1H), 6.84 (d, J=8.0 Hz, 1H), 6.74 (d, J=7.6 Hz, 1H), 5.98 (d, J=1.6 Hz, 2H), 3.76 (t, J=4.8 Hz, 4H), 3.39-3.37 (m, 1H), 2.97 (s, 6H), 2.44-2.43 (m, 2H), 2.37-2.35 (m, 2H), 1.28 (d, J=6.8 Hz, 3H). LCMS: (Method A) 384.2 (M+H), Rt. 2.44 min, 98.2% (Max). HPLC: (Method A) Rt. 2.44 min, 98.3% (Max). Chiral HPLC: (Method G) Rt. 6.98 min, 100.00%

Example 141: (S)-5-(4-(1-(benzo[d][1,3]dioxol-5-yl)ethyl)piperazin-1-yl)-N-ethyl-1,3,4-thiadiazol-2-amine

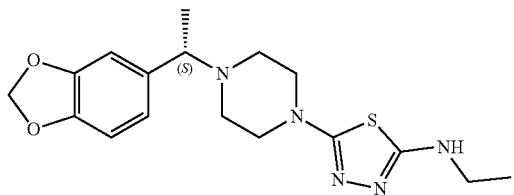

To a stirred solution of Example 132 (0.7 g, 2.1 mmol) in THF (14 mL), acetaldehyde (0.84 mL, 5M in THF) and titanium(IV)ethoxide (0.958 g, 4.2 mmol) were added and the resulting mixture was stirred at rt overnight. The completion of the reaction was confirmed by TLC. The reaction mixture was cooled to 0° C. and sodium borohydride (0.238 g, 6.3 mmol) was added. The reaction mixture was stirred 2 h at rt. It was quenched with water (10 mL) and filtered through celite. The celite bed washed with EtOAc (2×50 mL) and the filtrate was washed with water (10 mL), brine (10 mL), dried over Na₂SO₄. It was evaporated at 50° C. under vacuum. The crude product was purified by MD Autoprep HPLC (Method D) to give the title compound (off white solid). ¹H NMR (400 MHz, DMSO-d₆): δ 6.98 (t, J=5.2 Hz, 2H), 6.88 (d, J=1.2 Hz, 1H), 6.84 (d, J=8.0 Hz, 1H), 6.75 (dd, J=8.0, 1.2 Hz, 1H), 5.99-5.98 (m, 2H), 3.37 (q, J=6.8 Hz, 2H), 3.20-3.14 (m, 6H), 2.47-2.36 (m, 4H), 1.26 (d, J=6.8 Hz, 3H), 1.11 (t, J=7.2 Hz, 3H). LCMS: (Method A) 362.0 (M+H), Rt. 2.01 min, 99.75% (Max). HPLC: (Method A) Rt. 2.02 min, 97.69% (Max). Chiral HPLC: (Method B) Rt. 3.90 min, 100%

Example 142: (S)-5-(4-(1-(benzo[d][1,3]dioxol-5-yl)ethyl)piperazin-1-yl)-N-propyl-1,3,4-thiadiazol-2-amine

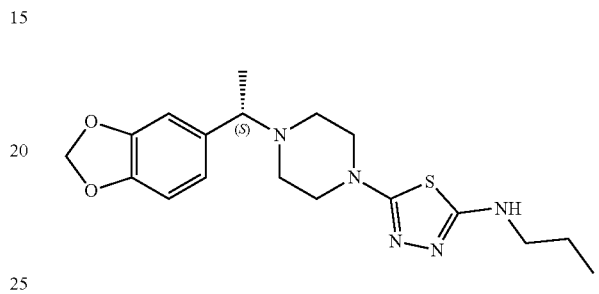

To a stirred solution of Example 132 (0.5 g, 1.5 mmol) in THF (10 mL), propionaldehyde (0.17 g, 3.0) and titanium (IV)ethoxide (0.684 g, 3.0 mmol) were added at rt and stirred overnight. The completion of the reaction was confirmed by TLC. The reaction mixture was cooled to 0° C. and sodium borohydride (0.17 g, 4.4 mmol) was added. The reaction mixture was stirred for 2 h at rt. It was quenched with water (10 mL) and filtered through celite. The celite bed washed with EtOAc (2×50 mL) and the filtrate was washed with water (10 mL), brine solution (10 mL) and dried over Na₂SO₄. It was evaporated at 50° C. under vacuum. The crude product was purified by MD Autoprep HPLC (Method D) to give the title compound (off white solid). ¹H NMR (400 MHz, DMSO-d₆): δ 7.02 (t, J=5.2 Hz, 2H), 6.88 (d, J=1.6 Hz, 1H), 6.84 (d, J=7.6 Hz, 1H), 6.75 (dd, J=7.6, 1.6 Hz, 1H), 5.99-5.98 (m, 2H), 3.41 (q, J=6.4 Hz, 2H), 3.20-3.17 (m, 4H), 3.11-3.06 (m, 2H), 2.45-2.32 (m, 4H), 1.56-1.47 (m, 2H), 1.26 (d, J=6.4 Hz, 3H), 0.86 (t, J=7.6 Hz, 3H). LCMS: (Method A) 376.0.0 (M+H), Rt. 2.23 min, 99.08% (Max). HPLC: (Method A) Rt. 2.21 min, 97.11% (Max). Chiral HPLC: (Method B) Rt. 3.61. min, 100%.

Example 144: 2-(4-(1-(Benzo[d][1,3]dioxol-5-yl)ethyl)piperazin-1-yl)-4-methylthiazole

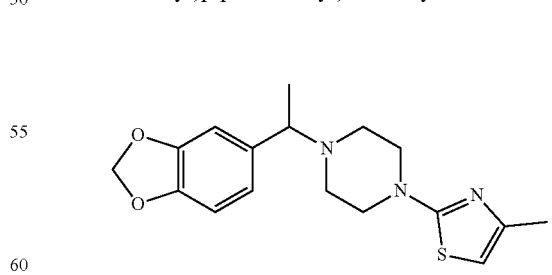

Step 1: tert-Butyl 4-(4-methylthiazol-2-yl)piperazine-1-carboxylate

To a stirred solution of tert-butyl 4-carbamothioylpiperazine-1-carboxylate (synthesized according to Example 5, Step 1, 1.0 g, 4.08 mmol) in dioxane (10 mL), TEA (0.58 g, 5.3 mmol) and bromo acetone (0.67 mL, 5.3 mmol) were added at rt and the resulting mixture was stirred at 90° C. for 16 h. The completion of the reaction was monitored by TLC. The reaction mixture was diluted with water (10 mL) and extracted with EtOAc (2×25 mL). The organic layer was dried over anhydrous $Na_2SO_4$, concentrated under vacuum. The crude product was taken as such for next step. Yield: 77% (0.9 g, pale yellow solid). LCMS: (Method A) 284.0 (M+H), Rt. 2.74 min, 83.2% (Max).

Step 2: 4-Methyl-2-(piperazin-1-yl)thiazole hydrochloride

To a stirred solution of tert-butyl 4-(4-methylthiazol-2-yl)piperazine-1-carboxylate (1.0 g, 3.53 mmol) in dry dioxane (2 mL), HCl in dioxane (4 N, 10 mL) was added at rt and the resulting mixture was stirred for 3 h. It was concentrated under vacuum and the resulting crude product was triturated in $Et_2O$, filtrated and dried under vacuum to afford the title compound. Yield: 75% (500 mg, off white solid).

Step 3: 2-(4-(1-(Benzo[d][1,3]dioxol-5-yl)ethyl) piperazin-1-yl)-4-methylthiazole The title compound was synthesized by following general procedure D, using 4-methyl-2-(piperazin-1-yl)thiazole hydrochloride (1.01 g, 5.41 mmol) and Intermediate 1 (1.0 g, 5.41 mmol). The crude product was purified by flash chromatography (1.2-1.5% MeOH in DCM) to afford the title compound (colorless oil). $^1$H NMR (400 MHz, DMSO-$d_6$): δ 6.88 (s, 1H), 6.83 (d, J=8.0 Hz, 1H), 6.75 (d, J=7.6 Hz, 1H), 6.34 (s, 1H), 5.97 (s, 2H), 3.39-3.37 (m, 1H), 3.32-3.29 (m, 4H), 2.46-2.43 (m, 2H), 2.41-2.37 (m, 2H), 2.10 (s, 1H), 1.26 (d, J=6.8 Hz, 3H). LCMS: (Method A) 332.0 (M+H), Rt. 2.04 min, 99.1% (Max). HPLC: (Method A) Rt. 2.02 min, 99.6% (Max).

Example 148: 2-(4-(1-(benzo[d][1,3]dioxol-5-yl)ethyl)piperazin-1-yl)-6,7-dihydrothiazolo[5,4-c]pyridin-4(5H)-one

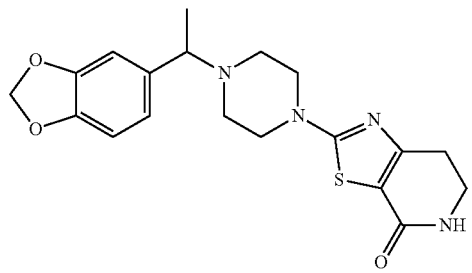 [SMILES: CC(c1ccc2c(c1)OCO2)N1CCN(c2nc3c(s2)C(=O)NCC3)CC1]

To a stirred solution of Intermediate 25 (0.75 g, 2.43 mmol) in dry DMF (7 mL), TEA (1.4 mL, 7.30 mmol) and Intermediate 1 (0.9 g, 4.87 mmol) were added at rt. The resulting mixture was stirred overnight at 120° C. It was cooled to rt and DMF was evaporated under reduced pressure. Resulting crude product was purified by flash column chromatography followed by MD Autoprep HPLC (Method B), affording the title product (off white solid). $^1$H NMR (400 MHz, DMSO-$d_6$): δ 7.32 (s, 1H), 6.86-6.84 (m, 3H), 5.99-5.98 (m, 2H), 3.45-3.44 (m, 4H), 3.38-3.34 (m, 2H), 2.70-2.67 (m, 2H), 2.50-2.59 (m, 4H), 1.28-1.23 (m, 3H). LCMS: (Method A) 387.2 (M+H), Rt. 2.15 min, 96.71% (Max). HPLC: (Method A) Rt. 2.11 min, 94.32% (Max).

Example 166: (S)-1-(1-(benzo[d][1,3]dioxol-5-yl) ethyl)-4-(5-(trifluoromethyl)pyridin-2-yl)piperazine

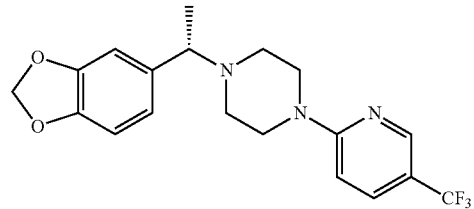 [SMILES: C[C@@H](c1ccc2c(c1)OCO2)N1CCN(c2ccc(C(F)(F)F)cn2)CC1]

To a stirred solution of Intermediate 16 (0.25 g, 0.93 mmol) in dry DMF (5 mL), TEA (0.4 mL, 2.7 mmol) and 2-chloro-5-fluoro methyl pyridine (0.16 g, 9.3 mmol) were added at rt. The resulting reaction mixture was stirred at 90° C. for 12 h. It was cooled to rt, concentrated and diluted with dichloromethane (30 mL). The resulting solution was washed with saturated NaCl solution (10 mL), dried over anhydrous $Na_2SO_4$ and concentrated. The resulting crude product was purified by flash chromatography affording the title compound (brown oil). $^1$H NMR (400 MHz, DMSO-$d_6$): δ 8.38 (s, 1H), 7.78 (dd, J=9.2, 2.4 Hz, 1H), 6.88 (d, J=8.0 Hz, 2H), 6.84 (d, J=8.0 Hz, 1H), 6.77-6.75 (m, 1H), 5.99-5.98 (m, 2H), 3.60 (t, J=4.8 Hz, 4H), 3.40-3.37 (m, 1H), 2.48-2.44 (m, 4H), 1.27 (d, J=6.4 Hz, 3H). LCMS: (Method A) 380.0 (M+H), Rt. 3.73 min, 98.89% (Max). HPLC: (Method A) Rt. 3.67 min, 99.06% (Max).

Example 167: (S)-1-(2-(4-(1-(benzo[d][1,3]dioxol-5-yl)ethyl)piperazin-1-yl)pyrimidin-5-yl)ethan-1-one

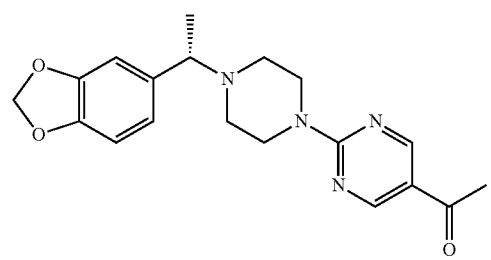 [SMILES: CC(=O)c1cnc(N2CCN([C@@H](C)c3ccc4c(c3)OCO4)CC2)nc1]

Step 1: 1-(2-chloropyrimidin-5-yl)ethan-1-one

5-Bromo 2-chloro pyrimidine (2 g, 10.33 mmol, Combi-Blocks) was degassed for 30 min. 1-Ethoxy vinyl tributyltin (4.1 mL, 11.3 mmol, Frontier Scientific) and bis(triphenylphosphine)palladium dichloride (0.36 g, 0.51 mmol) were added at rt. The resulting mixture was stirred overnight at 90° C. It was cooled to rt and filtered through celite. An aqueous HCl solution (6 N, 10 mL) was added and the mixture was stirred for 1 hour at rt. It was neutralized with sat.$NaHCO_3$ solution (15 mL), extracted with DCM (50 mL), dried over anhydrous $Na_2SO_4$ and concentrated. The crude product was purified by flash column chromatography to afford the title compound (pale yellow solid). $^1$H NMR (400 MHz, DMSO-d$_6$): δ 8.90 (s, 2H), 2.65 (s, 3H). LCMS: (Method B) 162.0 (M+H), Rt. 4.6 min, 98.01% (Max).

Step 2: (S)-1-(2-(4-(1-(benzo[d][1,3]dioxol-5-yl)ethyl)piperazin-1-yl)pyrimidin-5-yl)ethan-1-one To a stirred solution of Intermediate 16 (1.14 g, 4.24 mmol) in dry DMF (10 mL), TEA (1.1 mL, 16.5 mmol) and 1-(2-chloropyrimidin-5-yl)ethan-1-one obtained in the previous step (0.6 g, 3.85 mmol) were added at rt. The resulting mixture was heated to 90° C. for 12 h. It was cooled to rt and concentrated. Dichloromethane (50 mL) was added and was washed with a saturated NaCl solution (10 mL), dried over anhydrous Na$_2$SO$_4$ and concentrated. The crude product was purified by flash chromatography, affording the title compound (off white solid). $^1$H NMR (400 MHz, DMSO-d$_6$): δ 8.83 (s, 2H), 6.90 (s, 1H), 6.84 (d, J=7.6 Hz, 1H), 6.74 (dd, J=8.0, 1.2 Hz, 1H), 5.99-5.98 (m, 2H), 3.84 (t, J=4.8 Hz, 4H), 3.40-3.36 (m, 1H), 2.49-2.47 (m, 5H), 2.38-2.35 (m, 2H), 1.27 (d, J=6.8 Hz, 3H). LCMS: (Method A) 355.0 (M+H), Rt. 2.61 min, 99.78% (Max). HPLC: (Method A) Rt. 2.55 min, 99.51% (Max).

Example 168: 1-(2-(4-((S)-1-(benzo[d][1,3]dioxol-5-yl)ethyl)piperazin-1-yl)pyrimidin-5-yl)ethan-1-ol

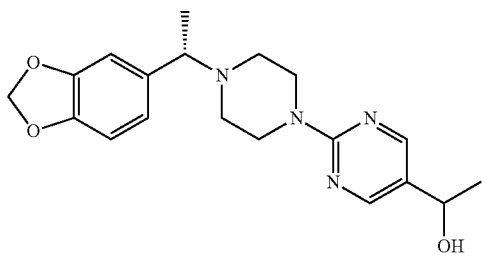 [SMILES: CC(O)c1cnc(N2CCN([C@@H](C)c3ccc4c(c3)OCO4)CC2)nc1]

To a stirred solution of Example 167 (0.2 g, 0.56 mmol) in dry MeOH (5 mL), sodium borohydride (0.48 g, 0.84 mmol, spectrochem) was added portion wise at 0° C. The resulting mixture was stirred at rt for 1 h. It was concentrated, diluted with DCM (20 mL) and washed with brine solution (5 mL) and dried over Na$_2$SO$_4$. After evaporation of the solvent, the crude product was purified by flash column chromatography to afford the titled compound. Yield: 77% (0.154 g, brown oil). $^1$H NMR (400 MHz, DMSO-d$_6$): δ 8.29 (s, 2H), 6.89 (s, 1H), 6.84 (d, J=8.0 Hz, 1H), 6.76 (dd, J=8.0, 1.6 Hz, 1H), 5.99-5.98 (m, 2H), 5.12 (d, J=4.4 Hz, 1H), 4.62-4.59 (m, 1H), 3.67 (t, J=5.2 Hz, 4H), 3.39-3.37 (m, 1H), 2.42-2.40 (m, 2H), 2.35-2.32 (m, 2H), 1.32-1.27 (m, 6H). LCMS: (Method A) 357.2 (M+H), Rt. 2.38 min, 99.04% (Max). HPLC: (Method A) Rt. 2.31 min, 98.15% (Max).

Example 171: 2-(4-(1-(benzo[d][1,3]dioxol-5-yl)ethyl)piperazin-1-yl)-6,7-dihydrothiazolo[5,4-c]pyridin-4(5H)-one

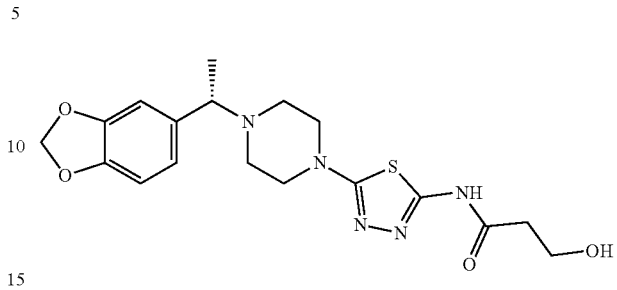

To a stirred solution of 3-hydroxypropionic acid (97 mg, 1.0 mmol) in dry NMP (5 mL), Example 132 (300 mg, 0.9 mmol), triethylamine (0.18 mg, 1.8 mmol) and HATU (513 mg, 1.3 mmol) were added at 0° C. The resulting mixture was stirred at rt for 1 h. It was was diluted with water (15 mL) and extracted with EtOAc (2×15 mL). Combined organic layers was dried over Na$_2$SO$_4$. After evaporation of the solvents, the crude product was further purified by MD Autoprep HPLC (Method B), affording the title compound (off white solid). $^1$H NMR (400 MHz, DMSO-d$_6$): δ11.98 (s, 1H), 6.88 (s, 1H), 6.84 (d, J=8.0 Hz, 1H), 6.75 (d, J=8.0 Hz, 1H), 5.98-5.97 (m, 2H), 4.71 (t, J=5.2 Hz, 1H), 3.69-3.64 (m, 2H), 3.40-3.32 (m, 5H), 2.54-2.32 (m, 6H), 1.25 (d, J=6.4 Hz, 3H). LCMS: (Method A) 406.0 (M+H), Rt. 2.15 min, 99.05% (Max). HPLC: (Method A) Rt. 2.11 min, 98.88% (Max).

Example 173: (S)-2-(4-(1-(benzo[d][1,3]dioxol-5-yl)ethyl)piperazin-1-yl)-5-fluoropyrimidine

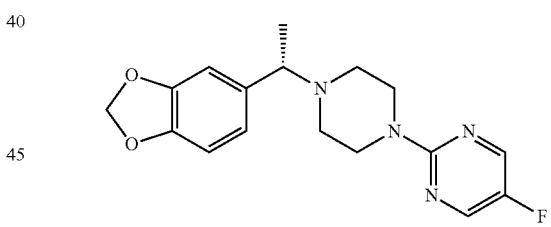

To a stirred solution of Intermediate 16 (0.4 g, 1.50 mmol) in dry DMF (10 mL), TEA (0.6 mL, 4.5 mmol) and 2-chloro-5-fluoro pyrimidine (0.2 g, 1.5 mmol) were added at rt and the reaction mixture was stirred at 90° C. for 12 h. It was cooled to rt and concentrated. Dichloromethane (50 mL) was added and the mixture was washed with sat NaCl solution (10 mL) dried over anhydrous Na$_2$SO$_4$. After evaporation of the solvents, the crude product was purified by flash chromatography to give the title compound (colourless oil). $^1$H NMR (400 MHz, DMSO-d$_6$): δ 8.42 (s, 2H), 7.43 (d, J=7.6 Hz, 1H), 6.89-6.85 (m, 1H), 6.75 (dd, J=7.6, 1.2 Hz, 1H), 5.99-5.98 (m, 2H), 3.65 (t, J=5.2 Hz, 4H), 3.37-3.35 (m, 1H), 2.43-2.41 (m, 2H), 2.37-2.35 (m, 2H), 1.28 (d, J=6.4 Hz, 3H). LCMS: (Method A) 331.0 (M+H), Rt. 2.88 min, 99.79% (Max). HPLC: (Method A) Rt. 2.82 min, 99.93% (Max).

Example 175: (S)-2-(4-(1-(benzo[d][1,3]dioxol-5-yl)ethyl)piperazin-1-yl)-5-bromopyrimidine

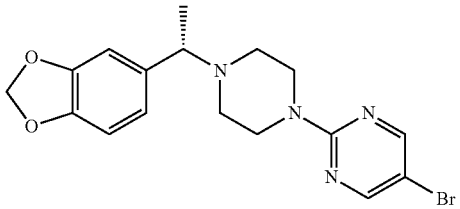 [SMILES: C[C@@H](c1ccc2c(c1)OCO2)N1CCN(c2ncc(Br)cn2)CC1]

To a stirred solution of Intermediate 16 (4.1 g, 15.5 mmol) in dry DMF (30 mL), TEA (6.4 mL, 46.5 mmol) and 5-bromo-2-chloro pyrimidine (3 g, 15.5 mmol) were added at rt and the reaction mixture was stirred at 90° C. for 12 h. It was cooled to rt and concentrated under reduced pressure. Dichloromethane (150 mL) was added. The solution was washed with brine (50 mL) and dried over anhydrous Na$_2$SO$_4$. After evaporation of the solvents, the crude product was purified by flash chromatography affording the title compound. Yield: 57% (3.5 g, white solid). $^1$H NMR (400 MHz, DMSO-d$_6$): δ 8.43 (s, 2H), 6.83-6.89 (m, 2H), 6.76 (d, J=7.8 Hz, 1H), 5.99-5.98 (m, 2H), 3.67 (t, J=4.8 Hz, 4H), 3.37-3.33 (m, 1H), 2.41-2.33 (m, 4H), 1.28 (d, J=6.6 Hz, 3H). LCMS: (Method A) 391.0 (M+H), Rt. 3.25 min, 99.9% (Max).

Example 176: (S)-2-(2-(4-(1-(benzo[d][1,3]dioxol-5-yl)ethyl)piperazin-1-yl)pyrimidin-5-yl)propan-2-ol

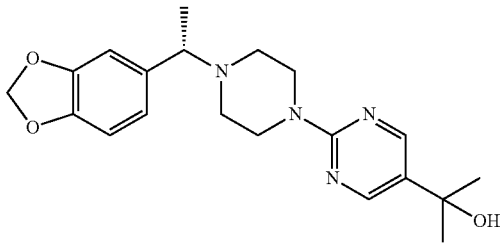 [SMILES: C[C@@H](c1ccc2c(c1)OCO2)N1CCN(c2ncc(C(C)(C)O)cn2)CC1]

To a stirred solution of Example 175 (0.5 g, 1.28 mmol) in dry THF (10 mL) cooled at –78° C., n-BuLi (1.6 M, 1.2 mL, 19.2 mmol, Aldrich) was added. The mixture was stirred at –78° C. for 1 h. Dry acetone in THF (0.89 g, 1.53 mmol, Aldrich) was then added at the same temperature and the mixture was stirred for 10 minutes. The temperature was increased to rt over 1 h. The reaction mixture was quenched with saturated ammonium chloride solution (10 mL). The desired product was extracted with EtOAc (50 mL), washed with sat NaCl solution (20 mL) and dried over anhydrous Na$_2$SO$_4$. After evaporation of the solvents, the crude product was purified by MD Autoprep HPLC (Method D), affording the title product (off white solid). $^1$H NMR (400 MHz, DMSO-d$_6$): 8.33 (s, 2H), 6.89-6.83 (m, 2H), 6.77-6.74 (m, 1H), 5.99-5.98 (m, 2H), 5.05 (s, 1H), 3.66 (d, J=4.8 Hz, 4H), 3.38-3.35 (m, 1H), 2.45-2.43 (m, 2H), 2.35-2.32 (m, 2H), 1.59 (s, 6H), 1.28 (d, J=6.8 Hz, 3H). LCMS: (Method A) 371.2 (M+H), Rt. 2.5 min, 99.51% (Max). HPLC: (Method A) Rt. 2.46 min, 98.9% (Max).

Example 177: (S)—N-(2-(4-(1-(benzo[d][1,3]dioxol-5-yl)ethyl)piperazin-1-yl)pyrimidin-5-yl)-3-hydroxypropanamide

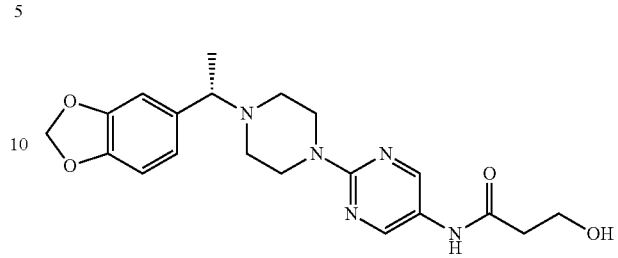

Step 1: (S)-2-(4-(1-(Benzo[d][1,3]dioxol-5-yl)ethyl)piperazin-1-yl)-4-nitropyrimidine To a stirred solution of Intermediate 16 (4.8 g, 18.7 mmol) in dry ACN (15 mL), Et$_3$N (10.5 mL, 75.0 mmol) and 2-chloro-5-nitropyrimidine (3.0 g, 18.7 mmol) were added at rt. The mixture was heated at 80° C. overnight. It was cooled to rt, diluted with DCM (20 mL), washed with water (15 mL) and brine (15 mL), and dried over anhydrous Na$_2$SO$_4$. After evaporation of the solvents, the crude product was triturated with MeOH, filtered and dried under vacuum, affording the title compound. Yield: 75% (3.8 g, pale yellow solid). LCMS: (Method A) 358.3 (M+H), Rt. 2.94 min, 98.07% (Max).

Step 2: (S)-2-(4-(1-(Benzo[d][1,3]dioxol-5-yl)ethyl)piperazin-1-yl)pyrimidin-5-amine To a stirred solution of (S)-2-(4-(1-(Benzo[d][1,3]dioxol-5-yl)ethyl)piperazin-1-yl)-4-nitropyrimidine obtained in the previous step (1.0 g, 62.9 mmol) in a mixture of methanol (100 mL) and THF (100 mL), 10% Pd/C (200 mg, 20% w/w) was added at rt. The reaction mixture was stirred under hydrogen atmosphere (1 kg/cm$^2$) at rt overnight. Completion of the reaction was confirmed by TLC. The reaction mixture was filtered through celite and washed with methanol. After evaporation of the solvents, the title compound was obtained and used in the next step without further purification. Yield: 96% (1.0 g, pale brown solid). LCMS: (Method A) 328.2 (M+H), Rt. 1.52 min, 90.58% (Max).

Step 3: (S)—N-(2-(4-(1-(benzo[d][1,3]dioxol-5-yl)ethyl)piperazin-1-yl)pyrimidin-5-yl)-3-hydroxypropanamide To a stirred solution of 3-hydroxypropionic acid (132 mg, 1.0 mmol) in dry DMF (2 mL), (S)-2-(4-(1-(benzo[d][1,3]dioxol-5-yl)ethyl)piperazin-1-yl)pyrimidin-5-amine obtained in the previous step (400 mg, 1.2 mmol), DIPA (236 mg, 1.83 mmol) and HATU (557 mg, 1.83 mmol) were added at 0° C. The reaction mixture was stirred at rt overnight. The completion of the reaction was monitored by TLC. The reaction mixture was diluted water (10 mL) and extracted with DCM (15 mL). The organic layer was dried over anhydrous Na$_2$SO$_4$ and evaporated. The crude product was purified by preparative HPLC (Method B), affording the title product (off white solid). $^1$H NMR (400 MHz, CDCl$_3$): δ 8.40 (s, 2H), 7.79 (br s, 1H), 6.88 (s, 1H), 6.75 (s, 2H), 5.96-5.95 (m, 2H), 3.97 (t, J=6.8 Hz, 2H), 3.77 (t, J=4.8 Hz, 4H), 3.35 (q, J=6.8 Hz, 1H), 2.56-2.62 (m, 2H), 2.48-2.55 (m, 2H), 2.42-2.51 (m, 2H), 1.37 (d, J=6.8 Hz, 3H). LCMS:

(Method A) 400.2 (M+H), Rt. 2.11 min, 99.42% (Max). HPLC: (Method A) Rt. 2.06 min, 98.9% (Max).

Example 180: (S)-1-(2-(4-(1-(benzo[d][1,3]dioxol-5-yl)ethyl)piperazin-1-yl)pyrimidin-5-yl)cyclohexan-1-ol

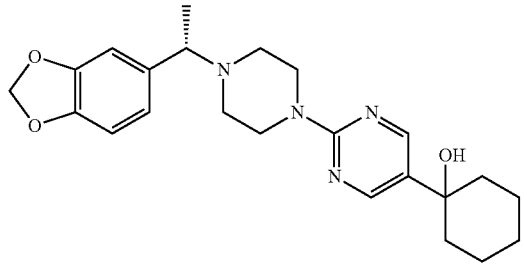 [SMILES: C[C@@H](c1ccc2c(c1)OCO2)N1CCN(c2ncc(C3(O)CCCCC3)cn2)CC1]

To a stirred solution of Example 175 (0.5 g, 1.28 mmol) in dry THF (10 mL) at −78° C., n-BuLi (1.6M, 0.9 mL, 15.3 mmol, Aldrich) was added and the reaction mixture was stirred at −78° C. for 1 h. Cyclohexanone (0.15 g, 1.53 mmol, Aldrich) in dry THF (1 mL) was added at −78° C. and the mixture was stirred for 10 minutes. The temperature was increased to rt over 1 h. The reaction completion was monitored by TLC. The reaction was quenched with saturated ammonium chloride solution (10 mL) and was extracted with EtOAc (50 mL). The organic layer was washed with sat NaCl solution (20 mL) dried over anhydrous $Na_2SO_4$ and the solvents were evaporated under reduced pressure. The crude product was purified by flash column chromatography to afford the title compound (off white solid). $^1$H NMR (400 MHz, DMSO-$d_6$): δ 8.38 (s, 2H), 6.88 (s, 1H), 6.83 (d, J=7.6 Hz, 1H), 6.74 (d, J=7.6 Hz, 1H), 5.98-5.97 (m, 2H), 4.73 (s, 1H), 3.65-3.63 (m, 4H), 3.33-3.31 (m, 1H), 2.40-2.38 (m, 2H), 2.34-2.32 (m, 2H), 1.65-1.60 (m, 6H), 1.45-1.42 (m, 2H), 1.28-1.22 (m, 5H). LCMS: (Method A) 411.2 (M+H), Rt. 3.25 min, 96.51% (Max). HPLC: (Method A) Rt. 3.14 min, 97.88% (Max).

Example 181: (S)-1-(2-(4-(1-(benzo[d][1,3]dioxol-5-yl)ethyl)piperazin-1-yl)pyrimidin-5-yl)cyclopentan-1-ol

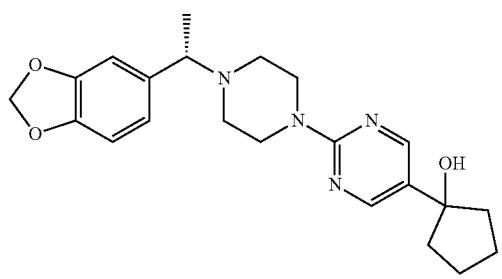 [SMILES: C[C@@H](c1ccc2c(c1)OCO2)N1CCN(c2ncc(C3(O)CCCC3)cn2)CC1]

The title compound was prepared according to the protocol described for the preparation of Example 180, replacing cyclohexanone with cyclopentanone (0.12 g, 1.53 mmol, Aldrich). The crude product was purified by flash column chromatography to afford the title compound (brown oil). $^1$H NMR (400 MHz, DMSO-$d_6$): δ 8.38 (s, 2H), 6.88 (s, 1H), 6.83 (d, J=7.6 Hz, 1H), 6.74 (d, J=7.6 Hz, 1H), 5.98-5.97 (m, 2H), 4.80 (s, 1H), 3.65-3.63 (m, 4H), 3.32-3.30 (m, 1H), 2.49-2.45 (m, 2H), 2.34-2.32 (m, 2H), 1.82-1.7 (m, 8H), 1.28 (d, J=6.8 Hz, 3H). LCMS: (Method A) 397.2 (M+H), Rt. 2.90 min, 98.83% (Max). HPLC: (Method A) Rt. 2.87 min, 99.10% (Max).

Example 183: Ethyl (S)-6-(4-(1-(benzo[d][1,3]dioxol-5-yl)ethyl)piperazin-1-yl)nicotinate

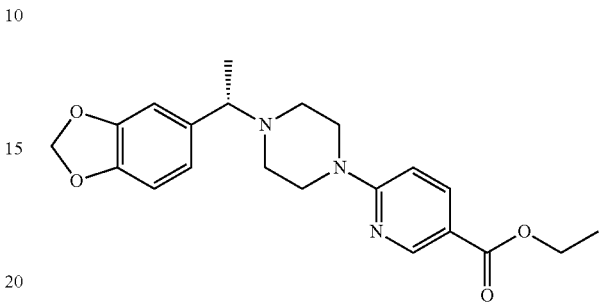

To a stirred solution of Intermediate 16 (1.0 g, 3.71 mmol) in dry DMF (10 mL), TEA (1.54 mL, 11.1 mmol) and ethyl-6-chloro nicotinate (0.69 g, 3.71 mmol) were added at rt and the reaction mixture was heated at 90° C. for 12 h. It was cooled to rt and concentrated. DCM (50 mL) was added and the resulting solution was washed with brine (30 mL) and dried over anhydrous $Na_2SO_4$. After evaporation of the solvents, the crude product was purified by flash chromatography to give the title compound (off white solid). $^1$H NMR (400 MHz, DMSO-$d_6$): δ 8.61 (d, J=2.4 Hz, 1H), 7.92-7.90 (m, 1H), 6.89 (d, J=1.6 Hz, 1H), 6.85-6.81 (m, 2H), 6.77-6.75 (m, 1H), 5.99-5.98 (m, 2H), 4.27 (q, J=7.2 Hz, 2H) 3.61 (t, J=4.8 Hz, 4H), 3.39-3.37 (m, 1H), 2.45-2.33 (m, 5H), 1.29-1.26 (m, 3H). LCMS: (Method A) 384.2 (M+H), Rt. 3.14 min, 98.30% (Max). HPLC: (Method A) Rt. 3.11 min, 98.88% (Max).

Example 185: (S)-(6-(4-(1-(benzo[d][1,3]dioxol-5-yl)ethyl)piperazin-1-yl)pyridin-3-yl)methanol

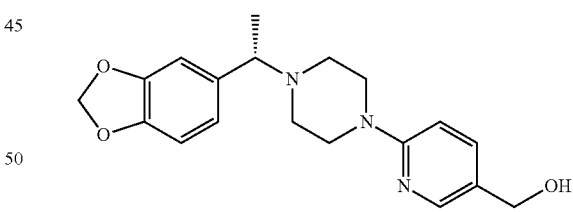

To a stirred solution of Example 183 (0.2 g, 0.56 mmol) in dry MeOH (5 mL) cooled at 0° C., was added lithium aluminium hydride (2.4 M, 0.24 mL, 1.17 mmol, spectrochem) dropwise and the mixture was stirred for 1 h at the same temperature. The reaction mixture was quenched with saturated ammonium chloride (5 mL) and extracted with ethyl acetate (20 mL). The organic phase was washed with brine solution (5 mL), dried over $Na_2SO_4$ and concentrated. The crude product was purified by flash column chromatography to afford the titled compound. Yield: 66% (88 mg, colorless oil). $^1$H NMR (400 MHz, DMSO-$d_6$): δ 8.04 (d, J=2.0 Hz, 1H), 7.46 (dd, J=8.8, 2.4 Hz, 1H), 6.88-6.86 (m, 1H), 6.84-6.82 (m, 1H), 6.76-6.73 (m, 2H), 5.98-5.97 (m, 2H), 4.96 (t, J=5.6 Hz, 1H) 4.32 (d, J=5.6 Hz, 2H), 3.41 (t, J=9.6 Hz, 4H), 3.34-3.32 (m, 1H), 2.49-2.45 (m, 2H), 2.39-2.37 (m, 2H), 1.28 (d, J=6.8 Hz, 3H). LCMS: (Method A) 342.3 (M+H), Rt. 1.74 min, 99.28% (Max). HPLC: (Method A) Rt. 1.71 min, 98.49% (Max).

Example 186: (S)-6-(4-(1-(benzo[d][1,3]dioxol-5-yl)ethyl)piperazin-1-yl)-N-methylnicotinamide

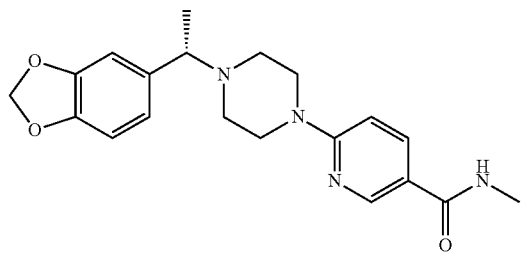 [SMILES: CNC(=O)c1ccc(N2CCN([C@@H](C)c3ccc4c(c3)OCO4)CC2)nc1]

Step 1: Lithium (S)-6-(4-(1-(benzo[d][1,3]dioxol-5-yl)ethyl)piperazin-1-yl)nicotinate Example 183 (1 g, 2.62 mmol) was dissolved in a mixture of MeOH (2 mL), THF (7 mL) and water (1 mL). The resulting mixture was cooled to 0° C. and lithium hydroxide (0.32 g, 7.86 mmol, spectrochem) was added. The resulting mixture was heated at 90° C. for 2 h. It was then concentrated and used as such in next step. Yield: 85% (0.8 g, off white solid). $^1$H NMR (400 MHz, DMSO-$d_6$): δ 8.52 (d, J=2.3 Hz, 1H), 7.89-7.86 (m, 1H), 6.88-6.59 (m, 4H), 5.97-5.96 (m, 2H), 3.43-3.33 (m, 5H), 2.36-2.28 (m, 4H), 1.26 (d, J=8.7 Hz, 3H). LCMS: (Method A) 354.0 (M+H), Rt. 3.639 min, 93.32% (Max).

Step 2: (S)-6-(4-(1-(benzo[d][1,3]dioxol-5-yl)ethyl)piperazin-1-yl)-N-methylnicotinamide To a stirred solution of lithium (S)-6-(4-(1-(benzo[d][1,3]dioxol-5-yl)ethyl)piperazin-1-yl)nicotinate (0.3 g, 8.32 mmol) in dry DCM (10 mL) cooled to 0° C., were added triethylamine (0.5 mL, 3.72 mmol), methylamine in THF (2 M, 2 mL, 2.24 mmol) followed by $T_3P$ (0.6 mL, 3.72 mmol). The resulting mixture was stirred at rt for 1 h. Reaction completion was monitored by TLC. The reaction mixture was washed with 10% sodium bicarbonate solution (10 mL). The organic layer was dried over $Na_2SO_4$, and evaporated to dryness. The crude product was purified by flash column chromatography (white solid). $^1$H NMR (400 MHz, DMSO-$d_6$): δ 8.54 (d, J=2.0 Hz, 1H), 8.18 (d, J=4.4 Hz, 1H), 7.89 (dd, J=2.4, 9.2 Hz, 1H), 6.89 (d, J=1.2 Hz, 1H), 6.85-6.77 (m, 1H), 6.77-6.74 (m, 2H), 5.99-5.98 (m, 2H), 3.54 (t, J=4.8 Hz, 4H), 3.37-3.35 (m, 1H), 2.73 (d, J=4.4 Hz, 3H), 2.45-2.43 (m, 2H), 2.39-2.32 (m, 2H), 1.28 (d, J=6.8 Hz, 3H). LCMS: (Method A) 369.2 (M+H), Rt. 2.05 min, 98.6% (Max). HPLC: (Method A) Rt. 2.00 min, 98.3% (Max).

Example 187: (S)-6-(4-(1-(benzo[d][1,3]dioxol-5-yl)ethyl)piperazin-1-yl)-N,N-dimethylnicotinamide

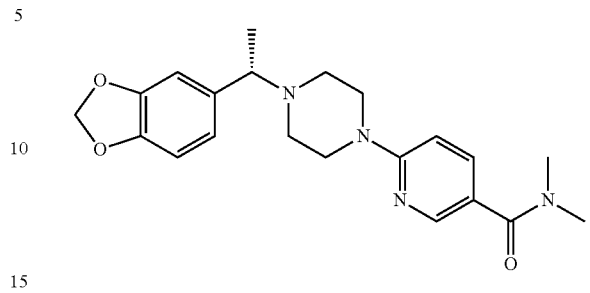

To a stirred solution of lithium (S)-6-(4-(1-(benzo[d][1,3]dioxol-5-yl)ethyl)piperazin-1-yl)nicotinate (Example 186, Step 1, 0.5 g, 1.38 mmol) in dry DCM (10 mL) at 0° C., were added triethylamine (2.6 mL, 4.14 mmol), dimethylamine in THF (2 M, 2 mL, 2.24 mmol) followed by $T_3P$ (2.6 mL, 4.14 mmol). The resulting mixture was stirred at rt for 1 h. Reaction completion was monitored by TLC. The reaction mixture was washed with 10% sodium bicarbonate solution (10 mL). The organic layer was dried over $Na_2SO_4$, and evaporated to dryness. The crude product was purified by flash column chromatography. Yield: 52% (279 mg, off white solid). $^1$H NMR (400 MHz, DMSO-$d_6$): δ 8.19 (d, J=2.4 Hz, 1H), 7.59 (dd, J=2.4, 8.8 Hz, 1H), 6.90 (s, 1H), 6.85 (d, J=8.0 Hz, 1H), 6.78 (t, J=7.2 Hz, 2H), 5.99-5.98 (m, 2H), 3.54-3.51 (m, 4H), 3.38-3.33 (m, 1H), 2.96 (s, 6H), 2.47-2.46 (m, 2H), 2.41-2.34 (m, 2H), 1.29 (d, J=6.8 Hz, 3H). LCMS: (Method A) 383.3 (M+H), Rt. 2.19 min, 99.8% (Max). HPLC: (Method A) Rt. 2.14 min, 99.6% (Max).

Example 188: (S)-4-(2-(4-(1-(benzo[d][1,3]dioxol-5-yl)ethyl)piperazin-1-yl)pyrimidin-5-yl)tetrahydro-2H-pyran-4-ol

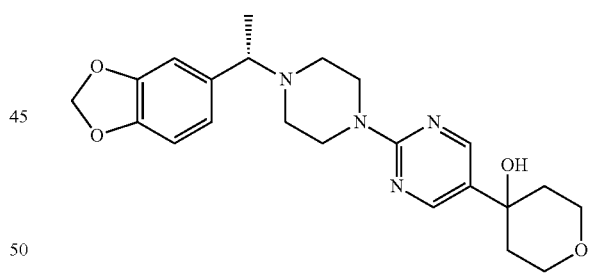

To a stirred solution of Example 175 (0.5 g, 1.28 mmol) in dry THF (10 mL) at −78° C. was added n-BuLi (1.6 M, 1.2 mL, 1.92 mmol, Aldrich) and the resulting mixture was stirred to −78° C. for 1 h. Tetrahydrofuran-4H-pyran-4-one (0.15 g, 1.53 mmol, Aldrich) in THF (5 mL) was added at −78° C. for 10 minutes. The temperature was increased to rt over 1 h. The reaction completion was monitored by TLC. The reaction mixture was quenched with saturated ammonium chloride solution (10 mL). It was extracted with EtOAc (50 mL). The organic phase was washed with saturated NaCl solution (20 mL) and dried over anhydrous $Na_2SO_4$. The crude product was purified by flash column chromatography to afford the title compound (off white solid). $^1$H NMR (400 MHz, DMSO-$d_6$): δ 8.42 (s, 2H), 6.90 (s, 1H), 6.84 (d, J=8.0 Hz, 1H), 6.76 (d, J=8.0 Hz, 1H), 5.99-5.98 (m, 2H), 5.07 (s, 1H), 3.77-3.66 (m, 8H), 3.39-3.37 (m, 1H), 2.44-2.40 (m, 2H), 2.37-2.33 (m, 2H), 1.95-1.87 (m, 2H), 1.57-1.54 (m, 2H), 1.28 (d, J=6.8 Hz, 3H). LCMS: (Method A) 413.3 (M+H), Rt. 2.32 min, 99.65% (Max). HPLC: (Method A) Rt. 2.27 min, 99.23% (Max).

Example 189: 3-(2-(4-((S)-1-(benzo[d][1,3]dioxol-5-yl)ethyl)piperazin-1-yl)pyrimidin-5-yl)tetrahydrofuran-3-ol

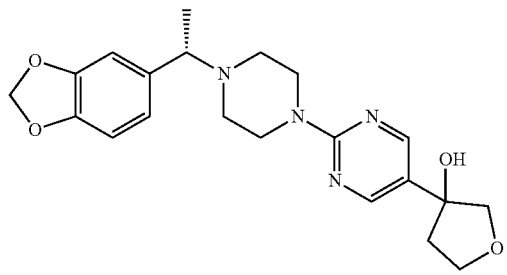 [SMILES: C[C@@H](c1ccc2c(c1)OCO2)N1CCN(c2ncc(C3(O)CCOC3)cn2)CC1]

Example 189 was prepared according the same procedure as Example 188, replacing tetrahydrofuran-4H-pyran-4-one with dihydrofuran(2H)-one (0.13 g, 1.53 mmol, Aldrich). The crude product was purified by flash column chromatography to afford the title compound (off white solid). $^1$H NMR (400 MHz, DMSO-$d_6$): δ 8.41 (s, 2H), 6.90 (d, J=1.2 Hz, 1H), 6.84 (d, J=7.6 Hz, 1H), 6.76 (d, J=7.6 Hz, 1H), 5.99-5.98 (m, 2H), 3.97-3.93 (m, 2H), 3.78-3.76 (m, 1H), 3.68-3.65 (m, 6H), 2.50-2.42 (m, 1H), 2.35-2.32 (m, 4H), 2.33-2.32 (m, 1H), 2.11-2.06 (m, 1H), 1.28 (d, J=6.4 Hz, 3H). LCMS: (Method A) 399.0 (M+H), Rt. 2.32 min, 97.39% (Max). HPLC: (Method A) Rt. 2.22 min, 97.15% (Max).

Example 190: (S)-2-(6-(4-(1-(benzo[d][1,3]dioxol-5-yl)ethyl)piperazin-1-yl)pyridin-3-yl)propan-2-ol

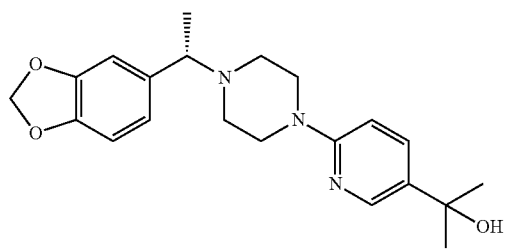 [SMILES: C[C@@H](c1ccc2c(c1)OCO2)N1CCN(c2ccc(C(C)(C)O)cn2)CC1]

To a stirred solution of Example 183 (0.3 g, 0.78 mmol) in dry THF (10 mL) at 0° C. was added methyl magnesium bromide solution in THF (1.4 M, 0.8 mL, 1.17 mmol, Aldrich). The resulting mixture was stirred at 0° C. for 1 h. The temperature was increased to rt and the mixture was stirred 12 h at that temperature. The reaction compleation was monitored by TLC. The reaction mixture was quenched with saturated ammonium chloride solution (10 mL) and extracted with EtOAc (50 mL). The organic layer was washed with sat NaCl solution (20 mL) and dried over anhydrous Na$_2$SO$_4$. The crude product was purified by flash column chromatography, yielding the title compound. Yield: 61% (0.178 g, colorless oil). $^1$H NMR (400 MHz, DMSO-$d_6$): δ 8.17 (d, J=2.0 Hz, 1H), 7.59-7.57 (m, 1H), 6.89-6.83 (m, 2H), 6.78-6.70 (m, 2H), 5.99-5.98 (m, 2H), 4.92 (s, 1H), 3.39 (t, J=4.8 Hz, 5H), 2.40-2.36 (m, 4H), 1.39 (s, 6H), 1.29 (d, J=6.8 Hz, 3H). LCMS: (Method A) 370.2 (M+H), Rt. 1.94 min, 99.3% (Max). HPLC: (Method A) Rt. 1.92 min, 99.60% (Max).

Example 191: (S)-1-(1-(benzo[d][1,3]dioxol-5-yl)ethyl)-4-(5-bromopyridin-2-yl)piperazine

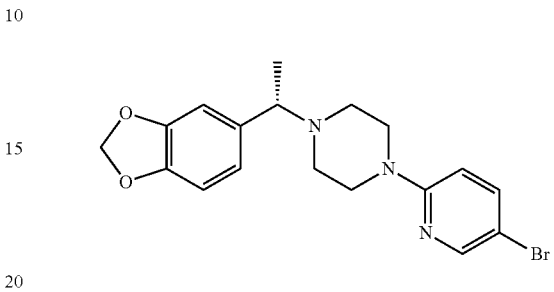

To a stirred solution of Intermediate 16 (5.5 g, 20.68 mmol) in dry DMF (50 mL), TEA (7.1 mL, 51.45 mmol) and 5-bromo-2-fluoropyridine (3 g, 17.24 mmol) were added at rt and the reaction mixture was stirred at 90° C. overnight. The reaction mixture was cooled to rt and concentrated under reduced pressure. Water (30 mL) was added and the compound was extracted with EtOAc (100 mL). The organic layer was dried over anhydrous Na$_2$SO$_4$ and concentrated. The resulting crude product was purified by flash chromatography to afford the title compound (white solid). $^1$H NMR (400 MHz, DMSO-$d_6$): δ 8.14 (d, J=2.4 Hz, 1H), 7.66-7.65 (m, 1H), 6.87 (d, J=1.2 Hz, 1H), 6.84 (d, J=7.6 Hz, 1H), 6.77-6.55 (m, 2H), 5.99-5.98 (m, 2H), 3.43 (t, J=4.8 Hz, 4H), 3.36-3.34 (m, 1H), 2.47-2.45 (m, 2H), 2.38-2.35 (m, 2H), 1.28 (d, J=6.8 Hz, 3H). LCMS: (Method A) 392.0 (M+H), Rt. 3.32 min, 99.88% (Max). HPLC: (Method A) Rt. 3.26 min, 99.96% (Max).

Example 192: (S)-1-(1-(benzo[d][1,3]dioxol-5-yl)ethyl)-4-(5-(methylthio)pyridin-2-yl)piperazine

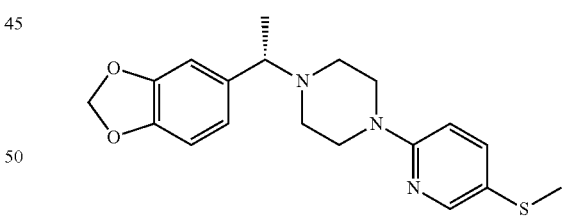

To a stirred solution of Example 191 (3.0 g, 7.71 mmol) in dry THF (30 mL), n-BuLi (6.0 mL, 9.2 mmol) was added at −78° C. and stirred for 1 h. Dimethyl disulphide (45 mL) was added at same temperature and stirred for 1 h at rt. The reaction mixture was quenched with saturated NH$_4$Cl and extracted with EtOAc. The organic layer was washed with water and dried over anhydrous Na$_2$SO$_4$ and concentrated. The resulting crude was purified by flash column chromatography to afford the title compound. Yield: 90% (2.58 g, yellow solid). $^1$H NMR (400 MHz, CDCl$_3$): δ 8.21 (d, J=2.4 Hz, 1H), 7.52-7.51 (m, 1H), 6.89 (s, 1H), 6.76 (s, 2H), 6.56 (d, J=8.8 Hz, 1H), 5.96-5.94 (m, 2H), 3.52 (m, 4H), 3.34 (d, J=6.0 Hz, 1H), 2.57-2.50 (m, 4H), 2.38 (s, 3H), 1.36 (d, J=6.4 Hz, 3H). LCMS: (Method A) 358.3.0 (M+H), Rt. 2.61 min, 97.99% (Max). HPLC: (Method A) Rt. 2.56 min, 97.57% (Max).

Example 195: (S)-2-(4-(1-(benzo[d][1,3]dioxol-5-yl)ethyl)piperazin-1-yl)-5-methoxypyrimidine

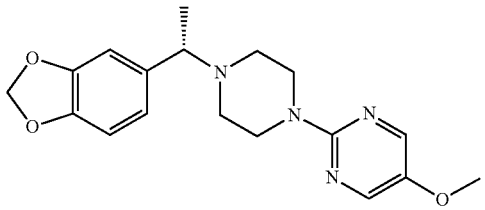 [SMILES: CSc1ccc(N2CCN([C@@H](C)c3ccc4c(c3)OCO4)CC2)nc1]

To a stirred solution of Intermediate 16 (0.55 g, 2.07 mmol) in dry DMF (5 mL), triethylamine (0.9 mL, 6.21 mmol, spectrochem) and 2-chloro-5-methoxy pyrimidine (0.3 g, 2.07 mmol, Combi-Blocks) were added and the resulting mixture was heated to 90° C. for 12 h. The reaction mixture was cooled down to rt and concentrated. Dichloromethane (25 mL) was added and the resulting solution was washed with water (20 mL), bind (20 mL) and dried over $Na_2SO_4$. After evaporation of the solvents, the crude product was purified by flash column chromatography to afford the title compound (brown solid). $^1$H NMR (400 MHz, DMSO-$d_6$): δ 8.18 (s, 2H), 6.87 (m, 2H), 6.76 (d, J=8.0 Hz, 1H), 5.99-5.98 (m, 2H), 3.76 (s, 3H), 3.58 (t, J=4.8 Hz, 4H), 3.38-3.36 (m, 1H), 2.45-2.42 (m, 2H), 2.36-2.33 (m, 2H), 1.28 (d, J=6.8 Hz, 3H). LCMS: (Method A) 343.2 (M+H), Rt. 2.73 min, 99.83% (Max). HPLC: (Method A) Rt. 2.71 min, 99.41% (Max).

Example 197 and 198: (S)-1-(2-(4-((S)-1-(benzo[d][1,3]dioxol-5-yl)ethyl)piperazin-1-yl)pyrimidin-5-yl)ethan-1-ol and (S)-1-(2-(4-((R)-1-(benzo[d][1,3]dioxol-5-yl)ethyl)piperazin-1-yl)pyrimidin-5-yl)ethan-1-ol

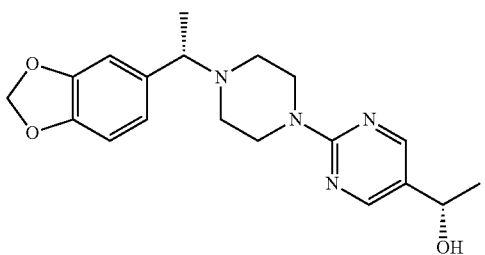

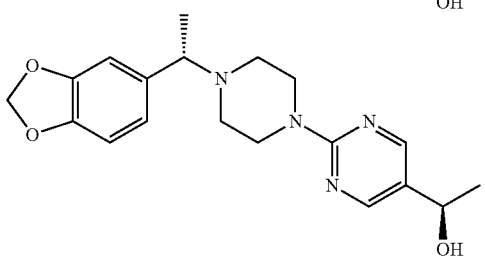

Example 168 was submitted to chiral preparative HPLC Method PK to separate both enantiomers. The first eluting compound was concentrated to give Example 198 (brown oil). $^1$H NMR (400 MHz, DMSO $d_6$): δ 8.29 (s, 2H), 6.89 (s, 1H), 6.84 (d, J=7.9 Hz, 1H), 6.75 (d, J=7.9 Hz, 1H), 5.99-5.98 (m, 2H), 5.12 (d, J=4.4 Hz, 1H), 4.62-4.61 (m, 1H), 3.67-3.65 (m, 4H), 3.38-3.36 (m, 1H), 2.51-2.33 (m, 4H), 1.31 (d, J=6.4 Hz, 3H), 1.28 (d, J=6.4 Hz, 3H). LCMS: (Method A) 357.2 (M+H), Rt. 2.30 min, 99.37% (Max). HPLC: (Method A) Rt. 2.30 min, 98.05% (Max). Chiral HPLC: (Method H) Rt. 7.06 min, 100%. The second eluting compound was concentrated to give Example 197 (brown oil). $^1$H NMR (400 MHz, DMSO $d_6$): δ 8.29 (s, 2H), 6.89 (s, 1H), 6.84 (d, J=8.0 Hz, 1H), 6.75 (d, J=8.0 Hz, 1H), 5.99-5.98 (m, 2H), 5.11 (d, J=4.4 Hz, 1H), 4.62-4.59 (m, 1H), 3.68-3.65 (m, 4H), 3.38-3.36 (m, 1H), 2.35-2.32 (m, 4H), 1.31 (d, J=6.4 Hz, 3H), 1.28 (d, J=6.8 Hz, 3H). LCMS: (Method A) 357.2 (M+H), Rt. 2.29 min, 99.93% (Max). HPLC: (Method N) Rt. 2.26 min, 99.62% (Max). Chiral HPLC: (Method H) Rt 7.60 min, 100%.

Example 199: 2-(4-(1-(2,3-dihydrobenzofuran-6-yl)ethyl)piperazin-1-yl)-6,7-dihydrothiazolo[5,4-c]pyridin-4(5H)-one

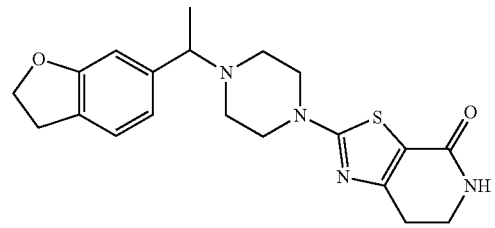 [SMILES: CC(c1ccc2c(c1)OCC2)N1CCN(c2nc3c(s2)C(=O)NCC3)CC1]

To a stirred solution of Intermediates 25 (0.5 g, 1.61 mmol) in DMF (5 mL, 10V), TEA (0.89 mL, 6.4 mmol) and Intermediate 21 (0.44 g, 2.41 mmol) were added at rt and the mixture was stirred at 80° C. for 12 h. It was concentrated under vacuum and resulting crude mixture was purified by MD Autoprep HPLC (Method C) to afford titled compound (off white solid). $^1$H NMR (400 MHz, DMSO-d6): δ 7.29 (s, 1H), 7.16 (d, J=7.2 Hz, 1H), 6.76 (d, J=7.6 Hz, 1H), 6.72 (s, 1H), 4.51 (t, J=8.8 Hz, 2H), 3.46-3.42 (m, 4H), 3.38-3.36 (m, 4H), 3.14 (t, J=8.8 Hz, 2H), 2.69 (t, J=7.2 Hz, 2H), 2.44-2.43 (m, 2H), 1.28 (d, J=6.80 Hz, 3H). LCMS: (Method A) 358.0 (M+H), Rt. 2.324 min, 97.963% (Max). HPLC: (Method A) Rt. 2.279 min, 99.224% (Max).

Example 200: Ethyl 5-(4-(1-(2,3-dihydrobenzofuran-6-yl)ethyl)piperazin-1-yl)-1,3,4-thiadiazole-2-carboxylate

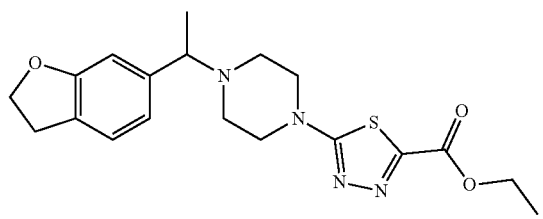 [SMILES: CCOC(=O)c1nnc(N2CCN(C(C)c3ccc4c(c3)OCC4)CC2)s1]

To a stirred solution of ethyl 5-chloro-1,3,4-thiadiazole-2-carboxylate (0.25 g, 1.29 mmol) in dry DMF (2.5 mL), $K_2CO_3$ (0.54 g, 3.89 mmol) and Intermediate 30 (0.59 g, 1.93 mmol) were added at rt. The reaction mixture was stirred overnight at 80° C. It was then concentrated under vacuum. EtOAc (10 mL) was added and the resulting solution was washed with water (10 mL), brine (10 mL), dried over anhydrous $Na_2SO_4$ and concentrated. The crude product was purified by flash chromatography to afford the title compound. Yield: 51% (0.26 g, off white solid). $^1$H NMR (400 MHz, DMSO-$d_6$): δ 7.15 (d, J=7.60 Hz, 1H), 6.75 (d, J=7.60 Hz, 1H), 6.71 (s, 1H), 4.50 (t, J=8.80 Hz, 2H), 4.33 (q, J=6.80 Hz, 2H), 3.54 (t, J=5.20 Hz, 4H), 3.43-3.41 (m, 1H), 3.13 (t, J=8.40 Hz, 2H), 2.45-2.32 (m, 4H), 1.31-1.27 (m, 6H). LCMS: (Method A) 389.2 (M+H), Rt. 2.88 min, 95.7% (Max). HPLC: (Method A) Rt 2.81 min, 96.5% (Max).

Example 201: 5-(4-(1-(2,3-dihydrobenzofuran-6-yl) ethyl)piperazin-1-yl)-N-methyl-1,3,4-thiadiazole-2-carboxamide

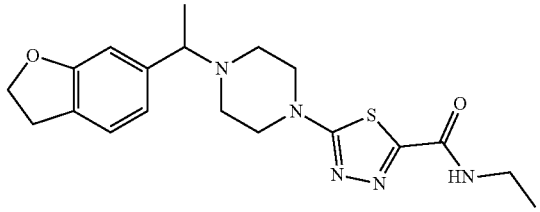 [SMILES: CCNC(=O)c1nnc(N2CCN(C(C)c3ccc4c(c3)OCC4)CC2)s1]

The title compound was synthesized according to the procedure described for Example 59 and 60, starting from Example 200 (brown thick oil). $^1$H NMR (400 MHz, DMSO-$d_6$): δ 8.74 (q, J=4.8 Hz, 1H), 7.16 (d, J=7.2 Hz, 1H), 6.76 (d, J=1.2 Hz, 1H), 6.72 (s, 1H), 4.51 (t, J=8.40 Hz, 2H), 3.49 (t, J=4.80 Hz, 4H), 3.43-3.41 (m, 1H), 3.14 (t, J=8.80 Hz, 2H), 2.75 (d, J=4.8 Hz, 3H), 2.53-2.51 (m, 2H), 2.46-2.42 (m, 2H), 1.28 (d, J=6.8 Hz, 3H). LCMS: (Method A) 374.0 (M+H), Rt. 2.35 min, 96.4% (Max). HPLC: (Method A) Rt 2.30 min, 98.2% (Max).

Examples 202 and 203: (R)—N-(5-(4-(1-(2,3-dihydrobenzofuran-6-yl)ethyl)piperazin-1-yl)-1,3,4-thiadiazol-2-yl)acetamide and (S)—N-(5-(4-(1-(2,3-dihydrobenzofuran-6-yl)ethyl)piperazin-1-yl)-1,3,4-thiadiazol-2-yl)acetamide

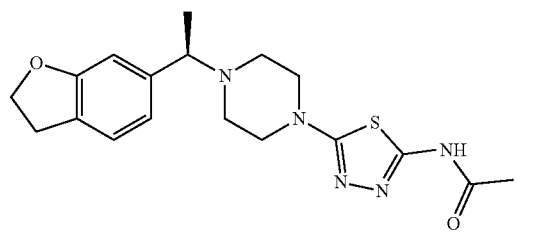

and

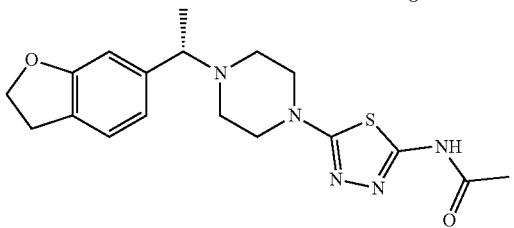

The racemic mixture of Example 128 was separated by SFC using the preparative chiral method PA.

The first eluting compound correspond to Example 202 (off white solid). $^1$H NMR (400 MHz, DMSO-$d_6$): δ 11.99 (s, 1H), 7.14 (d, J=7.6 Hz, 1H), 6.75 (d, J=7.2 Hz, 1H), 6.71 (s, 1H), 4.50 (t, J=8.8 Hz, 2H), 3.38-3.36 (m, 1H), 3.35-3.33 (m, 4H), 3.13 (t, J=8.4 Hz, 2H), 2.42-2.38 (m, 4H), 2.07 (s, 3H), 1.27 (d, J=6.80 Hz, 3H). LCMS: (Method A) 374.2 (M+H), Rt. 2.31 min, 99.4% (Max). HPLC: (Method A) Rt 2.34 min, 99.7% (Max). CHIRAL HPLC: (SFC Method AA) Rt. 2.81 min, 100% (Max).

The second eluting compound corresponds to Example 203 (white solid). $^1$H NMR (400 MHz, DMSO-$d_6$): δ 12.05 (s, 1H), 7.14 (d, J=7.6 Hz, 1H), 6.75 (d, J=7.6 Hz, 1H), 6.70 (s, 1H), 4.49 (t, J=8.8 Hz, 2H), 3.37-3.36 (m, 1H), 3.32-3.31 (m, 4H), 3.13 (t, J=8.8 Hz, 2H), 2.41-2.38 (m, 4H), 2.08 (s, 3H), 1.27 (d, J=6.40 Hz, 3H). LCMS: (Method A) 374.2 (M+H), Rt. 2.31 min, 99.37% (Max). HPLC: (Method A) Rt 2.35 min, 99.59% (Max). CHIRAL HPLC: (SFC Method AA) Rt. 3.45 min, 99.42% (Max).

Example B01: Human O-GlcNAcase Enzyme Inhibition Assay

5 µl of the appropriate concentration of a solution of inhibitor in McIlvaine's Buffer (pH 6.5) in 2% DMSO (for a dose response curve calculation) is added into each well of a 384-well plate (Greiner, 781900). Then, 20 nM of His-Tagged hOGA and 10 µM of FL-GlcNAc (Fluorescein mono-beta-D-(2-deoxy-2-N-acetyl) glucopyranoside; Marker Gene Technologies Inc, M1485) were added to the 384-well plate for a final volume of 20 µl. After incubation for 60 min at room temperature, the reaction was terminated by the addition of 10 µL of stop buffer (200 mM glycine, pH 10.75). The level of fluorescence ($\lambda_{exc}$ 485 nm; ($\lambda_{emm}$ 520 nm) was read on a PHERAstar machine. The amount of fluorescence measured was plotted against the concentration of inhibitor to produce a sigmoidal dose response curve to calculate an $IC_{50}$. All individual data was corrected by subtraction of the background (Thiamet 3 uM=100% inhibition) whilst 0.5% DMSO was considered as the control value (no inhibition).

Example B02: Pharmacodynamic Model: Total Protein O-GlcNAcylation Immunoassay (RL2 mAb, Meso Scale Electrochemiluminescence (ECL) Assay)

The test compound was administered orally to C57BL/6J mice. At defined time intervals after compound administration, typically a time ranging between 2 and 48 hours, preferably between 4 and 24 hours, mice were sacrificed by decapitation for blood collection and forebrain dissection. Right brain hemispheres were placed in 2 ml Precellys tubes, snap frozen in dry ice and stored at −80° C. Left hemispheres were placed in 2 ml Eppendorf tubes, snap frozen in dry ice and stored at −80° C. until further processing. Blood samples were collected in Sarstedt tubes containing 35 IU of Heparin and kept at 4° C. After centrifugation for 10 min at 3800×g, 4° C., 50 µL of plasma from each sample was transferred to a 1.5 ml Eppendorf tube and stored at −80° C.

For the preparation of soluble brain protein for the immunoassay the hemispheres were homogenized in ice-cold Cytobuster reagent (71009—Merck Millipore) buffer with protease inhibitor cocktail. After centrifugation for 15 min at 17000×g at 4° C. the supernatants were transferred into polycarbonate tubes (1 ml). The supernatants were cleared by centrifugation for 1 h. at 100000×g, 4° C., and the protein concentrations were determined by using the BCA kit (23227—Pierce, Rockford, IL) according to the manufacturer's instructions.

Total Protein O-GlcNAcylation Immunoassay:

Samples were randomised and 120 µg/ml (25 µl/well) of soluble brain protein was directly coated on a Multi-array 96-well high bind plate (L15XB-3 High bind—Meso Scale Discovery) overnight at 4° C. After washing (3× with PBS-T buffer), the plate was blocked with MSD blocker A solution for 1 h. at room temperature (RT) under agitation. After washing (3× with PBS-T buffer), the plate was incubated with 0.1 µg/ml of a mouse monoclonal antibody directed against O-GlcNAc moieties (RL2; MA1-072—Thermo Scientific) for 1 h. at RT under agitation. For the ECL assay, after washing (3× with PBS-T buffer), 1 µg/ml of a SULFO-TAG™ labeled anti-mouse secondary antibody (Meso Scale Discovery) was added and the plate was incubated for 1 h. at RT under agitation and protected from light. After washing (3× with PBS-T buffer), 150 µl/well of 1× Read Buffer T was added to the plates before reading on a Sector Imager 6000 (Meso Scale Discovery).

Example B03: Pharmaceutical Preparations (A) Injection vials: A solution of 100 g of an active ingredient according to the invention and 5 g of disodium hydrogen phosphate in 3 l of bi-distilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of $NaH_2PO_4.2 H_2O$, 28.48 g of $Na_2HPO_4.12 H_2O$ and 0.1 g of benzalkonium chloride in 940 ml of bi-distilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated tablets: Tablets were pressed analogously to EXAMPLE E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bi-distilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

Example C01: Physical Properties Characterization Methods

X-Ray Powder Diffraction (XRPD)

Approximately 5-10 mg of sample was gently compressed on the XRPD zero back ground single obliquely cut silica sample holder. The sample was then loaded into a Philips X-Pert PRO diffractometer and analysed using the following experimental conditions.

Tube anode: Cu
Generator tension: 40 kV
Tube current: 40 mA
Wavelength alpha1: 1.5406 Å
Wavelength alpha2: 1.5444 Å
Start angle [2 theta]: 5
End angle [2 theta]: 50
Continuous scan For suspected novel salts a slower scan speed was also used over a range of 4-40° 2q.

Raman Spectroscopy

Samples were analysed by a Nicolet Almega XR Dispersive Raman Microscope for its Raman spectrum using the following conditions:

Exposure Time: 1.0 s
Acquisition No: 50
Slit Size: 100 µm
Wavelength range: 2000–400 $cm^{-1}$ (single grating)
Laser: He—Ne 780 nm 100% power
Objective: 20×/0.40 (magnifier/numerical aperture number)

Baseline subtraction was performed on the Raman spectra. Nuclear Magnetic

Resonance (NMR)

The $^1H$ NMR was run in DMSO-d6 using a Bruker Avance III 400 instrument.

Simultaneous Thermal Analysis (STA)

Approximately 5 mg of sample was accurately weighed into a ceramic crucible and it was placed into the chamber of Perkin-Elmer STA 6000 TGA/DTA analyzer at ambient temperature. The sample was then heated at a rate of 10° C./min, typically from 30° C. to 300° C., during which time the change in weight was monitored as well as DTA signal. The purge gas used was nitrogen at a flow rate of 20 $cm^3$/min.

Differential Scanning Calorimetry (DSC)

Approximately, 5 mg of each sample was weighed into an aluminium DSC pan and sealed non-hermetically with an aluminium lid. The sample was then loaded into a Perkin-Elmer Jade DSC and held at 30° C. Once a stable heat-flow response was obtained, the sample was then heated to a 250 or 300° C. at a scan rate of 10° C./min and the resulting heat flow response was monitored. A 20 $cm^3$/min helium purge was used. Prior to analysis, the instrument was temperature and heat flow verified using an indium standard.

Example C02: Primary Salt Screen Procedure

Preferred compound of Structure I were selected for primary salt screen procedure.

If the respective acid was a solid (such as but not limited to maleic acid, fumaric acid, succinic acid, L-tartaric acid, citric acid, adipic acid, benzoic acid, p-toluene sulphonic acid), the Compound of formula (I) (~30 mg) was weighed into twelve separate vials with ~1.1 equivalents of the counter-ion as a physical solid mixture. 300 μL of the appropriate solvent was added.

If the respective acid, was in aqueous solution or a liquid (such as but not limited to 5M hydrochloric acid, 6M sulphuric acid, 85% orthophosphoric acid, methane sulphonic acid) the appropriate volume corresponding to ~1.1 equivalents was added to ~30 mg of the API in the appropriate solvent (300 μL) (mostly suspension).

The mixture was shaken well by hand. All slurries or solutions were temperature-cycled between ambient and 40° C. for ~18-24 hours. If enough solid was present the supernatant was decanted off, if possible, and the solid dried by evaporation. If a solution was observed, the solvent was allowed to evaporate under nitrogen then dried.

Diverse solvents or solvents mixture were selected for the primary salt screen, such as but not limited to methanol, acetone, ethyl acetate, acetonitrile, tetrahydrofuran, toluene, 50/50 methanol/water and 90/10 propan-2-ol/water. They were selected on the basis of structural diversity and acceptability. They were all commonly used in final step processes.

Any solids were examined by XRPD and are reported in FIGS. 1 to 6.

Example C03: Methods of Preparation

Example C03-1: Hydrochloride Salt Preparation

A preferred method of preparation of this salt was as follows:

Compound of Formula I (1.33 mmol) was suspended in ethanol (5 mL). 5M Hydrochloric acid (300 μL, 1.5 mmol, 1.25 equiv) was added and mixed well. The resulting suspension was temperature-cycled between 40° C. and ambient temperature overnight (18-24 hours). The product amassed and ethanol (2 mL) was added to mobilize before the product was filtered, washed with ethanol (2×2 mL) and dried in a vacuum oven at 50° C. for ~24 hours to constant weight. (Yield 88%).

Starting from 500 mg of Example 69, 480 mg of hydrochloride salt was obtained.

Example 69 hydrochloride salt was characterized by XRPD (FIG. 11), Raman (FIG. 12), $^1$H NMR (FIG. 13), STA (FIG. 14) and DSC (FIG. 15).

Example C03-2: Maleate Salt Preparation

A preferred method of preparation of this salt was as follows:

Compound of Formula I (1.33 mmol) was suspended in ethanol (5 mL). Maleic acid (170 mg, 1.46 mmol, 1.1 equiv) was added and mixed well. The resulting suspension was temperature-cycled between 40° C. and ambient temperature overnight (18-24 hours). The product was filtered, washed with ethanol (2×2 mL) and dried in a vacuum oven at 50° C. for ~24 hours to constant weight.

Starting from 500 mg of Example 69, 518 mg of maleate salt was obtained.

Example 69 maleate salt was characterized by XRPD (FIG. 16), $^1$H NMR (FIG. 17), STA (FIG. 18) and DSC (FIG. 19).

Example C03-3: L-Tartrate Salt Preparation

A preferred method of preparation of this salt was as follows:

Compound of Formula I (1.33 mmol) was suspended in ethanol (5 mL). L-tartaric acid (200 mg, 1.33 mmol, 1 equiv) was added and mixed well. The resulting suspension was temperature-cycled between 40° C. and ambient temperature overnight (18-24 hours). The product was filtered, washed with ethanol (2×2 mL) and dried in a vacuum oven at 50° C. for ~24 hours to constant weight.

Starting from 500 mg of Example 69, 599 mg of L-tartrate salt was obtained.

Example 69 L-tartrate salt was characterized by XRPD (FIG. 20), $^1$H NMR (FIG. 21).

Example C04: Visual Aqueous Solubility

The salts and free base (~10 mg) were weighed into glass vials and water was added in 0.1 mL portions up to 3 mL and 1 mL portions thereafter. Solubility was assessed visually following a brief period of equilibration.

The aqueous solubility of different salt of Example 69 was assessed, as reported in Table 1.

| Example 69 Salts | Visual aqueous solubility |
|---|---|
| L-Tartrate salt | ~20 mg/mL |
| Maleate salt | ~4.5 mg/mL |
| Hydrochloride salt | ~4.5 mg/mL |
| Free base | <0.5 mg/mL |

Salts of compounds of formula I with various other acids did not yield a useful improvement of aqueous solubility over the free base and/or have not been stable or solid or have other properties not suitable for pharmaceutical development, especially for solid oral dosage forms, such as tablets, e.g compressed tablets.

The invention claimed is:
1. An acid addition salt of a compound of formula (I):

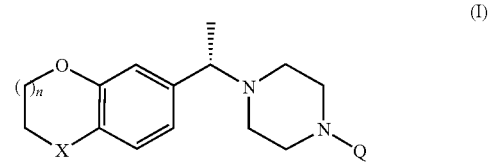

(I)

and an acid that is hydrochloric acid, maleic acid, tartaric acid, sulfuric acid, or p-toluolsulfonic acid;
wherein:
X is O or $CH_2$;
n is 0 or 1;
Q is:

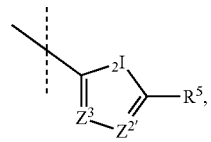
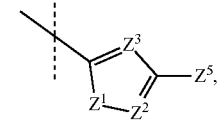

-continued

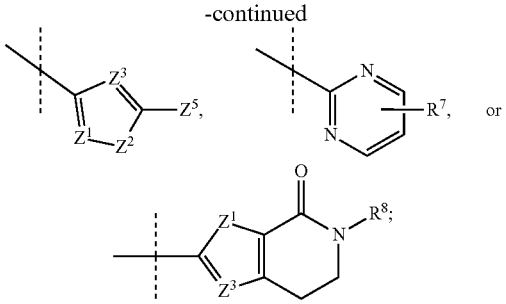

$Z^1$ is S, O, or $NR^3$;

each of $Z^2$, $Z^{2'}$, and $Z^3$, independently, are selected from $CR^5$, $CR^6$, and N;

each of $R^5$, $R^{5'}$, $R^6$, and $R^7$, independently, are selected from H, Hal, $NR^3R^4$, $NO_2$, Ar, Het, Cyc, and straight chain or branched alkyl having 1 to 12 carbon atoms, wherein 1 to 3 $CH_2$-groups may be replaced by a group selected from O, $NR^3$, S, SO, $SO_2$, CO, COO, OCO, $CONR^3$, and $NR^3CO$, and wherein 1 to 5 hydrogen atoms are optionally replaced by Hal, $NR^3R^4$, $NO_2$, $OR^3$, Het, Ar, or Cyc;

$R^8$ is H, methyl, or straight chain or branched alkyl having 2 to 12 carbon atoms, wherein 1 to 3 $CH_2$-groups are optionally replaced by a group selected from O, $NR^3$, S, SO, $SO_2$, CO, COO, OCO, $CONR^3$, and $NR^3CO$, and wherein 1 to 5 hydrogen atoms are optionally replaced by Hal, $NR^3R^4$, or $NO_2$;

each of $R^3$ and $R^4$, independently, are selected from H and straight chain or branched alkyl group having 1 to 12 carbon atoms;

Hal is F, Cl, Br, or I;

Het is a saturated, unsaturated, or aromatic ring, being monocyclic, bicyclic, or fused-bicyclic, and having 3- to 8-members and containing 1 to 4 heteroatoms selected from N, O and S, which may be substituted by 1 to 3 substituents selected from $R^5$, Hal, and $OR^3$;

Ar is a 6-membered carbocyclic aromatic ring or a fused or non-fused bicyclic aromatic ring system, which is optionally substituted by 1 to 3 substituents independently selected from $R^5$, $OR^3$, and Hal;

Cyc is a saturated or an unsaturated carbocyclic ring having from 3 to 8 carbon atoms which is optionally substituted by 1 to 3 substituents independently selected from $R^5$, Hal, or OH;

or a solid form thereof.

2. The acid addition salt of claim 1, or a solid form thereof, wherein the compound of formula (I) is formula (Ia):

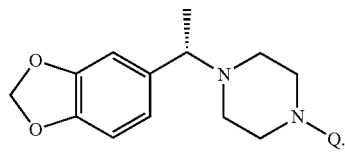

3. The acid addition salt of claim 1, or a solid form thereof, wherein Q is

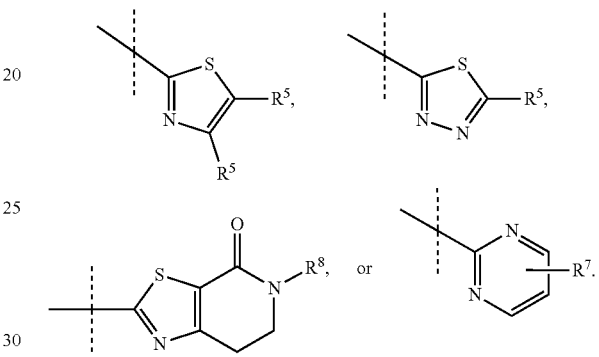

4. The acid addition salt of claim 1, or a solid form thereof, wherein the molar ratio of the compound of formula (I) to acid is 1:1.

5. A solid oral dosage form comprising the acid addition salt of claim 1 or a solid form thereof.

6. A method for the preparation of the acid addition salt of claim 1, comprising the following steps:
a) suspending or dissolving the compound of formula (I) and the acid in a suitable solvent or solvent mixture to prepare a mixture;
b) heating the mixture obtained in step a) to a temperature of between 30° C. to the boiling point of the selected solvent or solvent mixture, and then allowing the mixture to cool to room temperature;
c) optionally repeating step b) several times;
d) separating and drying the acid addition salt.

* * * * *